United States Patent
Tran et al.

(10) Patent No.: US 11,827,884 B2
(45) Date of Patent: Nov. 28, 2023

(54) CORE MASTER REGULATORS OF GLIOBLASTOMA STEM CELLS

(71) Applicant: University of Florida Research Foundation, Incorporated, Gainesville, FL (US)

(72) Inventors: David Tran, Gainesville, FL (US); Son B. Le, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/613,402

(22) PCT Filed: May 15, 2018

(86) PCT No.: PCT/IB2018/053365
§ 371 (c)(1),
(2) Date: Nov. 13, 2019

(87) PCT Pub. No.: WO2011/211409
PCT Pub. Date: Nov. 22, 2018

(65) Prior Publication Data
US 2020/0165614 A1 May 28, 2020

Related U.S. Application Data

(60) Provisional application No. 62/586,655, filed on Nov. 15, 2017, provisional application No. 62/506,413, filed on May 15, 2017.

(51) Int. Cl.
*C12N 15/113* (2010.01)
*A61K 45/06* (2006.01)

(52) U.S. Cl.
CPC .......... *C12N 15/1135* (2013.01); *A61K 45/06* (2013.01); *C12N 2310/14* (2013.01); *C12N 2310/531* (2013.01)

(58) Field of Classification Search
CPC ............ C12N 15/1135; C12N 2310/14; C12N 2310/531; A61K 45/06
See application file for complete search history.

(56) References Cited

U.S. PATENT DOCUMENTS 7,723,112 B2  5/2010  Clarke et al.
7,812,124 B2  10/2010  Palm
(Continued)

FOREIGN PATENT DOCUMENTS

EP  3118306 A1  1/2017
WO  WO-2004/096826 A2  11/2004
(Continued)

OTHER PUBLICATIONS

Rheinbay et al. (Cell Rep., 2013 vol. 5:1567-1579).*
(Continued)

*Primary Examiner* — Terra C Gibbs
(74) *Attorney, Agent, or Firm* — Wolf, Greenfield & Sacks, P.C.

(57) ABSTRACT

Provided herein are immunotherapy compositions for treating a subject with a glioblastoma, comprising a peptide formulation derived from at least one cancer or stemness factor, nanoparticles containing peptides derived from at least one cancer or stemness factor, dendritic cells containing peptides derived from at least one cancer or stemness factors, RNA coding at least one cancer or stemness factor, nanoparticles containing RNA coding at least one cancer or stemness factor, dendritic cells containing RNA coding at least one cancer factor or stemness factor, or an inhibitor of at least one cancer or stemness factor. Also provided are methods of inhibiting a glioblastoma stem-like cell (GSC), methods of treating a subject for glioblastoma, and methods
(Continued)

of reprogramming an astrocyte to a glioblastoma stem-like cell (GSC) using such immunotherapy compositions.

10 Claims, 33 Drawing Sheets

Specification includes a Sequence Listing.

(56) References Cited

U.S. PATENT DOCUMENTS

| | | | |
|---|---|---|---|
| 2004/0219575 | A1 | 11/2004 | Neuman et al. |
| 2006/0188484 | A1 | 8/2006 | Rabinowitz et al. |
| 2014/0005249 | A1 | 1/2014 | Hugnot et al. |
| 2015/0024036 | A1 | 1/2015 | Saydam et al. |
| 2016/0017005 | A1 | 1/2016 | Asokan et al. |
| 2016/0074389 | A1 | 3/2016 | Lisanto |
| 2016/0116474 | A1 | 4/2016 | Suva et al. |
| 2017/0051288 | A1 | 2/2017 | Byrne et al. |
| 2018/0066285 | A1 | 3/2018 | Ojala et al. |
| 2022/0135971 | A1 | 5/2022 | Tran et al. |
| 2022/0333136 | A1 | 10/2022 | Zolotukhin et al. |

FOREIGN PATENT DOCUMENTS

| | | |
|---|---|---|
| WO | WO-2005/028675 A2 | 3/2005 |
| WO | WO 2010/108126 A2 | 9/2010 |
| WO | WO-2013/188813 A2 | 12/2013 |
| WO | WO-2014/062454 A1 | 4/2014 |
| WO | WO-2017/032869 A1 | 3/2017 |
| WO | WO 2018/069891 A2 | 4/2018 |
| WO | WO 2018/211409 A1 | 11/2018 |

OTHER PUBLICATIONS

Haapa-Paananen et al. (Oncogene, 2012 vol. 31;1299-1310).*

Berezovsky et al. (Neoplasia, 2014 vol. 16:193-206).*

International Searching Authority, International Search Report and Written Opinion for International Application No. PCT/IB2018/053365, dated May 15, 2018, (16 pages), European Patent Office, Rijswijk, Netherlands.

Clavairoly, Adrien. *Ascl1 and Olig2 Transcriptional Regulations of Oligodendrogenesis*, Neurons and Cognition [q-bio.NC], Université Pierre et Marie Curie, Paris VI, (2014), (257 pages), English, NNT: 2014PA066316. [Retrieved from the Internet Feb. 5, 2020] <https://tel.archives-ouvertes.fr/tel-01133659/file/2014PA066316.pdf>.

Johansson, Térèse A. et al. *Identification of Achaete-Scute Complex-Like 1 (ASCL1) Target Genes and Evaluation of DKK1 and TPH1 Expression In Pancreatic Endocrine Tumours*, BMC Cancer, BioMed Central, vol. 9, No. 1, Sep. 10, 2009, pp. 1-13. XP021057699. ISSN: 1471-2407. DOI: 10.1186/1471-2407-9-321. [Retrieved from the Internet Feb. 5, 2020] < https://bmccancer.biomedcentral.com/articles/10.1186/1471-2407-9-321>.

Swartling, Fredrik J. *Myc Proteins In Brain Tumor Development and Maintenance*, Upsula Journal of Medical Sciences, vol. 117, No. 2, Feb. 2012, pp. 122-131. ISSN: 0300-9734. DOI: 10.3109/03009734.2012.658975. [Retrieved from the Internet Feb. 5, 2020] < https://www.tandfonline.com/doi/full/10.3109/03009734.2012.658975>.

Suvá, Mario L. et al. *Reconstructing and Reprogramming The Tumor-Propagating Potential of Glioblastoma Stem-Like Cells*, Cell Press, vol. 157, No. 3, Apr. 24, 2014, pp. 580-594. [Retrieved from the Internet Feb. 5, 2020] <https://www/sciencedirect.com/science/article/pii/S0092867414002293>.

Hoffman, Stephanie A. et al. *Stem Cell Factor Sox2 and Its Close Relative Sox3 Have Differentiation Functions In Oligodendrocytes*, The Compnay of Biologists Ltd. | Development, vol. 141, (2014), pp. 39-50. DOI: 10.1242/dev.098418. [Retrieved from the Internet Feb. 5, 2020] <https://dev.biologists.org/content/develop/141/1/39.full.pdf>.

Andersen, Jimena. *Study of Ascl1 Function In The Neurogenic Lineage Of The Adult Mouse Hippocampus*, Division of Molecular Neurobiology, MRC National Institute for Medical Research, Mar. 2015, pp. 1-212. [Retrieved from the Internet Feb. 5, 2020] <http://discovery.ucl.ac.uk/1469969/1/PhD%20thesis_Jimena%20Andersen_Reduced.pdf>.

International Search Report and Written Opinion for Application No. PCT/US2020/045526, dated Feb. 8, 2021.

International Preliminary Report on Patentability for Application No. PCT/IB2018/053365, dated Nov. 28, 2019.

International Search Report and Written Opinion for Application No. PCT/US2020/017090, dated Jun. 22, 2020.

International Preliminary Report on Patentability for Application No. PCT/US2020/017090, dated Aug. 19, 2021.

Lochrie et al., Mutations on the external surfaces of adeno-associated virus type 2 capsids that affect transduction and neutralization. J Virol. Jan. 2006;80(2):821-34. doi: 10.1128/JVI.80.2.821-834.2006.

Maguire et al., Directed evolution of adeno-associated virus for glioma cell transduction. J Neurooncol. Feb. 2010;96(3):337-47. doi: 10.1007/s11060-009-9972-7. Epub Jul. 19, 2009.

Zolotukhin et al., Improved Adeno-associated Viral Gene Transfer to Murine Glioma. J Genet Syndr Gene Ther. Apr. 29, 2013;4(133):12815. doi: 10.4172/2157-7412.1000133. Author Manuscript. 16 pages.

Invitation to Pay Additional Fees for Application No. PCT/US2020/045526 dated Nov. 16, 2020.

International Preliminary Report on Patentability for International Application No. PCT/US2020/045526, dated Feb. 17, 2022.

Invitation to Pay Additional Fees for International Application No. PCT/US2020/017090 dated Apr. 23, 2020.

Choudhury et al., Novel Methodology for Creating Macaque Retinas with Sortable Photoreceptors and Ganglion Cells. Front Neurosci. Dec. 1, 2016;10:551. eCollection 2016.

Crommentuijin et al., Systemically administered AAV9-sTRAIL combats invasive glioblastoma in a patient-derived orthotopic xenograft model. Mol Ther Oncolytics. Jun. 22, 2016;3:16017. doi: 10.1038/mto.2016.17.

Guhasarkar et al., Systemic AAV9-IFNβ gene delivery treats highly invasive glioblastoma. Neuro Oncol. Nov. 2016;18(11):1508-1518. doi: 10.1093/neuonc/now097. Epub May 18, 2016.

Gurda et al., Capsid antibodies to different adeno-associated virus serotypes bind common regions. J Virol. Aug. 2013;87(16):9111-24. doi: 10.1128/JVI.00622-13. Epub Jun. 12, 2013.

Koerber et al., DNA shuffling of adeno-associated virus yields functionally diverse viral progeny. Mol Ther. Oct. 2008;16(10):1703-9. doi: 10.1038/mt.2008.167. Epub Aug. 26, 2008. Author Manuscript, 17 pages.

Maheshri et al., Directed evolution of adeno-associated virus yields enhanced gene delivery vectors. Nat Biotechnol. Feb. 2006;24(2):198-204. doi: 10.1038/nbt1182. Epub Jan. 22, 2006.

Santiago-Ortiz Set al., Adeno-associated virus (AAV) vectors in cancer gene therapy. J Control Release. Oct. 28, 2016;240:287-301. doi: 10.1016/j.jconrel.2016.01.001. Epub Jan. 12, 2016. Author Manuscript, 39 pages.

Tseng et al., Mapping the AAV Capsid Host Antibody Response toward the Development of Second Generation Gene Delivery Vectors. Front Immunol. Jan. 30, 2014;5:9. doi: 10.3389/fimmu.2014.00009. eCollection 2014.

Partial Supplementary European Search Report dated Oct. 20, 2022 in connection with Application No. EP 20752092.5.

Muraguchi et al., NKX2.2 suppresses self-renewal of glioma-initiating cells. Cancer Res. Feb. 1, 2011;71(3):1135-45. doi: 10.1158/0008-5472.CAN-10-2304. +A56:N56.

Sebastian et al., Abstract 4072: Direct transdifferentiation of glioblastoma cells to antigen-presenting cells: A novel immunotherapeutic approach, Cancer Research, American Association for Cancer Research, Apr. 14, 2018 (Apr. 14, 2018), pp. 1-4, XP55969302, Retrieved from the Internet: URL:https://aacrjournals.org/cancerres/article/78/13Supplement/4072/628678/Abstract-4072-Direct-transdifferentiation-of [retrieved on Oct. 10, 2022].

* cited by examiner

| Factors/Combos | SOX2 | ASCL1 | OLIG2 | NGN2 | NEUROD1 | NEUROD4 |
|---|---|---|---|---|---|---|
| C1 | + | + | + | + | + | + |
| C2 | + | + | + | + | + |   |
| C3 | + | + | + | + |   | + |
| C4 | + | + | + | + |   |   |
| C5 | + | + | + |   | + | + |
| C6 | + | + | + |   |   | + |
| C7 |   | + | + | + | + | + |
| C8 | + |   | + |   | + | + |
| C9 | + |   |   | + | + | + |
| C10 | + | + |   |   | + | + |
| C11 | + |   | + | + | + |   |
| EV |   |   |   |   |   |   |

On -3 days, 1x10e5 human normal astrocytes was seeded into 6 well plate. On -2 days, astrocytes was infected by different virus combinations. Total cell counts were performed on day 16.

Cell Counts

| Combinations | Reprogrammed live cells |
|---|---|
| C1 | 45x10e4 |
| C2 | 2x10e4 |
| C3 | 13.5x10e4 |
| C4 | 2x10e4 |
| C5 | 13.5x10e4 |
| C6 | Not detected |
| C7 | 18x10e4 |
| C8 | Not detected |
| C9 | Not detected |
| C10 | 20x10e4 |
| C11 | 7x10e4 |
| EV | Not detected |

Figure 3

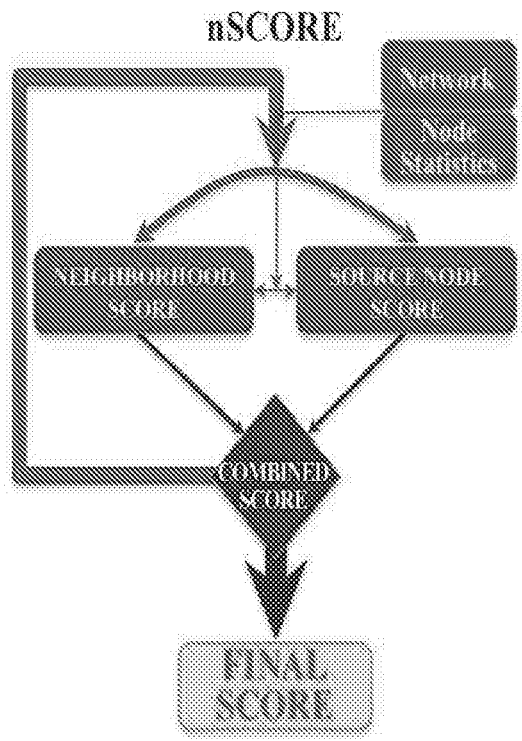

*Step 1:* Extract subnetworks of differentially expressed genes from the whole network using -top_genes_proportion and -g.

*Step 2:* Calculate individual node scores. If -k = TRUE, then the input node statistics are converted to rank value. Individual node score (indscore) of gene i: $indscore_i = \prod_{k=1}^{l} stat_i^k$, whereas $stat_i^k$ is k-th statistics in -l of gene i.

*Step 3:* Calculate the neighborhood score of gene i: $nbhscore_i = \sum_{s=1}^{step} \left( \frac{1}{s^p} * \sum_{j=1}^{n_s} w_{i,j}^c * indScore_j \right)$, where $w_{i,j}$ is weight of the closeness between nodes i and j (MI or rho), and $n_s$ is the number of neighbors of node i that requires s steps to reach the source node i.

If -a is TRUE, then $nbhscore_i = \sum_{s=1}^{step} \left( \frac{1}{s^p} * \left( \frac{1}{n_s} \right) * \sum_{j=1}^{n_s} w_{i,j}^c * indScore_j \right)$

*Step 4:* Combine nbhscore and the source node score to obtain the node importance score niscore. If -d = "n", then $niscore_i = nbhscore_i$. If -d = "m", then $niscore_i = indscore_i$. If -d = "s", then $niscore_i = nbhscore_i + ngene * indscore_i$, where ngene is the number of genes in the neighborhood of gene i in case of -a = FALSE to balance source node indscore with the nbhscore. If -a = TRUE, then ngene = 1. If -d = "p", then $niscore_i = nbhscore_i * indscore_i$.

*Step 5:* Iterative refinement of niscores. niscores from step 4 are used as new input to step 2 for iterative recalculation, repeated -r times or until convergence is reached. The sum of gene-level differences in ranking between consecutive iterations will be used as the objective function for monitoring convergence.

Figure 12

| Factors Comb | SOX8 | ASCL1 | OLIG2 | BASP1 | NKX6-2 | MYC-N |
|---|---|---|---|---|---|---|
| C1 | + | | + | + | + | |
| C2 | + | + | + | + | + | |
| C3 | | + | + | + | | + |
| C4 | + | + | + | + | | + |
| C5 | + | + | + | | + | + |
| C6 | | + | + | + | + | + |
| C7 | | + | + | | + | + |
| C8 | | + | + | + | + | + |
| C9 | | + | + | | + | |
| C10 | + | | + | + | + | |
| C11(EV) | | | | | | |

FIGURE 15

| Combinations | Transformed live cells |
|---|---|
| C1 | 50X10e4 |
| C2 | 8X10e4 |
| C3 | 22X10e4 |
| C4 | NA |
| C5 | 25X10e4 |
| C6 | NA |
| C7 | 33X10e4 |
| C8 | NA |
| C9 | NA |
| C10 | 10X10e4 |
| C11(EV) | NA |

FIGURE 17

At -3 days, 1X10e5 human normal astrocytes was seeded into 6 well plate. At -2 days, astrocytes was infected by different virus combination. Total cell counts were performed on day 16.

FIGURE 19

| Combinations | Transformed live cells |
|---|---|
| C1 | 45X10e4 |
| C2 | 2X10e4 |
| C3 | 13.5X10e4 |
| C4 | 2X10e4 |
| C5 | 13.5X10e4 |
| C6 | NA |
| C7 | 18X10e4 |
| C8 | NA |
| C9 | NA |
| C10 | 20X10e4 |
| C11 | 7X10e4 |
| C12(EV) | NA |

FIGURE 20

On -3 days, 1X10e5 human normal astrocytes was seeded into 6 well plate. On -2 days, astrocytes was infected by different virus combination. Total cell counts were performed on day 16.

| Combinations | Sphere count |
|---|---|
| C1 | 116 ● 0 |
| C2 | NA |
| C3 | NA |
| C4 | NA |
| C5 | NA |
| C6 | NA |
| C7 | ● 58 ● 11 |
| C8 | NA |
| C9 | NA |
| C10 | ● 42 ● 7 |
| C11 | NA |
| C12(EV) | NA |

On day 16, 7X10e4 transformed cells were seeded into 6 well plate with 2 ml of NSC media. Total neurosphere were counted on day 25.

FIGURE 22

| Combinations | Transformed live cells(1) | Transformed live cells(2) |
|---|---|---|
| C1(ABNMSO) | 6X10e4 | 21X10e4 |
| C7(ABNMO) | 24X10e4 | 9X10e4 |
| C10(ABNMS) | 96X10e4 | 126X10e4 |
| C13(ABNM) | 110X10e4 | 50X10e4 |
| C12(EV) | <1X10e4 | <1X10e4 |

On -3 days, 1X10e5 human normal astrocytes was seeded into 6 well plate. On -2 days, astrocytes was infected by different virus combination. Total cell counts were performed on day 16.

FIGURE 24

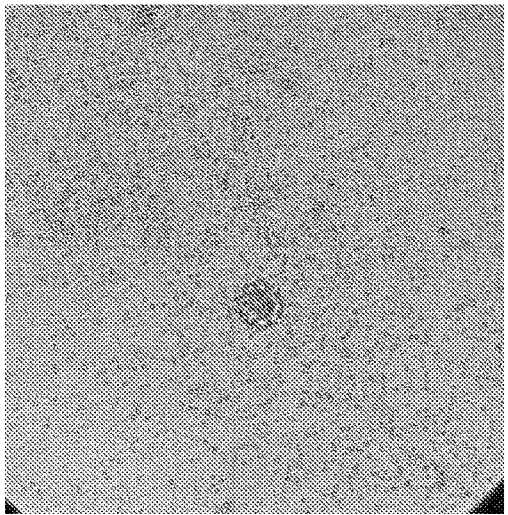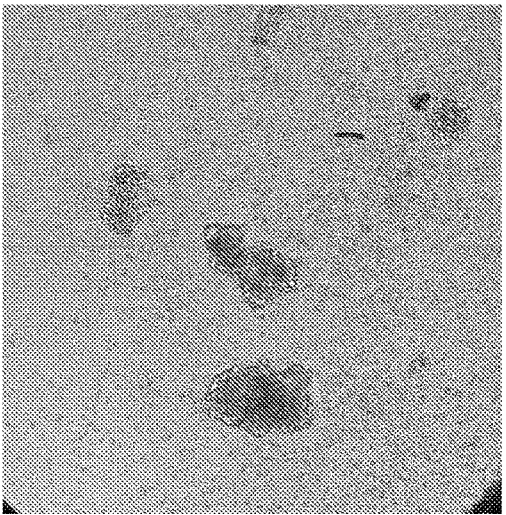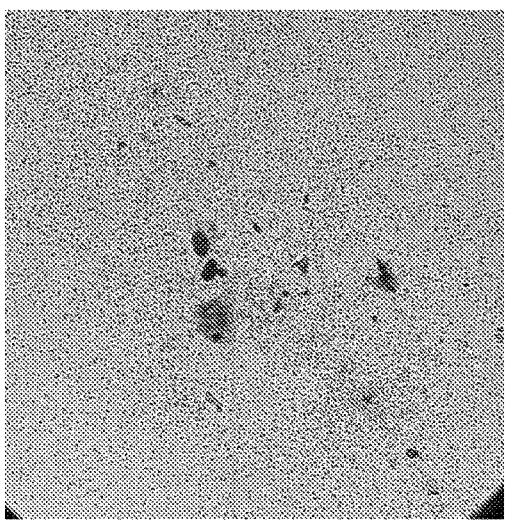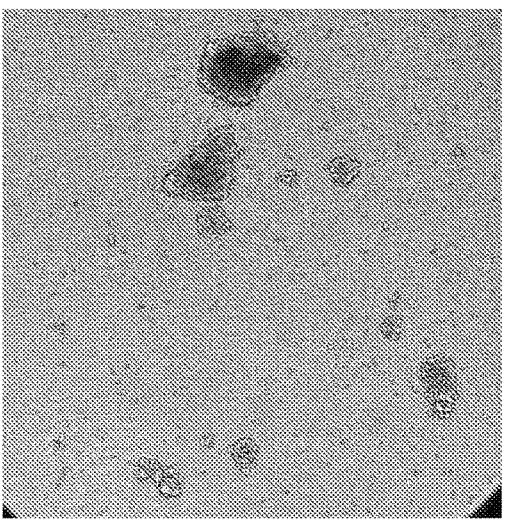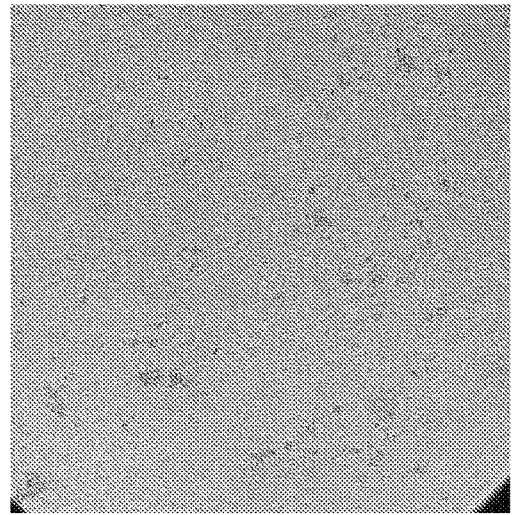
FIGURE 25
A: ASCL1
B: BASP1
N: NKX6.2
M: MYCN
S: SOX8
O: OLIG2

| Combinations | Sphere count |
|---|---|
| C1(ABNMSO) | 22+13 |
| C7(ABNMO) | 38+25 |
| C10(ABNMS) | 430+223 |
| C13(ABNM) | 216+122 |
| C12(EV) | NA |

On day 16, 2.5X10e5 transformed cells were seeded into 6 well plate with 2 ml of NSC media. Total neurosphere were counted on day 25.

FIGURE 26

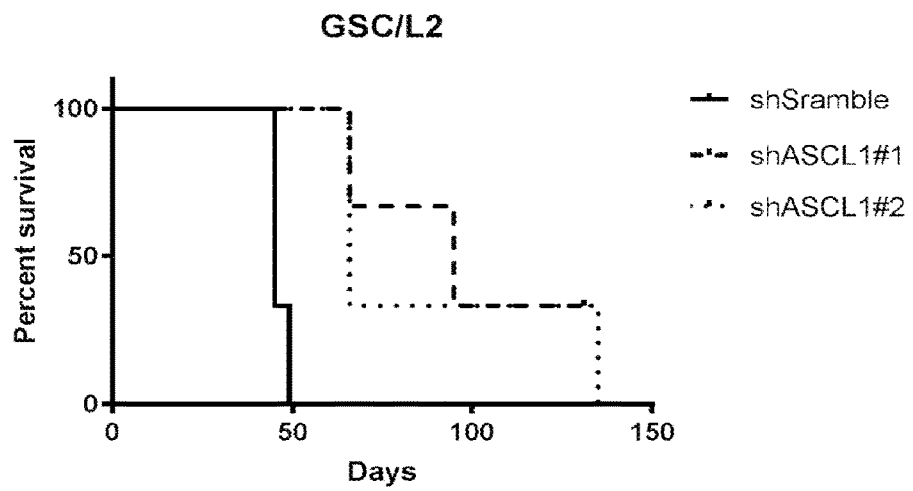
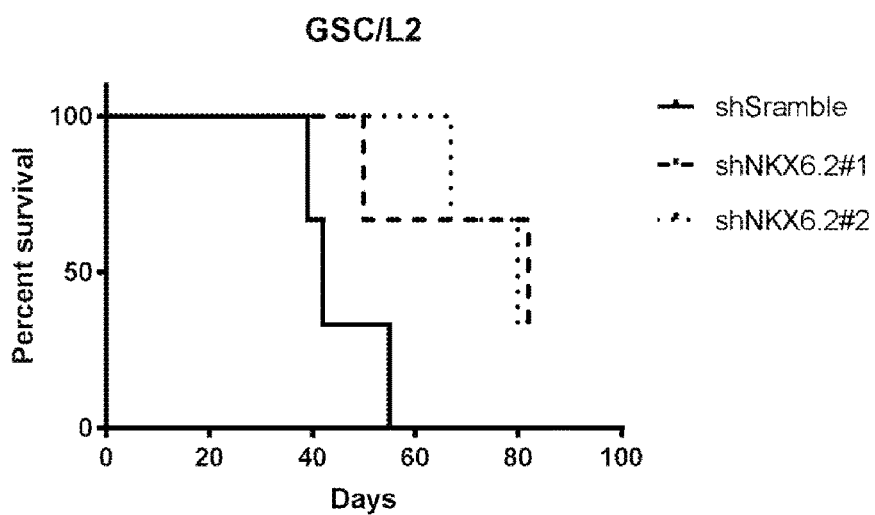
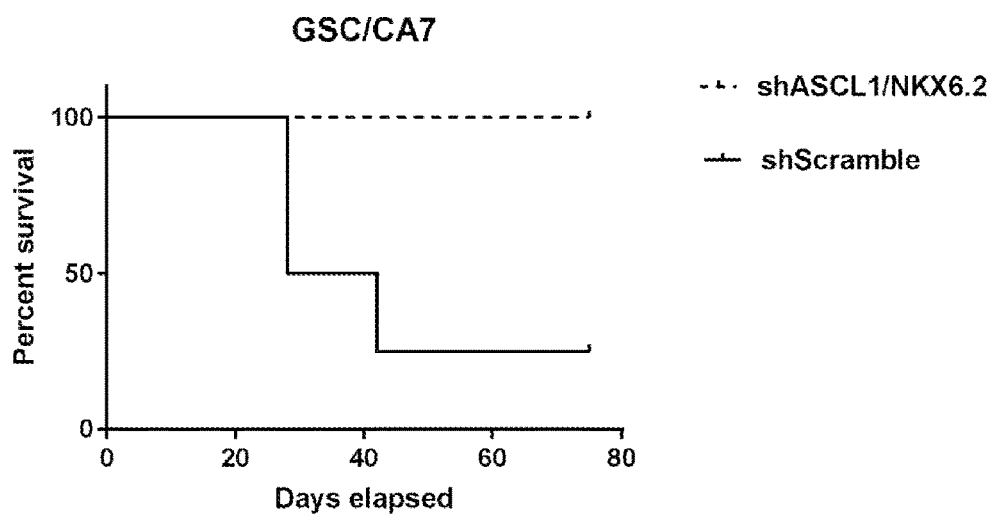
FIGURE 31

CORE MASTER REGULATORS OF GLIOBLASTOMA STEM CELLS

CROSS REFERENCE TO RELATED APPLICATIONS

This application is a national stage entry of PCT/IB2018/053365, filed May 15, 2018, which claims priority under 35 U.S.C. § 119 of U.S. Provisional Application Nos. 62/506,413, filed May 15, 2017 and 62/586,655, filed Nov. 15, 2017, the contents of which are incorporated herein by reference.

FEDERALLY SPONSORED RESEARCH OR DEVELOPMENT

This invention was made with government support K08CA160824 awarded by National Institute of Health (NIH). The government has certain rights in the invention.

REFERENCE TO A SEQUENCE LISTING

This application includes an electronic sequence listing in a file named 539532SEQLIST.TXT, created on Nov. 13, 2019, and containing 208,614 bytes, which is incorporated by reference.

BACKGROUND

Recent advances in treatment for patients with glioblastoma (GBM) have produced only a modest survival benefit with few long-term survivors. New effective, and safe therapies are urgently needed to enhance outcomes for GBM patients. GBMs are heterogeneous tumors that arise from astrocytes—the star-shaped cells that make up the "glue-like," or supportive tissue of the brain. Glioblastomas usually contain a mix of cell types. It is not unusual for these tumors to contain cystic mineral, calcium deposits, blood vessels, or a mixed grade of cells, and are nourished by an ample blood supply.

BRIEF DESCRIPTION OF THE SEVERAL VIEWS OF THE DRAWING(S)

Having thus described the invention in general terms, reference will now be made to the accompanying drawings, which are not necessarily drawn to scale.

FIG. 3 illustrates cell counts of astrocytes after reprogramming NHA into GSCs.

Figure 8:
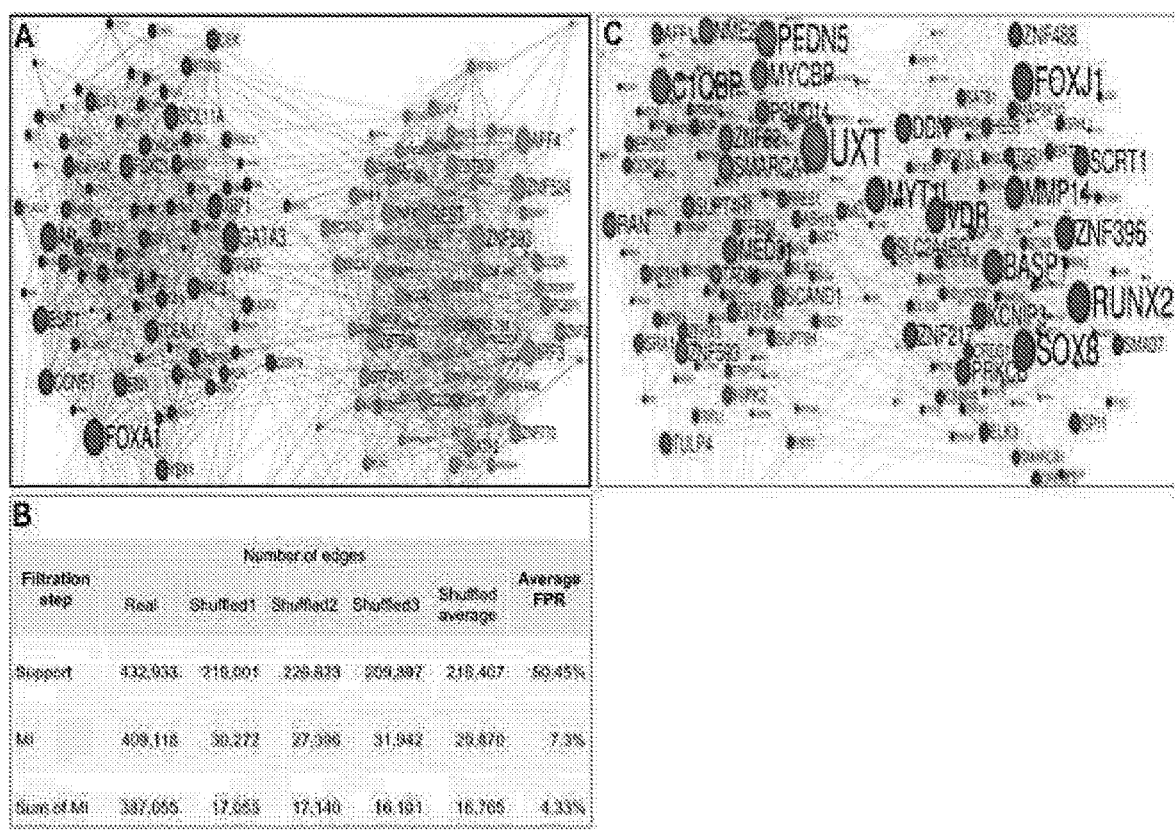

FIG. 8 illustrates GeneRep-created networks from TCGA breast (1222) (A) and brain (166) (C) cancer RNAseq datasets. 16,825 nodes with 387,055 edges (breast) and 17,528 nodes with 823,018 edges (brain) were recovered. Top 200 hubs by number of edges are shown showing well-known drivers in their respective cancers. (B) Numbers of nodes and edges in each filtration step show GeneRep decreased FPR from >50% to <5%. Node size=number of edges.

Figure 9:
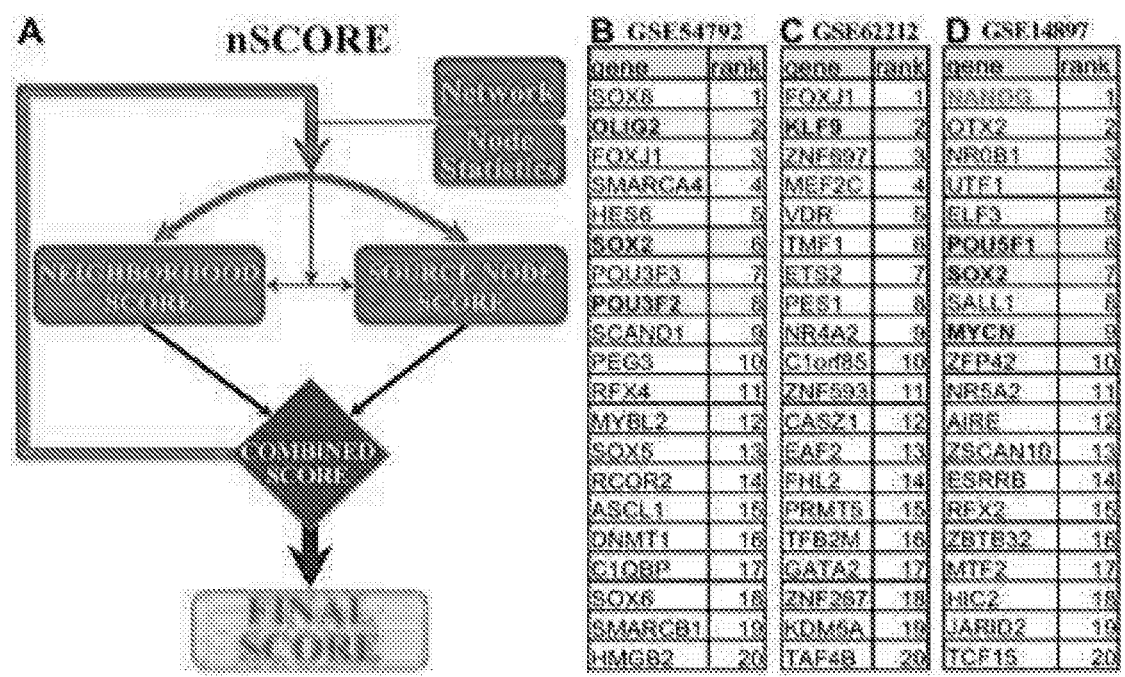

FIG. 9 illustrates nSCORE. (A) Inputs include network and node statistics. Neighborhood score is the aggregation score of the neighbors of the source node. Neighborhood and source scores are combined and the combined used as input for the next round of calculation and so on. nSCORE can accept 12 different parameters. (B) Training case: The best of 2000 scoring parameter sets predicted the most with highest ranks of previously validated master regulators in the GDC-to-GSC conversion, GSE54792 (OLIG2, SOX2, POU5F2). (C-D) Testing cases: The same best scoring set was applied to datasets GSE62212 (C—KFL9 was forcibly expressed in GSCs) and GSE14897 (D—OSKM were used to reprogram fibroblasts to iPSC). KFL9 and POU5F1 (Oct4), Sox2 and Mycn (3 of 4) were ranked 2nd and top 9th, respectively, of all genes. For OSKM, this is the highest ranked and most factors recovered compared to other prediction platforms. NANOG, another critical iPSC factor, was ranked 1st.

Figure 10:
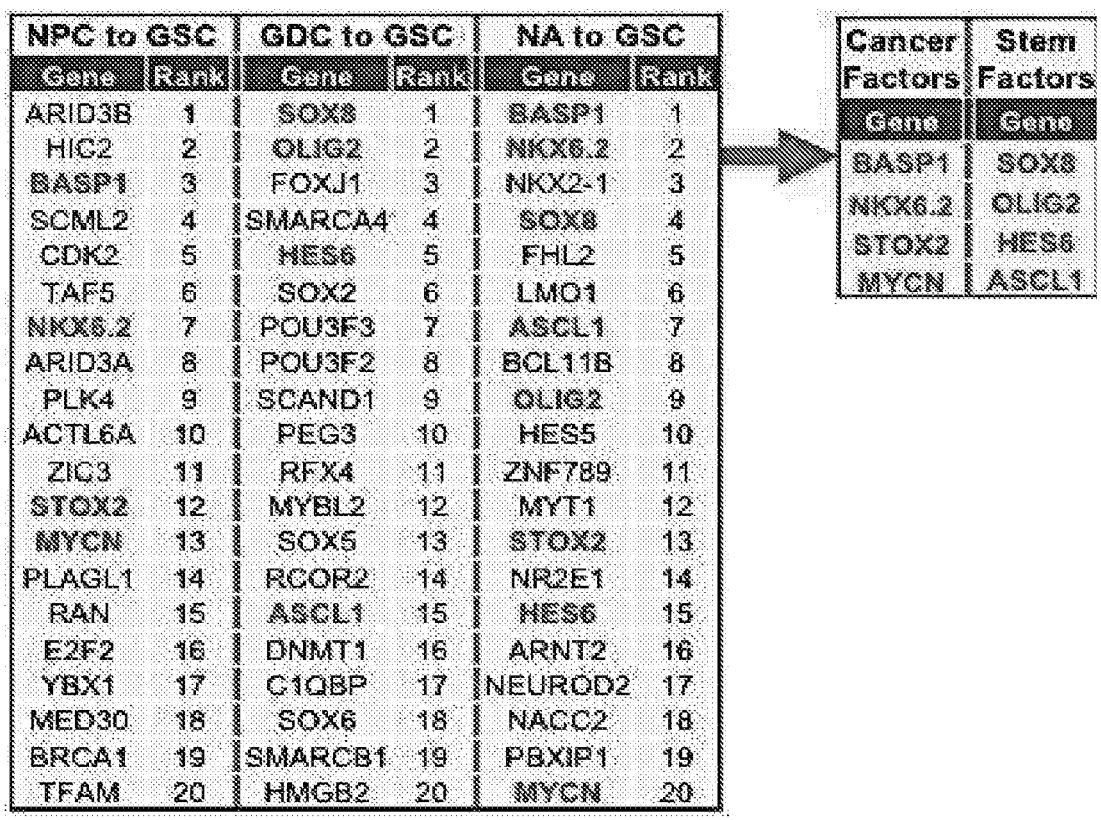

FIG. 10 illustrates 8 factors predicted by nSCORE to enable the NA-GSC conversion (right) are divided into 2 functional groups: Cancer and Stemness. At least 1 factor from each group is necessary for the conversion.

Figure 11:
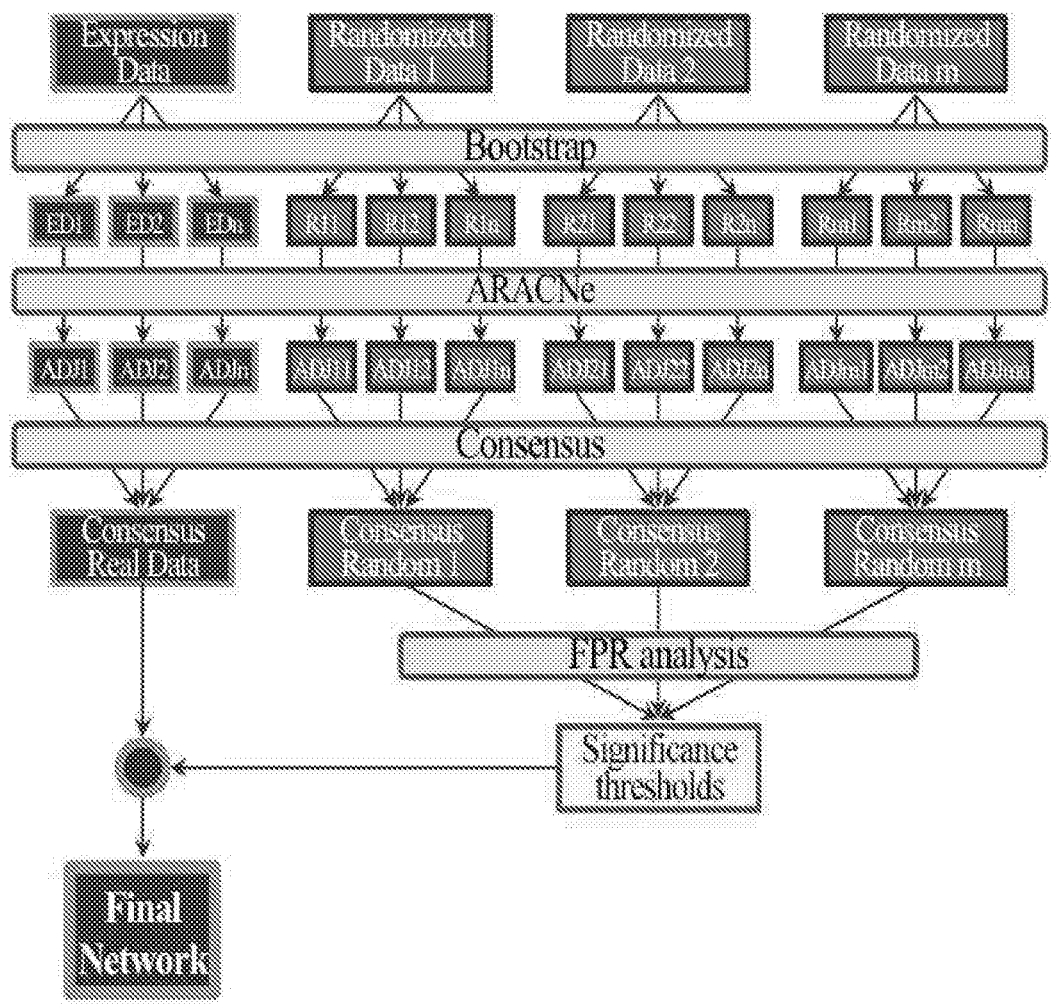

FIG. 11 illustrates GENEREP pipeline to reconstruction gene network significantly increases sensitivity and specificity by generation of true negative network using real data.

FIG. 12 illustrates NSCORE a generalized framework for node importance scoring.

Figure 13:
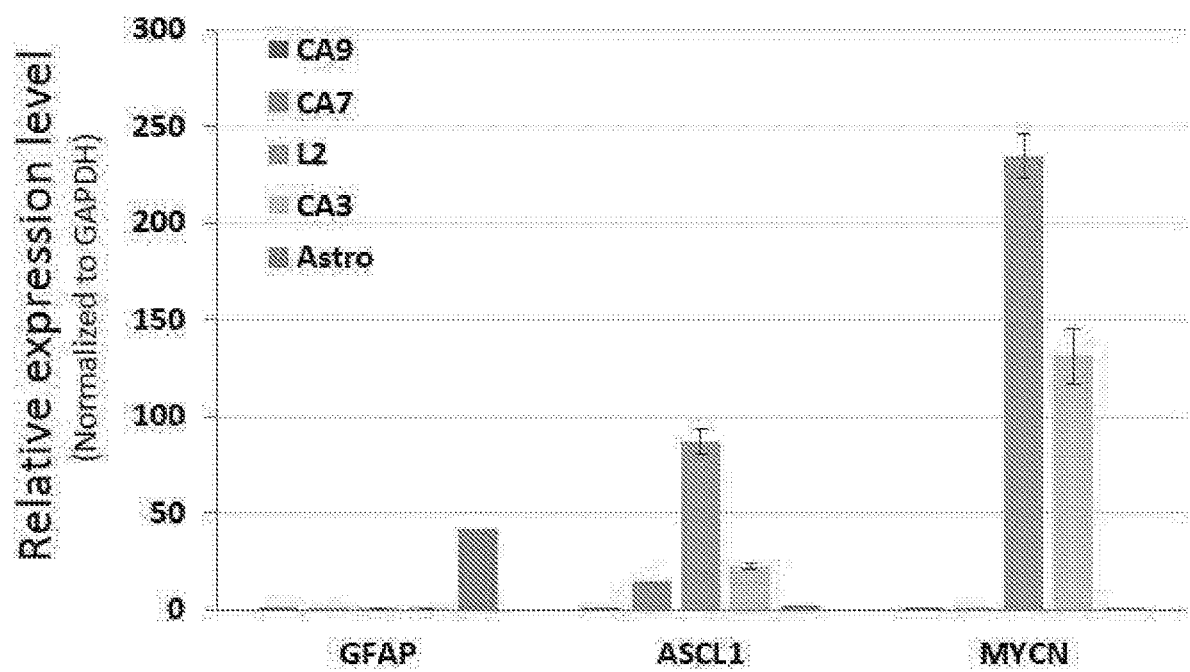

FIG. 13 illustrates higher expression level of regulators of core network in GBM stem cells.

Figure 14A:
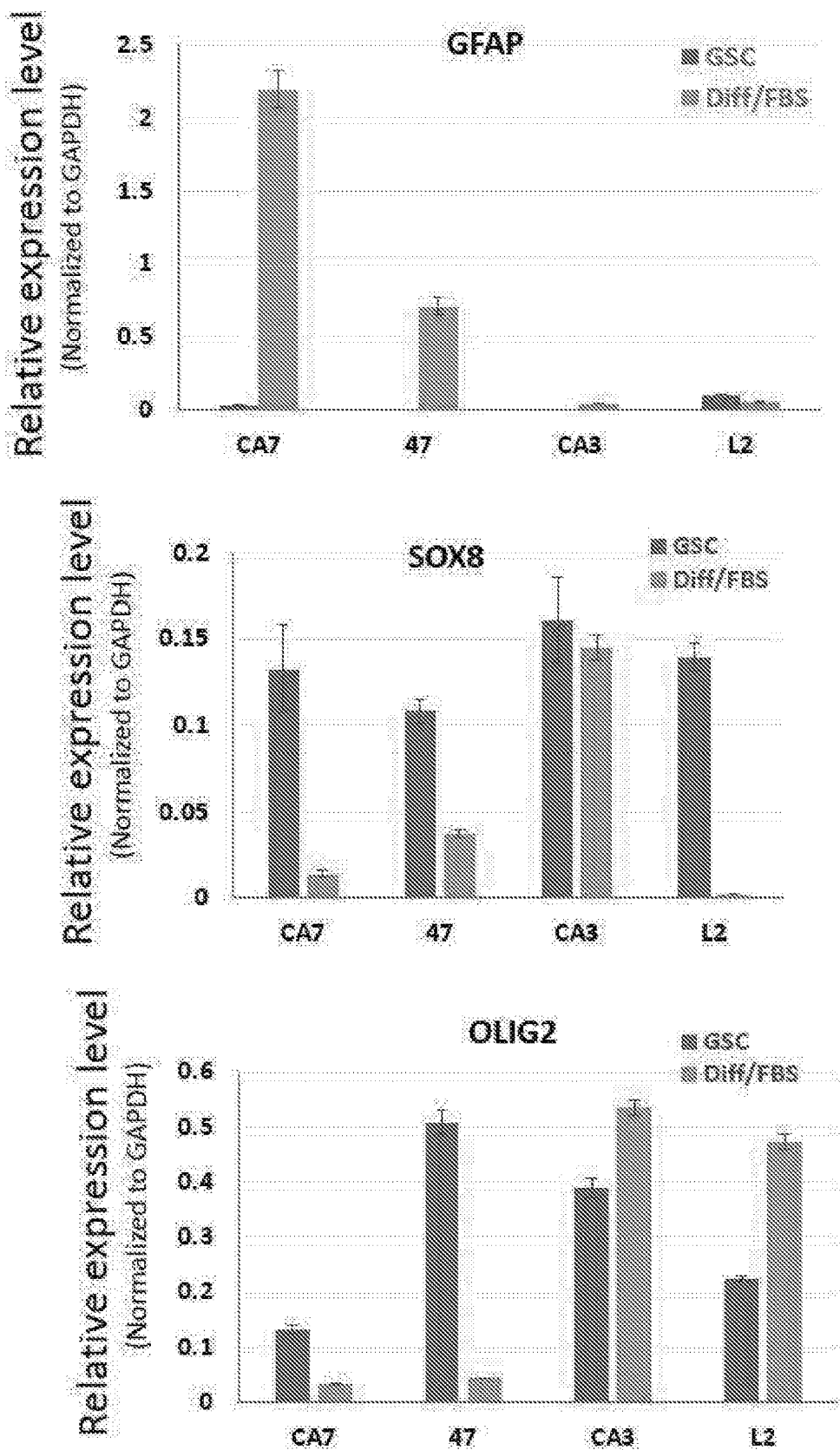
Figure 14B:
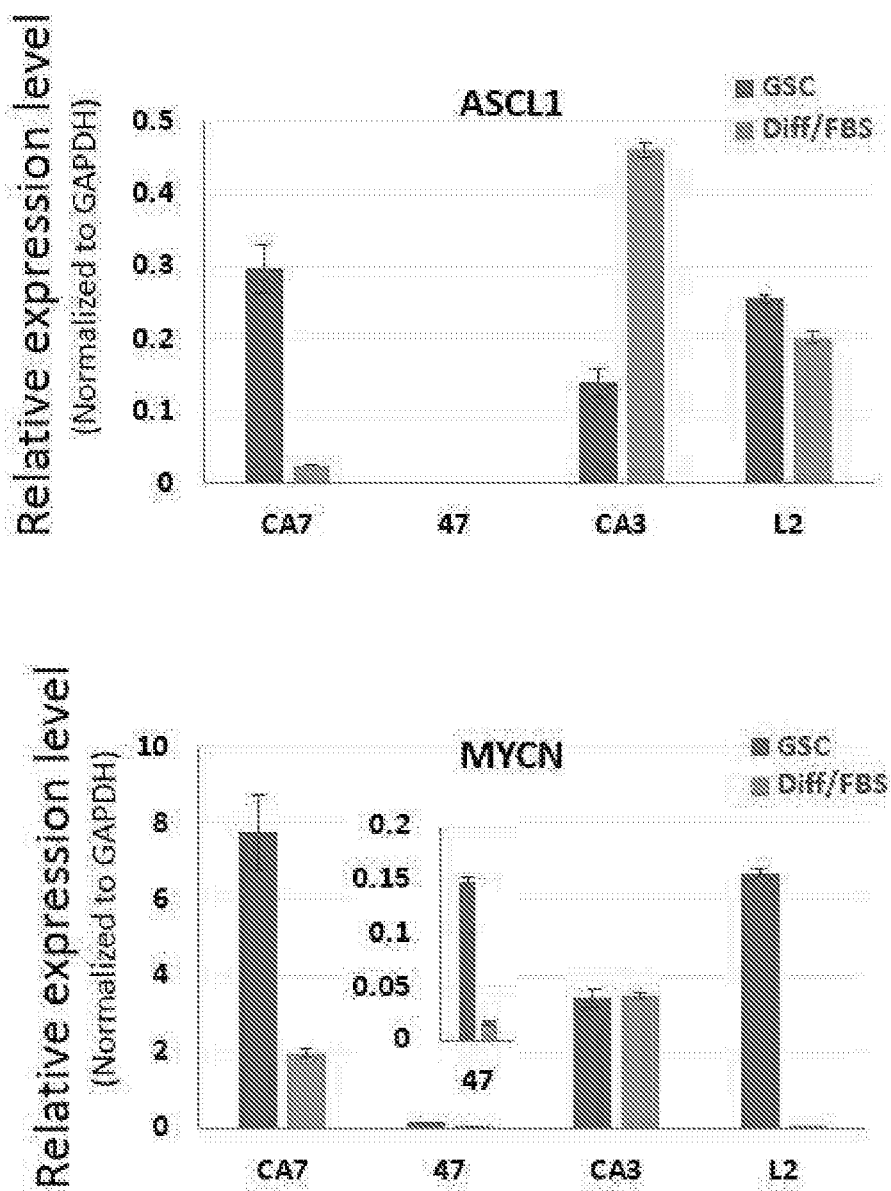
Figure 14C:
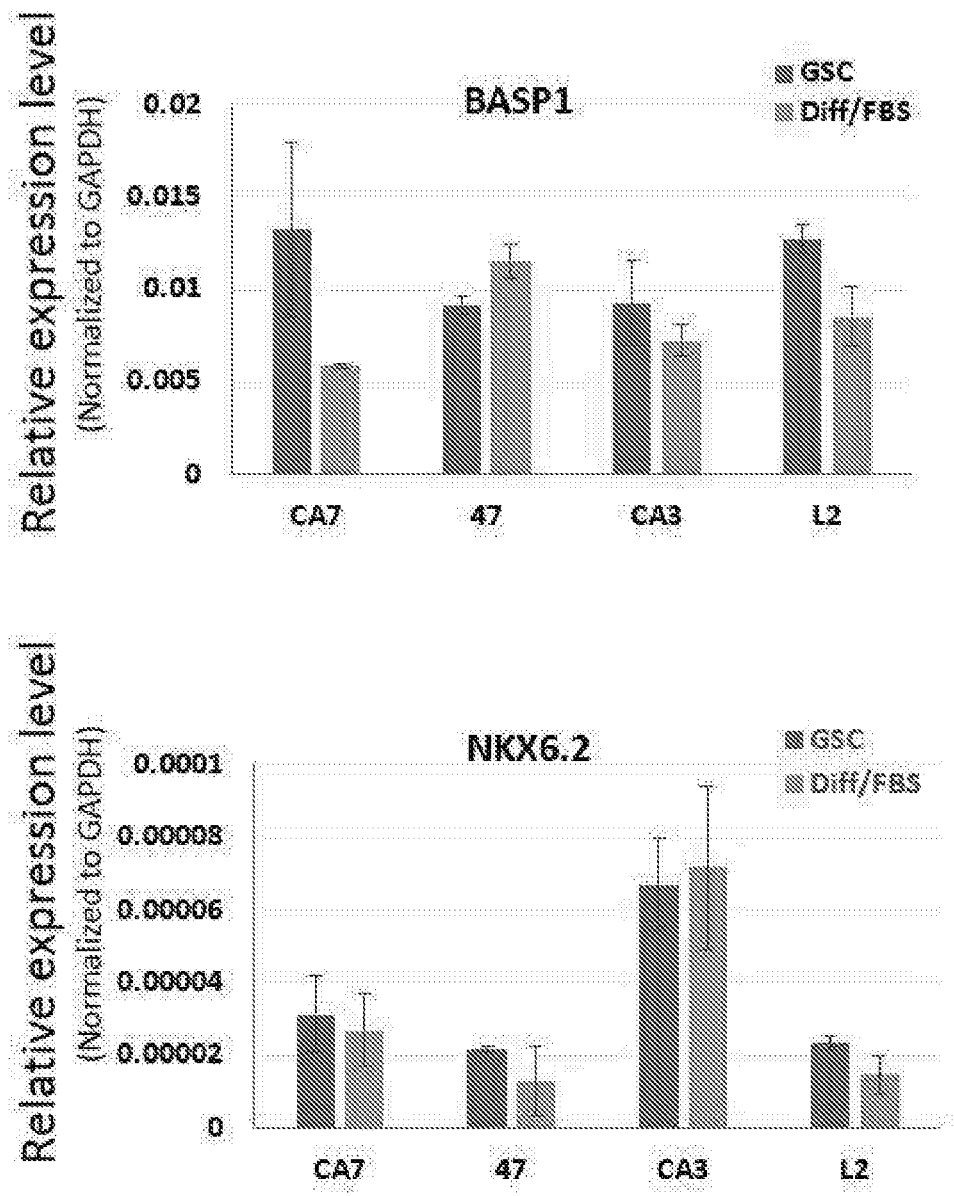

FIG. 14A, FIG. 14B, and FIG. 14C illustrates regulators of core network drop down after GBM stem cells differentiation.

FIG. 15 illustrates combination of reprogramming factors for experiment 1.

Figure 16:
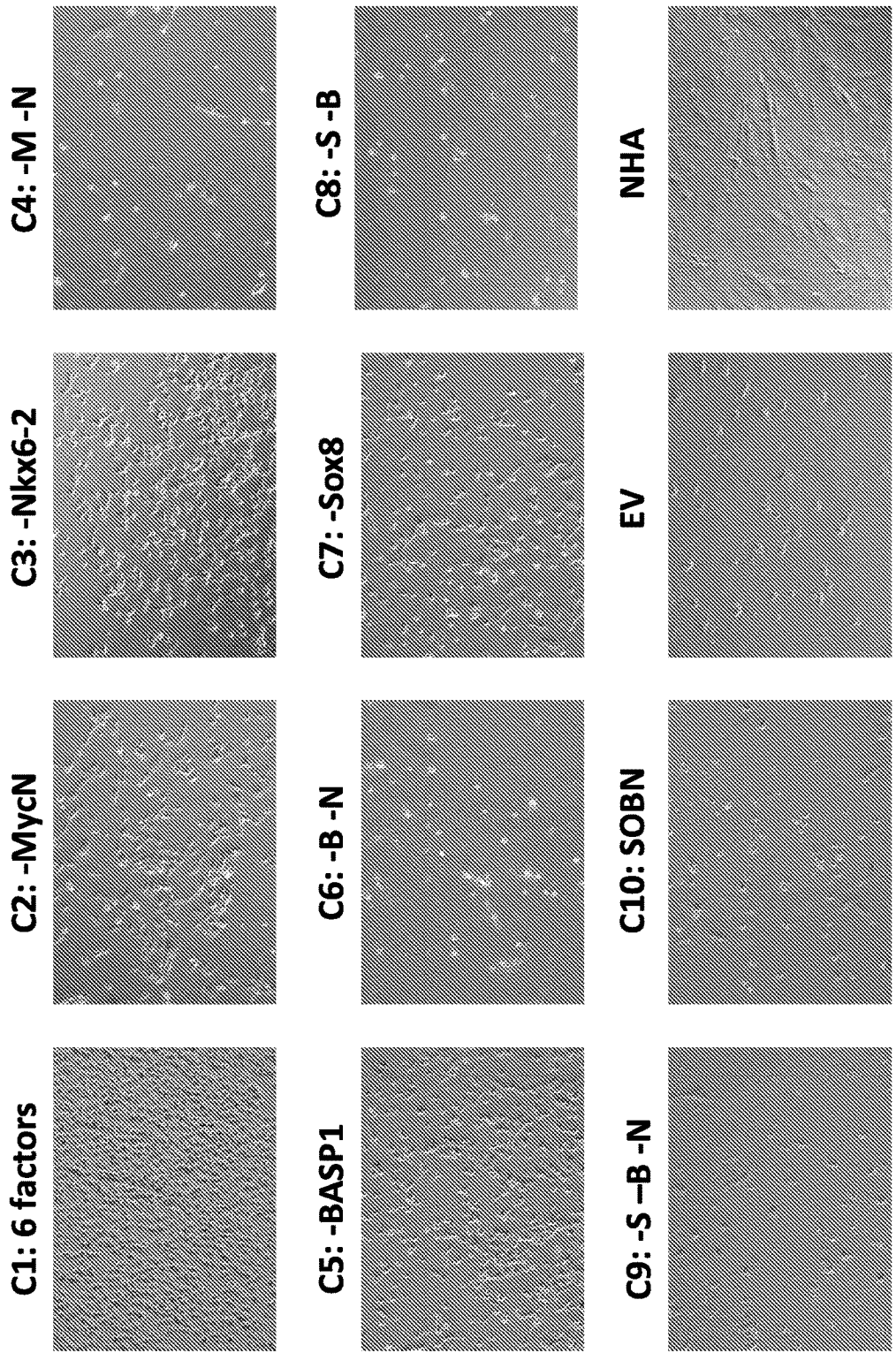

FIG. 16 illustrates Day 10 of reprograming experiment 2.

FIG. 17 illustrates total cell counts on Day 16 for experiment 2.

Figure 18:
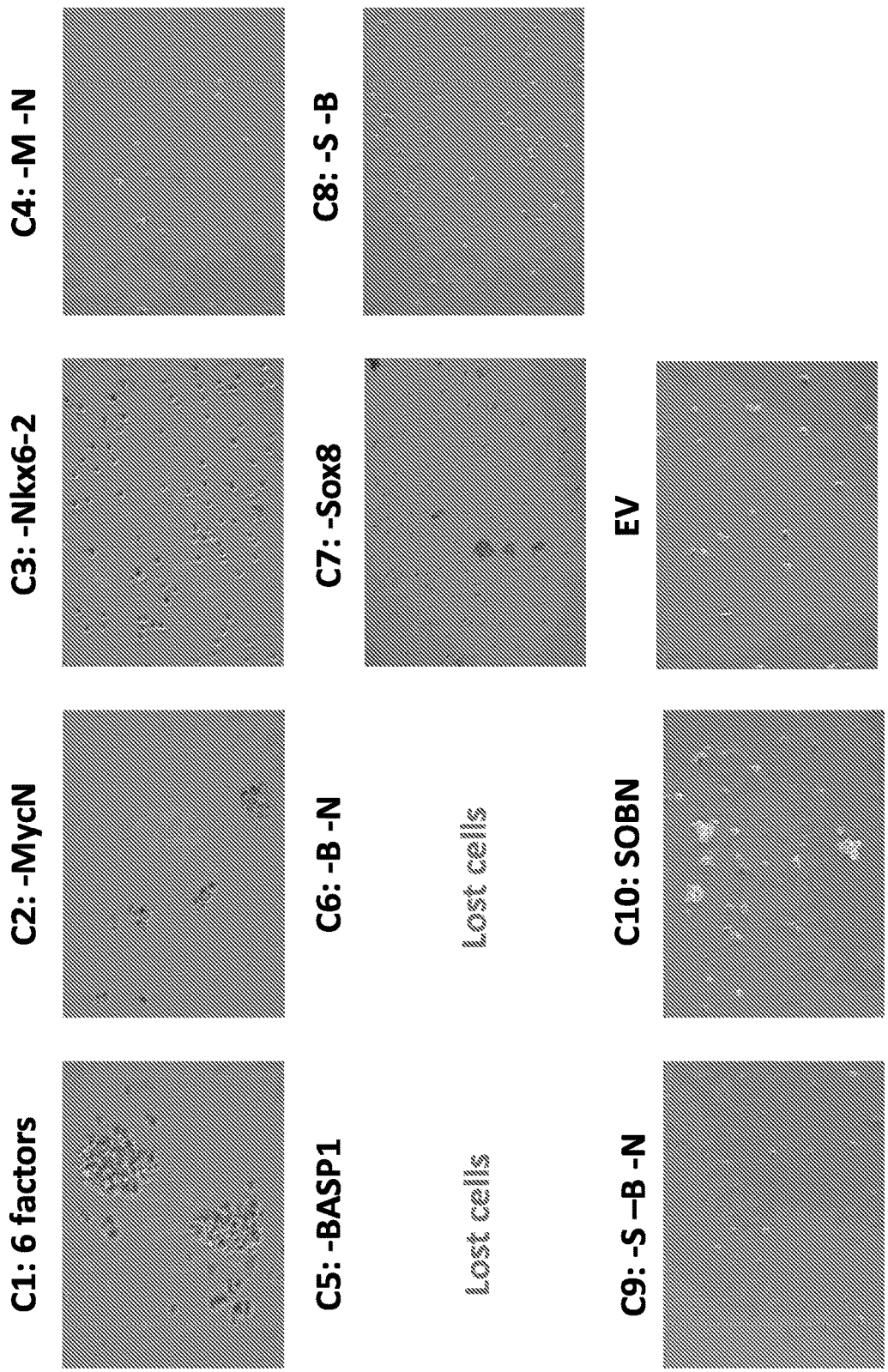

FIG. 18 illustrates Day 18 neurosphere formation assay for experiment 2.

FIG. 19 illustrates combination of reprogramming factors for experiment 3.

FIG. 20 illustrates total cell counts on Day 16 for experiment 3.

Figure 21:
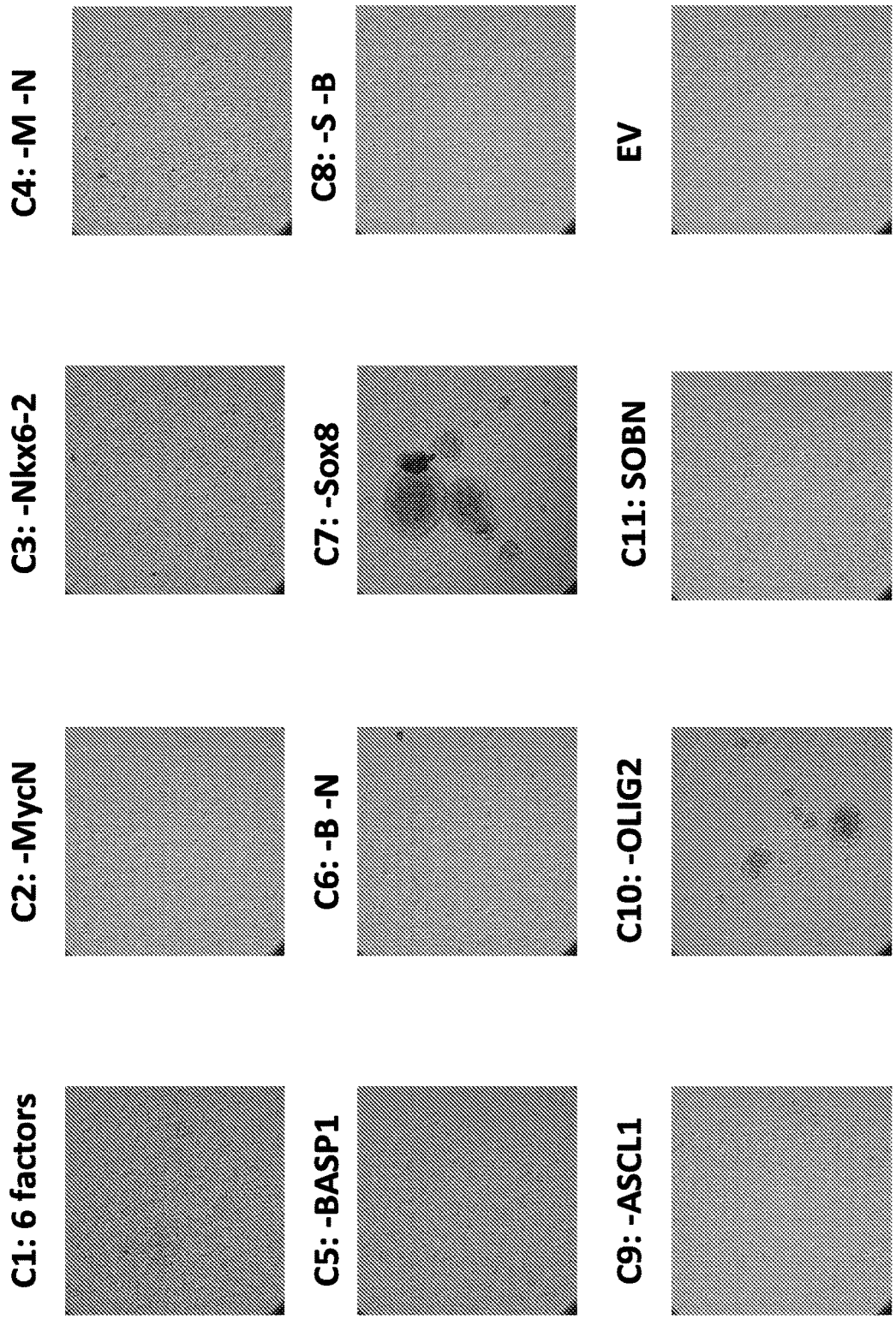

FIG. 21 illustrates Day 25 neurosphere formation assay for experiment 3.

FIG. 22 illustrates Day 25 neurosphere formation assay neurosphere count for experiment 3.

Figure 23:
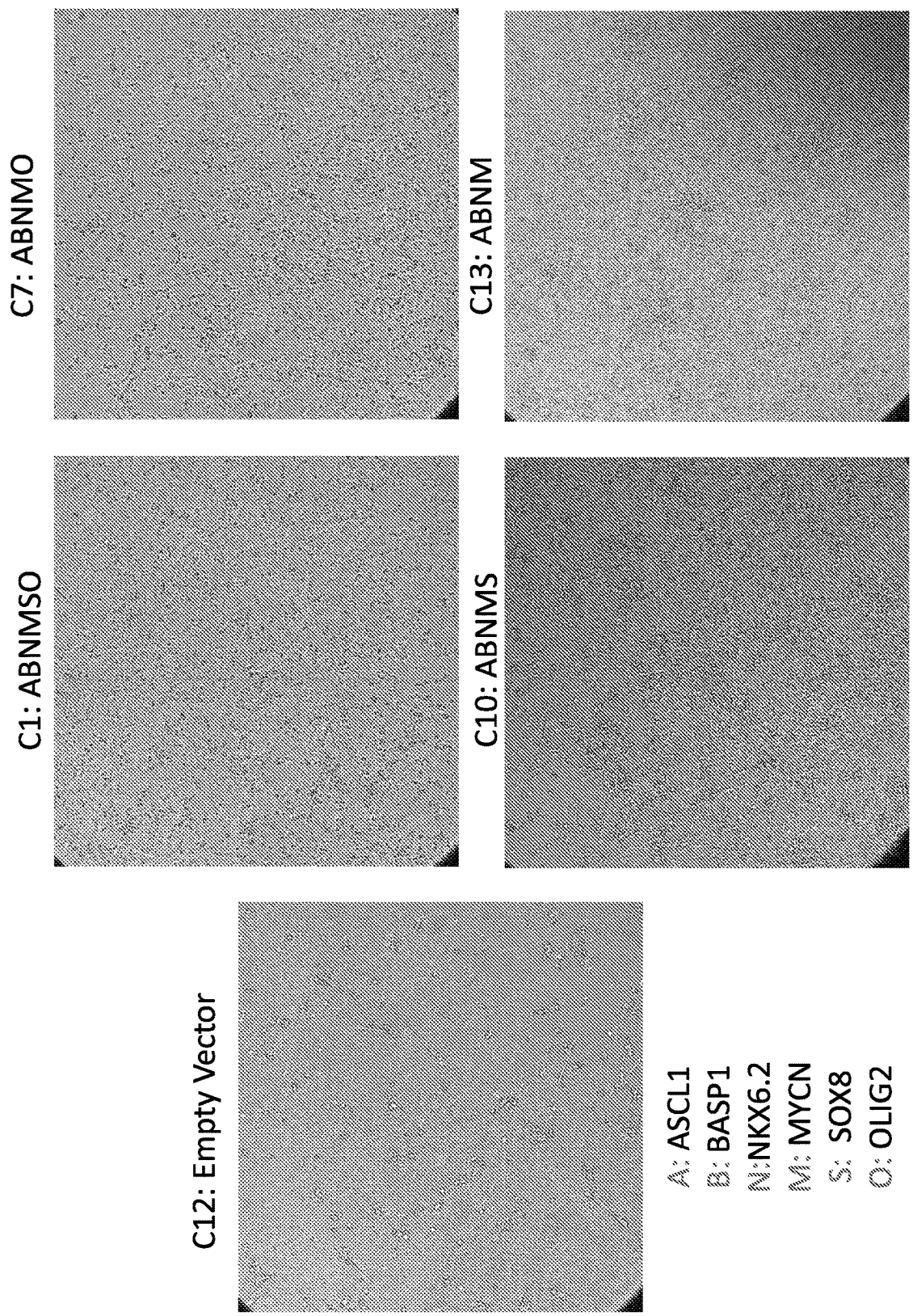

FIG. 23 illustrates combination of reprogramming factors for experiment 4.

FIG. 24 illustrates reprogrammed cell counts on Day 16 for experiment 4.

FIG. 25 illustrates Day 25 neurosphere formation assay for experiment 4.

FIG. 26 illustrates Day 25 neurosphere formation assay neurosphere count for experiment 4.

Figure 27A:
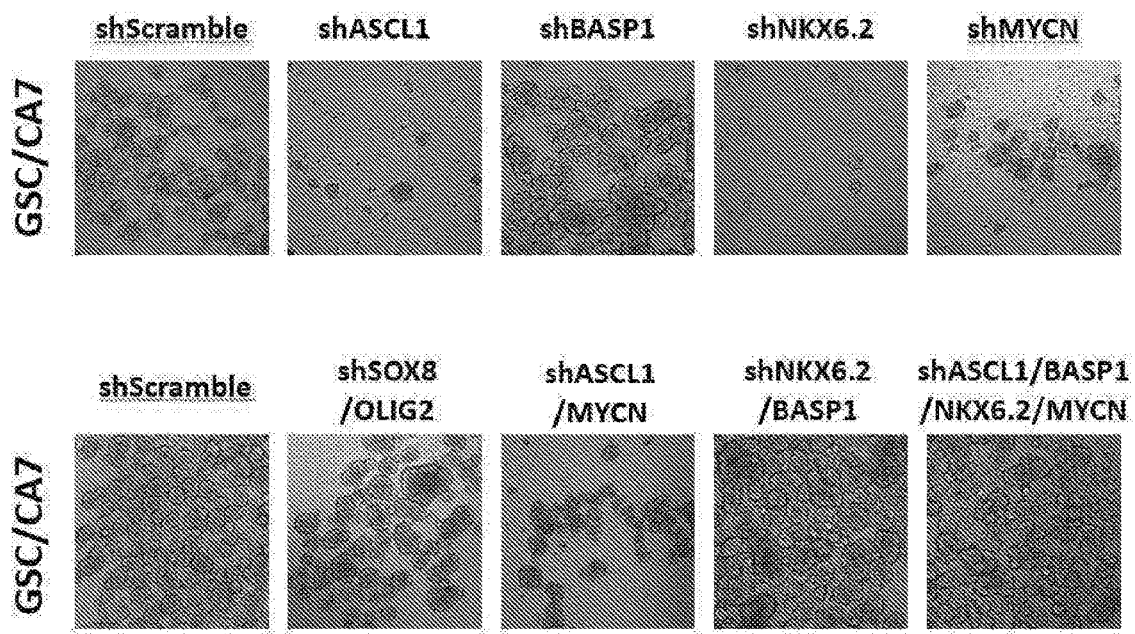
Figure 27B:
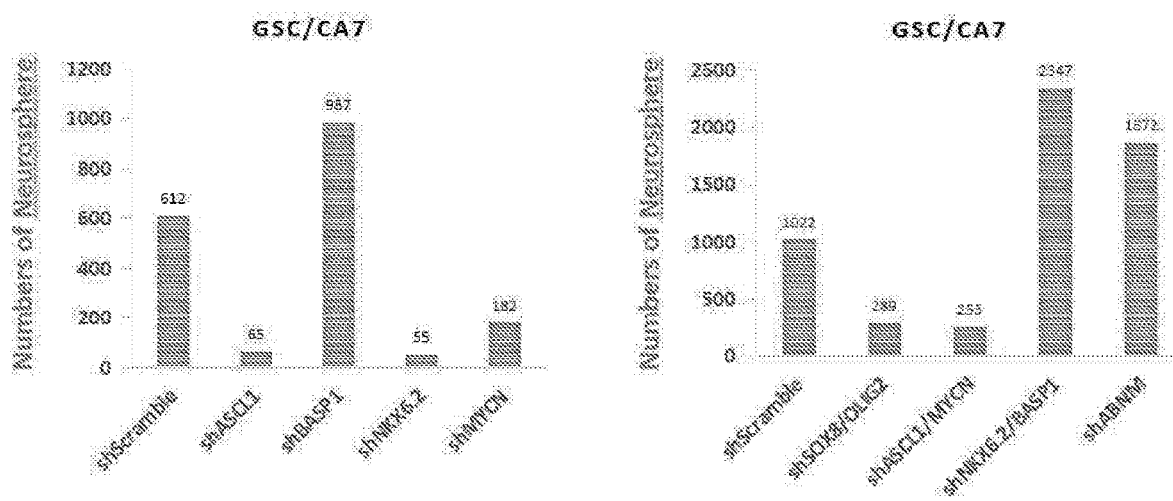

FIG. 27A and FIG. 27B illustrates combined KD of those factors that suppress GSCs growth and neurosphere formation for GSC/CA7 experiment 1.

Figure 28A:
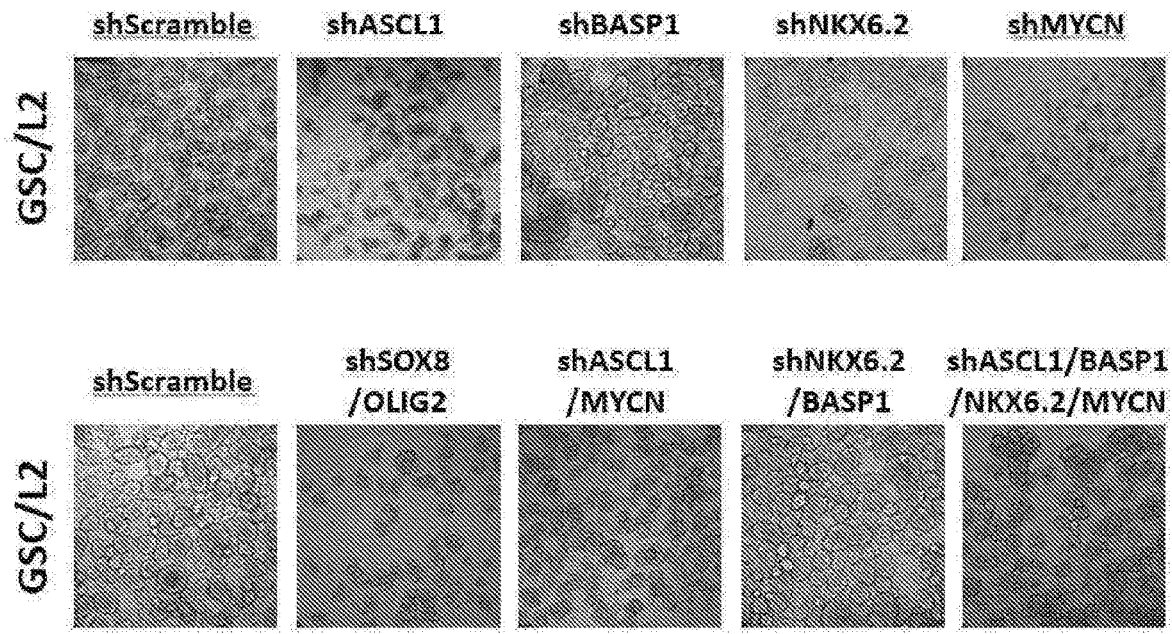
Figure 28B:
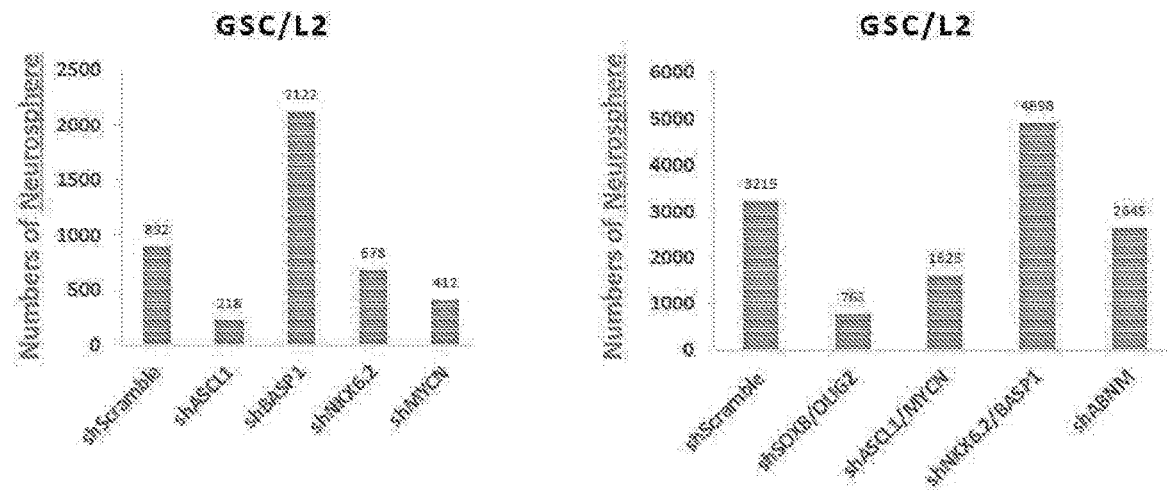

FIG. 28A and FIG. 28B illustrates combined KD of those factors that suppress GSCs growth and neurosphere formation for GSC/L2.

Figure 29A:
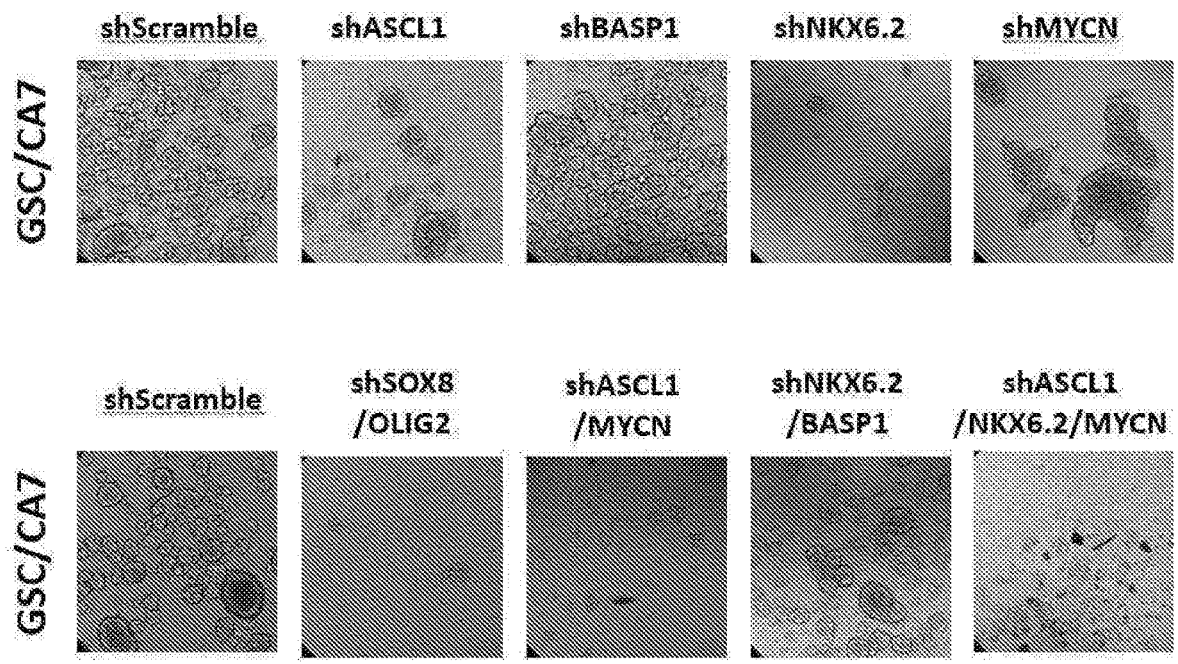
Figure 29B:
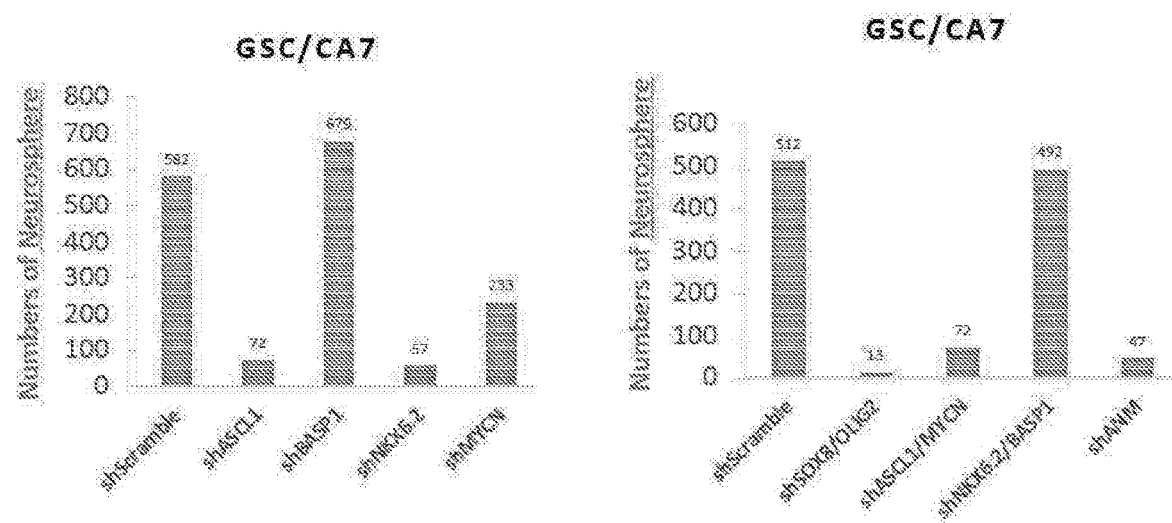

FIG. 29A and FIG. 29B illustrates combined KD of those factors that suppress GSCs growth and neurosphere formation for GSC/CA7 experiment 2.

Figure 30A:
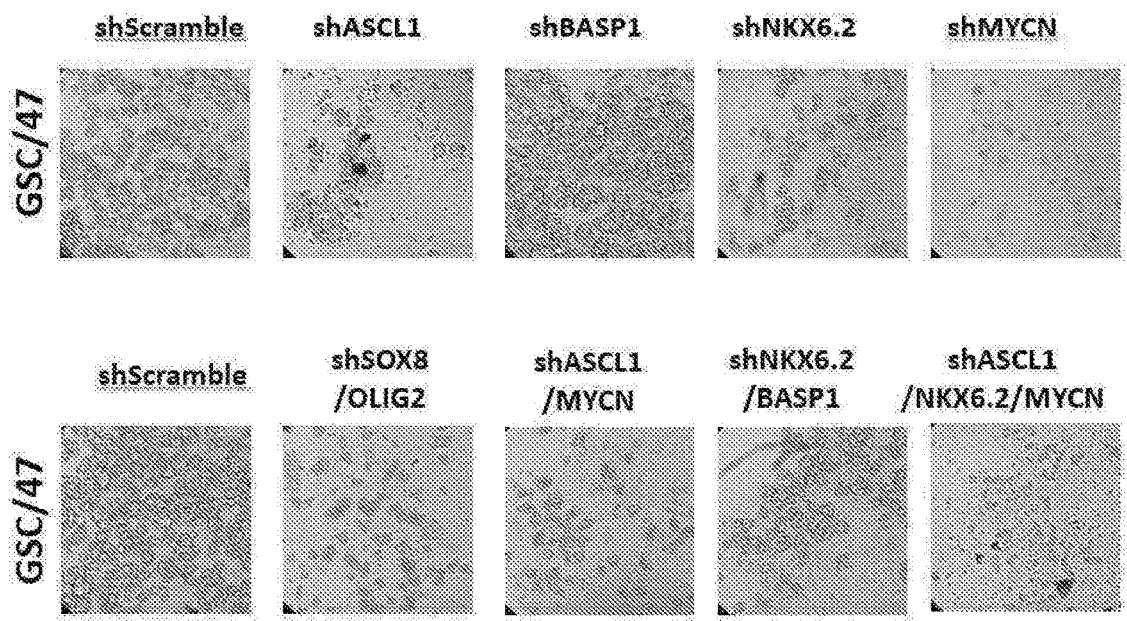
Figure 30B:
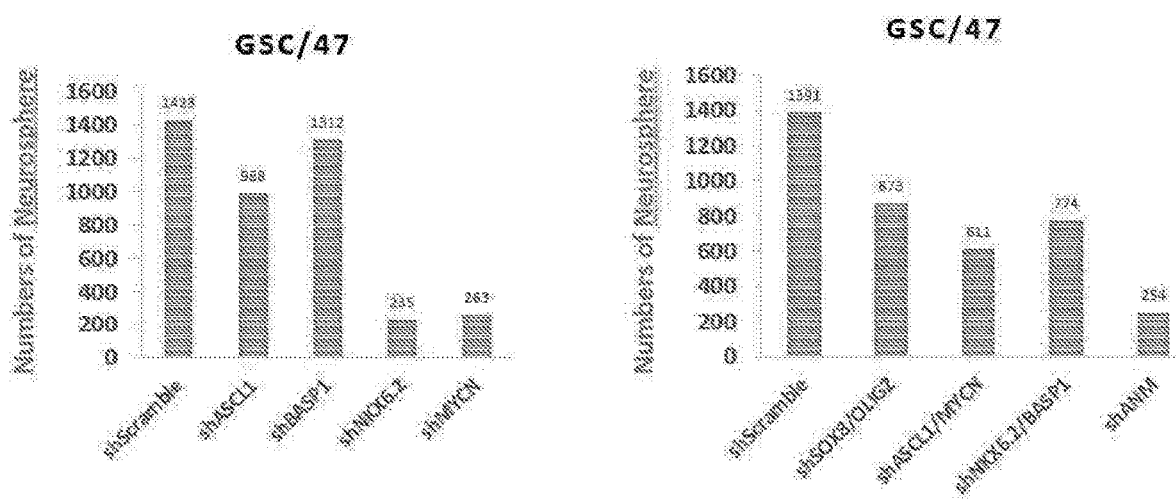

FIG. 30A and FIG. 31B illustrates combined KD of those factors that suppress GSCs growth and neurosphere formation for GSC/47.

FIG. 31 illustrates percent survival of mice with (A) individual knockdown of ASCL1, (B) individual knockdown of NKX6-2, or (C) simultaneous knockdown of ASCL1 and NKX6-2.

DEFINITIONS

The terms "protein," "polypeptide," and "peptide," used interchangeably herein, refer to polymeric forms of amino acids of any length, including coded and non-coded amino acids and chemically or biochemically modified or derivatized amino acids. The terms include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, refer to polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

"Codon optimization" refers to a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a fusion polypeptide can be modified to substitute codons having a higher frequency of usage in a given host cell as compared to the naturally occurring nucleic acid sequence. Codon usage tables are readily available, for example, at the "Codon Usage Database." The optimal codons utilized by L. monocytogenes for each amino acid are shown US 2007/0207170, herein incorporated by reference in its entirety for all purposes. These tables can be adapted in a number of ways. See Nakamura et al. (2000) Nucleic Acids Research 28:292, herein incorporated by reference in its entirety for all purposes. Computer algorithms for codon optimization of a particular sequence for expression in a particular host are also available (see, e.g., Gene Forge).

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" refers to the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) refers to a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence.

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment. A fragment can also be, for example, a functional fragment or an immunogenic fragment.

The term "in vitro" refers to artificial environments and to processes or reactions that occur within an artificial environment (e.g., a test tube).

The term "in vivo" refers to natural environments (e.g., a cell or organism or body) and to processes or reactions that occur within a natural environment.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value or variations ±0.5%, 1%, 5%, or 10% from a specified value.

The singular forms of the articles "a," "an," and "the" include plural references unless the context clearly dictates otherwise. For example, the term "an antigen" or "at least one antigen" can include a plurality of antigens, including mixtures thereof.

Statistically significant means p≤0.05.

DETAILED DESCRIPTION

Various embodiments of the inventions now will be described more fully hereinafter, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level.

Figure 7:
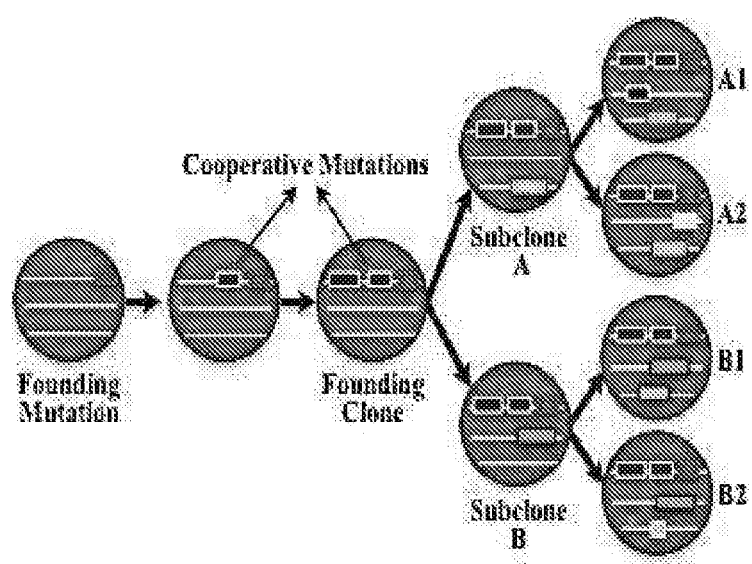
FIG. 7 illustrates clonal evolution in GBM. Mutations in the founding clone are passed on to subclones.

Details regarding various embodiments are described herein. By way of background, GBM is enriched in GBM stem-like cells (GSCs), a major contributor to tumor recurrence. Both GSCs and normal neuronal precursor cells (NPC) have the ability to form neurospheres when cultured in stem cell conditions, however only GSCs can regenerate all cancer cells in the tumor when implanted in vivo (e.g. in vivo tumorigenicity). GSCs also can differentiate into other cells of the brain, however these cells are often not functional compared to those produced by NPCs. In a mouse model of GBM, elimination of self-renewal by genetic means led to a loss of GSCs and prolonged survival. However as with other cancers, targeting GSCs has been a challenge because of the dearth of master regulators specific only to GSCs and not to NPCs or normal brain cells. The cell origin of GSCs remains unclear; both NPCs and normal astrocytes (NA) have been shown to contribute to GSCs. As a result, several survival and growth signals in GSCs share parallels in NPCs and NAs, increasing potential toxicity for therapies that target these pathways. Many of these targets are downstream signaling nodes with overlapping functions, allowing them to compensate for one another's blockade. Another challenge is the high intra- and inter-tumor heterogeneity in the GSC compartment, which necessitates the development of therapies that can target most, if not all, fractions of different subclones within and across many tumors. Recent genomics studies suggest that like other cancers, GBM originates from a founding GSC clone that emerged after sustaining a series of initiating and cooperative alterations that are passed on such that all subclones contain the founding alterations (i.e. the core common master regulators) and hence are targetable (FIG. 7). As the number of potential founding alterations is surprisingly small (i.e. 8-12), many founding alterations are expected to be common across different tumors of the same type or even of different types.

Founding alterations may produce "imprints" on the global gene regulatory network that may persist as the founding clone morphs into subclones and may be traceable across subclones. However, understanding the biological implications of these genomic alterations requires novel analytic tools that interrogate large-scale gene expression profiles to provide information on cancer cell's behaviors caused by interactions between the founding alterations and the tumor microenvironment. Gene expression profiles can then be used to infer the global and local networks that control such behaviors. This can be achieved using reverse engineering tools such as ARACNe (Algorithm for the Reconstruction of Accurate Cellular Networks), designed to scale up to the complexity of mammalian cells. ARACNe applies a theoretical information approach to infer gene networks using gene expression data, by calculating Mutual Information (MI).

In some embodiments, two computational engines GeneRep and nSCORE are applied to optimize the use of ARACNe and to quantitatively rank master regulators in any network, respectively. This strategy is greatly enhanced by the coupling with a multi-pronged compound-screening scheme.

GeneRep and nSCORE address 2 difficulties in computational biology: how to set a threshold cutoff level to maximize sensitivity while minimizing the false discovery rate (FDR) and how to incorporate various ranking parameters known individually to influence network hierarchy GeneRep employs innovative coupling of bootstrapping with a random networks generation procedure from the real data. Networks generated at the gene level by GeneRep contain ~20,000 nodes, while those generated at the transcript level contain ~50,000 nodes. The number of edges ranges from 300,000 to 1 million, far higher than what is often obtained with current methods. nSCORE creates an automated node importance scoring framework that incorporates limitless sets of existing parameters and thus can be applied to any type of networks and node statistics inputs.

The master regulator identification and targeting workflow integrates key aspects to optimize success: GeneRep-nSCORE to rapidly identify GSC-specific master regulators at apices of signaling networks; intra- and inter-tumor heterogeneity analyses to identify master regulators common among GSC subclones; mutational and survival analyses to capture additional relevant master regulators; a 2-pronged compound screening platform combining in silico and ultra-high throughput functional screens; evaluation of the clinical timeframe from surgery to drug identification; and development of a quantitative, network-based predictive biomarker for treatment response in GSCs.

In some embodiments, to achieve therapeutic success, core master regulators specific only to GSCs are first systemically identified across multiple GBM tumors and functionally validated, followed by simultaneous targeting of these core factors to achieve maximal efficacy with minimal toxicity.

The presently disclosed subject matter provides factors, such as cancer factors (e.g., factors encoded by genes BASP1, NKX6.2, STOX2, and MYCN) and stemness factors (e.g., factors encoded by genes SOX8, OLIG2, HES6, and ASCL1) that when inhibited, can reduce or inhibit GSCs. In some embodiments, inhibition of at least one of these factors can be used to inhibit GSCs. In some embodiments, inhibition of a combination of at least two of these factors can be used to inhibit GSCs. In some embodiments, a combination of inhibition of at least one cancer factor and at least one stemness factor can be used to inhibit GSCs. In some embodiments, inhibition of at least one of these factors can be used to treat a subject with glioblastoma. In some embodiments, a combination of inhibition of at least two of these factors can be used to treat a subject with glioblastoma. In some embodiments, the presently disclosed subject matter provides a method of reprogramming normal human astrocytes to GSCs by introducing a combination of cancer and/or stemness factors. In some embodiments, inhibition of a combination of the factors BASP1, NKX6.2, MYCN, and ASCL1 can be used to inhibit GSCs or in therapeutic methods for treating glioblastoma.

In some embodiments, a method of inhibiting GSCs or treating glioblastoma comprising using or administering an immunotherapy composition against individual or combinations of cancer and/or stemness factors. Also provided are immunotherapy compositions that target at least one cancer factor or stemness factor. In one embodiment, the immunotherapy composition comprises a peptide formulation derived from at least one cancer or stemness factor. In one embodiment, the immunotherapy composition comprises nanoparticle or dendritic cell containing peptides derived from at least one cancer or stemness factor. In one embodiment, the immunotherapy composition comprises RNAs coding for at least one cancer or stemness factor. In one embodiment, the immunotherapy composition comprises nanoparticles or dendritic cells containing RNAs coding for at least one cancer or stemness factor. In one embodiment, the RNAs coding for factors are electroporated into dendritic cells.

Also provided are pharmaceutical compositions that inhibit at least one cancer factor or stemness factor. In one embodiment, the inhibitor is a RNA interference agent or a small molecule.

In one embodiment, delivery of the composition is by direct injection into the brain. In one embodiment, delivery is by gene therapy, for example by adeno-associated virus (AAV) or retroviral replication vector (RRV) vector. In one embodiment, delivery is by systemic intravenous delivery.

In one embodiment, the stemness factor is SOX8. In one embodiment, SOX8 has the sequence of SEQ ID Nos: 13 or 14. In one embodiment, a method of treating a cancer or tumor by administering and inhibitor of SOX8 to a subject in need thereof. In one embodiment, the inhibitor that targets SOX8 targets SEQ ID Nos: 13 or 14 or a fragment thereof. In one embodiment, the stemness factor is ASCL1. In one embodiment, ASCL1 has the sequence of SEQ ID Nos: 15 or 16. In one embodiment, a method of treating a cancer or tumor by administering and inhibitor of ASCL1 to a subject in need thereof. In one embodiment, the inhibitor that targets ASCL1 targets SEQ ID Nos: 15 or 16 or a fragment thereof. In one embodiment, the stemness factor is OLIG2. In one embodiment, OLIG2 has the sequence of SEQ ID Nos: 17, 18, 19, or 20. In one embodiment, a method of treating a cancer or tumor by administering and inhibitor of OLIG2 to a subject in need thereof. In one embodiment, the inhibitor that targets OLIG2 targets SEQ ID Nos: 17, 18, 19, 20, or a fragment thereof. In one embodiment, the stemness factor is HES6. In one embodiment, HES6 has the sequence of SEQ ID Nos: 39, 40, 41, 42, 43, or 44. In one embodiment, a method of treating a cancer or tumor by administering and inhibitor of HES6 to a subject in need thereof. In one embodiment, the inhibitor that targets HES6 targets SEQ ID Nos: 39, 40, 41, 42, 43, 44, or a fragment thereof.

In one embodiment, the cancer factor is STOX2. In one embodiment, STOX2 has the sequence of SEQ ID Nos: 1, 2, 3, 4, 5, 6, 7, 8, 9, 10, 11, or 12. In one embodiment, a method of treating a cancer or tumor by administering and inhibitor of STOX2 to a subject in need thereof. In one embodiment, the inhibitor that targets STOX2 targets SEQ ID Nos: 1, 2, 3, 4, 5, 6, 7, 8, 9, 10, 11, 12, or a fragment thereof. In one embodiment, the cancer factor is BASP1. In one embodiment, BASP1 has the sequence of SEQ ID Nos: 21, 22, 23, or 24. In one embodiment, the inhibitor that targets BASP1 targets SEQ ID Nos: 21, 22, 23, 24, or a fragment thereof.

In one embodiment, the cancer factor is NKX6.2. In one embodiment, NKX6.2 has the sequence of SEQ ID Nos: 25, 26, 27, or 28. In one embodiment, a method of treating a cancer or tumor by administering and inhibitor of NKX6.2 to a subject in need thereof. In one embodiment, the inhibitor that targets NKX6.2 targets SEQ ID Nos: 25, 26, 27, 28, or a fragment thereof. In one embodiment, the cancer factor is MYC-N. In one embodiment, MYC-N has the sequence of SEQ ID Nos: 29, 30, 31, 32, 33, 34, 35, 36, 37, or 38. In one embodiment, a method of treating a cancer or tumor by administering and inhibitor of MYC-N to a subject in need thereof. In one embodiment, the inhibitor that targets MYC-N targets SEQ ID Nos: 29, 30, 31, 32, 33, 34, 35, 36, 37, 38, or a fragment thereof.

In one embodiment, a method of treating a subject with a cancer or tumor comprising administering a composition comprising at least one stemness factor inhibitor and at least one cancer factor inhibitor. In one embodiment, the cancer factor is selected from the group consisting of BASP1, NKX6.2, STOX2, and MYCN and the stemness factor is selected from the group consisting of SOX8, OLIG2, HES6, and ASCL1.

In one embodiment, a method of treating a subject with a cancer or tumor. In one embodiment, the cancer or tumor is a glioblastoma. In one embodiment, the tumor is a glioma. In one embodiment, the tumor is from brain. In one embodiment, the cancer or tumor is non-small cell lung cancer or cancer where the cell type of origin are from neurodectoderm.

In one embodiment, an immunotherapy composition treating a subject with a glioblastoma, comprising an inhibitor of at least one cancer or stemness factor, wherein the cancer factor is selected from the group consisting of BASP1, NKX6.2, STOX2, and MYCN and the stemness factor is selected from the group consisting of SOX8, OLIG2, HES6, and ASCL1.

In one embodiment, an immunotherapy composition for treating a subject with a glioblastoma, comprising a peptide formulation derived from at least one cancer or stemness factor, nanoparticles containing peptides derived from at least one cancer or stemness factor, dendritic cells containing peptides derived from at least one cancer or stemness factors, RNA coding at least one cancer or stemness factor, nanoparticles containing RNA coding at least one cancer or stemness factor, or dendritic cells containing RNA coding at least one cancer factor or stemness factor.

In one embodiment, an immunotherapy composition for inhibiting a glioblastoma stem-like cell (GSC), comprising an inhibitor of at least one cancer or stemness factor, wherein the cancer factor is selected from the group consisting of BASP1, NKX6.2, STOX2, and MYCN and the stemness factor is selected from the group consisting of SOX8, OLIG2, HES6, and ASCL1.

In one embodiment, an immunotherapy composition for reprogramming an astrocyte to a glioblastoma stem-like cell (GSC), comprising at least one cancer or stemness factor, wherein the cancer factor is selected from the group consisting of BASP1, NKX6.2, STOX2, and MYCN and the stemness factor is selected from the group consisting of SOX8, OLIG2, HES6, and ASCL1.

In one embodiment, a kit, comprising a first container and a second container, wherein the first container comprises at least one dose of a composition comprising an inhibitor of at least one cancer factor selected from the group consisting of: BASP1, NKX6.2, STOX2, and MYCN, wherein the second container comprises at least one dose of a composition comprising an inhibitor of at least one stemness factor selected from the group consisting of: SOX8, OLIG2, HES6, and ASCL1.

EXAMPLES

Example 1: GeneRep Maximize Sensitivity while Minimizing the False Discovery Rate (FDR)

GeneRep employs innovative coupling of robustness enhancing bootstrap procedure with a maximally realistic random networks generation. Network edges are pruned through multiple filtration steps aimed at eliminating spurious while preserve true relationships, effectively reducing FDR from >50% to <5%. Networks generated at the gene level by GeneRep contain ~20,000 nodes, while those generated at the transcript level contain ~50,000 nodes. The number of edges ranges from 300,000 to 1 million, far higher than what often obtained with current methods.

We applied GeneRep to the RNAseq datasets for breast (1222 samples) and brain (166 samples) cancers from the Cancer Genome Atlas (TCGA) to establish gene networks. 16,825 nodes with 387,055 edges (breast—FIG. 8B) and 17,528 nodes with 823,018 edges (brain) were recovered. The top 200 hubs with the highest number of connections contained well-known tumorigenic drivers in their respective cancers, e.g. in one cluster are transcription factors [Estrogen receptor 1 (ESR1), GATA3 (breast); SOX8 and MYT1 (brain)]; in the other cluster are histone modifiers (ARID2, EZH2, and TRIP13—breast) and chromatin remodelers (DNMT1 and BRCA2—breast; SMARCA4—brain) (FIG. 8).

Example 2: Identifying and Ranking Master Regulators of Gene Networks nSCORE addresses this by creating an automated node importance scoring framework incorporating limitless sets of ranking parameters known individually to influence hierarchy and thus can be applied to any type of networks and node statistics inputs and to predict master regulators controlling any network of any biological process. The node importance score (niscore) is the aggregation of source node and neighborhood scores. The score is calculated iteratively with the output of the previous calculation serving as the input for the next and so on. Inputs include networks (e.g. GeneRep, STRING) and node statistics (e.g. log FC, FDR, or pvalue).

Retrospective datasets: We applied nSCORE to the training RNAseq dataset #GSE54792. In this study, GBM differentiated cancer cells (GDC) were successfully reprogrammed into GSCs using a set of 4 transcription factors (TF): Olig2, Sox2, Pouf3f2, and Sall2. We generated approximately 2000 scoring sets of parameters. The best-fit results are shown in FIG. 9B, where we recovered 3 of 4 TF (Olig2, Sox2, Pouf3f2) in the top 8 ranked genes (FIG. 9B, highlighted).

Using the best parameter set of the training case above, we applied nSCORE to 2 testing RNAseq cases; i) #GSE62212, in which two human GSC lines with a tet-inducible Klf9 transgene were treated with doxycycline, and ii) #GSE14897, in which mouse fibroblasts were reprogrammed into iPS cells with OSKM. Compared to controls, network changes in treated cells' profile ranked KFL9 as the 2nd highest target of all genes by nSCORE (FIG. 9C) and 3 of 4 OSKM factors (Oct4, aka Pou5f1, Myc and Sox2) were ranked 6th, 7th, and 9th, respectively (of note, Klf4 is transiently expressed and not amenable to computational prediction).

This represents the most factors recovered and collectively the highest ranking compared to existing platforms. In addition, Nanog, another critical iPSC factor, was also recovered and ranked 1st.

Prospective datasets: We used GeneRep-nSCORE to predict GSC maintenance factors in the nicotinamide adenine dinucleotide (NAD+) metabolic pathways, and identified E2F2 at its signaling apex. The critical role of E2F2 was subsequently validated experimentally.

Example 3: Identification and Validation of Core Master Regulators of GSCs

Using gene expression profiles of patient-derived GSCs and GBM differentiating cells (GDC), NPC, and NA, GeneRep-nSCORE predicted the top 20 genes required for fate conversion between these cell types. Notably, two functional groups (stemness and cancer phenotype) of master regulators emerged (FIG. 10, bolded). Sox8, Olig2, Hes6 and Ascl1 were predicted to establish the stemness program, while Basp1, Nkx6.2, Stox2, and Mycn the cancer/proliferative phenotype. To validate these predictions, we introduced various combinations of the 6 factors (SOABNM) into NA using a lentiviral vector and determined the effect on the NA-GSC conversion as measured in a standard neurosphere formation assay (see below) and tumorigenicity in immunocompromised mice. When 6 factors were introduced simultaneously, the largest number of spheres was produced. Any combination lacking ABNM individually led to severely impaired sphere formation, similar to the empty virus control, while SO were dispensable for this process. Taken together these results establish ABNM as the core master determinants of the general GSC fate.

To further confirm the critical requirement of ABNM in GSC in humans, we transduced 8 independent patient-derived GSC lines (results from 2 are shown), established at UF Brain Tumor Center, with lentiviruses encoding for shRNAs specific against these factors. Importantly, knockdown of individual factors showed significant loss of GSCs consistently across all cell lines tested with ASCL1 and Nkx6.2 KD compared to the other factors. However, knockdown of many combinations of 2 or more factors, except for the Sox8 and Olig2 combination in some cell lines, profoundly suppressed sphere formation in these GSC lines.

Figure 1:
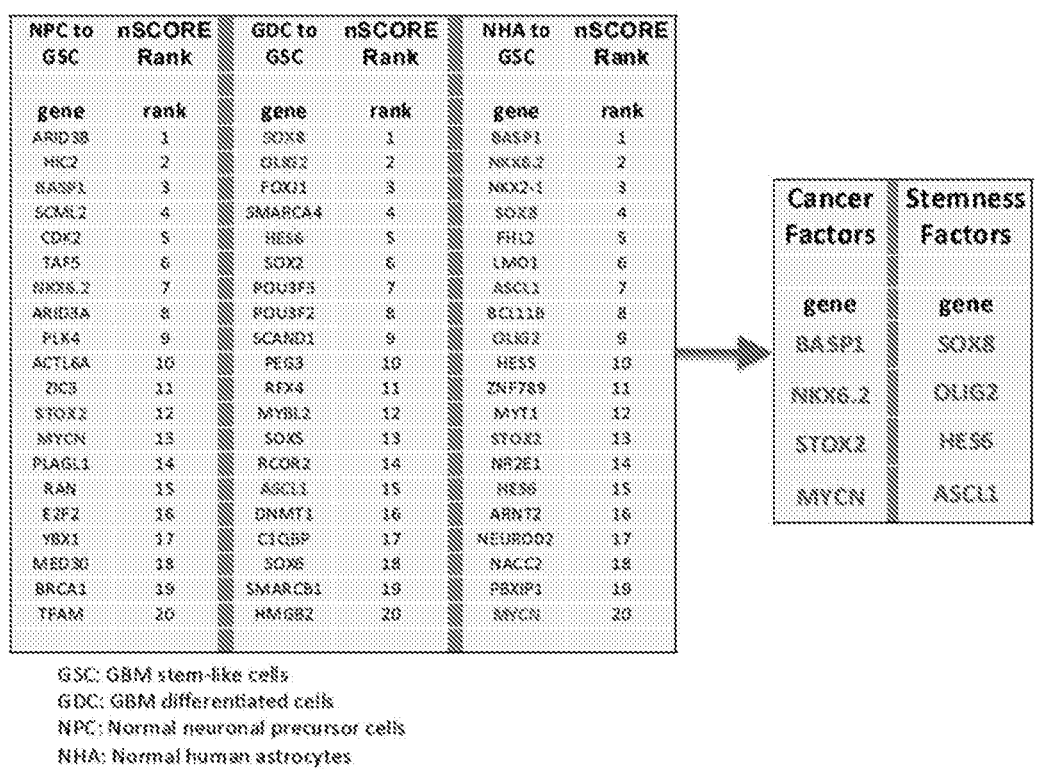
FIG. 1 illustrates GeneRep-nSCORE predicted master regulators of GSCs.

Example 4: Targeting Glioblastoma Stem Cells by Perturbing a Novel Gene Regulatory Cluster to Reduce Tumor Recurrence Core GSC-specific master regulators are those that when at least one being absent will result in a loss of stem-like behaviors (neurosphere formation and tumorigenicity) of GSCs, and/or that only when all are present will reprogram non-GSCs into GSCs. To this end, we applied the GeneRep-nSCORE platform to gene expression profiles of GSCs and GBM differentiating cells (GDC), normal neuronal precursor cells (NPC), and normal human astrocytes (NHA) and predicted the top 20 genes involved in fate conversions between these cell types. Two functional groups of master regulators of stemness and cancer phenotype that are shared among these conversions emerged (FIG. 1). 4 master regulators SOX8, OLIG2, HES6 and ASCL1 are predicted to induce and maintain the stemness program, while BASP1, NKX6.2, STOX2, and MYCN confer the cancer program to GSCs.

Figure 2:
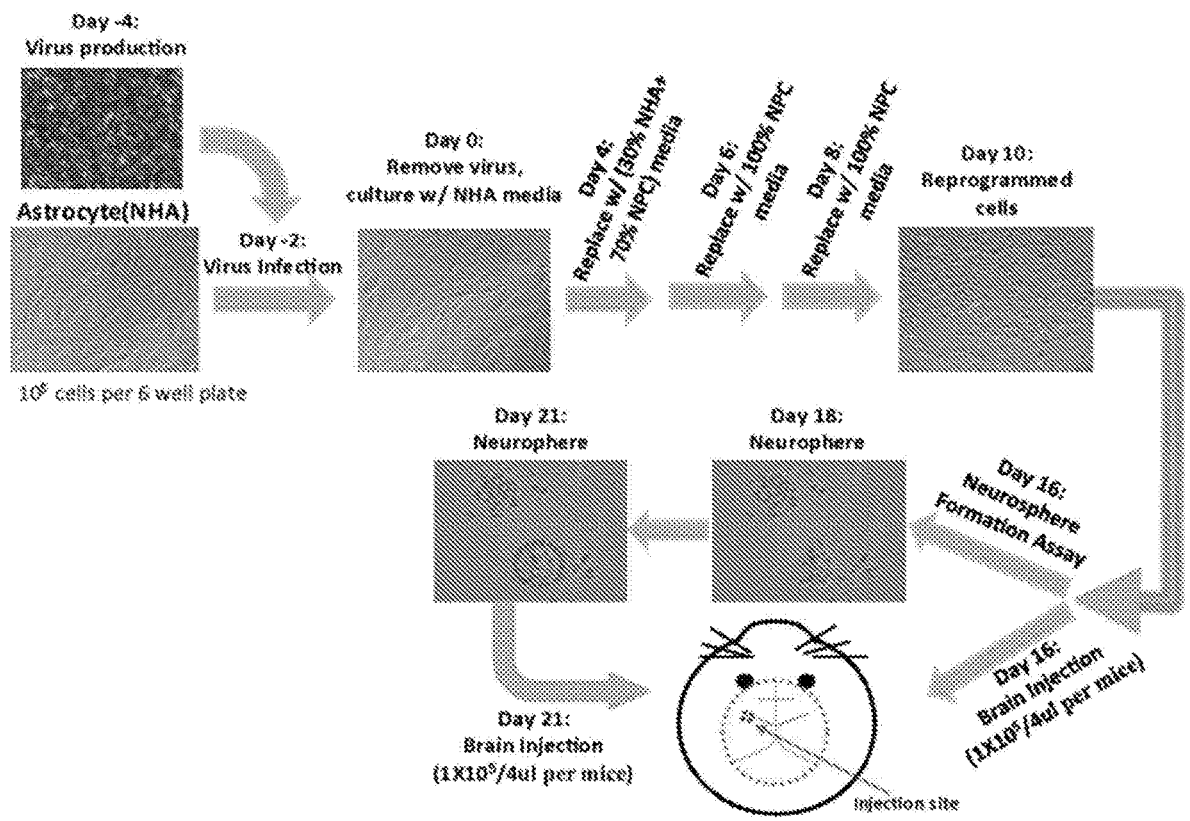
FIG. 2 illustrates the experimental plan for reprogramming NHA to GSA.
Figure 4:
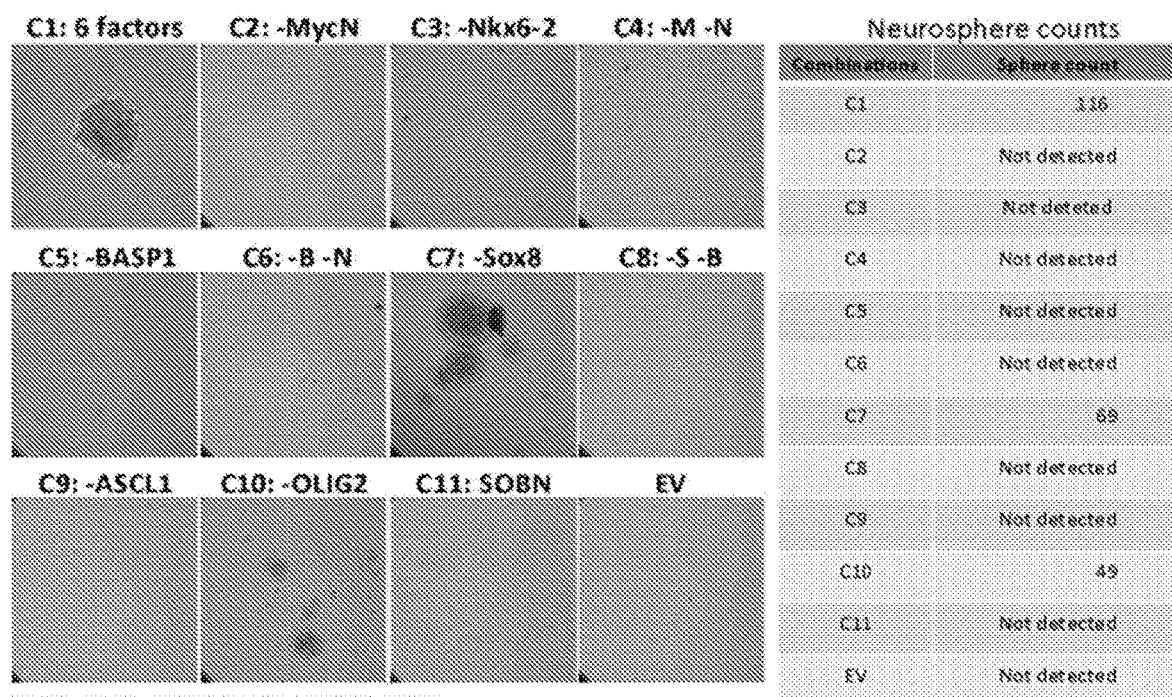
FIG. 4 illustrates the core factors required for NHA-GSC reprogramming.

We introduced various combinations of these 6 factors (SOX8, OLIG2, ASCL1, BASP1, NKX6.2, and MYCN) into NHA using a lentiviral vector and determined the minimal combination needed to reprogram NHA to GSCs as measured by neurosphere formation and tumorigenic potential in an orthotopic model in mice (FIG. 2). HES6 and STOX2 were not tested although they are predicted to behave similarly as other genes in their respective functional groups. When all 6 factors were introduced simultaneously, the largest number of cells were produced that could survive in neural stem cell media. Lacking any one of these 6 factors significantly decreased the number of cells by 3 to 10 fold and lacking any 2 factors brought the number of cells to an undetectable level, similar to the empty virus control (FIG. 3). To measure stemness potential of these cells, we performed a standard neurosphere assay. Any combination that lacked ASCL1, BASP1, NKX6.2 or MYCN severely impaired neurosphere formation, while SOX8 and OLIG2 were dispensable for this process (FIG. 4). Taken together these results indicated that ASCL1, BASP1, NKX6.2 and MYCN are the core GSC master regulators.

Figure 5:
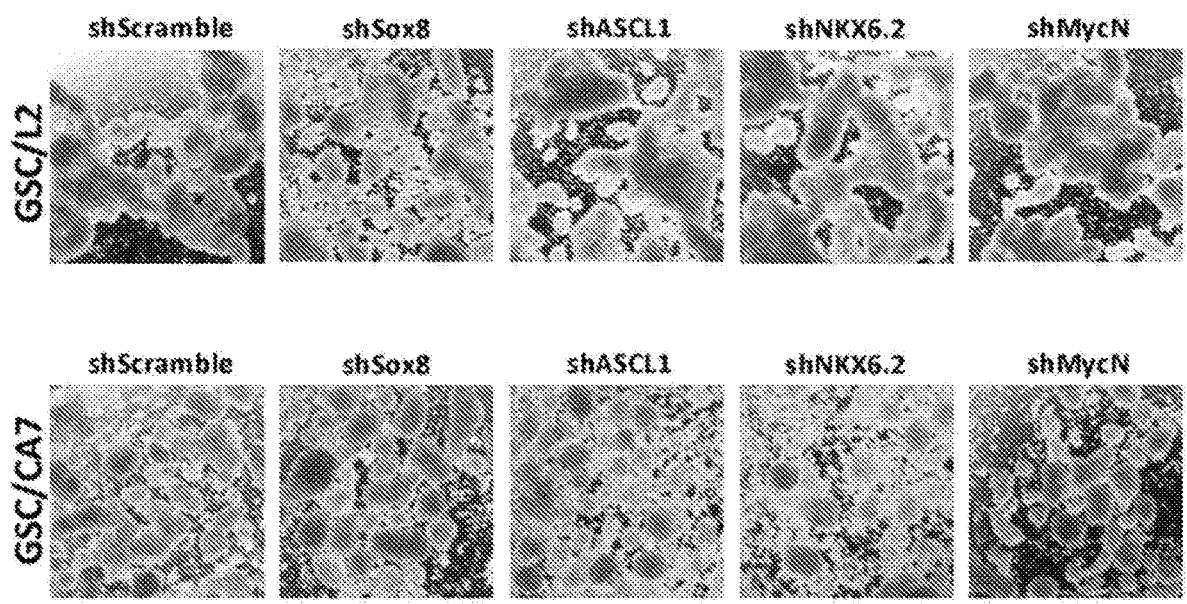
FIG. 5 illustrates that knockdown of individual factors alone minimally impact maintenance of patient-derived GSCs.
Figure 6:
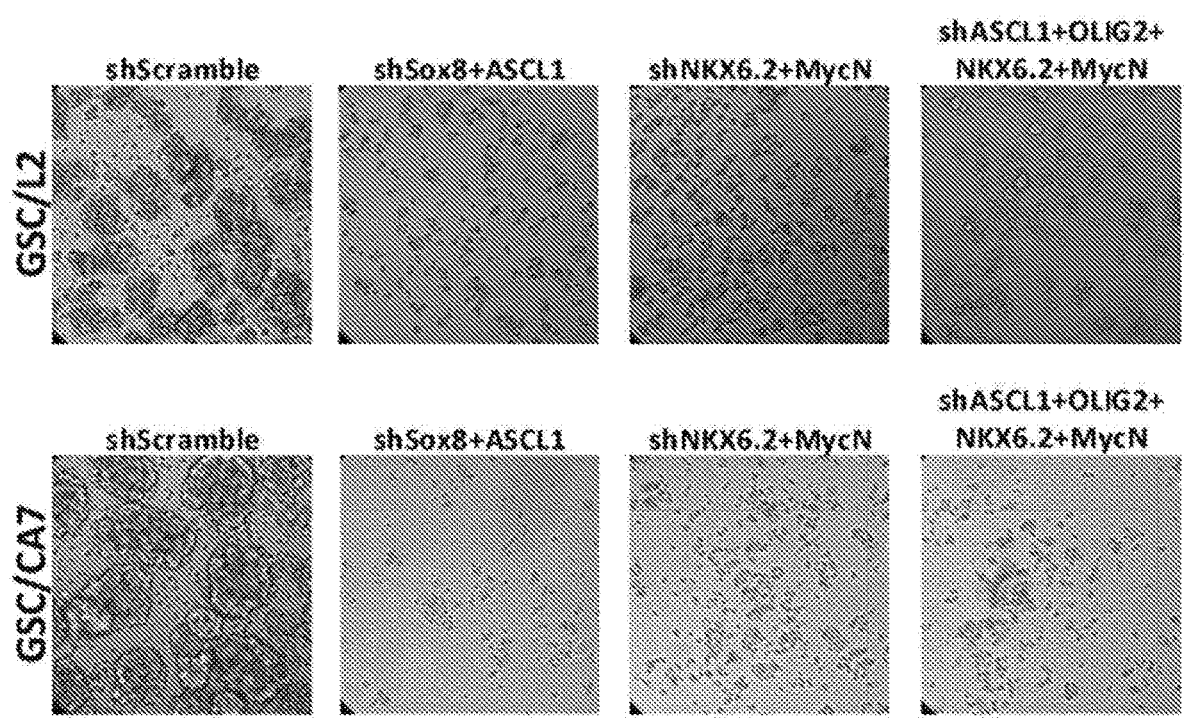
FIG. 6 illustrates that core factors are required for GSC maintenance of neurosphere formation.

To further confirm the functions of these 4 master regulators and to test the potential for therapeutic development, we used lentiviruses encoding for shRNA specific for one of these 6 factors and transduced 4 independent patient-derived GSC lines. Representative results from 2 GSC lines are shown in FIGS. 5 and 6. SiRNA knockdown of individual factors alone had no significant impact on GSC neurosphere formation (FIG. 5), indicating that these factors do not function independently of each other. However, knockdown of any combination of 2 or more factors, except for the SOX8 and OLIG2 combination, profoundly suppressed neurosphere formation in these 4 patient-derived GSC lines (FIG. 6). These results confirmed the reprogramming observations above that SOX8 and OLIG2 together were dispensable for GSC maintenance, that ASCL1, BASP1, NKX6.2 and MYCN represented core master regulators of GSCs in general, and that effective inhibition of any combination of 2 or more of these 4 core master regulators, either by genetic means (si/shRNA) or perhaps small molecule inhibitors, would have significant therapeutic potential as a GSC-specific treatment of GBM, and possibly for other cancers whose stem cells share similar regulatory pathways.

These experiments were performed in 3 individual patient derived GSC cell lines and to the same result. Together, these findings show that these factors may serve as important pharmacologically targets that and may reduce tumorigenicity (i.e., reduced tumor size or number of tumors).

Example 5: In Vivo Experimentation Targeting Glioblastoma Stem Cells by Perturbing a Novel Gene Regulatory Cluster to Reduce Tumor Recurrence GBM mice are administered a combination of an inhibitor of at least one cancer factor selected from the group consisting of BASP1, NKX6.2, STOX2, and MYCN and an inhibitor of at least one stemness factor is selected from the group consisting of SOX8, OLIG2, HES6, and ASCL1 by direct injection to the brain, gene therapy, or viral delivery (treatment groups).

GBM mice tumor number and size are analyzed and compared to control non-treatment GBM mice.

It is expected that mice in the treatment group will have significantly reduce tumorigenicity (i.e., reduced tumor size or number of tumors), especially in mice administered inhibitors of BASP1, NKX6.2, MYCN, and ASCL1 or mice administered inhibitors of NKX6.2 and ASCL1.

Example 6: In Vivo Experimentation with ASCL1 and NKX6-2 Knockdown in Mice

Patient derived GBM stem cells with knockdown (by shRNA) of ASCL1 and NKX6-2 either individually (FIGS. 31A and 31B, respectively) or simultaneously (FIG. 31C) were implanted into the brain of immunosuppressed mice, whose survival was compared to mice implanted with the same GBM stem cells containing a scrambled control shRNA. Simultaneous knockdown of ASCL1 and NKX6-2 resulted in cure of GBM-bearing mice as compared to only partial rescue with individual knockdown, which in turn fared significantly better than scrambled controls.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

| Gene ID | Gene Name | Accession Numbers |
| --- | --- | --- |
| STOX2 | storkhead box 2 (STOX2), | NP_064610 (GenBank; protein; SEQ ID NO: 1); NM_020225 (GenBank; mRNA; SEQ ID NO: 2)<br>XP_011530431 (GenBank; protein isoform X1; SEQ ID NO: 3)<br>XM_011532129 (GenBank; mRNA isoform X1; SEQ ID NO: 4)<br>XP_011530432 (GenBank; protein isoform X2; SEQ ID NO: 5)<br>XM_011532130 (GenBank; mRNA isoform X2; SEQ ID NO: 6)<br>XP_016863955 (GenBank; protein isoform X3; SEQ ID NO: 7)<br>XM_017008466 (GenBank; mRNA isoform X3; SEQ ID NO: 8)<br>XP_011530433 (GenBank; protein isoform X4; SEQ ID NO: 9)<br>XM_011532131 (GenBank; mRNA isoform X4; SEQ ID NO: 10)<br>XP_016863956 (GenBank; protein isoform X5; SEQ ID NO: 11)<br>XM_017008467 (GenBank; mRNA isoform X5; SEQ ID NO: 12) |
| SOX8 | SRY-box 8 | NP_055402 (GenBank; protein; SEQ ID NO: 13); NM_014587 (GenBank; mRNA; SEQ ID NO: 14) |
| ASCL1 | achaete-scute homolog 1 | NP_004307 (GenBank; protein; SEQ ID NO: 15); NM_001080391 (GenBank, mRNA; SEQ ID NO: 16) |
| OLIG2 | oligodendrocyte transcription factor 2 | NP_005797(GenBank; protein; SEQ ID NO: 17);<br>NM_005806(GenBank; mRNA; SEQ ID NO: 18)<br>XP_005260965 (GenBank; mRNA; isoform X1; SEQ ID NO: 19), XM_005260908 (GenBank; mRNA; isoform X1; SEQ ID NO: 20) |
| BASP1 | brain abundant membrane attached signal protein 1 | NP_006308 (GenBank; protein; variant 1; SEQ ID NO: 21);<br>NM_006317(GenBank; mRNA; variant 1; SEQ ID NO: 22)<br>NP_001258535 (GenBank; protein; variant 2; SEQ ID NO: 23);<br>NM_001271606 (GenBank; mRNA; variant 2; SEQ ID NO: 24) |
| NKX6-2 | NK6 homeobox 2 | NP_796374 (GenBank; protein; SEQ ID NO: 25);<br>NM_177400 (GenBank; mRNA; SEQ ID NO: 26)<br>XP_016872278 (GenBank; protein; isoform X1; SEQ ID NO: 27), XM_017016789 (GenBank; mRNA; isoform X1; SEQ ID NO: 28) |
| MYC-N | MYCN proto-oncogene, bHLH transcription factor | NP_001280157 (GenBank; protein; Isoform 1, variant 1; SEQ ID NO: 29); NM_001293228 (GenBank; mRNA; isoform 1, variant 1; SEQ ID NO: 30)<br>NP_005369 (GenBank; protein; Isoform 1, variant 2; SEQ ID NO: 31); NM_005378 (GenBank; mRNA; isoform 1, variant 2; SEQ ID NO: 32)<br>NP_001280160 (GenBank; protein; isoform 2; SEQ ID NO: 33); NM_001293231 (GenBank; mRNA; isoform 2; SEQ ID NO: 34)<br>NP_001280162 (GenBank; protein; isoform 3; SEQ ID NO: 35); NM_001293233 (GenBank; mRNA; isoform 3; SEQ ID NO: 36)<br>XP_016859657(GenBank; protein; isoform X1; SEQ ID NO: 37), XM_017004168(GenBank; mRNA; isoform X1; SEQ ID NO: 38) |
| HES6 | hes family bHLH transcription factor 6 | NP_061115 (GenBank; protein; Isoform a; SEQ ID NO: 39); NM_018645(GenBank; mRNA; isoform a; SEQ ID NO: 40)<br>NP_001136325 (GenBank; protein; Isoform b; SEQ ID NO: 41); NM_001142853(GenBank; mRNA; isoform b; SEQ ID NO: 42)<br>NP_001269363 (GenBank; protein; isoform c; SEQ ID NO: 43); NM_001282434 (GenBank; mRNA; isoform c; SEQ ID NO: 44) |

```
SEQ ID NO: 1-STOX2:
Protein sequence:
    1  mkktrsttlr rawpssdfsd rasdrmrsrs ekdyrlhkrf paafapqasr gymtsgdvsp
   61  ismspisqsq fiplgeilcl aisamnsark pvtqealmeh lttcfpgvpt psgeilrhtl
  121  ntivrerkiy ptpdgyfivt pqtyfitpsl irtnskwyhl deripdrsqc tspqpgtitp
  181  sasgcvrert lprnhcdsch ccredvhsth aptlqrksak dckdpycpps lcqvppteks
  241  kstvnfsykt etlskpkdse kqskkfglkl frlsfkkdkt kqlanfsaqf ppeewplrde
  301  dtpatiprev emeiirrinp dltvenvmrh talmkkleee kaqrskagss ahhsgrskks
  361  rthrkshgks rshsktrvsk gdpsdgshld ipaereydfc dpltrvpreg cfiiehkgdn
  421  fimhsntnvl eshfpmtpew dvsgelakrr tempfpepsr gsshskvhrs hshtqdrrsr
  481  nersnkaker srsmdnskgp lgasslgtpe dlaegcsqdd qtpsasyidd stlrpaqtvs
  541  lqrahissts ykevcipeiv sgskepssac sllepgkppe slpsygelns cptktatddy
  601  fqcntssetv ltapsplgkn kedhdtltla egvkklspsd rqvphssrep vghkeespkg
  661  pgggpaasgg vaegiangrl vqhhgaepss ldkrkeifsk dtlfkplhst lsvnsyhkss
  721  lsllkshpkt padtlpgrce klepslgtsa aqampasqrq gesggngeas fdyynvsddd
  781  dseeganknt eeeknredvg tmqwllerek erdlqrkfek nitllapket dsssnqrath
  841  sarldsmdss sitvdsgfns prtreslasn tssivesnrr qnpalspahg gagpafnfra
  901  saepptneae klqkpsnclq asvtsv SEQ ID NO: 2-STOX2:
mRNA sequence:
    1  gcagcgtagc gggctggcgg tgacttacac cgggactcca gagggagaga ggaagcgctg
   61  caggccactt gcattgcgtc ttccaggctg cgtggacccg cgccccggc gtgtgcggtt
  121  gtgggggagc tcgccgtggc ctcccctccc tctggcttta gcttcctttg gggttggcgc
  181  aggtgggcca ggcagcgcac cgcagatctc cccgttccca cgaaggctgg ctcgctgtct
  241  ctctccgagc gggagggacc atcctaaaaa tatgtaaata tccaagcgct ggctccaggc
  301  tggggcagct gccaaggtcc ccgcgccgcc gccgggtgtt ttacatgaaa atgagaagcc
  361  tgatgggaac cgcgttctaa cttaaggcag cctggtgatt agcatgagac tgggcggctg
  421  tcctgcttcc tgcccttcaa tagccgttcc gcgcgctcgc gccggagcag cgctgccgcc
  481  gcgcgggggt cgatcgcagg ctcggcgtcc ttggcagcca tggctccggc gccgctcgg
  541  ccagtaagta ggagcatgca tgtgtagggg gcacatgcgt gtcggcgcac ccacccagcc
  601  atccacccgc gcgcacgcac agcgcccgga gcctcggcaa ggggaagatt gacgaggcgc
  661  tgcagtcgcg gggacgacgc gggctcttcc tggattccgc aggagcccgc ccgccgcagc
  721  tgctgtctgc agagcctgct cggatcctgt gcacgcgc ccccgctcg agcctctgtg
  781  atgaagactg tctcccgggg actgcagcgg aggcagagcc agccagcgcc ggggactgcg
  841  ggccgtgcgg ctgataggcc gcgggggaca cgactcggac actgtcatcc ccacgcctcg
  901  cgctgagctg cccggcgcgg agggtctgcc gccgccctc cggcctcccg cacgcccgat
  961  cccgggtcag ccccggaggc ctcggctgcc tcatttgttt gggtcttttg tgccgtggct
 1021  cccagttggc caagcactcc tgcgctgaat cggccattg tctgcgctcc cattgccttc
 1081  acgctgcaag tctcggcgcc ccaccccgc ccgccccctc ccgcctcct cccggccggg
 1141  gagcctccta acgtgccttt cccccccagga atctggaagc ataagccgg gcggattgca
 1201  aatgaagtgt aatgcattgt gggacgtgtg taaatcgga gccttcgccg tggggtgtg
 1261  gggggcgtg gggagggccg gaccgccgc tggcggtgta gacgccgacg aggaggggct
 1321  gggaaaatgt gcgcagagtc cgcccgggtc gtgcccgccg tagacggatg aaggagcgcg
```

-continued

```
1381  ctgcgccccg gcgctgaggc cccgaggatc ggggcggcag gtcgccctcc ccaccatgaa
1441  gaagacccgg agcacaacct tgcggcgagc ctggcctagc tcggatttct cggaccgggc
1501  ctcggaccgc atgaggtccc gcagcgagaa ggactaccgc ctgcacaagc gtttccccgc
1561  ggccttcgcg ccccaggctt cgcggggcta catgacatca ggtgatgtat cacccatcag
1621  tatgtctccc atcagtcagt ctcagtttat tccactcggg gagatcctct gcttggccat
1681  ctcagcaatg aactcggcaa gaaagcctgt cacccaagaa gcactgatgg agcacctgac
1741  cacgtgcttc ccaggtgttc caacgccaag ccaagaaatt ctgcggcaca cgctgaacac
1801  gctggtacgg gagaggaaga tctacccaac tccagatggc tacttcatcg tgaccccaca
1861  gacttatttc ataactcctt ccctcataag aactaacagt aaatggtacc atttggacga
1921  gaggatacct gaccggtctc agtgcacctc tccgcaaccc gggaccatca cgccctctgc
1981  ctcaggctgt gtcagggaaa ggacattgcc ccgaaaccac tgcgactctt gccactgctg
2041  cagagaagac gtgcacagca cgcatgcacc caccctgcaa aggaagtctg ccaaggactg
2101  caaagaccct tactgtcccc cttctctgtg ccaggtgcca cccactgaaa agagcaaaag
2161  tactgtaaat ttttcctata agacagaaac tctctcaaaa cctaaagata gtgaaaagca
2221  gtcaaaaaaa ttcgggctaa agttattccg gttaagtttt aaaaaagaca agaccaaaca
2281  gctggccaat ttttctgccc agtttcctcc tgaagagtgg ccctgcgag acgaggacac
2341  gccagctacg atccctcggg aagtagagat ggaaatcatt aggcgcatta acccagacct
2401  gaccgtggaa aatgtcatgc ggcacaccgc gctcatgaag aaactggaag aagaaaaggc
2461  ccagaggagt aaagccgggt cctctgccca tcacagcgga aggagtaaaa agagtaggac
2521  tcatcggaag tcccatggaa agtctcggtc tcacagcaag acacgggtgt ctaaaggaga
2581  cccttccgac ggttcacatc tggatatccc agctgaaaga gagtatgact tttgtgatcc
2641  tcttaccagg gtgcccaggg agggctgctt catcattgaa cacaaaggag ataacttcat
2701  catgcacagc aacacaaacg tgctcgagtc ccacttcccc atgacaccag aatgggatgt
2761  gtctggtgaa ttggctaaaa ggagaactga gatgcctttt cctgaacctt ctaggggaag
2821  ctcccactca aaagtgcacc gaagccacag ccatacacag gaccggaggt ccaggaatga
2881  gagatccaac aaagccaagg agagatccag gtcgatggat aactccaaag gccctctggg
2941  tgcttcttct ctagggacgc cggaagacct tgctgaaggc tgcagccaag acgaccagac
3001  ccccagccaa tcctacattg acgacagtac tttaaggcct gcacagaccg ttagtctcca
3061  aagggctcac atttcgtcca caagctataa agaggtgtgt attccagaga tagtcagtgg
3121  cagcaaggaa ccgtccagcg cttgcagcct tttggagcca ggaaaaccac ccgagagttt
3181  gccatcctat ggcgaactca actcttgtcc aacaaaaaca gccacagatg actatttcca
3241  gtgcaacacc tctagtgaga cggtgctcac ggcaccatca cctctgggaa agaataagga
3301  ggaccatgac actctgactt tggcagaagg ggtgaaaaag ctctccccctt ctgataggca
3361  ggtcccccac tcctccaggg agcctgtggg gcacaaggag gagtcaccaa aagggccggg
3421  tggggccccc gctgcttcgg gaggagtggc tgaagggatc gccaacggac gcctcgtcca
3481  gcaccatggt gccgagccca gcagcttgga caagaggaaa gagatattta gcaaagacac
3541  actgttcaaa cctcttcaca gcaccttgtc tgtaaacagc tatcacaagt cgagcctgtc
3601  cctcctcaaa tctcacccga agacacctgc tgacacattg ccaggccgat gtgagaaact
3661  ggaaccgtcc ctggggacct cggcggcaca agccatgcct gcttcccagc gtcagcagga
```

```
3721   gtcaggaggg aaccaggaag cctcttttga ctattacaac gtctctgatg atgacgactc
3781   tgaggaaggg gcaaacaaga acacagagga ggagaaaaat agagaggacg taggcaccat
3841   gcagtggctc ctcgagcggg agaaggaaag agacttgcag aggaaatttg aaaagaacct
3901   cacccttctt gctccaaaag aaaccgacag cagcagcaac cagagagcca cccattcagc
3961   ccggctcgac agcatggaca gcagcagcat cacagtggac agtggattca actccccacg
4021   tactcgggag agcctggctt ccaacacatc aagcattgtt gaaagtaacc gtcgtcagaa
4081   ccccgctttg agcccggccc atggtggagc tggtccagcc ttcaacttcc gagcgagcgc
4141   ggagcccccg acaaatgaag ctgagaagct acagaaacct tccaactgct tgcaagcttc
4201   tgttactagc gtgtgattgt ccttctgcct cagatcttct gtctcattcg atacagcaaa
4261   gtttacgaca ctgggactga tgtttacatc tttggaaaga caagcatctc aaccacagtt
4321   tttgtgttta cttaaactgt gctgctaagt agggctaggg caaaaaaaca aaaaatcttt
4381   atttcagagt attgcttttc acatttatgg ctctgtagca actgagtaac agtaggggtg
4441   atatgtatac ttttgcttca ctaattgtat ctgagcacac ataggaaagt ctagacactg
4501   taagtgtaat acgcattttc aatgtcatgc agttgccaat tccattttaa aatgccacag
4561   atgcgtgttg ctcccagtct gtggttaaac ggtgccacag aactgatcct tgacacttcc
4621   aaaaaaaaaa aaacaaaaca aaacaaaaaa aatttaaaaa aaaaaacaa aaaacaaaac
4681   taagctacca cgaaatgtca aatgcaaggg tccaccttga gggaaataga tgccaaacta
4741   actagaaggg acccccggccc tttgtgtgtg aattgtttat gcaccagtca ttttcactg
4801   tgagttttcg tgacactatt ttgcaggagc ccatggaagt gtgtgagaag gggtcgcaat
4861   ggagatcact gggagtgaat gttttcaggg ttttgttttg aagtgtcaca gatgcttgtc
4921   tgattttttt aaccttccgt gatcacaaac aggaatatag gcctttgaat ctgaagtgga
4981   caaaggaaag caatttccag tctggctggg gcacagcatt aggtgattga aaaggtgatg
5041   tggacttgta aaggtgttta ctcaaatatt gaaggaagag aatttcctcc ttgtgatact
5101   taggatgacc ctatcttact ctaatagata caataattag tttgtttaaa agcaaaatgt
5161   tctttgtgat acaaatgaag agtagggcct gaggatgtta ttctttctaa tggaaggaca
5221   taaatctatt ttatgtagtt ttaaatagaa tgcctaaatt aggctgtggg agataatttt
5281   tagtggttgt aggaaagagc aaatttaggg agtgttgaac ttcaggcctt ttattcctgg
5341   gaagatatgt atagagaaaa cttttaaaat aattttgat tagaaatata catgtgccca
5401   tgtaataaac aacagaatgt gctcattctg ctagtgcggt ataatccgaa tttgtactcc
5461   cctaaaattt atcagaataa caattatgca tacatgaact atgccagagt aatgtttaca
5521   gatactttgt aaccaatttc aggaggcgtt tttagctgga tgtgtagtta attagaccaa
5581   cttatttcca aatggtttgt taacattttg ctttggttta caatgtcatg ttgaacacaa
5641   agaagaccca gcagcaaagg gatgaccaat aatttcatct tatagcaagg agacattcca
5701   acgttcccat gttttatttt ctgagaacag tgggacagat ctgtagtaat ggaatattat
5761   ttgcaaaagg gttacatatg acacaagtaa gtgttctgac ataaagtttt atttagttca
5821   gtggcatgtg ctgttgggag ccatacacca taaatatat atatcccaaa ataaatctag
5881   aatattttca cctccaattt cagtaattgg catatgattt gtgagacgca tctgttttttg
5941   tatgaggttt aatcactagc aatctgttta aagaatccag tcctatacac agttggactc
6001   attcttgaaa cctttaaatg ctccctcata gttttcagt tatttggaag ttgcattggg
6061   tcaaactgaa ctccttgagt ttggtgtaaa ttccttttttt ctgcttatta tagtgaaact
```

-continued

```
6121  tcagcatgtt tcttagtaaa ctcccatacc attgaaatgc ttaagccagt tggctttcag
6181  tctcatgcct tatttcctcc aaggcatgcc tcaacgcatt gtttgtctca ttgcttaaat
6241  atgtccagaa ggaatgatca tgtatctaat agactacata gttggttccc ttggggagtt
6301  atatatcata cagttactaa atatttgtct aaattcattt tttccaaaaa cctgctctca
6361  aattttctt ctactctcag ttcataaata ataaccat tgaaacaaca catcagcctc
6421  tagctgatcc tctgaaagta gccattgaaa taatcgaata ctgtgtgaac aggaaaggaa
6481  agcgttacct ttaagagaag ctttaaaata ggaatttatt gatatttcac aagatatagg
6541  tttacagaag acattattca aataaatatg tacactattt gcctgatgct atggggtaca
6601  taatttttta aaaactccct tagaccagca gccattagtg tagaaatgat ggactttaaa
6661  ggtgatacca tgtaagcaga tgttgcatat aaaaatattc ctgcctgaat ctgatcgaga
6721  ttcttgaatg ggggaggagt ggcagccggc agcacattgc aaatgtcatt cgaggtcacg
6781  gtgaggctct cggtcccgga acagtggggg cctcgccagg cgttgccagt atccctttcc
6841  tcctgtaaaa tcatagcttt gtgttacacg actgcttatc cagtcttagg gtttagcagc
6901  tgaaaggttt acaaaactga atctggttga atctctgtga aagggtcaac acatctgtcg
6961  gcattttgca cacttatgta ttattatgat acaacatatt actttatggt aatttttatt
7021  tttacatata actacctcca taaatttgat gaaatggcag ccgtgtgtta aagtgtatcg
7081  ttcagaagag caaagttgaa cacttccttc aacattaggg catggcgtgc tgtgtgtgtc
7141  agtgattgcc tctgtggact catgactttc catcgccatg gctttctctt acgccgctgt
7201  ttggctttca gatgtaatcc tgtcttctcc tctcttcccc acgaaagcgc actcgatttt
7261  gttaggaatg aacggaagtt taaaaattct tgtgcccacc cccgccctcc acccattcct
7321  gttaaaagtt ctctggcgaa gagccaatgg gtgaacgtaa ttgaaagagc tatttactct
7381  tttggaaatc tgatttgaag tctaagtttt cagtaacaga agacacacaa gcaatgtgga
7441  ctgccaagct tgaagcactt cgggctctgc cttcactcgc atgctaccat gtcgagccca
7501  aactccactt taattaaaag agctgtgctg tgaattccac aacttctgtt aaataatttg
7561  tattccatta tatatatttt gcacatctca ggggaccata atgaacatat gaaaggggggg
7621  ggggtgccat caaatagaga aaacaaatag aagaggtgaa tggagactag ctggataaaa
7681  ataacaaatt acttcttctc tgatgttgtg aaggtcaggt tcaggaagca tcaattcaca
7741  gttaatccgg agtaacaatg atctgaacac cagctgttcc caggtccctc tttttcatag
7801  cccaaccagc atctaaaatg taaatttaaa ttacattgca gtcaccatgg ggagaagaaa
7861  cctgttcagt ggaagcagaa gcattgttcc ttttttaggt tggcgcagct ttgcaaaact
7921  ctacccagga taaaccactt atcaccacca agtgtacttg aaaataaagt ttttaactta
7981  aattacaagc atattgctca taatacaata gtgatcattt tttgaaagtc ttgccattta
8041  taacatgggc agtatttgga gcttcattta aaaaccaaca caaccgata atgactttgc
8101  acgattcact ttgggatctc aaagtgcttc caaagcattc agatttacaa acaattcaca
8161  agacaggtca tctttgtaat acgcatactt acaacgaatt aacaaaagga gtgacttaag
8221  attctccagg aacacagtgg cagctattga tgatctgttt tctatctgtt tgatagagca
8281  tcatgagaaa tcacaaaata caatgctatt tttctgatgt gtgctaataa agtcaaagaa
8341  aacaaataca tcttgacact tttgtccatt tcattaaaa aaaaaaagt tcagggtgtt
8401  tggaatttta catctcagca caccttactg gtatcaatgg ataaagcggg tgattgacag
```

-continued

```
   8461 atccacccaa atgccactgc agtcagaagc agatctggac acacccttgt ttacagtttc
   8521 atattgggtt gctatagttc ccgtgctaaa tcaccagctt tcaggaacat gactgctcct
   8581 ggcagtggaa ggtgctgaaa cagaaatttt aattaaaaac tttatcaagt actcttcaca
   8641 gtgctgcttg caccataga aaatcagtac aatatatcga gccctacttt ggaggagctg
   8701 gatttctgag ggagctgatc cagttctaag tgtcttctcg aattaggaga tagatgatct
   8761 ttgatgggga tctcctccgt caccacaggc cagtcacaga accaactagc cacgtgctgc
   8821 cagacctcag tgggcccaag caggagcaat ctcttctatc ccccatctcc cccaggacca
   8881 tcccgcccat tgtcaacgtc atccagggct cttctggtag tgagtgactt ttctgcacat
   8941 gtttagggct tgggggagct agaacacagg aaacatgaat gcaaaaggca tggaaaacac
   9001 tgttttgctt tgggttagta aaatgtgggc aggacaaaga ttactattgg tctgagcttt
   9061 gccaagtgag atagaatcaa ctgtcacccc attcctttcc cagaaggtct tatggtatta
   9121 aggatacatc cagtattttc ccacagattt ttattcaggc gatgtttcat aaattacata
   9181 tatgaaaaca ttcattatta catttccttg tgtgtttcaa acagacattg gcaccttcct
   9241 attgagttaa ttctctgcat cttttgcagc agcagcccac aaggagattc ccagagatgg
   9301 ctcccctaac acacagtcct gtgattttac agttctatga cttacagttg atgattcaca
   9361 agattcagga ttctacaaga ctcaggggg aactaaactt tcttacgatt gtacatgatc
   9421 agttataggg ctgtaatcat taattgttgg cttcaaatgt ggacacacac acacacacat
   9481 catgccaagg agggaatggg gtgtttcaag tcaggcagcg atgattctgg aaggttggaa
   9541 atgtaaggtt agaagcttgg ctggtcttag taaacttgtt cccttgctcc caccaagaag
   9601 aggtaccaaa tgtgagacct gagatctcct ccaatatctg tcctctgcag ttccgggaaa
   9661 ctaatcatga agtacacatg cagcagctcc tccacttcct ttcctccgag gtcctccttt
   9721 ccattctccc acctagatac tgacacaccg ccacggtttc cacattggaa gggcagaaca
   9781 ctgtgcagta tcgtgcacac ttgctgggtt aggaatagag ctgccctagg gtcaccttca
   9841 tgcaagtatt gacagctaca aattaaagtc cttagagcag ttgacacaga tactacgttc
   9901 tagaagagaa ttaaatttaa acgtcaagtt taaagggatc ataattctgc aggtatcttt
   9961 ctctgagtga ctgaatgtga ctattgcatt agggtaaatg aattaagacg tgcaagtggg
  10021 atttactgta tgttagaaag gagttttgca gccaagactg ccttgaataa aatgtgtttg
  10081 cactgaaaaa aaattttaaa ttacttggtc tctggttgct gtaaaggtca tccaagatgg
  10141 atgttctgtt tatattgtat agtatttcat atgaaataat tacagttcat gaaatgtctt
  10201 ccctaatgtt actgatttat aacagcacat ttgtaacatg ttttttatcg tgtcagtgta
  10261 ccatactgta aatgatgatt acttgtcatg cttagtataa taacttaaaa gaaaaaaaag
  10321 gacagggatt tttgtaagtc tatatttgaa agtccctccc tatggtgata ctgtgttcat
  10381 gttgtttatg tagtgttgtg tgaaatatcc attttggatt gtgttacttt ttaagatatt
  10441 aaataacatt tggttatatg tcaaaaaaaa aaaa
```

SEQ ID NO: 3-STOX2, isoform X1
Protein sequence:

```
     1 mpgkmekflq iaphslaivl gpaeapager pgaarpappa qprqlarhhi gyeifadfka
    61 enmqhfwnkk vtaavaetff lgwideqvll iqgkeehlea lregwtrral rppsgfhirc
   121 lgdvspisms pisqsqfipl geilclaisa mnsarkpvtq ealmehlttc fpgvptpsqe
   181 ilrhtlntiv rerkiyptpd gyfivtpqty fitpslirtn skwyhlderi pdrsqctspq
   241 pgtitpsasg cvrertlprn hcdschccre dvhsthaptl qrksakdckd pycppslcqv
```

```
301  pptekskstv  nfsyktetls  kpkdsekqsk  kfglklfrls  fkkdktkqla  nfsaqfppee
361  wplrdedtpa  tiprevemei  irrinpdltv  envmrhtalm  kkleeekaqr  skagssahhs
421  grskksrthr  kshgksrshs  ktrvskgdps  dgshldipae  reydfcdplt  rvpregcfii
481  ehkgdnfimh  sntnvleshf  pmtpewdvsg  elakrrtemp  fpepsrgssh  skvhrshsht
541  qdrrsrners  nkakersrsm  dnskgplgas  slgtpedlae  gcsqddqtps  qsyiddstlr
601  paqtvslqra  hisstsykev  cipeivsgsk  epssacslle  pgkppeslps  ygelnscptk
661  tatddyfqcn  tssetvltap  splgknkedh  dtltlaegvk  klspsdrqvp  hssrepvghk
721  eespkgpggg  paasggvaeg  iangrlvqhh  gaepssldkr  keifskdtlf  kplhstlsvn
781  syhksslsll  kshpktpadt  lpgrceklep  slgtsaaqam  pasqrqqesg  gnqeasfdyy
841  nvsddddsee  gankneeek   nredvgtmqw  llerekerdl  qrkfeknitl  lapketdsss
901  nqrathsarl  dsmdsssitv  dsgfnsprtr  eslasntssi  vesnrrqnpa  lspahggagp
961  afnfrasaep  ptneaeklqk  psnclqasvt  sv
```

SEQ ID NO: 4-STOX2, isoform X1  
mRNA sequence:

```
   1  acagtgagac  ctcgtctcaa  cacaaaaca   aaacaaaaca  aaacaaaaca  aaccaaaaca
  61  aaacaaaaca  aacacctcag  gtctttagac  ccgggtttag  tgactttttc  atgataataa
 121  aatcacagga  cgccagcgga  aaacagttca  gttatttcta  ttccccaaaa  ctaggctgga
 181  cattctgtgt  ttttcacggt  gtggtccgag  accaccagca  gcagcagtag  cagcagcatc
 241  tgggaatttc  ttagaaattt  aaaaaaccgg  gttcctctag  acctactgaa  tcagaaactc
 301  tgggaatggg  gcccagatac  ctgcgtttta  atacgtgttc  aggtgacggt  gatgcacgtt
 361  gaaatttaaa  taccgctctg  ggtaaatgta  gcataactct  taatgcttct  tatgacaatc
 421  atctctttc   acatatgact  actagcctct  ctcgattaaa  atataagtca  tacagaattt
 481  ggcacagaaa  caaacgtaag  gaattttctt  aaaagcatca  tcgttacctt  tcctggtaaa
 541  tttctgtaac  ctcttcataa  accgagggtt  aatggttgat  tgggtttcct  ctagggtagg
 601  ccaaagtata  tgctgaagac  aagagagtag  aattcctcaa  gagtttggga  ggagggactg
 661  atgacaattt  tggtggttg   actaagtttt  ttaaaaagcc  acttctaagg  gtacattcat
 721  taaccagtca  gcgaatccac  ttgttccagc  gagaggtggg  aagtgggggc  aggggtggag
 781  cgtggggagg  agcgacactc  gccgctccgg  aatccgtgcc  ttccaagtgt  cgccgttgcg
 841  tccccgcaa   ccccgctttt  ctgatctccc  tcgaggccca  acacccaaag  gctcacccct
 901  aggccatccg  cgctccccga  ccacctccct  cataggactc  cttgggattc  ctcaggccgc
 961  gtccagccga  gggggttccc  gggcgcggtg  cgcactgccc  gccccctcac  tgcctcctcc
1021  cgcgtctccg  cccccgcggg  gccgctgggc  gcccggggag  gcgagggtgc  cgaggccgga
1081  aaatgagcgc  tgcccgaagg  gtggcccgga  gctgcaggta  acgcggtcca  gagctcaggc
1141  cggagcgggc  cccgcacacc  gtcccttccc  cgcagcgacc  cgcgggctgc  gcccagggac
1201  tgcgccgggc  gccgggctg   cagggacgcg  ggcgcggggg  aggcgcggcc  agccctgccc
1261  tggggggacgg  tcgcgctccc  cgctggtctt  gcagccacgt  cccggcggct  gttcctggga
1321  gcggcgggag  gcggcctcgg  tgagccaggt  cggcgcggca  gatgcctggg  aagatggaga
1381  agtttctgca  gatcgcgcct  cactccctgg  ccatcgtcct  gggcccggca  gaggcgccgg
1441  cgggggaaag  gccaggggca  gcccggcccg  cgcccccggc  ccagcccgc   cagctcgccc
1501  ggcaccacat  cggctacgag  atcttcgccg  acttcaaagc  cgagaacatg  cagcacttct
```

-continued

```
1561  ggaacaagaa ggtcacggcc gcggtggccg agaccttctt cctgggctgg atcgacgagc
1621  aggtcctgct gatccagggc aaggaggaac atctggaggc gctgcgcgaa ggctggacgc
1681  gccgggccct gcggccgccc tcgggcttcc acatccgctg cctgggtgat gtatcaccca
1741  tcagtatgtc tcccatcagt cagtctcagt ttattccact cggggagatc tctctgcttgg
1801  ccatctcagc aatgaactcg gcaagaaagc ctgtcaccca agaagcactg atggagcacc
1861  tgaccacgtg cttcccaggt gttccaacgc caagccaaga aattctgcgg cacacgctga
1921  acacgctggt acgggagagg aagatctacc caactccaga tggctacttc atcgtgaccc
1981  cacagactta tttcataact ccttccctca taagaactaa cagtaaatgg taccatttgg
2041  acgagaggat acctgaccgg tctcagtgca cctctccgca acccgggacc atcacgccct
2101  ctgcctcagg ctgtgtcagg gaaaggacat tgccccgaaa ccactgcgac tcttgccact
2161  gctgcagaga agacgtgcac agcacgcatg cacccaccct gcaaaggaag tctgccaagg
2221  actgcaaaga cccttactgt ccccccttctc tgtgccaggt gccacccact gaaaagagca
2281  aaagtactgt aaattttccc tataagacag aaactctctc aaaacctaaa gatagtgaaa
2341  agcagtcaaa aaaattcggg ctaaagttat tccggttaag ttttaaaaaa gacaagacca
2401  aacagctggc caatttttct gcccagtttc ctcctgaaga gtggcccctg cgagacgagg
2461  acacgccagc tacgatccct cgggaagtag agatggaaat cattaggcgc attaacccag
2521  acctgaccgt ggaaaatgtc atgcggcaca ccgcgctcat gaagaaactg aagaagaaa
2581  aggcccagag gagtaaagcc gggtcctctg cccatcacag cggaaggagt aaaaagagta
2641  ggactcatcg gaagtccat ggaaagtctc ggtctcacag caagacacgg gtgtctaaag
2701  gagacccttc cgacggttca catctggata tcccagctga agagagtat gacttttgtg
2761  atcctcttac cagggtgccc agggagggct gcttcatcat tgaacacaaa ggagataact
2821  tcatcatgca cagcaacaca aacgtgctcg agtcccactt ccccatgaca ccagaatggg
2881  atgtgtctgg tgaattggct aaaaggagaa ctgagatgcc ttttcctgaa ccttctaggg
2941  gaagctccca ctcaaaagtg caccgaagcc acagccatac acaggaccgg aggtccagga
3001  atgagagatc caacaaagcc aaggagagat ccaggtcgat ggataactcc aaaggccctc
3061  tgggtgcttc ttctctaggg acgccggaag accttgctga aggctgcagc caagacgacc
3121  agacccccag ccaatcctac attgacgaca gtactttaag gcctgcacag accgttagtc
3181  tccaaagggc tcacatttcg tccacaagct ataaagaggt gtgtattcca gagatagtca
3241  gtggcagcaa ggaaccgtcc agcgcttgca gcctttttgga gccaggaaaa ccacccgaga
3301  gtttgccatc ctatggcgaa ctcaactctt gtccaacaaa acagccaca gatgactatt
3361  tccagtgcaa cacctctagt gagacggtgc tcacggcacc atcacctctg ggaaagaata
3421  aggaggacca tgacactctg actttggcag aaggggtgaa aaagctctcc ccttctgata
3481  ggcaggtccc ccactcctcc agggagcctg tggggcacaa ggaggagtca ccaaaagggc
3541  cgggtggggg cccgctgct tcggaggag tggctgaagg gatcgccaac ggacgcctcg
3601  tccagcacca tggtgccgag cccagcagct tggacaagag gaaagagata tttagcaaag
3661  acacactgtt caaacctctt cacagcacct tgtctgtaaa cagctatcac aagtcgagcc
3721  tgtccctcct caaatctcac ccgaagacac ctgctgacac attgccaggc cgatgtgaga
3781  aactggaacc gtccctgggg acctcggcgg cacaagccat gcctgcttcc cagcgtcagc
3841  aggagtcagg agggaaccag gaagcctctt ttgactatta caacgtctct gatgatgacg
3901  actctgagga aggggcaaac aagaacacag aggaggagaa aaatagagag gacgtaggca
```

```
-continued 3961  ccatgcagtg gctcctcgag cgggagaagg aaagagactt gcagaggaaa tttgaaaaga
4021  acctcaccct tcttgctcca aaagaaaccg acagcagcag caaccagaga gccacccatt
4081  cagcccggct cgacagcatg gacagcagca gcatcacagt ggacagtgga ttcaactccc
4141  cacgtactcg ggagagcctg gcttccaaca catcaagcat tgttgaaagt aaccgtcgtc
4201  agaaccccgc tttgagcccg gcccatggtg gagctggtcc agccttcaac ttccgagcga
4261  gcgcggagcc cccgacaaat gaagctgaga agctacagaa accttccaac tgcttgcaag
4321  cttctgttac tagcgtgtga ttgtccttct gcctcagatc ttctgtctca ttcgatacag
4381  caaagtttac gacactggga ctgatgttta catctttgga aagacaagca tctcaaccac
4441  agttttttgtg tttacttaaa ctgtgctgct aagtagggct agggcaaaaa aacaaaaaat
4501  ctttatttca gagtattgct tttcacattt atggctctgt agcaactgag taacagtagg
4561  ggtgatatgt atacttttgc ttcactaatt gtatctgagc acacatagga aagtctagac
4621  actgtaagtg taatacgcat tttcaatgtc atgcagttgc caattccatt ttaaaatgcc
4681  acagatgcgt gttgctccca gtctgtggtt aaacggtgcc acagaactga tccttgacac
4741  ttccaaaaaa aaaaaacaa aacaaaacaa aaaaaattta aaaaaaaaaa acaaaaaaca
4801  aaactaagct accacgaaat gtcaaatgca agggtccacc ttgagggaaa tagatgccaa
4861  actaactaga agggaccccg gccctttgtg tgtgaattgt ttatgcacca gtcattttc
4921  actgtgagtt tcgtgacac tatttttgcag gagcccatgg aagtgtgtga aaggggtcg
4981  caatggagat cactgggagt gaatgttttc agggttttgt tttgaagtgt cacagatgct
5041  tgtctgattt ttttaacctt ccgtgatcac aaacaggaat ataggccttt gaatctgaag
5101  tggacaaagg aaagcaattt ccagtctggc tggggcacag cattaggtga ttgaaaaggt
5161  gatgtggact tgtaaaaggt gttactcaaa tattgaagga agagaatttc ctccttgtga
5221  tacttaggat gaccctatct tactctaata gatacaataa ttagtttgtt taaaagcaaa
5281  atgttctttg tgatacaaat gaagagtagg gcctgaggat gttattcttt ctaatggaag
5341  gacataaatc tattttatgt agttttaaat agaatgccta aattaggctg tgggagataa
5401  ttttttagtgg ttgtaggaaa gagcaaattt agggagtgtt gaacttcagg cctttattc
5461  ctgggaagat atgtatagag aaaactttta aaataatttt tgattagaaa tatacatgtg
5521  cccatgtaat aaacaacaga atgtgctcat tctgctagtg cggtataatc cgaatttgta
5581  ctcccctaaa atttatcaga ataacaatta tgcatacatg aactatgcca gagtaatgtt
5641  tacagatact ttgtaaccaa tttcaggagg cgttttagc tggatgtgta gttaattaga
5701  ccaacttatt tccaaatggt ttgttaacat tttgctttgg tttacaatgt catgttgaac
5761  acaaagaaga cccagcagca aagggatgac caataatttc atcttatagc aaggagacat
5821  tccaacgttc ccatgtttta ttttctgaga acagtgggac agatctgtag taatggaata
5881  ttatttgcaa aagggttaca tatgacacaa gtaagtgttc tgacataaag ttttatttag
5941  ttcagtggca tgtgctgttg ggagccatac accataaaat atatatatcc caaaataaat
6001  ctagaatatt ttcacctcca atttcagtaa ttggcatatg atttgtgaga cgcatctgtt
6061  tttgtatgag gtttaatcac tagcaatctg tttaaagaat ccagtcctat acacagttgg
6121  actcattctt gaaacctta aatgctccct catagttttt cagttatttg gaagttgcat
6181  tgggtcaaac tgaactcctt gagtttggtg taaattcctt ttttctgctt attatagtga
6241  aacttcagca tgtttcttag taaactccca taccattgaa atgcttaagc cagttggctt
```

```
-continued 6301  tcagtctcat gccttatttc ctccaaggca tgcctcaacg cattgtttgt ctcattgctt 6361  aaatatgtcc agaaggaatg atcatgtatc taatagacta catagttggt tcccttgggg 6421  agttatatat catacagtta ctaaatattt gtctaaattc attttttcca aaaacctgct 6481  ctcaaatttt tcttctactc tcagttcata ataatataa ccattgaaac aacacatcag 6541  cctctagctg atcctctgaa agtagccatt gaaataatcg aatactgtgt gaacaggaaa 6601  ggaaagcgtt acctttaaga gaagctttaa ataggaatt tattgatatt cacaagata 6661  taggtttaca gaagacatta ttcaaataaa tatgtacact atttgcctga tgctatgggg 6721  tacataattt tttaaaaact cccttagacc agcagccatt agtgtagaaa tgatggactt 6781  taaaggtgat accatgtaag cagatgttgc atataaaaat attcctgcct gaatctgatc 6841  gagattcttg aatgggggag gagtggcagc cggcagcaca ttgcaaatgt cattcgaggt 6901  cacggtgagg ctctcggtcc cggaacagtg ggggcctcgc caggcgttgc cagtatccct 6961  ttcctcctgt aaaatcatag ctttgtgtta cacgactgct tatccagtct tagggtttag 7021  cagctgaaag gtttacaaaa ctgaatctgg ttgaatctct gtgaaagggt caacacatct 7081  gtcggcattt tgcacactta tgtattatta tgatacaaca tattacttta tggtaatttt 7141  tattttaca tataactacc tccataaatt tgatgaaatg gcagccgtgt gttaaagtgt 7201  atcgttcaga agagcaaagt tgaacacttc cttcaacatt agggcatggc gtgctgtgtg 7261  tgtcagtgat tgcctctgtg gactcatgac tttccatcgc catggctttc tcttacgccg 7321  ctgtttggct ttcagatgta atcctgtctt ctcctctctt ccccacgaaa gcgcactcga 7381  ttttgttagg aatgaacgga agtttaaaaa ttcttgtgcc cacccccgcc ctccacccat 7441  tcctgttaaa agttctctgg cgaagagcca atgggtgaac gtaattgaaa gagctattta 7501  ctcttttgga aatctgattt gaagtctaag ttttcagtaa cagaagacac acaagcaatg 7561  tggactgcca agcttgaagc acttcgggct ctgccttcac tcgcatgcta ccatgtcgag 7621  cccaaactcc actttaatta aaagagctgt gctgtgaatt ccacaacttc tgttaaataa 7681  tttgtattcc attatatata ttttgcacat ctcaggggac cataatgaac atatgaaagg 7741  ggggggggtg ccatcaaata gagaaaacaa atagaagagg tgaatggaga ctagctggat 7801  aaaaataaca aattacttct tctctgatgt tgtgaaggtc aggttcagga agcatcaatt 7861  cacagttaat ccggagtaac aatgatctga acaccagctg ttcccaggtc cctcttttc 7921  atagcccaac cagcatctaa aatgtaaatt taaattacat tgcagtcacc atggggagaa 7981  gaaacctgtt cagtggaagc agaagcattg ttccttttt aggttggcgc agctttgcaa 8041  aactctaccc aggataaacc acttatcacc accaagtgta cttgaaaata aagtttttaa 8101  cttaaattac aagcatattg ctcataatac aatagtgatc attttttgaa agtcttgcca 8161  tttataacat gggcagtatt tggagcttca tttaaaaacc aacaacaacc gataatgact 8221  ttgcacgatt cactttggga tctcaaagtg cttccaaagc attcagattt acaaacaatt 8281  cacaagacag gtcatctttg taatacgcat acttacaacg aattaacaaa aggagtgact 8341  taagattctc caggaacaca gtggcagcta ttgatgatct gttttctatc tgtttgatag 8401  agcatcatga gaaatcacaa aatacaatgc tattttttctg atgtgtgcta ataaagtcaa 8461  agaaaacaaa tacatcttga cacttttgtc cattttcatt aaaaaaaaaa aagttcaggg 8521  tgtttggaat ttacatctc agcacacctt actggtatca atggataaag cgggtgattg 8581  acagatccac ccaaatgcca ctgcagtcag aagcagatct ggacacaccc ttgtttacag 8641  tttcatattg ggttgctata gttcccgtgc taaatcacca gctttcagga acatgactgc
```

```
   8701   tcctggcagt ggaaggtgct gaaacagaaa ttttaattaa aaactttatc aagtactctt 8761   cacagtgctg cttggcacca tagaaaatca gtacaatata tcgagcccta ctttggagga 8821   gctggatttc tgagggagct gatccagttc taagtgtctt ctcgaattag agatagatg 8881   atctttgatg gggatctcct ccgtcaccac aggccagtca cagaaccaac tagccacgtg 8941   ctgccagacc tcagtgggcc caagcaggag caatctcttc tatcccccat ctcccccagg 9001   accatcccgc ccattgtcaa cgtcatccag ggctcttctg gtagtgagtg acttttctgc 9061   acatgtttag ggcttggggg agctagaaca caggaaacat gaatgcaaaa ggcatggaaa 9121   acactgtttt gctttgggtt agtaaaatgt gggcaggaca agattacta ttggtctgag 9181   ctttgccaag tgagatagaa tcaactgtca ccccattcct ttcccagaag gtcttatggt 9241   attaaggata catccagtat tttcccacag attttattc aggcgatgtt tcataaatta 9301   catatatgaa acattcatt attacatttc cttgtgtgtt tcaaacagac attggcacct 9361   tcctattgag ttaattctct gcatcttttg cagcagcagc ccacaaggag attcccagag 9421   atggctcccc taacacacag tcctgtgatt ttacagttct atgacttaca gttgatgatt 9481   cacaagattc aggattctac aagactcaag ggggaactaa actttcttac gattgtacat 9541   gatcagttat agggctgtaa tcattaattg ttggcttcaa atgtggacac acacacacac 9601   acatcatgcc aaggagggaa tggggtgttt caagtcaggc agcgatgatt ctggaaggtt 9661   ggaaatgtaa ggttagaagc ttggctggtc ttagtaaact tgttcccttg ctcccaccaa 9721   gaagaggtac caaatgtgag acctgagatc tcctccaata tctgtcctct gcagttccgg 9781   gaaactaatc atgaagtaca catgcagcag ctcctccact tcctttcctc cgaggtcctc 9841   ctttccattc tcccacctag atactgacac accgccacgg tttccacatt ggaagggcag 9901   aacactgtgc agtatcgtgc acacttgctg ggttaggaat agagctgccc tagggtcacc 9961   ttcatgcaag tattgacagc tacaaattaa agtccttaga gcagttgaca cagatactac 10021   gttctagaag agaattaaat ttaaacgtca agtttaaagg gatcataatt ctgcaggtat 10081   ctttctctga gtgactgaat gtgactattg cattagggta aatgaattaa gacgtgcaag 10141   tgggatttac tgtatgttag aaaggagttt tgcagccaag actgccttga ataaaatgtg 10201   tttgcactga aaaaaaattt taaattactt ggtctctggt tgctgtaaag gtcatccaag 10261   atggatgttc tgtttatatt gtatagtatt tcatatgaaa taattacagt tcatgaaatg 10321   tcttccctaa tgttactgat ttataacagc acatttgtaa catggttttt atcgtgtcag 10381   tgtaccatac tgtaaatgat gattacttgt catgcttagt ataataactt aaaagaaaaa 10441   aaaggacagg gattttgta agtctatatt tgaaagtccc tccctatggt gatactgtgt 10501   tcatgttgtt tatgtagtgt tgtgtgaaat atccattttg gattgtgtta ctttttaaga 10561   tattaaataa catttggtta ta SEQ ID NO: 5-STOX2, isoform X2
Protein sequence:
     1   mpgkmekflq iaphslaivl gpaeapager pgaarpappa qprqlarhhi gyeifadfka 61   enmqhfwnkk vtaavaetff lgwideqvll iqgkeehlea lregwtrral rppsgfhirc 121   lgdvspisms pisqsqfipl geilclaisa mnsarkpvtq ealmehlttc fpgvptpsqe 181   ilrhtlntiv rerkiyptpd gyfivtpqty fitpslirtn skwyhlderi pdrsqctspq 241   pgtitpsasg cvrertlprn hcdschccre dvhsthaptl qrksakdckd pycppslcqv 301   pptekskstv nfsyktetls kpkdsekqsk kfglklfrls fkkdktkqla nfsaqfppee
```

-continued

```
    361  wplrdedtpa tiprevemei irrinpdltv envmrhtalm kkleeekaqr skagssahhs
    421  grskksrthr kshgksrshs ktrvskgdps dgshldipae reydfcdplt rvpregcfii
    481  ehkgdnfimh sntnvleshf pmtpewdvsg elakrrtemp fpepsrgssh skvhrshsht
    541  qdrrsrners nkakersrsm dnskgplgas slgtpedlae gcsqddqtps qsyiddstlr
    601  paqtvslqra hisstsykev cipeivsgsk epssacslle pgkppeslps ygelnscptk
    661  tatddyfqcn tssetvltap splgknkedh dtltlaegvk klspsdrqvp hssrepvghk
    721  eespkgpggg paasggvaeg iangrlvqhh gaepssldkr keifskdtlf kplhstlsvn
    781  syhksslsll kshpktpadt lpgrceklep slgtsaaqam pasqrqqesg gnqeasfdyy
    841  nvsddddsee gankntereek nredvgtmqw llerekerdl qrkfeknitl lapketdsss
    901  nqrathsarl dsmdsssitv dsgfnsprn
```

SEQ ID NO: 6-STOX2, isoform X2
mRNA sequence:

```
       1  acagtgagac ctcgtctcaa acacaaaaca aaacaaaaca aaacaaaaca aaccaaaaca
      61  aaacaaaaca aacacctcag gtctttagac ccgggtttag tgactttttc atgataataa
     121  aatcacagga cgccagcgga aaacagttca gttatttcta ttccccaaaa ctaggctgga
     181  cattctgtgt ttttcacggt gtggtccgag accaccagca gcagcagtag cagcagcatc
     241  tgggaatttc ttagaaattt aaaaaaccgg gttcctctag acctactgaa tcagaaactc
     301  tgggaatggg gcccagatac ctgcgtttta atacgtgttc aggtgacggt gatgcacgtt
     361  gaaatttaaa taccgctctg ggtaaatgta gcataactct taatgcttct tatgacaatc
     421  atctcttttc acatatgact actagcctct ctcgattaaa atataagtca tacagaattt
     481  ggcacagaaa caaacgtaag gaatttttctt aaaagcatca tcgttaccttt tcctggtaaa
     541  tttctgtaac ctcttcataa accgagggtt aatggttgat tgggtttcct ctagggtagg
     601  ccaaagtata tgctgaagac aagagagtag aattcctcaa gagtttggga ggagggactg
     661  atgacaattt ttggtggttg actaagttttt ttaaaaagcc acttctaagg gtacattcat
     721  taaccagtca gcgaatccac ttgttccagc gagaggtggg aggtggggc aggggtggag
     781  cgtggggagg agcgacactc gccgctccgg aatccgtgcc ttccaagtgt cgccgttgcg
     841  tcccccgcaa ccccccgcttt ctgatctccc tcgaggccca acacccaaag gctcacccct
     901  aggccatccg cgctccccga ccacctccct cataggactc cttgggattc ctcaggccgc
     961  gtccagccga gggggttccc gggcgcggtg cgcactgccc gccccctcac tgcctcctcc
    1021  cgcgtctccg cccccgcggg gccgctgggc gccggggag gcgagggtgc cgaggccgga
    1081  aaatgagcgc tgcccgaagg gtggcccgga gctgcaggta acgcggtcca gagctcaggc
    1141  cggagcgggc cccgcacacc gtcccttccc cgcagcgacc cgcgggctgc gcccagggac
    1201  tgcgccgggc gccgggctg cagggacgcg ggcgcgggg aggcgcggcc agccctgccc
    1261  tgggggacgg tcgcgctccc cgctggtctt gcagccacgt cccggcggct gttcctggga
    1321  gcggcgggag gcggcctcgg tgagccaggt cggcgcggca gatgcctggg aagatggaga
    1381  agtttctgca gatcgcgcct cactccctgg ccatcgtcct gggcccggca gaggcgccgg
    1441  cggggaaag gccaggggca gcccggcccg cgccccggc ccagcccgc cagctcgccc
    1501  ggcaccacat cggctacgag atcttcgccg acttcaaagc cgagaacatg cagcacttct
    1561  ggaacaagaa ggtcacggcc gcggtggccg agaccttctt cctgggctgg atcgacgagc
    1621  aggtcctgct gatccagggc aaggaggaac atctggaggc gctgcgcgaa ggctggacgc
    1681  gccgggccct gcggccgccc tcgggcttcc acatccgctg cctgggtgat gtatcaccca
```

-continued

| | | | | |
|---|---|---|---|---|
| 1741 | tcagtatgtc | tcccatcagt | cagtctcagt | ttattccact cggggagatc ctctgcttgg |
| 1801 | ccatctcagc | aatgaactcg | gcaagaaagc | ctgtcaccca agaagcactg atggagcacc |
| 1861 | tgaccacgtg | cttcccaggt | gttccaacgc | caagccaaga aattctgcgg cacacgctga |
| 1921 | acacgctggt | acgggagagg | aagatctacc | caactccaga tggctacttc atcgtgaccc |
| 1981 | cacagactta | tttcataact | ccttccctca | taagaactaa cagtaaatgg taccatttgg |
| 2041 | acgagaggat | acctgaccgg | tctcagtgca | cctctccgca acccgggacc atcacgccct |
| 2101 | ctgcctcagg | ctgtgtcagg | gaaaggacat | tgccccgaaa ccactgcgac tcttgccact |
| 2161 | gctgcagaga | agacgtgcac | agcacgcatg | cacccaccct gcaaaggaag tctgccaagg |
| 2221 | actgcaaaga | cccttactgt | ccccttctc | tgtgccaggt gccacccact gaaaagagca |
| 2281 | aaagtactgt | aaattttcc | tataagacag | aaactctctc aaaacctaaa gatagtgaaa |
| 2341 | agcagtcaaa | aaaattcggg | ctaaagttat | tccggttaag ttttaaaaaa gacaagacca |
| 2401 | aacagctggc | caattttct | gcccagtttc | ctcctgaaga gtggcccctc cgagacgagg |
| 2461 | acacgccagc | tacgatccct | cgggaagtag | agatggaaat cattaggcgc attaacccag |
| 2521 | acctgaccgt | ggaaaatgtc | atgcggcaca | ccgcgctcat gaagaaactg aagaagaaa |
| 2581 | aggcccagag | gagtaaagcc | gggtcctctg | cccatcacag cggaaggagt aaaaagagta |
| 2641 | ggactcatcg | gaagtcccat | ggaaagtctc | ggtctcacag caagacacgg gtgtctaaag |
| 2701 | gagacccttc | cgacggttca | catctggata | tcccagctga agagagtat gacttttgtg |
| 2761 | atcctcttac | cagggtgccc | agggagggct | gcttcatcat tgaacacaaa ggagataact |
| 2821 | tcatcatgca | cagcaacaca | aacgtgctcg | agtcccactt ccccatgaca ccagaatggg |
| 2881 | atgtgtctgg | tgaattggct | aaaaggagaa | ctgagatgcc ttttcctgaa ccttctaggg |
| 2941 | gaagctccca | ctcaaaagtg | caccgaagcc | acagccatac acaggaccgg aggtccagga |
| 3001 | atgagagatc | caacaaagcc | aaggagagat | ccaggtcgat ggataactcc aaaggccctc |
| 3061 | tgggtgcttc | ttctctaggg | acgccggaag | accttgctga aggctgcagc caagacgacc |
| 3121 | agacccccag | ccaatcctac | attgacgaca | gtactttaag gcctgcacag accgttagtc |
| 3181 | tccaagggc | tcacatttcg | tccacaagct | ataaagaggt gtgtattcca gagatagtca |
| 3241 | gtggcagcaa | ggaaccgtcc | agcgcttgca | gccttttgga gccaggaaaa ccacccgaga |
| 3301 | gtttgccatc | ctatggcgaa | ctcaactctt | gtccaacaaa acagccaca gatgactatt |
| 3361 | tccagtgcaa | cacctctagt | gagacggtgc | tcacggcacc atcacctctg ggaaagaata |
| 3421 | aggaggacca | tgacactctg | actttggcag | aaggggtgaa aaagctctcc ccttctgata |
| 3481 | ggcaggtccc | ccactcctcc | agggagcctg | tggggcacaa ggaggagtca ccaaaagggc |
| 3541 | cgggtggggg | cccgctgct | tcggaggag | tggctgaagg gatcgccaac ggacgcctcg |
| 3601 | tccagcacca | tggtgccgag | cccagcagct | tggacaagag gaaagagata tttagcaaag |
| 3661 | acacactgtt | caaacctctt | cacagcacct | tgtctgtaaa cagctatcac aagtcgagcc |
| 3721 | tgtccctcct | caaatctcac | ccgaagacac | ctgctgacac attgccaggc cgatgtgaga |
| 3781 | aactggaacc | gtccctgggg | acctcggcgg | cacaagccat gcctgcttcc cagcgtcagc |
| 3841 | aggagtcagg | agggaaccag | gaagcctctt | ttgactatta caacgtctct gatgatgacg |
| 3901 | actctgagga | aggggcaaac | aagaacacag | aggaggagaa aaatagagag gacgtaggca |
| 3961 | ccatgcagtg | gctcctcgag | cgggagaagg | aaagagactt gcagaggaaa tttgaaaaga |
| 4021 | acctcaccct | tcttgctcca | aaagaaaccg | acagcagcag caaccagaga gccacccatt |

```
4081  cagcccggct cgacagcatg gacagcagca gcatcacagt ggacagtgga ttcaactccc
4141  cacggaattg aaaaaaatgt ttctgcacct gtagagatca ccaatctgga ctgtactcgg
4201  gagagcctgg cttccaacac atcaagcatt gttgaaagta accgtcgtca gaacccgct
4261  ttgagcccgg cccatggtgg agctggtcca gccttcaact ccgagcgag cgcggagccc
4321  ccgacaaatg aagctgagaa gctacagaaa ccttccaact gcttgcaagc ttctgttact
4381  agcgtgtgat tgtccttctg cctcagatct tctgtctcat tcgatacagc aaagtttacg
4441  acactgggac tgatgtttac atctttggaa agacaagcat ctcaaccaca gttttttgtgt
4501  ttacttaaac tgtgctgcta agtagggcta gggcaaaaaa acaaaaaatc tttatttcag
4561  agtattgctt ttcacattta tggctctgta gcaactgagt aacagtaggg gtgatatgta
4621  tacttttgct tcactaattg tatctgagca cataggaa agtctagaca ctgtaagtgt
4681  aatacgcatt ttcaatgtca tgcagttgcc aattccattt taaaatgcca cagatgcgtg
4741  ttgctcccag tctgtggtta acggtgcca cagaactgat ccttgacact tccaaaaaaa
4801  aaaaaacaaa acaaaacaaa aaaaattaa aaaaaaaaaa caaaaaacaa aactaagcta
4861  ccacgaaatg tcaaatgcaa gggtccacct tgagggaaat agatgccaaa ctaactagaa
4921  gggaccccgg cccttgtgt gtgaattgtt tatgcaccag tcattttca ctgtgagttt
4981  tcgtgacact attttgcagg agcccatgga agtgtgtgag aaggggtcgc aatggagatc
5041  actgggagtg aatgttttca gggttttgtt ttgaagtgtc acagatgctt gtctgatttt
5101  tttaaccttc cgtgatcaca acaggaata taggcctttg aatctgaagt ggacaaagga
5161  aagcaatttc cagtctggct ggggcacagc attaggtgat tgaaaaggtg atgtggactt
5221  gtaaaggtg ttactcaaat attgaaggaa gagaatttcc tccttgtgat acttaggatg
5281  accctatctt actctaatag atacaataat tagtttgttt aaaagcaaaa tgttctttgt
5341  gatacaaatg aagagtaggg cctgaggatg ttattctttc taatggaagg acataaatct
5401  attttatgta gttttaaata gaatgcctaa attaggctgt gggagataat ttttagtggt
5461  tgtaggaaag agcaaattta gggagtgttg aacttcaggc cttttattcc tgggaagata
5521  tgtatagaga aaacttttaa aataattttt gattagaaat atacatgtgc ccatgtaata
5581  aacaacagaa tgtgctcatt ctgctagtgc ggtataatcc gaatttgtac tcccctaaaa
5641  tttatcagaa taacaattat gcatacatga actatgccag agtaatgttt acagatactt
5701  tgtaaccaat ttcaggaggc gttttagct ggatgtgtag ttaattagac caacttattt
5761  ccaaatggtt tgttaacatt ttgctttggt ttacaatgtc atgttgaaca caaagaagac
5821  ccagcagcaa agggatgacc aataatttca tcttatagca aggagacatt ccaacgttcc
5881  catgttttat tttctgagaa cagtgggaca gatctgtagt aatgaatat tatttgcaaa
5941  agggttacat atgacacaag taagtgttct gacataaagt tttatttagt tcagtggcat
6001  gtgctgttgg gagccataca ccataaaata tatatatccc aaaataaatc tagaatattt
6061  tcacctccaa tttcagtaat tggcatatga tttgtgagac gcatctgttt ttgtatgagg
6121  tttaatcact agcaatctgt ttaaagaatc cagtcctata cacagttgga ctcattcttg
6181  aaacctttaa atgctccctc atagttttc agttatttgg aagttgcatt gggtcaaact
6241  gaactccttg agtttggtgt aaattccttt tttctgctta ttatagtgaa acttcagcat
6301  gtttcttagt aaactcccat accattgaaa tgcttaagcc agttggcttt cagtctcatg
6361  ccttatttcc tccaaggcat gcctcaacgc attgtttgtc tcattgctta aatatgtcca
6421  gaaggaatga tcatgtatct aatagactac atagttggtt cccttgggga gttatatatc
```

-continued

```
6481  atacagttac taaatatttg tctaaattca ttttttccaa aaacctgctc tcaaattttt
6541  cttctactct cagttcataa ataatataac cattgaaaca acacatcagc ctctagctga
6601  tcctctgaaa gtagccattg aaataatcga atactgtgtg aacaggaaag gaaagcgtta
6661  cctttaagag aagctttaaa ataggaattt attgatattt cacaagatat aggtttacag
6721  aagacattat tcaaataaat atgtacacta tttgcctgat gctatggggt acataatttt
6781  ttaaaaactc ccttagacca gcagccatta gtgtagaaat gatggacttt aaaggtgata
6841  ccatgtaagc agatgttgca tataaaaata ttcctgcctg aatctgatcg agattcttga
6901  atgggggagg agtggcagcc ggcagcacat tgcaaatgtc attcgaggtc acggtgaggc
6961  tctcggtccc ggaacagtgg gggcctcgcc aggcgttgcc agtatccctt tcctcctgta
7021  aaatcatagc tttgtgttac acgactgctt atccagtctt agggtttagc agctgaaagg
7081  tttacaaaac tgaatctggt tgaatctctg tgaaagggtc aacacatctg tcggcatttt
7141  gcacacttat gtattattat gatacaacat attactttat ggtaattttt attttacat
7201  ataactacct ccataaattt gatgaaatgg cagccgtgtg ttaaagtgta tcgttcagaa
7261  gagcaaagtt gaacacttcc ttcaacatta gggcatggcg tgctgtgtgt gtcagtgatt
7321  gcctctgtgg actcatgact ttccatcgcc atggctttct cttacgccgc tgtttggctt
7381  tcagatgtaa tcctgtcttc tcctctcttc cccacgaaag cgcactcgat tttgttagga
7441  atgaacggaa gtttaaaaat tcttgtgccc accccgccc tccacccatt cctgttaaaa
7501  gttctctggc gaagagccaa tgggtgaacg taattgaaag agctatttac tcttttggaa
7561  atctgatttg aagtctaagt tttcagtaac agaagacaca caagcaatgt ggactgccaa
7621  gcttgaagca cttcgggctc tgccttcact cgcatgctac catgtcgagc ccaaactcca
7681  ctttaattaa aagagctgtg ctgtgaattc cacaacttct gttaaataat ttgtattcca
7741  ttatatatat tttgcacatc tcaggggacc ataatgaaca tatgaaaggg gggggggtgc
7801  catcaaatag agaaaacaaa tagaagaggt gaatggagac tagctggata aaaataacaa
7861  attacttctt ctctgatgtt gtgaaggtca ggttcaggaa gcatcaattc acagttaatc
7921  cggagtaaca atgatctgaa caccagctgt tcccaggtcc ctcttttca tagcccaacc
7981  agcatctaaa atgtaaattt aaattacatt gcagtcacca tggggagaag aaacctgttc
8041  agtggaagca gaagcattgt tcctttttta ggttggcgca gctttgcaaa actctaccca
8101  ggataaacca cttatcacca ccaagtgtac ttgaaaataa agttttaac ttaaattaca
8161  agcatattgc tcataataca atagtgatca ttttttgaaa gtcttgccat ttataacatg
8221  ggcagtattt ggagcttcat ttaaaaacca acaacaaccg ataatgactt tgcacgattc
8281  actttgggat ctcaaagtgc ttccaaagca ttcagattta caacaattc acaagacagg
8341  tcatctttgt aatacgcata cttacaacga attaacaaaa ggagtgactt aagattctcc
8401  aggaacacag tggcagctat tgatgatctg ttttctatct gtttgataga gcatcatgag
8461  aaatcacaaa atacaatgct attttttctga tgtgtgctaa taaagtcaaa gaaaacaaat
8521  acatcttgac acttttgtcc attttcatta aaaaaaaaaa agttcagggt gtttggaatt
8581  ttacatctca gcacacctta ctggtatcaa tggataaagc gggtgattga cagatccacc
8641  caaatgccac tgcagtcaga agcagatctg gacacaccct tgtttacagt ttcatattgg
8701  gttgctatag ttcccgtgct aaatcaccag ctttcaggaa catgactgct cctggcagtg
8761  gaaggtgctg aaacagaaat tttaattaaa aactttatca agtactcttc acagtgctgc
```

-continued

```
 8821 ttggcaccat agaaaatcag tacaatatat cgagccctac tttggaggag ctggatttct
 8881 gagggagctg atccagttct aagtgtcttc tcgaattagg agatagatga tctttgatgg
 8941 ggatctcctc cgtcaccaca ggccagtcac agaaccaact agccacgtgc tgccagacct
 9001 cagtgggccc aagcaggagc aatctcttct atcccccatc tcccccagga ccatcccgcc
 9061 cattgtcaac gtcatccagg gctcttctgg tagtgagtga cttttctgca catgtttagg
 9121 gcttggggga gctagaacac aggaaacatg aatgcaaaag gcatggaaaa cactgttttg
 9181 ctttgggtta gtaaaatgtg ggcaggacaa agattactat tggtctgagc tttgccaagt
 9241 gagatagaat caactgtcac cccattcctt tcccagaagg tcttatggta ttaaggatac
 9301 atccagtatt ttcccacaga tttttattca ggcgatgttt cataaattac atatatgaaa
 9361 acattcatta ttacatttcc ttgtgtgttt caaacagaca ttggcacctt cctattgagt
 9421 taattctctg catcttttgc agcagcagcc cacaaggaga ttcccagaga tggctcccct
 9481 aacacacagt cctgtgattt tacagttcta tgacttacag ttgatgattc acaagattca
 9541 ggattctaca agactcaagg gggaactaaa ctttcttacg attgtacatg atcagttata
 9601 gggctgtaat cattaattgt tggcttcaaa tgtggacaca cacacacaca catcatgcca
 9661 aggagggaat ggggtgtttc aagtcaggca gcgatgattc tggaaggttg gaaatgtaag
 9721 gttagaagct tggctggtct tagtaaactt gttcccttgc tcccaccaag aagaggtacc
 9781 aaatgtgaga cctgagatct cctccaatat ctgtcctctg cagttccggg aaactaatca
 9841 tgaagtacac atgcagcagc tcctccactt cctttcctcc gaggtcctcc tttccattct
 9901 cccacctaga tactgacaca ccgccacggt ttccacattg gaagggcaga acactgtgca
 9961 gtatcgtgca cacttgctgg gttaggaata gagctgccct agggtcacct tcatgcaagt
10021 attgacagct acaaattaaa gtccttagag cagttgacac agatactacg ttctagaaga
10081 gaattaaatt taaacgtcaa gtttaaaggg atcataattc tgcaggtatc tttctctgag
10141 tgactgaatg tgactattgc attagggtaa atgaattaag acgtgcaagt gggatttact
10201 gtatgttaga aaggagtttt gcagccaaga ctgccttgaa taaaatgtgt ttgcactgaa
10261 aaaaaatttt aaattacttg gtctctggtt gctgtaaagg tcatccaaga tggatgttct
10321 gtttatattg tatagtattt catatgaaat aattacagtt catgaaatgt cttccctaat
10381 gttactgatt tataacagca catttgtaac atggttttta tcgtgtcagt gtaccatact
10441 gtaaatgatg attacttgtc atgcttagta taataactta aaagaaaaaa aaggacaggg
10501 atttttgtaa gtctatattt gaaagtccct ccctatggtg atactgtgtt catgttgttt
10561 atgtagtgtt gtgtgaaata tccatttggg attgtgttac ttttttaagat attaaataac
10621 atttggttat a
```

SEQ ID NO: 7-STOX2, isoform X3
Protein sequence:
```
    1 mpgkmekflq iaphslaivl gpaeapager pgaarpappa qprqlarhhi gyeifadfka
   61 enmqhfwnkk vtaavaetff lgwideqvll iqgkeehlea lregwtrral rppsgfhirc
  121 lgdvspisms pisqsqfipl geilclaisa mnsarkpvtq ealmehlttc fpgvptpsqe
  181 ilrhtlntiv rerkiyptpd gyfivtpqty fitpslirtn skwyhlderi pdrsqctspq
  241 pgtitpsasg cvrertlprn hcdschccre dvhsthaptl qrksakdckd pycppslcqv
  301 pptekskstv nfsyktetls kpkdsekqsk kfglklfrls fkkdktkqla nfsaqfppee
  361 wplrdedtpa tiprevemei irrinpdltv envmrhtalm kkleeekaqr skagssahhs
  421 grskksrthr kshgksrshs ktrvskgdps dgshldipae reydfcdplt rvpregcfii
```

```
481  ehkgdnfimh sntnvleshf pmtpewdvsg elakrrtemp fpepsrgssh skvhrshsht
541  qdrrsrners nkakersrsm dnskgplgas slgtpedlae gcsqddqtps qsyiddstlr
601  paqtvslqra hisstsykev cipeivsgsk epssacslle pgkppeslps ygelnscptk
661  tatddyfqcn tssetvltap splgknkedh dtltlaegvk klspsdrqvp hssrepvghk
721  eespkgpggg paasggvaeg iangrlvqhh gaepssldkr keifskdtlf kplhstlsvn
781  syhksslsll kshpktpadt lpgrceklep slgtsaaqam pasqrqqesg gnqeasfdyy
841  nvsddddsee ganknteeek nredvgtmqw llerekerdl qrkfeknitl lapketdsss
901  nqrathsarl dsmdsssitv dsgfnspr
```

SEQ ID NO: 8-STOX2, isoform X3
mRNA sequence:

```
   1  acagtgagac ctcgtctcaa acacaaaaca aaacaaaaca aaacaaaaca aaccaaaaca
  61  aaacaaaaca aacacctcag gtctttagac ccgggtttag tgacttttc atgataataa
 121  aatcacagga cgccagcgga aaacagttca gttatttcta ttccccaaaa ctaggctgga
 181  cattctgtgt ttttcacggt gtggtccgag accaccagca gcagcagtag cagcagcatc
 241  tgggaatttc ttagaaattt aaaaaaccgg gttcctctag acctactgaa tcagaaactc
 301  tgggaatggg gcccagatac ctgcgtttta atacgtgttc aggtgacggt gatgcacgtt
 361  gaaatttaaa taccgctctg ggtaaatgta gcataactct taatgcttct tatgacaatc
 421  atctctttc acatatgact actagcctct ctcgattaaa atataagtca tacagaattt
 481  ggcacagaaa caaacgtaag gaatttctt aaaagcatca tcgttacctt tcctggtaaa
 541  tttctgtaac ctcttcataa accgagggtt aatggttgat tgggtttcct ctagggtagg
 601  ccaaagtata tgctgaagac aagagagtag aattcctcaa gagtttggga ggagggactg
 661  atgacaattt tggtggttg actaagtttt ttaaaaagcc acttctaagg gtacattcat
 721  taaccagtca gcgaatccac ttgttccagc gagaggtggg aagtgggggc aggggtggag
 781  cgtggggagg agcgacactc gccgctccgg aatccgtgcc ttccaagtgt cgccgttgcg
 841  tccccgcaa ccccgctt ctgatctccc tcgaggccca acacccaaag gctcacccct
 901  aggccatccg cgctccccga ccacctccct cataggactc cttgggattc ctcaggccgc
 961  gtccagccga gggggttccc gggcgcggtg cgcactgccc gccccctcac tgcctcctcc
1021  cgcgtctccg cccccgcggg gccgctgggc gccggggag cgagggtgc cgaggccgga
1081  aaatgagcgc tgcccgaagg gtggcccgga gctgcaggta acgcggtcca gagctcaggc
1141  cggagcgggc cccgcacacc gtcccttccc cgcagcgacc cgcgggctgc gcccagggac
1201  tgcgccgggc gcccgggctg cagggacgcg ggcgcggggg aggcgcggcc agccctgccc
1261  tgggggacgg tcgcgctccc cgctggtctt gcagccacgt cccggcggct gttcctggga
1321  gcggcgggag gcggcctcgg tgagccaggt cggcgcggca gatgcctggg aagatggaga
1381  agtttctgca gatcgcgcct cactccctgg ccatcgtcct gggccggca gaggcgccgg
1441  cggggaaag gccaggggca gcccggcccg cgccccggc ccagcccgc cagctcgccc
1501  ggcaccacat cggctacgag atcttcgccg acttcaaagc cgagaacatg cagcacttct
1561  ggaacaagaa ggtcacggcc gcggtggccg agaccttctt cctgggctgg atcgacgagc
1621  aggtcctgct gatccagggc aaggaggaac atctggaggc gctgcgcgaa ggctggacgc
1681  gccggcccct gcggccgccc tcgggcttcc acatccgctg cctgggtgat gtatcaccca
1741  tcagtatgtc tcccatcagt cagtctcagt ttattccact cggggagatc ctctgcttgg
```

-continued

```
1801  ccatctcagc aatgaactcg gcaagaaagc ctgtcaccca agaagcactg atggagcacc
1861  tgaccacgtg cttcccaggt gttccaacgc caagccaaga aattctgcgg cacacgctga
1921  acacgctggt acgggagagg aagatctacc caactccaga tggctacttc atcgtgaccc
1981  cacagactta tttcataact ccttccctca taagaactaa cagtaaatgg taccatttgg
2041  acgagaggat acctgaccgg tctcagtgca cctctccgca acccgggacc atcacgccct
2101  ctgcctcagg ctgtgtcagg gaaaggacat gcccccgaaa ccactgcgac tcttgccact
2161  gctgcagaga agacgtgcac agcacgcatg cacccaccct gcaaaggaag tctgccaagg
2221  actgcaaaga cccttactgt ccccttctc tgtgccaggt gccacccact gaaaagagca
2281  aaagtactgt aaatttttcc tataagacag aaactctctc aaaacctaaa gatagtgaaa
2341  agcagtcaaa aaattcggg ctaaagttat tccggttaag ttttaaaaaa gacaagacca
2401  aacagctggc caattttct gcccagtttc ctcctgaaga gtggcccctg cgagacgagg
2461  acacgccagc tacgatccct cgggaagtag agatggaaat cattaggcgc attaacccag
2521  acctgaccgt ggaaaatgtc atgcggcaca ccgcgctcat gaagaaactg aagaagaaa
2581  aggcccagag gagtaaagcc gggtcctctg cccatcacag cggaaggagt aaaaagagta
2641  ggactcatcg gaagtcccat ggaaagtctc ggtctcacag caagacacgg gtgtctaaag
2701  gagacccttc cgacggttca catctggata tcccagctga agagagtat gactttttgtg
2761  atcctcttac cagggtgccc agggagggct gcttcatcat tgaacacaaa ggagataact
2821  tcatcatgca cagcaacaca aacgtgctcg agtcccactt ccccatgaca ccagaatggg
2881  atgtgtctgg tgaattggct aaaaggagaa ctgagatgcc ttttcctgaa ccttctaggg
2941  gaagctccca ctcaaaagtg caccgaagcc acagccatac acaggaccgg aggtccagga
3001  atgagagatc caacaaagcc aaggagagat ccaggtcgat ggataactcc aaaggccctc
3061  tgggtgcttc ttctctaggg acgccggaag accttgctga aggctgcagc caagacgacc
3121  agaccccag ccaatcctac attgacgaca gtactttaag gcctgcacag accgttagtc
3181  tccaaaggg tcacattttcg tccacaagct ataagaggt gtgtattcca gagatagtca
3241  gtggcagcaa ggaaccgtcc agcgcttgca gccttttgga gccaggaaaa ccacccgaga
3301  gtttgccatc ctatggcgaa ctcaactctt gtccaacaaa acagccaca gatgactatt
3361  tccagtgcaa cacctctagt gagacggtgc tcacggcacc atcacctctg ggaaagaata
3421  aggaggacca tgacactctg actttggcag aagggggtgaa aaagctctcc ccttctgata
3481  ggcaggtccc ccactcctcc agggagcctg tggggcacaa ggaggagtca ccaaaagggc
3541  cgggtggggg cccgctgct tcgggaggag tggctgaagg gatcgccaac ggacgcctcg
3601  tccagcacca tggtgccgag cccagcagct tggacaagag gaaagagata tttagcaaag
3661  acacactgtt caaacctctt cacagcacct tgtctgtaaa cagctatcac aagtcgagcc
3721  tgtccctcct caaatctcac ccgaagacac ctgctgacac attgccaggc cgatgtgaga
3781  aactggaacc gtccctgggg acctcggcgg cacaagccat gctgcttcc cagcgtcagc
3841  aggagtcagg agggaaccag gaagcctctt ttgactatta caacgtctct gatgatgacg
3901  actctgagga aggggcaaac aagaacacag aggaggagaa aaatagagag gacgtaggca
3961  ccatgcagtg gctcctcgag cgggagaagg aaagagactt gcagaggaaa tttgaaaaga
4021  acctcacccct tcttgctcca aaagaaaccg acagcagcag caaccagaga gccacccatt
4081  cagcccggct cgacagcatg gacagcagca gcatcacagt ggacagtgga ttcaactccc
4141  cacggtag
```

SEQ ID NO: 9-STOX2, isoform X4
Protein sequence:

```
  1  mfgqkkhkhg dvspismspi sqsqfiplge ilclaisamn sarkpvtqea lmehlttcfp
 61  gvptpsqeil rhtlntivre rkiyptpdgy fivtpqtyfi tpslirtnsk wyhlderipd
121  rsqctspqpg titpsasgcv rertlprnhc dschccredv hsthaptlqr ksakdckdpy
181  cppslcqvpp tekskstvnf syktetlskp kdsekqskkf glklfrlsfk kdktkqlanf
241  saqfppeewp lrdedtpati prevemeiir rinpdltven vmrhtalmkk leeekaqrsk
301  agssahhsgr skksrthrks hgksrshskt rvskgdpsdg shldipaere ydfcdpltry
361  pregcfiieh kgdnfimhsn tnvleshfpm tpewdvsgel akrrtempfp epsrgsshsk
421  vhrshshtqd rrsrnersnk akersrsmdn skgplgassl gtpedlaegc sqddqtpsqs
481  yiddstlrpa qtvslqrahi sstsykevci peivsgskep ssacsllepg kppeslpsyg
541  elnscptkta tddyfqcnts setvltapsp lgknkedhdt ltlaegvkkl spsdrqvphs
601  srepvghkee spkgpgggpa asggvaegia ngrlvqhhga epssldkrke ifskdtlfkp
661  lhstlsvnsy hksslsllks hpktpadtlp grceklepsl gtsaaqampa sqrqqesggn
721  qeasfdyynv sddddseega nknteeeknr edvgtmqwll erekerdlqr kfeknitlla
781  pketdsssnq rathsarlds mdsssitvds gfnsprtres lasntssive snrrqnpals
841  pahggagpaf nfrasaeppt neaeklqkps nclqasvtsv
```

SEQ ID NO: 10-STOX2, isoform X4
mRNA sequence:

```
   1  ggtgctgggt gagctccacc gctgcccggg ctgcgagcct gacggctgtg tgtcgggaat
  61  gacgagaccc aggcttgcaa agacttgcac ggcaactgga atttatgaca aatagctcac
 121  tgcagctaaa ctttgataca gtgtacagta gaaccgcctg ttacacacag gagggagacg
 181  cgtccttcgt caccatgcaa agccagcctt aacacaacat aggaaaatgt ggcaggtctc
 241  taattacgga ctgagaacaa gcagaagagg agtgacactg cagattccga ggcactgcag
 301  tgggatgttg gctcagcaag tggctgtgat gtacgggata ggcatggaac aggattccag
 361  ctgttccatg caaataggat aaaagaatgg taaagaggat tcctttttt ttccctcctc
 421  aaaacgttac cagcaaagta cattcacaga gcctttttaa ggtgcctttt gccagctttt
 481  gaactgaact tgtaccagta tctcaagccc tgaattgtaa gaagagctga gagttctgga
 541  actcattttt aaaaagtaga tctacgaaga ttctaggacg tccgtttctg ttactggctc
 601  cttcttgtgc ttggatgcag ctccctagca tgcaccaggc tttagcgtca gtgctacctg
 661  ggggatggag ccagtccaga aagggccagt cacatcatc tcatagctca ccctgtcaca
 721  gaagaaaaga gagcatgttt cctttctcca ctgtcagagg tctcttcttt ctgcatagca
 781  gtttgcatct tcagagcaac gttgaggatg ctgagtcagg tttaaaggat gtttggtcag
 841  aaaaaacaca agcatggtga tgtatcaccc atcagtatgt ctcccatcag tcagtctcag
 901  tttattccac tcggggagat cctctgcttg gccatctcag caatgaactc ggcaagaaag
 961  cctgtcaccc aagaagcact gatggagcac ctgaccacgt gcttccagg tgttccaacg
1021  ccaagccaag aaattctgcg gcacacgctg aacacgctgg tacgggagag aagatctac
1081  ccaactccag atggctactt catcgtgacc ccacagactt atttcataac tccttccctc
1141  ataagaacta acagtaaatg gtaccatttg gacgagagga tacctgaccg gtctcagtgc
1201  acctctccgc aacccgggac catcacgccc tctgcctcag gctgtgtcag ggaaaggaca
1261  ttgccccgaa accactgcga ctcttgccac tgctgcagag aagacgtgca cagcacgcat
```

-continued

```
1321  gcacccaccc tgcaaaggaa gtctgccaag gactgcaaag acccttactg tcccccttct
1381  ctgtgccagg tgccacccac tgaaaagagc aaaagtactg taaattttc  ctataagaca
1441  gaaactctct caaaacctaa agatagtgaa aagcagtcaa aaaaattcgg gctaaagtta
1501  ttccggttaa gttttaaaaa agacaagacc aaacagctgg ccaattttc  tgcccagttt
1561  cctcctgaag agtggcccct gcgagacgag gacacgccag ctacgatccc tcgggaagta
1621  gagatggaaa tcattaggcg cattaaccca gacctgaccg tggaaaatgt catgcggcac
1681  accgcgctca tgaagaaact ggaagaagaa aaggcccaga ggagtaaagc cgggtcctct
1741  gcccatcaca gcggaaggag taaaaagagt aggactcatc ggaagtccca tggaaagtct
1801  cggtctcaca gcaagacacg ggtgtctaaa ggagacccct tccgacggttc acatctggat
1861  atcccagctg aaagagagta tgacttttgt gatcctctta ccagggtgcc cagggagggc
1921  tgcttcatca ttgaacacaa aggagataac ttcatcatgc acagcaacac aaacgtgctc
1981  gagtcccact tccccatgac accagaatgg gatgtgtctg gtgaattggc taaaaggaga
2041  actgagatgc cttttcctga accttctagg ggaagctccc actcaaaagt gcaccgaagc
2101  cacagccata cacaggaccg gaggtccagg aatgagagat ccaacaaagc caaggagaga
2161  tccaggtcga tggataactc caaaggccct ctgggtgctt cttctctagg gacgccggaa
2221  gaccttgctg aaggctgcag ccaagacgac cagaccccca gccaatccta cattgacgac
2281  agtactttaa ggcctgcaca gaccgttagt ctccaaaggg ctcacatttc gtccacaagc
2341  tataaagagg tgtgtattcc agagatagtc agtggcagca aggaaccgtc cagcgcttgc
2401  agccttttgg agccaggaaa accacccgag agtttgccat cctatggcga actcaactct
2461  tgtccaacaa aaacagccac agatgactat ttccagtgca cacctctag  tgagacggtg
2521  ctcacggcac catcacctct gggaaagaat aaggaggacc atgacactct gactttggca
2581  gaagggtga  aaaagctctc cccttctgat aggcaggtcc cccactcctc cagggagcct
2641  gtggggcaca aggaggagtc accaaaaggg ccgggtgggg gccccgctgc ttcgggagga
2701  gtggctgaag ggatcgccaa cggacgcctc gtccagcacc atggtgccga gcccagcagc
2761  ttggacaaga ggaaagagat atttagcaaa gacacactgt tcaaacctct tcacagcacc
2821  ttgtctgtaa acagctatca aagtcgagc  ctgtccctcc tcaaatctca cccgaagaca
2881  cctgctgaca cattgccagg ccgatgtgag aaactggaac cgtccctggg gacctcggcg
2941  gcacaagcca tgcctgcttc ccagcgtcag caggagtcag gagggaacca ggaagcctct
3001  tttgactatt acaacgtctc tgatgatgac gactctgagg aaggggcaaa caagaacaca
3061  gaggaggaga aaaatagaga ggacgtaggc accatgcagt ggctcctcga gcgggagaag
3121  gaaagagact gcagaggaa  atttgaaaag aacctcaccc ttcttgctcc aaaagaaacc
3181  gacagcagca gcaaccagag agccacccat tcagcccggc tcgacagcat ggacagcagc
3241  agcatcacag tggacagtgg attcaactcc ccacgtactc gggagagcct ggcttccaac
3301  acatcaagca ttgttgaaag taaccgtcgt cagaaccccg ctttgagccc ggcccatggt
3361  ggagctggtc cagccttcaa cttccgagcg agcgcggagc ccccgacaaa tgaagctgag
3421  aagctacaga aaccttccaa ctgcttgcaa gcttcgtta  ctagcgtgtg attgtccttc
3481  tgcctcagat cttctgtctc attcgataca gcaaagttta cgacactggg actgatgttt
3541  acatctttgg aaagacaagc atctcaacca cagttttgt  gtttacttaa actgtgctgc
3601  taagtagggc tagggcaaaa aaacaaaaaa tctttatttc agagtattgc ttttcacatt
3661  tatggctctg tagcaactga gtaacagtag gggtgatatg tatactttg  cttcactaat
```

-continued

```
3721  tgtatctgag cacacatagg aaagtctaga cactgtaagt gtaatacgca ttttcaatgt
3781  catgcagttg ccaattccat tttaaaatgc cacagatgcg tgttgctccc agtctgtggt
3841  taaacggtgc cacagaactg atccttgaca cttccaaaaa aaaaaaaaca aaacaaaaca
3901  aaaaaatttt aaaaaaaaaa aacaaaaaac aaaactaagc taccacgaaa tgtcaaatgc
3961  aagggtccac cttgagggaa atagatgcca aactaactag aagggaccc ggccctttgt
4021  gtgtgaattg tttatgcacc agtcattttt cactgtgagt tttcgtgaca ctattttgca
4081  ggagcccatg gaagtgtgtg agaaggggtc gcaatggaga tcactgggag tgaatgtttt
4141  cagggttttg ttttgaagtg tcacagatgc ttgtctgatt tttttaacct tccgtgatca
4201  caaacaggaa tataggcctt tgaatctgaa gtggacaaag gaaagcaatt ccagtctgg
4261  ctggggcaca gcattaggtg attgaaaagg tgatgtggac ttgtaaaagg tgttactcaa
4321  atattgaagg aagagaattt cctccttgtg atacttagga tgaccctatc ttactctaat
4381  agatacaata attagtttgt ttaaaagcaa aatgttcttt gtgatacaaa tgaagagtag
4441  ggcctgagga tgttattctt tctaatggaa ggacataaat ctattttatg tagttttaaa
4501  tagaatgcct aaattaggct gtgggagata atttttagtg gttgtaggaa agagcaaatt
4561  tagggagtgt tgaacttcag gcctttatt cctgggaaga tatgtataga gaaaacttt
4621  aaaataattt ttgattagaa atatacatgt gcccatgtaa taaacaacag aatgtgctca
4681  ttctgctagt gcggtataat ccgaatttgt actcccctaa aatttatcag aataacaatt
4741  atgcatacat gaactatgcc agagtaatgt ttacagatac tttgtaacca atttcaggag
4801  gcgttttag ctggatgtgt agttaattag accaacttat ttccaaatgg tttgttaaca
4861  ttttgctttg gtttacaatg tcatgttgaa cacaaagaag acccagcagc aaagggatga
4921  ccaataattt catcttatag caaggagaca ttccaacgtt cccatgtttt attttctgag
4981  aacagtggga cagatctgta gtaatggaat attatttgca aaagggttac atatgacaca
5041  agtaagtgtt ctgacataaa gtttttattta gttcagtggc atgtgctgtt gggagccata
5101  caccataaaa tatatatatc ccaaaataaa tctagaatat tttcacctcc aatttcagta
5161  attggcatat gatttgtgag acgcatctgt ttttgtatga ggtttaatca ctagcaatct
5221  gtttaaagaa tccagtccta tacacagttg gactcattct tgaaacctt aaatgctccc
5281  tcatagtttt tcagttattt ggaagttgca ttgggtcaaa ctgaactcct tgagtttggt
5341  gtaaattcct ttttctgct tattatagtg aaacttcagc atgtttctta gtaaactccc
5401  ataccattga aatgcttaag ccagttggct ttcagtctca tgccttattt cctccaaggc
5461  atgcctcaac gcattgtttg tctcattgct taaatatgtc cagaaggaat gatcatgtat
5521  ctaatagact acatagttgg ttcccttggg gagttatata tcatacagtt actaaatatt
5581  tgtctaaatt cattttttcc aaaaacctgc tctcaaattt ttcttctact ctcagttcat
5641  aaataatata accattgaaa caacacatca gcctctagct gatcctctga agtagccat
5701  tgaaataatc gaatactgtg tgaacaggaa aggaaagcgt tacctttaag agaagcttta
5761  aaataggaat ttattgatat ttcacaagat ataggtttac agaagacatt attcaaataa
5821  atatgtacac tatttgcctg atgctatggg gtacataatt ttttaaaaac tcccttagac
5881  cagcagccat tagtgtagaa atgatggact ttaaaggtga taccatgtaa gcagatgttg
5941  catataaaaa tattcctgcc tgaatctgat cgagattctt gaatggggga ggagtggcag
6001  ccggcagcac attgcaaatg tcattcgagg tcacggtgag gctctcggtc ccggaacagt
```

-continued

```
6061  gggggcctcg ccaggcgttg ccagtatccc tttcctcctg taaaatcata gctttgtgtt
6121  acacgactgc ttatccagtc ttagggttta gcagctgaaa ggtttacaaa actgaatctg
6181  gttgaatctc tgtgaaaggg tcaacacatc tgtcggcatt ttgcacactt atgtattatt
6241  atgatacaac atattacttt atggtaattt ttattttac atataactac ctccataaat
6301  ttgatgaaat ggcagccgtg tgttaaagtg tatcgttcag aagagcaaag ttgaacactt
6361  ccttcaacat tagggcatgg cgtgctgtgt gtgtcagtga ttgcctctgt ggactcatga
6421  ctttccatcg ccatggcttt ctcttacgcc gctgtttggc tttcagatgt aatcctgtct
6481  tctcctctct tccccacgaa agcgcactcg attttgttag gaatgaacgg aagtttaaaa
6541  attcttgtgc ccaccccgc cctccaccca ttcctgttaa aagttctctg gcgaagagcc
6601  aatgggtgaa cgtaattgaa agagctattt actcttttgg aaatctgatt tgaagtctaa
6661  gttttcagta acagaagaca cacaagcaat gtggactgcc aagcttgaag cacttcgggc
6721  tctgccttca ctcgcatgct accatgtcga gcccaaactc cactttaatt aaaagagctg
6781  tgctgtgaat tccacaactt ctgttaaata atttgtattc cattatatat attttgcaca
6841  tctcagggga ccataatgaa catatgaaag gggggggggt gccatcaaat agagaaaaca
6901  aatagaagag gtgaatggag actagctgga taaaaataac aaattacttc ttctctgatg
6961  ttgtgaaggt caggttcagg aagcatcaat tcacagttaa tccggagtaa caatgatctg
7021  aacaccagct gttcccaggt ccctcttttt catagcccaa ccagcatcta aaatgtaaat
7081  ttaaattaca ttgcagtcac catggggaga agaaacctgt tcagtggaag cagaagcatt
7141  gttccttttt taggttggcg cagctttgca aaactctacc caggataaac cacttatcac
7201  caccaagtgt acttgaaaat aaagttttta acttaaatta caagcatatt gctcataata
7261  caatagtgat catttttga aagtcttgcc atttataaca tgggcagtat ttggagcttc
7321  atttaaaaac caacaacaac cgataatgac tttgcacgat tcactttggg atctcaaagt
7381  gcttccaaag cattcagatt tacaaacaat tcacaagaca ggtcatcttt gtaatacgca
7441  tacttacaac gaattaacaa aaggagtgac ttaagattct ccaggaacac agtggcagct
7501  attgatgatc tgttttctat ctgtttgata gagcatcatg agaaatcaca aaatacaatg
7561  ctattttct gatgtgtgct aataaagtca agaaaacaa atacatcttg acacttttgt
7621  ccattttcat taaaaaaaaa aaagttcagg gtgtttggaa ttttacatct cagcacacct
7681  tactggtatc aatggataaa gcgggtgatt gacagatcca cccaaatgcc actgcagtca
7741  gaagcagatc tggacacacc cttgtttaca gtttcatatt gggttgctat agttcccgtg
7801  ctaaatcacc agctttcagg aacatgactg ctcctggcag tggaaggtgc tgaaacagaa
7861  attttaatta aaaactttat caagtactct tcacagtgct gcttggcacc atagaaaatc
7921  agtacaatat atcgagccct actttggagg agctggattt ctgagggagc tgatccagtt
7981  ctaagtgtct tctcgaatta ggagatagat gatctttgat ggggatctcc tccgtcacca
8041  caggccagtc acagaaccaa ctagccacgt gctgccagac tcagtgggc caagcagga
8101  gcaatctctt ctatccccca tctcccccag gaccatcccg cccattgtca acgtcatcca
8161  gggctcttct ggtagtgagt gacttttctg cacatgttta gggcttgggg gagctagaac
8221  acaggaaaca tgaatgcaaa aggcatggaa aacactgttt tgctttgggt tagtaaaatg
8281  tgggcaggac aaagattact attggtctga gctttgccaa gtgagataga atcaactgtc
8341  accccattcc tttcccagaa ggtcttatgg tattaaggat acatccagta ttttcccaca
8401  gattttatt caggcgatgt ttcataaatt acatatatga aaacattcat tattacattt
```

```
8461  ccttgtgtgt ttcaaacaga cattggcacc ttcctattga gttaattctc tgcatctttt 8521  gcagcagcag cccacaagga gattcccaga gatggctccc ctaacacaca gtcctgtgat 8581  tttacagttc tatgacttac agttgatgat tcacaagatt caggattcta caagactcaa 8641  gggggaacta aactttctta cgattgtaca tgatcagtta tagggctgta atcattaatt 8701  gttggcttca aatgtggaca cacacacaca cacatcatgc caaggaggga atggggtgtt 8761  tcaagtcagg cagcgatgat tctggaaggt tggaaatgta aggttagaag cttggctggt 8821  cttagtaaac ttgttccctt gctcccacca agaagaggta ccaaatgtga gacctgagat 8881  ctcctccaat atctgtcctc tgcagttccg ggaaactaat catgaagtac acatgcagca 8941  gctcctccac ttcctttcct ccgaggtcct cctttccatt ctcccaccta gatactgaca 9001  caccgccacg gtttccacat tggaagggca gaacactgtg cagtatcgtg cacacttgct 9061  gggttaggaa tagagctgcc ctagggtcac cttcatgcaa gtattgacag ctacaaatta 9121  aagtccttag agcagttgac acagatacta cgttctagaa gagaattaaa tttaaacgtc 9181  aagtttaaag ggatcataat tctgcaggta tctttctctg agtgactgaa tgtgactatt 9241  gcattagggt aaatgaatta agacgtgcaa gtgggattta ctgtatgtta gaaaggagtt 9301  ttgcagccaa gactgccttg aataaaatgt gtttgcactg aaaaaaaatt taaattact 9361  tggtctctgg ttgctgtaaa ggtcatccaa gatggatgtt ctgtttatat tgtatagtat 9421  ttcatatgaa ataattacag ttcatgaaat gtcttcccta atgttactga tttataacag 9481  cacatttgta acatggtttt tatcgtgtca gtgtaccata ctgtaaatga tgattacttg 9541  tcatgcttag tataataact taaaagaaaa aaaaggacag ggattttgt aagtctatat 9601  ttgaaagtcc ctccctatgg tgatactgtg ttcatgttgt ttatgtagtg ttgtgtgaaa 9661  tatccatttt ggattgtgtt acttttaag atattaaata acatttggtt ata
```

SEQ ID NO: 11-STOX2, isoform X5
Protein sequence:

```
  1  mepvqkgpgd vspismspis qsqfiplgei lclaisamns arkpvtqeal mehlttcfpg 61  vptpsqeilr htlntivrer kiyptpdgyf ivtpqtyfit pslirtnskw yhlderipdr 121  sqctspqpgt itpsasgcvr ertlprnhcd schccredvh sthaptlqrk sakdckdpyc 181  ppslcqvppt ekskstvnfs yktetlskpk dsekqskkfg lklfrlsfkk dktkqlanfs 241  aqfppeewpl rdedtpatip revemeiirr inpdltvenv mrhtalmkkl eeekaqrska 301  gssahhsgrs kksrthrksh gksrshsktr vskgdpsdgs hldipaerey dfcdpltrvp 361  regcfiiehk gdnfimhsnt nvleshfpmt pewdvsgela krrtempfpe psrgsshskv 421  hrshshtqdr rsrnersnka kersrsmdns kgplgasslg tpedlaegcs qddqtpsqsy 481  iddstlrpaq tvslqrahis stsykevcip eivsgskeps sacsllepgk ppeslpsyge 541  lnscptktat ddyfqcntss etvltapspl gknkedhdtl taegvkkls psdrqvphss 601  repvghkees pkgpgggpaa sggvaegian grlvqhhgae pssldkrkei fskdtlfkpl 661  hstlsvnsyh ksslsllksh pktpadtlpg rceklepslg tsaaqampas qrqqesggnq 721  easfdyynvs ddddseegan knteeeknre dvgtmqwlle rekerdlqrk feknitllap 781  ketdsssnqr athsarldsm dsssitvdsg fnsprtresl asntssives nrrqnpalsp 841  ahggagpafn frasaepptn eaeklqkpsn clqasvtsv
```

SEQ ID NO: 12-STOX2, isoform X5
mRNA sequence:

```
  1  tcaattttaa tgtgtgtgtt ctctcttcaa gcatctggag gtatgtgccc tttttacctt
```

-continued

```
  61   tttcatgatt aaaaaaatat gagttggtgc taatgcatgg gaggggacct gggccccttg
 121   gagaggagag tgtgcccctc gccacccngc gcctgggta cattctgacc tcgcgtctcc
 181   gcactgcaca gacaaaggag cctgcacaga caaacagagg ctgtagcttt tcttggagcg
 241   atgactcatt tcagttcaca aaggattctg gcagggcag tgagaagtca ggttggctga
 301   tccgtccctg tgacttcact ttgcagagaa caagcagaag aggagtgaca ctgcagattc
 361   cgaggcactg cagtgggatg ttggctcagc aagtggctgt gatgtacggg ataggcatgg
 421   aacaggattc cagctgttcc atgcaaatag gataaagaa tggtaaagag gattccttt
 481   tttttccctc ctcaaaacgt taccagcaaa gtacattcac agagccttt taaggtgcct
 541   tttgccagct tttgaactga acttgtacca gtatctcaag ccctgaattg taagaagagc
 601   tgagagttct ggaactcatt tttaaaaagt agatctacga agattctagg acgtccgttt
 661   ctgttactgg ctccttcttg tgcttggatg cagctcccta gcatgcacca ggctttagcg
 721   tcagtgctac ctgggggatg gagccagtcc agaaagggcc aggtgatgta tcacccatca
 781   gtatgtctcc catcagtcag tctcagttta ttccactcgg ggagatcctc tgcttggcca
 841   tctcagcaat gaactcggca agaaagcctg tcacccaaga agcactgatg gagcacctga
 901   ccacgtgctt cccaggtgtt ccaacgccaa gccaagaaat tctgcggcac acgctgaaca
 961   cgctggtacg ggagaggaag atctacccaa ctccagatgg ctacttcatc gtgaccccac
1021   agacttattt cataactcct tccctcataa gaactaacag taaatggtac catttggacg
1081   agaggatacc tgaccggtct cagtgcacct ctccgcaacc cgggaccatc acgccctctg
1141   cctcaggctg tgtcagggaa aggacattgc cccgaaacca ctgcgactct tgccactgct
1201   gcagagaaga cgtgcacagc acgcatgcac ccaccctgca aaggaagtct gccaaggact
1261   gcaaagaccc ttactgtccc ccttctctgt gccaggtgcc acccactgaa aagagcaaaa
1321   gtactgtaaa ttttccctat aagacagaaa ctctctcaaa acctaaagat agtgaaaagc
1381   agtcaaaaaa attcgggcta agttattcc ggttaagttt taaaaaagac aagaccaaac
1441   agctggccaa ttttctgcc cagtttcctc ctgaagagtg gccctgcga gacgaggaca
1501   cgccagctac gatccctcgg gaagtagaga tggaaatcat taggcgcatt aacccagacc
1561   tgaccgtgga aaatgtcatg cggcacaccg cgctcatgaa gaaactggaa gaagaaaagg
1621   cccagaggag taaagccggg tcctctgccc atcacagcgg aaggagtaaa aagagtagga
1681   ctcatcggaa gtcccatgga aagtctcggt ctcacagcaa gacacgggtg tctaaaggag
1741   acccttccga cggttcacat ctggatatcc cagctgaaag agagtatgac ttttgtgatc
1801   ctcttaccag ggtgcccagg gagggctgct tcatcattga acacaaagga gataacttca
1861   tcatgcacag caacacaaac gtgctcgagt cccacttccc catgacacca gaatgggatg
1921   tgtctggtga attggctaaa aggagaactg agatgccttt tcctgaacct tctagggggaa
1981   gctcccactc aaaagtgcac cgaagccaca gccatacaca ggaccggagg tccaggaatg
2041   agagatccaa caaagccaag gagagatcca ggtcgatgga taactccaaa ggccctctgg
2101   gtgcttcttc tctagggacg ccggaagacc ttgctgaagg ctgcagccaa gacgaccaga
2161   ccccagcca atcctacatt gacgacagta ctttaaggcc tgcacagacc gttagtctcc
2221   aaagggctca catttcgtcc acaagctata agaggtgtg tattccagag atagtcagtg
2281   gcagcaagga accgtccagc gcttgcagcc ttttggagcc aggaaaacca cccgagagtt
2341   tgccatccta tggcgaactc aactcttgtc caacaaaaac agccacagat gactatttcc
2401   agtgcaacac ctctagtgag acggtgctca cggcaccatc acctctggga aagaataagg
```

-continued

```
2461  aggaccatga cactctgact ttggcagaag gggtgaaaaa gctctcccct tctgataggc
2521  aggtccccca ctcctccagg gagcctgtgg ggcacaagga ggagtcacca aaagggccgg
2581  gtgggggccc cgctgcttcg ggaggagtgg ctgaagggat cgccaacgga cgcctcgtcc
2641  agcaccatgg tgccgagccc agcagcttgg acaagaggaa agagatattt agcaaagaca
2701  cactgttcaa acctcttcac agcaccttgt ctgtaaacag ctatcacaag tcgagcctgt
2761  ccctcctcaa atctcacccg aagacacctg ctgacacatt gccaggccga tgtgagaaac
2821  tggaaccgtc cctggggacc tcggcggcac aagccatgcc tgcttcccag cgtcagcagg
2881  agtcaggagg gaaccaggaa gcctcttttg actattacaa cgtctctgat gatgacgact
2941  ctgaggaagg ggcaaacaag aacacagagg aggagaaaaa tagagaggac gtaggcacca
3001  tgcagtggct cctcgagcgg gagaaggaaa gagacttgca gaggaaattt gaaaagaacc
3061  tcacccttct tgctccaaaa gaaaccgaca gcagcagcaa ccagagagcc acccattcag
3121  cccggctcga cagcatggac agcagcagca tcacagtgga cagtggattc aactccccac
3181  gtactcggga gagcctggct tccaacacat caagcattgt tgaaagtaac cgtcgtcaga
3241  accccgcttt gagcccggcc catggtggag ctggtccagc cttcaacttc cgagcgagcg
3301  cggagccccc gacaaatgaa gctgagaagc tacagaaacc ttccaactgc ttgcaagctt
3361  ctgttactag cgtgtgattg tccttctgcc tcagatcttc tgtctcattc gatacagcaa
3421  agtttacgac actgggactg atgtttacat ctttggaaag acaagcatct caaccacagt
3481  ttttgtgttt acttaaactg tgctgctaag tagggctagg gcaaaaaaac aaaaaatctt
3541  tatttcagag tattgctttt cacatttatg gctctgtagc aactgagtaa cagtaggggt
3601  gatatgtata cttttgcttc actaattgta tctgagcaca cataggaaag tctagacact
3661  gtaagtgtaa tacgcatttt caatgtcatg cagttgccaa ttccatttta aaatgccaca
3721  gatgcgtgtt gctcccagtc tgtggttaaa cggtgccaca gaactgatcc ttgacacttc
3781  caaaaaaaaa aaaacaaaac aaaacaaaaa aaatttaaaa aaaaaaaaca aaaaacaaaa
3841  ctaagctacc acgaaatgtc aaatgcaagg gtccaccttg agggaaatag atgccaaact
3901  aactagaagg gaccccggcc ctttgtgtgt gaattgttta tgcaccagtc atttttcact
3961  gtgagttttc gtgacactat tttgcaggag cccatggaag tgtgtgagaa ggggtcgcaa
4021  tggagatcac tgggagtgaa tgttttcagg gttttgtttt gaagtgtcac agatgcttgt
4081  ctgattttt taaccttccg tgatcacaaa caggaatata ggcctttgaa tctgaagtgg
4141  acaaaggaaa gcaatttcca gtctggctgg ggcacagcat taggtgattg aaaaggtgat
4201  gtggacttgt aaaaggtgtt actcaaatat tgaaggaaga gaatttcctc cttgtgatac
4261  ttaggatgac cctatcttac tctaatagat acaataatta gtttgtttaa agcaaaatg
4321  ttctttgtga tacaaatgaa gagtagggcc tgaggatgtt attctttcta atggaaggac
4381  ataaatctat tttatgtagt tttaaataga atgcctaaat taggctgtgg gagataattt
4441  ttagtggttg taggaaagag caaatttagg gagtgttgaa cttcaggcct tttattcctg
4501  ggaagatatg tatagagaaa acttttaaaa taattttga ttagaaatat acatgtgccc
4561  atgtaataaa caacagaatg tgctcattct gctagtgcgg tataatccga atttgtactc
4621  ccctaaaatt tatcagaata acaattatgc atacatgaac tatgccagag taatgtttac
4681  agatactttg taaccaattt caggaggcgt ttttagctgg atgtgtagtt aattagacca
4741  acttatttcc aaatggtttg ttaacatttt gctttggttt acaatgtcat gttgaacaca
```

```
4801  aagaagaccc agcagcaaag ggatgaccaa taatttcatc ttatagcaag gagacattcc
4861  aacgttccca tgttttattt tctgagaaca gtgggacaga tctgtagtaa tggaatatta
4921  tttgcaaaag ggttacatat gacacaagta agtgttctga cataaagttt tatttagttc
4981  agtggcatgt gctgttggga gccatacacc ataaaatata tatatcccaa aataaatcta
5041  gaatattttc acctccaatt tcagtaattg gcatatgatt tgtgagacgc atctgttttt
5101  gtatgaggtt taatcactag caatctgttt aaagaatcca gtcctataca cagttggact
5161  cattcttgaa acctttaaat gctccctcat agttttttcag ttatttggaa gttgcattgg
5221  gtcaaactga actccttgag tttggtgtaa attccttttt tctgcttatt atagtgaaac
5281  ttcagcatgt ttcttagtaa actcccatac cattgaaatg cttaagccag ttggctttca
5341  gtctcatgcc ttatttcctc caaggcatgc ctcaacgcat tgtttgtctc attgcttaaa
5401  tatgtccaga aggaatgatc atgtatctaa tagactacat agttggttcc cttggggagt
5461  tatatatcat acagttacta aatatttgtc taaattcatt ttttccaaaa acctgctctc
5521  aaattttttct tctactctca gttcataaat aatataacca ttgaaacaac acatcagcct
5581  ctagctgatc ctctgaaagt agccattgaa ataatcgaat actgtgtgaa caggaaagga
5641  aagcgttacc tttaagaaa gctttaaaat aggaatttat tgatatttca caagatatag
5701  gtttacagaa gacattattc aaataaatat gtacactatt tgcctgatgc tatggggtac
5761  ataatttttt aaaaactccc ttagaccagc agccattagt gtagaaatga tggactttaa
5821  aggtgatacc atgtaagcag atgttgcata taaaaatatt cctgcctgaa tctgatcgag
5881  attcttgaat gggggaggag tggcagccgg cagcacattg caaatgtcat tcgaggtcac
5941  ggtgaggctc tcggtcccgg aacagtgggg gcctcgccag gcgttgccag tatccctttc
6001  ctcctgtaaa atcatagctt tgtgttacac gactgcttat ccagtcttag ggtttagcag
6061  ctgaaaggtt tacaaaactg aatctggttg aatctctgtg aaagggtcaa cacatctgtc
6121  ggcattttgc acacttatgt attattatga tacaacatat tacttttatg taatttttat
6181  ttttacatat aactacctcc ataaatttga tgaaatggca gccgtgtgtt aaagtgtatc
6241  gttcagaaga gcaaagttga acacttcctt caacattagg gcatggcgtg ctgtgtgtgt
6301  cagtgattgc ctctgtggac tcatgacttt ccatcgccat ggctttctct tacgccgctg
6361  tttggctttc agatgtaatc ctgtcttctc ctctcttccc cacgaaagcg cactcgattt
6421  tgttaggaat gaacggaagt ttaaaaattc ttgtgcccac ccccgccctc cacccattcc
6481  tgttaaaagt tctctggcga agagccaatg ggtgaacgta attgaaagag ctatttactc
6541  ttttggaaat ctgatttgaa gtctaagttt tcagtaacag aagacacaca agcaatgtgg
6601  actgccaagc ttgaagcact tcgggctctg ccttcactcg catgctacca tgtcgagccc
6661  aaactccact ttaattaaaa gagctgtgct gtgaattcca caacttctgt taaataattt
6721  gtattccatt atatatattt tgcacatctc aggggaccat aatgaacata tgaaagggggg
6781  gggggtgcca tcaaatagag aaaacaaata gaagaggtga atggagacta gctggataaa
6841  aataacaaat tacttcttct ctgatgttgt gaaggtcagg ttcaggaagc atcaattcac
6901  agttaatccg gagtaacaat gatctgaaca ccagctgttc ccaggtccct cttttttcata
6961  gcccaaccag catctaaaat gtaaatttaa attacattgc agtcaccatg gggagaagaa
7021  acctgttcag tggaagcaga agcattgttc cttttttagg ttggcgcagc tttgcaaaac
7081  tctacccagg ataaaccact tatcaccacc aagtgtactt gaaaataaag ttttttaactt
7141  aaattacaag catattgctc ataatacaat agtgatcatt ttttgaaagt cttgccattt
```

-continued

```
7201  ataacatggg cagtatttgg agcttcattt aaaaaccaac aacaaccgat aatgactttg
7261  cacgattcac tttgggatct caaagtgctt ccaaagcatt cagatttaca aacaattcac
7321  aagacaggtc atctttgtaa tacgcatact tacaacgaat taacaaaagg agtgacttaa
7381  gattctccag gaacacagtg gcagctattg atgatctgtt ttctatctgt ttgatagagc
7441  atcatgagaa atcacaaaat acaatgctat ttttctgatg tgtgctaata aagtcaaaga
7501  aaacaaatac atcttgacac ttttgtccat tttcattaaa aaaaaaaaag ttcagggtgt
7561  ttggaatttt acatctcagc acaccttact ggtatcaatg gataaagcgg gtgattgaca
7621  gatccaccca aatgccactg cagtcagaag cagatctgga cacacccttg tttacagttt
7681  catattgggt tgctatagtt cccgtgctaa atcaccagct tcaggaaca  tgactgctcc
7741  tggcagtgga aggtgctgaa acagaaattt taattaaaaa ctttatcaag tactcttcac
7801  agtgctgctt ggcaccatag aaaatcagta caatatatcg agccctactt tggaggagct
7861  ggatttctga gggagctgat ccagttctaa gtgtcttctc gaattaggag atagatgatc
7921  tttgatgggg atctcctccg tcaccacagg ccagtcacag aaccaactag ccacgtgctg
7981  ccagacctca gtgggcccaa gcaggagcaa tctcttctat cccccatctc ccccaggacc
8041  atcccgccca ttgtcaacgt catccagggc tcttctggta gtgagtgact tttctgcaca
8101  tgtttagggc ttgggggagc tagaacacag gaaacatgaa tgcaaaaggc atggaaaaca
8161  ctgttttgct ttgggttagt aaaatgtggg caggacaaag attactattg gtctgagctt
8221  tgccaagtga gatagaatca actgtcaccc cattcctttc ccagaaggtc ttatggtatt
8281  aaggatacat ccagtatttt cccacagatt tttattcagg cgatgtttca taaattacat
8341  atatgaaaac attcattatt acatttcctt gtgtgtttca aacagacatt ggcaccttcc
8401  tattgagtta attctctgca tcttttgcag cagcagccca caaggagatt cccagagatg
8461  gctcccctaa cacacagtcc tgtgatttta cagttctatg acttacagtt gatgattcac
8521  aagattcagg attctacaag actcaagggg gaactaaact ttcttacgat tgtacatgat
8581  cagttatagg gctgtaatca ttaattgttg gcttcaaatg tggacacaca cacacacaca
8641  tcatgccaag gagggaatgg ggtgtttcaa gtcaggcagc gatgattctg gaaggttgga
8701  aatgtaaggt tagaagcttg gctggtctta gtaaacttgt tcccttgctc ccaccaagaa
8761  gaggtaccaa atgtgagacc tgagatctcc tccaatatct gtcctctgca gttccgggaa
8821  actaatcatg aagtacacat gcagcagctc ctccacttcc tttcctccga ggtcctcctt
8881  tccattctcc cacctagata ctgacacacc gccacggttt ccacattgga agggcagaac
8941  actgtgcagt atcgtgcaca cttgctgggt taggaataga gctgccctag ggtcaccttc
9001  atgcaagtat tgacagctac aaattaaagt ccttagagca gttgacacag atactacgtt
9061  ctagaagaga attaaattta aacgtcaagt ttaaagggat cataattctg caggtatctt
9121  tctctgagtg actgaatgtg actattgcat tagggtaaat gaattaagac gtgcaagtgg
9181  gatttactgt atgttagaaa ggagttttgc agccaagact gccttgaata aaatgtgttt
9241  gcactgaaaa aaaattttaa attacttggt ctctggttgc tgtaaaggtc atccaagatg
9301  gatgttctgt ttatattgta tagtatttca tatgaaataa ttacagttca tgaaatgtct
9361  tccctaatgt tactgattta taacagcaca tttgtaacat ggttttatc  gtgtcagtgt
9421  accatactgt aaatgatgat tacttgtcat gcttagtata ataacttaaa agaaaaaaaa
9481  ggacagggat ttttgtaagt ctatatttga aagtccctcc ctatggtgat actgtgttca
```

```
9541  tgttgtttat gtagtgttgt gtgaaatatc cattttggat tgtgttactt tttaagatat 9601  taaataacat ttggttata
```

SEQ ID NO: 13-SOX8
Protein sequence:
```
   1  mldmsearsq ppcspsgtas smshvedsds dappspagse glgragvavg gargdpaeaa 61  derfpacird aysqvlkgyd wslvpmpvrg ggggalkakp hvkrpmnafm vwaqaarrkl 121  adqyphlhna elsktlgklw rllsesekrp fveeaerlry qhkkdhpdyk yqprrrksak 181  aghsdsdsga elgphpggga vykaeaglgd ghhhgdhtgq thgpptpptt pktelqqaga 241  kpelklegrr pvdsgrqnid fsnvdisels sevmgtmdaf dvhefdqylp lggpappepg 301  qayggayfha gaspvwahks apsasaspte tgpprphikt eqpspghygd qprgspdygs 361  csgqssatpa apagpfagsq gdygdlqass yygaypgyap glyqypcfhs prrpyaspll 421  nglalppahs ptshwdqpvy ttltrp
```

SEQ ID NO: 14-SOX8
mRNA sequence:
```
   1  ggcgagggtc ggggccaccg cgcggcgacc tcgggtcccg gagcgaccgc agggcagccc 61  cgggcgccgg ccccggtgcg cgtctcctgt gcgcgcccct ccgcgcgcgg ccccgatgct 121  ggacatgagc gaggcccgct cccagccgcc ctgcagcccg tccggcaccg ccagctccat 181  gtcgcacgtg gaggactcgg actcggacgc gccgccgtct cccgccggct ccgagggcct 241  gggccgcgcg ggggtcgcgg tgggggcgcg ccggggcgac ccggcggagg cggcggacga 301  gcgcttcccg gcctgcatcc gcgacgccgt gtcgcaggtg ctcaagggct acgactggag 361  tctggtgccc atgccggtgc gcggcggcgg cggcggcgcg ctcaaagcca agccgcatgt 421  gaagcggccc atgaacgcat tcatggtgtg ggcgcaggcg gcgcgccgca agctggccga 481  ccagtacccg cacctgcaca acgccgagct cagcaagacg ctgggcaagc tgtggcgctt 541  gctgagcgag agcgagaagc ggcccttcgt ggaggaggca gagcgccttc gcgtgcagca 601  caagaaggac caccccgact acaagtacca gccacggcgc aggaagagcg ccaaagccgg 661  ccacagcgac tccgactcgg gcgcggagct gggaccccac cctggcggcg tgccgtgta 721  caaggctgaa gcagggcttg agatgggcca ccaccatggc gaccacacag ggcagaccca 781  cgggccgccc accccgccca ccaccccaa gacggagctg cagcaggcgg gcgccaagcc 841  ggagctgaag ctggagggac gccggcggt ggacagcggg cgccagaaca tcgacttcag 901  caacgtggac atctcggagc tcagcagcga ggtcatgggc accatggacg ccttcgacgt 961  ccacgagttc gaccagtacc tgccctggg cggccccgcc cacccgagc cgggccaggc 1021  ctatggggc gcctacttcc acgccggggc gtccccgtg tgggcccaca agagtgcccc 1081  gtcggcctcc gcgtcgccca ccgagacggg tccccacgg ccgcacatca agacgagca 1141  gccgagccc ggccactacg gcgaccagcc ccgaggctcg cccgactacg gttcctgcag 1201  cggccagtcc agcgccaccc cggccgcccc cgccgccccc ttcgccggct cacagggcga 1261  ctatggcgac ctgcaggcct ccagctacta tggtgcctac cctggctacg cacccggcct 1321  ctaccagtac ccctgcttcc actcgccgcg ccggccctac gcctcacccc tgctcaacgg 1381  cctggccctg ccgccgccc acagccccac cagtcactgg gaccagccgg tgtacaccac 1441  cctgaccagg ccctgagggc ccagccgcgg ggagggactc gcaggcgtca gggggcagcc 1501  ttgtcccggc ccagtgtgtg tgaccaggc ggggagggcc ccagtggctg agctccaagt 1561  gcctgctgaa gtctgcaggg aaacacgctt gctgccgtg gccctcggcc tccagatggc 1621  cacacctctg ccgacgacgg accagctccc tctcccttct atctttcttt ttgaggtggt
```

```
1681  gggattattc cacaaagaag ggctgccgtt tggtccctct tccgtgagga ctggcggcac
1741  cagcaccttc gctttgcatc tcggtagagg agaaacggca gcacagccca aggaccaaag
1801  gagggggtgg caggggcctt gcagggcgct gtgaggtcca ggccggtctt ggcgccgaga
1861  gcccctgcac tcaaggccac attccctcga caacggctgc acgggctgtc cggatccgg
1921  ggtgtctgtc cgcagactgg gatgagtcta ctcgagcatc tccgggacct gcctgtcaga
1981  tctgaggtgt ctccttgctg gcagagtgcg ctcacgcgag ggctggcgt gatgaacaca
2041  tctctctttt atttttatgt ttttgataat ttttattttt gaagcttaaa tgtgtttctt
2101  ctgaaagctg ttaaagatgt atttatgttc tgtgttattt tatctttaat taatgaggta
2161  attcgggcaa agagtagaat ttaagacaaa acggaagctg gaagcttcc cttgagggca
2221  ggcaggaggt ggagttgcag ctgttggccg gcatcacgtt gctcgttgct cggcttatgg
2281  gaggccgccc tggagggccc ggaggtccca aggtccctgg gaggactggg cccctcatgc
2341  ctcgagcttg gcaaccgaaa acccgagggg ggagaaggga cctgccttgt gacatctctg
2401  atcaggttgg ggtgccccag cacccagtac cagtttgggg tttgggaagc aggactccgt
2461  ccctgtcccc gactgtgcca cgtggtagga cataggac acaggaattc ctgggtcctt
2521  gcccatgact gtgccatgtg gtaggacaca ggacacagga attcctggaa agtggtggct
2581  tcagaagtga tcttggctcg caggcaccag tgccacctac caagctgtga aactaaacct
2641  tctccactaa acgtcgttag ggcctcagtt ctagacgagt catacctgat tcacctgcac
2701  tgcttcccct gtgtgctgag catagagcat acaatagcgc ctacttcacg gaaacttgtg
2761  cctttaaact ttgtaaactt aaacacagcc gagaagttgc ttctttgtac tttttctact
2821  tttcctactt ttttgtagaa aaaaaagata atgcctctgc ttctatttct ctgggggtgg
2881  gggtgggggc cgggagccgt cgcagacccg tttcatgcag cgtctccctt ggcaccgcgt
2941  tcggaggacg caccctcact ccctgctgc cttcactcct ttctgaccaa gcaacgctaa
3001  cttttgtaca gatcgatttg ataaaattaa acaaagtgct ttttatgga
```

SEQ ID NO: 15-ASCL1
Protein sequence:
```
  1   messakmesg gagqqpqpqp qqpflppaac ffataaaaaa aaaaaaaqsa qqqqqqqqq
 61   qqapqlrpaa dgqpsggghk sapkqvkrqr ssspelmrck rrinfsgfgy slpqqqpaav
121   arrnerernr vklvnlgfat lrehvpngaa nkkmskvetl rsaveyiral qqlldehdav
181   saafgagvls ptispnysnd lnsmagspvs syssdegsyd plspeeqell dftnwf
```

SEQ ID NO: 16-ASCL1
mRNA sequence:
```
  1   agcactctct cacttctggc cagggaacgt ggaaggcgca ccgacaggga tccggccagg
 61   gagggcgagt gaaagaagga aatcagaaag gaagggagtt aacaaaataa taaaaacagc
121   ctgagccacg gctggagaga ccgagacccg gcgcaagaga gcgcagcctt agtaggagag
181   gaacgcgaga gcggcagag gcgttcagc actgactttt gctgctgctt ctgcttttt
241   ttttcttaga aacaagaagg cgccagcggc agcctcacac gcgagcgcca cgcgaggctc
301   ccgaagccaa cccgcgaagg gaggagggga gggaggagga ggcggcgtgc agggaggaga
361   aaaagcattt tcactttttt tgctcccact ctaagaagtc tcccgggat tttgtatata
421   ttttttaact tccgtcaggg ctcccgcttc atatttcctt ttctttccct ctctgttcct
481   gcacccaagt tctctctgtg tcccctcgc gggccccgca cctcgcgtcc cggatcgctc
541   tgattccgcg actccttggc cgccgctgcg catggaaagc tctgccaaga tggagagcgg
```

-continued

```
 601 cggcgccggc cagcagcccc agccgcagcc ccagcagccc ttcctgccgc ccgcagcctg
 661 tttctttgcc acggccgcag ccgcggcggc cgcagccgcc gcagcggcag cgcagagcgc
 721 gcagcagcag cagcagcagc agcagcagca gcagcaggcg ccgcagctga ccggcggc
 781 cgacggccag ccctcagggg gcggtcacaa gtcagcgccc aagcaagtca agcgacagcg
 841 ctcgtcttcg cccgaactga tgcgctgcaa acgccggctc aacttcagcg gctttggcta
 901 cagcctgccg cagcagcagc cggccgccgt ggcgcgccgc aacgagcgcg agcgcaaccg
 961 cgtcaagttg gtcaacctgg gctttgccac ccttcgggag cacgtcccca acggcgcggc
1021 caacaagaag atgagtaagg tggagacact cgctcggcg gtcgagtaca tccgcgcgct
1081 gcagcagctg ctggacgagc atgacgcggt gagcgccgcc ttccaggcag gcgtcctgtc
1141 gcccaccatc tcccccaact actccaacga cttgaactcc atggccggct cgccggtctc
1201 atcctactcg tcggacgagg gctcttacga cccgctcagc cccgaggagc aggagcttct
1261 cgacttcacc aactggttct gaggggctcg gcctggtcag gccctggtgc gaatggactt
1321 tggaagcagg gtgatcgcac aacctgcatc tttagtgctt tcttgtcagt ggcgttggga
1381 ggggagaaa aggaaaagaa aaaaaaaga agaagaagaa gaaaagagaa gaagaaaaaa
1441 acgaaaacag tcaaccaacc ccatcgccaa ctaagcgagg catgcctgag agacatggct
1501 ttcagaaaac gggaagcgct cagaacagta tctttgcact ccaatcattc acggagatat
1561 gaagagcaac tgggacctga gtcaatgcgc aaaatgcagc ttgtgtgcaa aagcagtggg
1621 ctcctggcag aagggagcag cacacgcgtt atagtaactc ccatcacctc taacacgcac
1681 agctgaaagt tcttgctcgg gtcccttcac ctcctcgccc tttcttaaag tgcagttctt
1741 agccctctag aaacgagttg gtgtctttcg tctcagtagc ccccacccca ataagctgta
1801 gacattggtt tacagtgaaa ctatgctatt ctcagccctt tgaaactctg cttctcctcc
1861 agggcccgat tcccaaaccc catggcttcc ctcacactgt cttttctacc attttcatta
1921 tagaatgctt ccaatctttt gtgaattttt tattataaaa aatctatttg tatctatcct
1981 aaccagttcg gggatatatt aagatatttt tgtacataag agagaaagag agagaaaaat
2041 ttatagaagt tttgtacaaa tggtttaaaa tgtgtatatc ttgatacttt aacatgtaat
2101 gctattacct ctgcatattt tagatgtgta gttcacctta caactgcaat tttccctatg
2161 tggttttgta aagaactctc ctcataggtg agatcaagag gccaccagtt gtacttcagc
2221 accaatgtgt cttactttat agaaatgttg ttaatgtatt aatgatgtta ttaaatactg
2281 ttcaagaaga acaaagttta tgcagctact gtccaaactc aaagtggcag ccagttggtt
2341 ttgataggtt gccttttgga gatttctatt actgcctttt tttttcttac tgttttatta
2401 caaacttaca aaaatatgta taaccctgtt ttatacaaac tagtttcgta ataaaacttt
2461 ttcctttttt taaaatgaaa ataaaaaaaa
```

SEQ ID NO: 17-OLIG2
Protein sequence:

```
   1 mdsdaslvss rpsspepddl flparskgss gsaftggtvs sstpsdcppe lsaelrgamg
  61 sagahpgdkl ggsgfkssss stsssstssaa asstkkdkkq mtepelqqlr lkinsrerkr
 121 mhdlniamdg lrevmpyahg psvrklskia tlllarnyil mltnsleemk rlvseiyggh
 181 hagfhpsacg glahsaplpa atahpaaaah aahhpavhhp ilppaaaaaa aaaaaayss
 241 aslpgsglps vgsirpphgl lkspsaaaaa plgggggggsg asggfqhwgg mpcpcsmcqv
 301 ppphhhvsam gagslprlts dak
```

SEQ ID NO: 18-OLIG2

-continued

```
mRNA sequence:
   1 aaaaaccggc cgagccccta aaggtgcgga tgcttattat agatcgacgc gacaccagcg
  61 cccggtgcca ggttctcccc tgaggctttt cggagcgagc tcctcaaatc gcatccagat
 121 tttcgggtcc gagggaagga ggaccctgcg aaagctgcga cgactatctt ccctgggc
 181 catggactcg gacgccagcc tggtgtccag ccgcccgtcg tcgccagagc ccgatgacct
 241 ttttctgccg gcccggagta agggcagcag cggcagcgcc ttcactgggg gcaccgtgtc
 301 ctcgtccacc ccgagtgact gcccgccgga gctgagcgcc gagctgcgcg gcgctatggg
 361 ctctgcgggc gcgcatcctg gggacaagct aggaggcagt ggcttcaagt catcctcgtc
 421 cagcacctcg tcgtctacgt cgtcggcggc tgcgtcgtcc accaagaagg acaagaagca
 481 aatgacagag ccggagctgc agcagctgcg tctcaagatc aacagccgcg agcgcaagcg
 541 catgcacgac ctcaacatcg ccatggatgg cctccgcgag gtcatgccgt acgcacacgg
 601 cccttcggtg cgcaagcttt ccaagatcgc cacgctgctg ctggcgcgca actacatcct
 661 catgctcacc aactcgctgg aggagatgaa cgactggtg agcgagatct acgggggcca
 721 ccacgctggc ttccacccgt cggcctgcgg cggcctggcg cactccgcgc ccctgcccgc
 781 cgccaccgcg caccccggcag cagcagcgca cgccgcacat caccccgcgg tgcaccaccc
 841 catcctgccg cccgccgccg cagcggctgc tgccgccgct gcagccgcgg ctgtgtccag
 901 cgcctctctg cccggatccg ggctgccgtc ggtcggctcc atccgtccac cgcacggcct
 961 actcaagtct ccgtctgctg ccgcggccgc cccgctgggg ggcggggcg gcggcagtgg
1021 ggcgagcggg ggcttccagc actggggcgg catgccctgc ccctgcagca tgtgccaggt
1081 gccgccgccg caccaccacg tgtcggctat gggcgccggc agcctgccgc gcctcacctc
1141 cgacgccaag tgagccgact ggcgccggcg cgttctgcg acaggggagc caggggccgc
1201 ggggaagcga ggactggcct gcgctgggct cgggagctct gtcgcgagga ggggcgcagg
1261 accatggact gggggtgggg catggtgggg attccagcat ctgcgaaccc aagcaatggg
1321 ggcgcccaca gagcagtggg gagtgagggg atgttctctc cgggacctga tcgagcgctg
1381 tctggcttta acctgagctg gtccagtaga catcgtttta tgaaaaggta ccgctgtgtg
1441 cattcctcac tagaactcat ccgaccccg accccacct ccgggaaaag attctaaaaa
1501 cttctttccc tgagagcgtg gcctgacttg cagactcggc ttgggcagca cttcgggggg
1561 ggaggggtg ttatgggagg gggacacatt ggggccttgc tcctcttcct ccttctttgg
1621 cgggtgggag actccgggta gccgcactgc agaagcaaca gcccgaccgc gccctccagg
1681 gtcgtccctg gcccaaggcc aggggccaca agttagttgg aagccggcgt tcggtatcag
1741 aagcgctgat ggtcatatcc aatctcaata tctgggtcaa tccacaccct cttagaactg
1801 tggccgttcc tccctgtctc tcgttgattt gggagaatat ggttttctaa taaatctgtg
1861 gatgttcctt cttcaacagt atgagcaagt ttatagacat tcagagtaga accacttgtg
1921 gattggaata acccaaaact gccgatttca ggggcgggtg cattgtagtt attatttaa
1981 aatagaaact accccaccga ctcatctttc cttctctaag cacaaagtga tttggttatt
2041 ttggtacctg agaacgtaac agaattaaaa ggcagttgct gtggaaacag tttgggttat
2101 ttgggggttc tgttggcttt ttaaaatttt cttttttgga tgtgtaaatt tatcaatgat
2161 gaggtaagtg cgcaatgcta agctgtttgc tcacgtgact gccagcccca tcggagtcta
2221 agccggcttt cctctatttt ggtttatttt tgccacgttt aacacaaatg gtaaactcct
2281 ccacgtgctt cctgcgttcc gtgcaagccg cctcggcgct gcctgcgttg caaactgggc
```

```
2341  tttgtagcgt ctgccgtgta acacccttcc tctgatcgca ccgcccctcg cagagagtgt
2401  atcatctgtt ttattttgt aaaaacaaag tgctaaataa tatttattac ttgtttggtt
2461  gcaaaaacgg aataaatgac tgagtgttga gattttaaat aaaatttaaa gtaaaaaaaa
2521  a
```

SEQ ID NO: 19-OLIG2, Isoform X1
Protein sequence:
```
  1  mdsdaslvss rpsspepddl flparskgss gsaftggtvs sstpsdcppe lsaelrgamg
 61  sagahpgdkl ggsgfkssss stsssstssaa asstkkdkkq mtepelqqlr lkinsrerkr
121  mhdlniamdg lrevmpyahg psvrklskia tlllarnyil mltnsleemk rlvseiyggh
181  hagfhpsacg glahsaplpa atahpaaaah aahhpavhhp ilppaaaaaa aaaaaaayss
241  aslpgsglps vgsirpphgl lkspsaaaaa plgggggsg asggfqhwgg mpcpcsmcqv
301  ppphhhvsam gagslprlts dak
```

SEQ ID NO: 20-OLIG2, Isoform X1
mRNA sequence:
```
   1  ggatgcttat tatagatcga cgcgacacca gcgcccggtg ccaggttctc ccctgaggct
  61  tttcggagcg agctcctcaa atcgcatcca gagtaagtgt ccccgcccca cagcagccgc
 121  agcctagatc ccagggacag actctcctca actcggctgt gacccagaat gctccgatac
 181  aggggggtctg gatccctact ctgcgggcca tttctccaga gcgactttgc tcttctgtcc
 241  tccccacact caccgctgca tctcccctcac caaaagcgag aagtcggagc gacaacagct
 301  ctttctgccc aagccccagt cagctgtttt cgggtccgag gaaggagga ccctgcgaaa
 361  gctgcgacga ctatcttccc ctggggccat ggactcggac gccagcctgg tgtccagccg
 421  cccgtcgtcg ccagagcccg atgaccttt tctgccggcc cggagtaagg gcagcagcgg
 481  cagcgccttc actggggca ccgtgtcctc gtccaccccg agtgactgcc cgccggagct
 541  gagcgccgag ctgcgcggcg ctatgggctc tgcgggcgcg catcctgggg acaagctagg
 601  aggcagtggc ttcaagtcat cctcgtccag cacctcgtcg tctacgtcgt cggcggctgc
 661  gtcgtccacc aagaaggaca agaagcaaat gacagagccg agctgcagc agctgcgtct
 721  caagatcaac agccgcgagc gcaagcgcat gcacgacctc aacatcgcca tggatggcct
 781  ccgcgaggtc atgccgtacg cacacggccc ttcggtgcgc aagctttcca agatcgccac
 841  gctgctgctg cgcgcaact acatcctcat gctcaccaac tcgctggagg agatgaagcg
 901  actggtgagc gagatctacg ggggccacca cgctggcttc caccgtcgg cctgcggcgg
 961  cctggcgcac tccgcgcccc tgccgccgc caccgcgcac ccggcagcag cagcgcacgc
1021  cgcacatcac cccgcggtgc accacccat cctgccgccc gccgccgcag cggctgctgc
1081  cgccgctgca gccgcggctg tgtccagcgc ctctctgccc ggatccgggc tgccgtcggt
1141  cggctccatc cgtccaccgc acggcctact caagtctccg tctgctgccg cggccgcccc
1201  gctgggggggc ggggcggcg gcagtgggc gagcggggc ttccagcact ggggcggcat
1261  gccctgcccc tgcagcatgt gccaggtgcc ccgccgcac caccacgtgt cggctatggg
1321  cgccggcagc ctgccgcgcc tcacctccga cgccaagtga gccgactggc gccggcgcgt
1381  tctggcgaca ggggagccag gggccgcggg gaagcgagga ctggcctgcg ctgggctcgg
1441  gagctctgtc gcgaggaggg gcgcaggacc atggactggg ggtggggcat ggtggggatt
1501  ccagcatctg cgaacccaag caatggggc gcccacagag cagtggggag tgaggggatg
1561  ttctctccgg gacctgatcg agcgctgtct ggctttaacc tgagctggtc cagtagacat
1621  cgtttttatga aaaggtaccg ctgtgtgcat tcctcactag aactcatccg accccccgacc
```

-continued

```
1681 cccacctccg ggaaaagatt ctaaaaactt ctttccctga gagcgtggcc tgacttgcag
1741 actcggcttg ggcagcactt cgggggggga gggggtgtta tgggaggggg acacattggg
1801 gccttgctcc tcttcctcct ttcttggcgg gtgggagact ccgggtagcc gcactgcaga
1861 agcaacagcc cgaccgcgcc ctccagggtc gtccctggcc caaggccagg ggccacaagt
1921 tagttggaag ccggcgttcg gtatcagaag cgctgatggt catatccaat ctcaatatct
1981 gggtcaatcc acaccctctt agaactgtgg ccgttcctcc ctgtctctcg ttgatttggg
2041 agaatatggt tttctaataa atctgtggat gttccttctt caacagtatg agcaagttta
2101 tagacattca gagtagaacc acttgtggat tggaataacc caaaactgcc gatttcaggg
2161 gcgggtgcat tgtagttatt attttaaaat agaaactacc ccaccgactc atctttcctt
2221 ctctaagcac aaagtgattt ggttattttg gtacctgaga cgtaacaga attaaaaggc
2281 agttgctgtg gaaacagttt gggttatttg ggggttctgt tggctttta aaattttctt
2341 ttttggatgt gtaaatttat caatgatgag gtaagtgcgc aatgctaagc tgtttgctca
2401 cgtgactgcc agccccatcg gagtctaagc cggctttcct ctattttggt ttattttgc
2461 cacgtttaac acaaatggta aactcctcca cgtgcttcct gcgttccgtg caagccgcct
2521 cggcgctgcc tgcgttgcaa actgggcttt gtagcgtctg ccgtgtaaca cccttcctct
2581 gatcgcaccg cccctcgcag agagtgtatc atctgtttta tttttgtaaa aacaaagtgc
2641 taaataatat ttattacttg tttggttgca aaaacggaat aaatgactga gtgttgagat
2701 tttaaataaa atttaaagta aa
```

SEQ ID NO: 21-BASP1, variant 1
Protein sequence:
```
  1 mggklskkkk gynvndekak ekdkkaegaa teeegtpkes epqaaaepae akegkekpdq
 61 daegkaeeke gekdaaaake eapkaepekt egaaeakaep pkapeqeqaa pgpaaggeap
121 kaaeaaaapa esaapaagee pskeegepkk teapaapaaq etksdgapas dskpgsseaa
181 pssketpaat eapsstpkaq gpaasaeepk pveapaansd qtvtvke
```

SEQ ID NO: 22-BASP1, variant 1
mRNA sequence:
```
  1 ggcactgggc aggaaggggga gggggagcga gcgcgagaaa tgcagaggct gcagcggcgg
 61 cggcggcggc agtagcggca gcggcgacga cggcggcggc agcgctccaa ctggctcctc
121 gctccgggct ccgccgtcga gcgggagag agcctccgcc agcggccagg caccagccag
181 acgacgccag cgaccccggc ctctcggcgg caccgcgcta actcaggggc tgcataggca
241 cccagagccg aactccaaga tgggaggcaa gctcagcaag aagaagaagg gctacaatgt
301 gaacgacgag aaagccaagg agaaagacaa gaaggccgag ggcgcggcga cggaagagga
361 ggggaccccg aaggagagtg agccccaggc ggccgcagag cccgccgagg ccaaggaggg
421 caaggagaag cccgaccagg acgccgaggg caaggccgag gagaaggagg gcgagaagga
481 cgcggcggct gccaaggagg aggccccgaa ggcggagccc gagaagacg agggcgcggc
541 agaggccaag gctgagcccc cgaaggcgcc cgagcaggag caggcggccc ccggccccgc
601 tgcgggcggc gaggccccca agctgctga gccgccgcg gccccggccg agagcgcggc
661 ccctgccgcc ggggaggagc ccagcaagga ggaaggggaa cccaaaaaga ctgaggcgcc
721 cgcagctcct gccgcccagg agaccaaaag tgacgggggcc ccagcttcag actcaaaacc
781 cggcagctcg gaggctgccc cctcttccaa ggagacccc gcagccacg aagcgcctag
841 ttccacaccc aaggcccagg gccccgcagc ctctgcagaa gagcccaagc cggtggaggc
```

-continued

```
 901 cccggcagct aattccgacc aaaccgtaac cgtgaaagag tgacaaggac agcctatagg
 961 aaaaacaata ccacttaaaa caatctcctc tctctctctc tctctctctc tctatctctc
1021 tctctatctc ctctctctct ctcctctcct atctctcctc tctctctctc ctatactaac
1081 ttgtttcaaa ttggaagtaa tgatatgtat tgcccaagga aaaatacagg atgttgtccc
1141 atcaagggag ggaggggtg ggagaatcca aatagtattt ttgtggggaa atatctaata
1201 taccttcagt caactttacc aagaagtcct ggatttccaa gatccgcgtc tgaaagtgca
1261 gtacatcgtt tgtacctgaa actgccgcca catgcactcc tccaccgctg agagttgaat
1321 agcttttctt ctgcaatggg agttgggagt gatgcgtttg attctgccca cagggcctgt
1381 gccaaggcaa tcagatcttt atgagagcag tattttctgt gttttctttt taatttacag
1441 cctttcttat tttgatattt ttttaatgtt gtggatgaat gccagctttc agacagagcc
1501 cacttagctt gtccacatgg atctcaatgc caatcctcca ttcttcctct ccagatattt
1561 ttgggagtga caaacattct ctcatcctac ttagcctacc tagatttctc atgacgagtt
1621 aatgcatgtc cgtggttggg tgcacctgta gttctgttta ttggtcagtg aaatgaaaa
1681 aaaaaaaaaa aaaagtctg cgttcattgc agttccagtt tctcttccat tctgtgtcac
1741 agacaccaac acaccactca ttggaaaatg gaaaaaaaaa acaaaaaaaa aacaaaaaaa
1801 tgtacaatgg atgcattgaa attatatgta attgtataaa tggtgcaaca gtaataaagt
1861 taaacaatta aaagaagta ataagacaa aaaaaaaaa aa
```

SEQ ID NO: 23-BASP1, variant 2
Protein sequence:

```
  1 mggklskkkk gynvndekak ekdkkaegaa teeegtpkes epqaaaepae akegkekpdq
 61 daegkaeeke gekdaaaake eapkaepekt egaaaeakaep pkapeqeqaa pgpaaggeap
121 kaaeaaaapa esaapaagee pskeegepkk teapaapaaq etksdgapas dskpgsseaa
181 pssketpaat eapsstpkaq gpaasaeepk pveapaansd qtvtvke
```

SEQ ID NO: 24-BASP1, variant 2
mRNA sequence:

```
  1 gcgcaactcg tttgcagcgg cgcagcccag acgcgcctgc agctggggct cacccccaacc
 61 tcgctgccag ccgagaactc caagatggga ggcaagctca gcaagaagaa gaagggctac
121 aatgtgaacg acgagaaagc caaggagaaa gacaagaagg ccgagggcgc ggcgacggaa
181 gaggagggga ccccgaagga gagtgagccc caggcggccg cagagcccgc gaggccaag
241 gagggcaagg agaagcccga ccaggacgcc gagggcaagg ccgaggagaa ggagggcgag
301 aaggacgcgg cggctgccaa ggaggaggcc ccgaaggcgg agcccgagaa gacggagggc
361 gcggcagagg ccaaggctga gccccccgaag gcgcccgagc aggagcaggc ggcccccggc
421 cccgctgcgg gcggcgaggc ccccaaagct gctgaggccg ccgcggcccc ggccgagagc
481 gcggcccctg ccgccgggga ggagcccagc aaggaggaag gggaacccaa aaagactgag
541 gcgcccgcag ctcctgccgc ccaggagacc aaaagtgacg gggcccagc ttcagactca
601 aaacccggca gctcggaggc tgccccctct tccaaggaga ccccgcagc acggaagcg
661 cctagttcca cacccaaggc ccagggcccc gcagcctctg cagaagagcc caagccggtg
721 gaggccccgg cagctaattc cgaccaaacc gtaaccgtga aagagtgaca aggacagcct
781 ataggaaaaa caataccact taaaacaatc tcctctctct ctctctctct ctctctctat
841 ctctctctct atctcctctc tctctctcct ctcctatctc tcctctctct ctcctata
901 ctaacttgtt tcaaattgga agtaatgata tgtattgccc aaggaaaat acaggatgtt
961 gtcccatcaa gggagggagg gggtgggaga atccaaatag tattttttgtg gggaaatatc
```

-continued

```
1021  taatatacct tcagtcaact ttaccaagaa gtcctggatt tccaagatcc gcgtctgaaa
1081  gtgcagtaca tcgtttgtac ctgaaactgc cgccacatgc actcctccac cgctgagagt
1141  tgaatagctt ttcttctgca atgggagttg ggagtgatgc gtttgattct gcccacaggg
1201  cctgtgccaa ggcaatcaga tctttatgag agcagtattt tctgtgtttt ctttttaatt
1261  tacagccttt cttattttga tatttttta atgttgtgga tgaatgccag ctttcagaca
1321  gagcccactt agcttgtcca catggatctc aatgccaatc ctccattctt cctctccaga
1381  tattttgg agtgacaaac attctctcat cctacttagc ctacctagat ttctcatgac
1441  gagttaatgc atgtccgtgg ttgggtgcac ctgtagttct gtttattggt cagtggaaat
1501  gaaaaaaaaa aaaaaaaaa gtctgcgttc attgcagttc cagtttctct tccattctgt
1561  gtcacagaca ccaacacacc actcattgga aaatggaaaa aaaaaacaaa aaaaaaacaa
1621  aaaaatgtac aatggatgca ttgaaattat atgtaattgt ataaatggtg caacagtaat
1681  aaagttaaac aattaaaaag aagtaataaa gacaaaaaaa aaaaaaa
```

SEQ ID NO: 25-NKX6-2
Protein sequence:

```
  1  mdtnrpgafv lssaplaalh nmaemktslf pyalqgpagf kapalgglga qlplgtphgi
 61  sdilgrpvga agggllgglp ringlassag vyfgpaaava rgypkplael pgrppifwpg
121  vvqgapwrdp rlagapagg vldkdgkkkh srptfsgqqi falektfeqt kylagperar
181  layslgmtes qvkvwfqnrr tkwrkrhaae masakkkqds daeklkvggs daedddeynr
241  pldpnsddek itrllkkhkp snlalvspcg ggagdal
```

SEQ ID NO: 26-NKX6-2
mRNA sequence:

```
  1  gccgcgcgca aacttcccgg gccggcgggc aggggcggcg cggcggggc ccggatggga
 61  gcccgggccg gcggcggcgg cgcccatgga cactaaccgc ccgggcgcgt tcgtgctgag
121  cagtgccccg ctggccgcgc tgcacaacat ggccgagatg aagacgtcgc tgttcccccta
181  cgcgctgcag gtccggccg gcttcaaggc gcccgcgctg ggggcctgg gcgcgcagct
241  cccgctcggg accccgcacg gcatcagcga catcctgggc cggcccgtgg gcgcggcggg
301  cgggggcctc ctgggggggc tgccccggct caacgggctc gcgtcgtccg ccggcgttta
361  cttcgggccc gcggccgctg tggcgcgcgg ctaccccaag cccctggccg agctgccggg
421  gcgcccgccc atcttctggc ccggcgtggt gcagggcgcg ccctggaggg acccgcgtct
481  ggctggcccg gccccggccg gcggcgtcct ggacaaggac gggaagaaga agcactcgcg
541  cccgaccttc tcgggccagc agatcttcgc gctggagaaa accttcgagc agaccaagta
601  cctggcgggc ccggagcgcg cgcgtctcgc ctactcgctg gcatgaccg agagccaggt
661  gaaggtctgg ttccagaacc gccgaccaa gtggcgcaag cggcacgcgg cggagatggc
721  gtcggccaag aagaagcagg actcggacgc cgagaagctg aaggtgggcg gctcggacgc
781  ggaggacgac gacgaataca accgccccct ggaccccaac tcggacgacg agaagatcac
841  gcggctgctc aagaagcaca aaccctcgaa cttggcgctg gtcagcccgt gcggcggcgg
901  cgcggggac gccttgtgag gacccgcggg gtggggcga atctattttt gcagaatccg
961  gggcggccc cggtggggcg cgagtcgctt tgtatcatca ataaattatt taacgggtc
```

SEQ ID NO: 27-NKX6-2, isoform X1
Protein sequence:

```
  1  mdtnrpgafv lssaplaalh nmaemktslf pyalqgpagf kapalgglga qlplgtphgi
 61  sdilgrpvga agggllgglp ringlassag vyfgpaaava rgypkplael pgrppifwpg
```

-continued

```
     121   vvqgapwrdp rlagpapagg vldkdgkkkh srptfsgqqi falektfeqt kylagperar 181   layslgmtes qvkvwfqnrr tkwrkrhave masakkkqds daeklkvggs daedddeynr 241   pldpnsddek itrllkkhkp snlalvspcg ggagdal
```

SEQ ID NO: 28-NKX6-2, isoform X1
mRNA sequence:
```
       1   cgcaaacttc ccgggccggc gggcaggggc ggcggcggcg gggcccggat gggagcccgg 61   gccggcggcg gcggcgccca tggacactaa ccgcccgggc gcgttcgtgc tgagcagtgc 121   cccgctggcc gcgctgcaca acatggccga gatgaagacg tcgctgttcc cctacgcgct 181   gcagggtccg gccggcttca aggcgcccgc gctgggggc ctgggcgcgc agctcccgct 241   cgggaccccg cacggcatca gcgacatcct gggccggccc gtgggcgcgg cgggcggggg 301   cctcctgggg gggctgcccc ggctcaacgg gctcgcgtcg tccgccggcg tttacttcgg 361   gcccgcggcc gctgtggcgc gcggctaccc caagcccctg ccgagctgc cggggcgccc 421   gcccatcttc tggcccggcg tggtgcaggg cgcgccctgg agggaccccgc gtctggctgg 481   cccggccccg gccggcggcg tcctggacaa ggacgggaag aagaagcact cgcgcccgac 541   cttctcgggc cagcagatct tcgcgctgga gaaaaccttc gagcagacca agtacctggc 601   gggcccggag cgcgcgcgtc tcgcctactc gctgggcatg accgagagcc aggtgaaggt 661   ctggttccag aaccgccgga ccaagtggcg caagcggcac gcggtggaga tggcgtcggc 721   caagaagaag caggactcgg acgccgagaa gctgaaggtg gcggctcgg acgcggagga 781   cgacgacgaa tacaaccggc ccctggaccc caactcggac gacgagaaga tcacgcggct 841   gctcaagaag cacaaaccct cgaacttggc gctggtcagc ccgtgcggcg gcggcgcggg 901   ggacgccttg tgaggacccg cggggtgggg gcgaatctat ttttgcagaa tccggggcg 961   gccccgggtg ggcgcgagtc gctttgtatc atcaataaat tatttaacgg tccccgtcg 1021   gagccgtcgc tccggagcct gcgccgcgtg tttcttccgt ctcgaacccg gagcgaggcg 1081   gccctcccc ggccccggct tcgcccctgc gccgcctcg ggtcctccgg gttcccggtg 1141   cggaggctgc gggccccggg caggcgcgag gaggcggcga aggcgcaggg aaggggcccg 1201   gcccgcggga aggaaccgca gcgacagccg ccaggagccc gggacggagc cggggacgga 1261   gcagcaggaa ccagaccggt cacttccaaa ggcccctcag aacgaccaac agctgaaacc 1321   cgcggggcgg actccgtgtt gaaccgcgga cagcggcaac cacagcagcg cacgcgacct 1381   gtgcttccac caagaacaga ttccgcagcg gacagcagtc acttgcagtg gtagtattta 1441   tcccacacaa acacccagct aatgccttca cccggtccag gaactctgta gtgttctaaa 1501   gtaaaatcaa taaaacatac atttgtgttt catcaaca
```

SEQ ID NO: 29-MYCN, isoform 1, variant 1
Protein sequence:
```
       1   mpscststmp gmicknpdle fdslqpcfyp deddfyfggp dstppgediw kkfellptpp 61   lspsrgfaeh sseppswvte mllenelwgs paeedafglg glggltpnpv ilqdcmwsgf 121   sareklerav seklqhgrgp ptagstaqsp gagaaspagr ghggaagagr agaalpaela 181   hpaaecvdpa vvfpfpvnkr epapvpaapa sapaagpava sgagiaapag apgvapprpg 241   grqtsggdhk alstsgedtl sdsddeddee edeeeeidvv tvekrrsssn tkavttftit 301   vrpknaalgp graqsselil krclpihqqh nyaapspyve sedappqkki kseasprplk 361   svippkaksl sprnsdseds errrnhnile rqrrndlrss fltlrdhvpe lvknekaakv 421   vilkkateyv hslqaeehql llekeklqar qqqllkkieh artc
```

SEQ ID NO: 30-MYCN, isoform 1, variant 1

-continued

```
mRNA sequence:
   1 gctttcctct cctttctccc tccccttgt ctgcgccaca gcccccttct ctccccgccc
  61 cccgggtgtg tcagatttt cagttaataa tatcccccga gcttcaaagc gcaggctgtg
 121 acagtcatct gtctggacgc gctgggtgga tgcgggggc tcctgggaac tgtgttggag
 181 ccgagcaagc gctagccagg cgcaagcgcg cacagactgt agccatccga ggacaccccc
 241 gccccccgg cccacccgga gacacccgcg cagaatcgcc tccggatccc ctgcagtcgg
 301 cgggaggtaa ggagcagggc ttgcaaaccg cccggcgccc agggaagcga cgagcgccgg
 361 ggcaaggcaa gccctggacg ggattgcgac gtgcgcaccg ggcgccctaa tatgcccggg
 421 ggactgtttc tgcttccgaa acaaaaccat ctctgggttt cccagaaaa gccagttcca
 481 gccccgaagg catcctggct agaggagacc cgccctaatc cttttgcagc ccttaccggg
 541 gggagtaatg gcttctgcga aaagaaattc cctcggctct agaagatctg tctgtgtttg
 601 agctgtcgga gagccgtgtt ggaggtcggc gccggccccc gccttccgcg ccccccacgg
 661 gaaggaagca cccccggtat taaaacgaac ggggcggaaa gagcccctca gtcgccggcc
 721 gggaggcgag ccgatgccga gctgctccac gtccaccatg ccgggcatga tctgcaagaa
 781 cccagacctc gagtttgact cgctacagcc ctgcttctac ccggacgaag atgacttcta
 841 cttcggcggc cccgactcga ccccccggg ggaggacatc tggaagaagt ttgagctgct
 901 gcccacgccc ccgctgtcgc cagccgtgg cttcgcggag cacagctccg agccccgag
 961 ctgggtcacg gagatgctgc ttgagaacga gctgtggggc agcccggccg aggaggacgc
1021 gttcggcctg gggggactgg gtggcctcac ccccaacccg gtcatcctcc aggactgcat
1081 gtggagcggc ttctccgccc gcagaagct ggagcgcgcc gtgagcgaga agctgcagca
1141 cggccgcggg ccgccaaccg ccggttccac cgcccagtcc ccgggagccg gcgccgccag
1201 ccctgcgggt cgcgggcacg gcggggctgc gggagccggc cgcgccgggg ccgccctgcc
1261 cgccgagctc gcccaccggg ccgccgagtg cgtggatccc gccgtggtct tcccctttcc
1321 cgtgaacaag cgcgagccag cgcccgtgcc cgcagcccg gccagtgccc cggcggcggg
1381 ccctgcggtc gcctcggggg cgggtattgc cgcccagcc ggggcccgg gggtcgcccc
1441 tccgcgccca gcggccgcc agaccagcgg cggcgaccac aaggccctca gtacctccgg
1501 agaggacacc ctgagcgatt cagatgatga agatgatgaa gaggaagatg aagaggaaga
1561 aatcgacgtg gtcactgtgg agaagcggcg ttcctcctcc aacaccaagg ctgtcaccac
1621 attcaccatc actgtgcgtc ccaagaacgc agccctgggt cccggagggg ctcagtccag
1681 cgagctgatc ctcaaacgat gccttcccat ccaccagcag cacaactatg ccgccccctc
1741 tccctacgtg gagagtgagg atgcaccccc acagaagaag ataaagagcg aggcgtcccc
1801 acgtccgctc aagagtgtca tccccccaaa ggctaagagc ttgagccccc gaaactctga
1861 ctcggaggac agtgagcgtc gcagaaacca caacatcctg gagcgccagc gccgcaacga
1921 ccttcggtcc agctttctca cgctcaggga ccacgtgccg gagttggtaa agaatgagaa
1981 ggccgccaag gtggtcattt tgaaaaaggc cactgagtat gtccactccc tccaggccga
2041 ggagcaccag cttttgctgg aaaaggaaaa attgcaggca agacagcagc agttgctaaa
2101 gaaaattgaa cacgctcgga cttgctagac gcttctcaaa actggacagt cactgccact
2161 ttgcacattt tgatttttt tttaaacaaa cattgtgttg acattaagaa tgttggttta
2221 ctttcaaatc ggtcccctgt cgagttcggc tctgggtggg cagtaggacc accagtgtgg
2281 ggtctgctgg gaccttgga gagcctgcat cccaggatgc tgggtggccc tgcagcctcc
```

-continued

```
2341  tccacctcac ctccatgaca gcgctaaacg ttggtgacgg ttgggagcct ctggggctgt 2401  tgaagtcacc ttgtgtgttc caagtttcca aacaacagaa agtcattcct tcttttttaaa 2461  atggtgctta agttccagca gatgccacat aaggggtttg ccatttgata cccctgggga 2521  acatttctgt aaataccatt gacacatccg ccttttgtat acatcctggg taatgagagg 2581  tggcttttgc ggccagtatt agactggaag ttcataccta agtactgtaa taatacctca 2641  atgtttgagg agcatgtttt gtatacaaat atattgttaa tctctgttat gtactgtact 2701  aattcttaca ctgcctgtat actttagtat gacgctgata cataactaaa tttgatactt 2761  atattttcgt atgaaaatga gttgtgaaag ttttgagtag atattacttt atcactttt 2821  gaactaagaa acttttgtaa agaaatttac tatatatata tgccttttc ctagcctgtt 2881  tcttcctgtt aatgtatttg ttcatgtttg gtgcatagaa ctgggtaaat gcaaagttct 2941  gtgtttaatt tcttcaaaat gtatatattt agtgctgcat cttatagcac tttgaaatac 3001  ctcatgttta tgaaaataaa tagcttaaaa ttaaatgaaa aaaaaa
```

SEQ ID NO: 31-MYCN, isoform 1, variant 2
Protein sequence:
```
  1  mpscststmp gmicknpdle fdslqpcfyp deddfyfggp dstppgediw kkfellptpp 61  lspsrgfaeh sseppswvte mllenelwgs paeedafglg glggltpnpv ilqdcmwsgf 121  sareklerav seklqhgrgp ptagstaqsp gagaaspagr ghggaagagr agaalpaela 181  hpaaecvdpa vvfpfpvnkr epapvpaapa sapaagpava sgagiaapag apgvapprpg 241  grqtsggdhk alstsgedtl sdsddeddee edeeeeidvv tvekrrsssn tkavttftit 301  vrpknaalgp graqsselil krclpihqqh nyaapspyve sedappqkki kseasprplk 361  svippkaksl sprnsdseds errrnhnile rqrrndlrss fltlrdhvpe lvknekaakv 421  vilkkateyv hslqaeehql llekeklqar qqqllkkieh artc
```

SEQ ID NO: 32-MYCN, isoform 1, variant 2
mRNA sequence:
```
   1  gctttcctct cctttctccc tcccccttgt ctgcgccaca gccccttct ctccccgccc 61  cccgggtgtg tcagattttt cagttaataa tatccccga gcttcaaagc gcaggctgtg 121  acagtcatct gtctggacgc gctgggtgga tgcgggggc tcctgggaac tgtgttggag 181  ccgagcaagc gctagccagg cgcaagcgcg cacagactgt agccatccga ggacaccccc 241  gccccccgg cccaccccgga gacacccgcg cagaatcgcc tccggatccc ctgcagtcgg 301  cgggagtgtt ggaggtcggc gccggccccc gccttccgcg cccccacgg gaaggaagca 361  ccccggtat taaaacgaac ggggcggaaa gaagccctca gtcgccggcc gggaggcgag 421  ccgatgccga gctgctccac gtccaccatg ccgggcatga tctgcaagaa cccagacctc 481  gagtttgact cgctacagcc ctgcttctac ccggacgaag atgacttcta cttcggcggc 541  cccgactcga ccccccgggg ggaggacatc tggaagaagt ttgagctgct gcccacgccc 601  ccgctgtcgc ccagccgtgg cttcgcggag cacagctccg agcccccgag ctgggtcacg 661  gagatgctgc ttgagaacga gctgtggggc agcccggccg aggaggacgc gttcggcctg 721  gggggactgg gtggcctcac ccccaacccg gtcatcctcc aggactgcat gtggagcggc 781  ttctccgccc gcgagaagct ggagcgcgcc gtgagcgaga agctgcagca cggccgcggg 841  ccgccaaccg ccggttccac cgcccagtcc ccgggagccg cgccgccag ccctgcgggt 901  cgcggcacg gcggggctg gggagccgg cgccgggg ccgcctgcc cgccgagctc 961  gcccaccgg ccgccgagtg cgtggatccc gccgtggtct tccccttcc cgtgaacaag 1021  cgcgagccag cgcccgtgcc cgcagccccg gccagtgccc cggcggcggg ccctgcggtc
```

```
1081   gcctcggggg cgggtattgc cgccccagcc ggggccccgg gggtcgcccc tccgcgccca
1141   ggcggccgcc agaccagcgg cggcgaccac aaggccctca gtacctccgg agaggacacc
1201   ctgagcgatt cagatgatga agatgatgaa gaggaagatg aagaggaaga aatcgacgtg
1261   gtcactgtgg agaagcggcg ttcctcctcc aacaccaagg ctgtcaccac attcaccatc
1321   actgtgcgtc ccaagaacgc agccctgggt cccgggaggg ctcagtccag cgagctgatc
1381   ctcaaacgat gccttcccat ccaccagcag cacaactatg ccgcccctc tccctacgtg
1441   gagagtgagg atgcaccccc acagaagaag ataaagagcg aggcgtcccc acgtccgctc
1501   aagagtgtca tcccccaaa ggctaagagc ttgagccccc gaaactctga ctcggaggac
1561   agtgagcgtc gcagaaacca caacatcctg cagcgccagc gccgcaacga ccttcggtcc
1621   agctttctca cgctcaggga ccacgtgccg gagttggtaa agaatgagaa ggccgccaag
1681   gtggtcattt tgaaaaaggc cactgagtat gtccactccc tccaggccga ggagcaccag
1741   cttttgctgg aaaggaaaa attgcaggca agacagcagc agttgctaaa gaaaattgaa
1801   cacgctcgga cttgctagac gcttctcaaa actggacagt cactgccact ttgcacattt
1861   tgattttttt tttaaacaaa cattgtgttg acattaagaa tgttggttta ctttcaaatc
1921   ggtcccctgt cgagttcggc tctgggtggg cagtaggacc accagtgtgg ggttctgctg
1981   ggaccttgga gagcctgcat cccaggatgc tgggtggccc tgcagcctcc tccacctcac
2041   ctccatgaca gcgctaaacg ttggtgacgg ttgggagcct ctggggctgt tgaagtcacc
2101   ttgtgtgttc caagtttcca acaacagaa agtcattcct tctttttaaa atggtgctta
2161   agttccagca gatgccacat aaggggtttg ccatttgata cccctgggga acatttctgt
2221   aaataccatt gacacatccg ccttttgtat acatcctggg taatgagagg tggcttttgc
2281   ggccagtatt agactggaag ttcataccta agtactgtaa taatacctca atgtttgagg
2341   agcatgtttt gtatacaaat atattgttaa tctctgttat gtactgtact aattcttaca
2401   ctgcctgtat actttagtat gacgctgata cataactaaa tttgatactt atattttcgt
2461   atgaaaatga gttgtgaaag ttttgagtag atattacttt atcactttt gaactaagaa
2521   actttgtaa agaaatttac tatatatata tgccttttc ctagcctgtt tcttcctgtt
2581   aatgtatttg ttcatgtttg gtgcatagaa ctgggtaaat gcaaagttct gtgtttaatt
2641   tcttcaaaat gtatatattt agtgctgcat cttatagcac tttgaaatac ctcatgttta
2701   tgaaaataaa tagcttaaaa ttaaatgaaa aaaaa
```

SEQ ID NO: 33-MYCN, isoform 2
Protein sequence:
```
  1   mrgapgncvg aeqalarrkr aqtvairghp rppgppgdtr aesppdplqs agddeddeee
 61   deeeeidvvt vekrrsssnt kavttftitv rpknaalgpg raqsselilk rclpihqqhn
121   yaapspyves edappqkkik seasprplks vippkaksls prnsdsedse rrrnhniler
181   qrrndlrssf ltlrdhvpel vknekaakvv ilkkateyvh slqaeehqll lekeklqarq
241   qqllkkieha rtc
```

SEQ ID NO: 34-MYCN, isoform 2
mRNA sequence:
```
  1   gctttcctct cctttctccc tccccttgt ctgcgccaca gccccttct ctccccgccc
 61   cccgggtgtg tcagattttt cagttaataa tatccccga gcttcaaagc gcaggctgtg
121   acagtcatct gtctggacgc gctgggtgga tgcgggggc tcctgggaac tgtgttggag
181   ccgagcaagc gctagccagg cgcaagcgcg cacagactgt agccatccga ggacaccccc
```

-continued

```
 241   gccccccgg  cccacccgga  gacacccgcg  cagaatcgcc  tccggatccc  ctgcagtcgg
 301   cgggagatga  tgaagatgat  gaagaggaag  atgaagagga  agaaatcgac  gtggtcactg
 361   tggagaagcg  gcgttcctcc  tccaacacca  aggctgtcac  cacattcacc  atcactgtgc
 421   gtcccaagaa  cgcagccctg  ggtcccggga  gggctcagtc  cagcgagctg  atcctcaaac
 481   gatgccttcc  catccaccag  cagcacaact  atgccgcccc  ctctccctac  gtggagagtg
 541   aggatgcacc  cccacagaag  aagataaaga  gcgaggcgtc  cccacgtccg  ctcaagagtg
 601   tcatcccccc  aaaggctaag  agcttgagcc  ccgaaactc  tgactcggag  gacagtgagc
 661   gtcgcagaaa  ccacaacatc  ctggagcgcc  agcgccgcaa  cgaccttcgg  tccagctttc
 721   tcacgctcag  ggaccacgtg  ccggagttgg  taaagaatga  aaggccgcc  aaggtggtca
 781   ttttgaaaaa  ggccactgag  tatgtccact  ccctccaggc  cgaggagcac  cagcttttgc
 841   tggaaaagga  aaaattgcag  gcaagacagc  agcagttgct  aaagaaaatt  gaacacgctc
 901   ggacttgcta  gacgcttctc  aaaactggac  agtcactgcc  actttgcaca  ttttgatttt
 961   tttttaaac  aaacattgtg  ttgacattaa  gaatgttggt  ttactttcaa  atcggtcccc
1021   tgtcgagttc  ggctctgggt  gggcagtagg  accaccagtg  tggggttctg  ctgggacctt
1081   ggagagcctg  catcccagga  tgctgggtgg  ccctgcagcc  tcctccacct  cacctccatg
1141   acagcgctaa  acgttggtga  cggttgggag  cctctggggc  tgttgaagtc  accttgtgtg
1201   ttccaagttt  ccaaacaaca  gaaagtcatt  ccttcttttt  aaatggtgc  ttaagttcca
1261   gcagatgcca  cataaggggt  ttgccatttg  ataccctgg  ggaacatttc  tgtaaatacc
1321   attgacacat  ccgccttttg  tatacatcct  gggtaatgag  aggtggcttt  tgcggccagt
1381   attagactgg  aagttcatac  ctaagtactg  taataatacc  tcaatgtttg  aggagcatgt
1441   tttgtataca  aatatatagt  taatctctgt  tatgtactgt  actaattctt  acactgcctg
1501   tatactttag  tatgacgctg  atacataact  aaatttgata  cttatatttt  cgtatgaaaa
1561   tgagttgtga  agttttgag  tagatattac  tttatcactt  tttgaactaa  gaaacttttg
1621   taaagaaatt  tactatatat  atatgccttt  ttcctagcct  gtttcttcct  gttaatgtat
1681   ttgttcatgt  ttggtgcata  gaactgggta  aatgcaaagt  tctgtgttta  atttcttcaa
1741   aatgtatata  tttagtgctg  catcttatag  cactttgaaa  tacctcatgt  ttatgaaaat
1801   aaatagctta  aaattaaatg  aaaaaaaaa
```

SEQ ID NO: 35-MYCN, isoform 3
Protein sequence:
```
   1   mrgapgncvg  aeqalarrkr  aqtvairghp  rppgppgdtr  aesppdplqs  agvlevgagp
  61   rlprppregs  tpgiktngae  rspqspagrr  adaellhvhh  aghdlqeprp  rv
```

SEQ ID NO: 36-MYCN, isoform 3
mRNA sequence:
```
   1   gctttcctct  cctttctccc  tcccccttgt  ctgcgccaca  gccccttct   ctccccgccc
  61   cccgggtgtg  tcagatttt   cagttaataa  tatccccga   gcttcaaagc  gcaggctgtg
 121   acagtcatct  gtctggacgc  gctgggtgga  tgcgggggc   tcctgggaac  tgtgttggag
 181   ccgagcaagc  gctagccagg  cgcaagcgcg  cacagactgt  agccatccga  ggacaccccc
 241   gccccccgg   cccacccgga  gacacccgcg  cagaatcgcc  tccggatccc  ctgcagtcgg
 301   cgggagtgtt  ggaggtcggc  gccggcccc   gccttccgcg  cccccacgg   gaaggaagca
 361   ccccggtat   taaaacgaac  ggggcggaaa  gaagccctca  gtcgccggcc  gggaggcgag
 421   ccgatgccga  gctgctccac  gtccaccatg  ccgggcatga  tctgcaagaa  cccagacctc
 481   gagtttgact  cgctacagcc  ctgcttctac  ccggacgaag  atgacttcta  cttcggcggc
```

```
  541  cccgactcga cccccccggg ggaggacatc tggaagaagt ttgagctgct gcccacgccc
  601  ccgctgtcgc ccagccgtgg cttcgcggag cacagctccg agcccccgag ctgggtcacg
  661  gagatgctgc ttgagaacga gctgtggggc agcccggccg aggaggacgc gttcggcctg
  721  gggggactgg gtggcctcac ccccaacccg gtcatcctcc aggactgcat gtggagcggc
  781  ttctccgccc gcgagaagct ggagcgcgcc gtgagcgaga agctgcagca cggccgcggg
  841  ccgccaaccg ccggttccac cgcccagtcc ccgggagccg cgccgccag ccctgcgggt
  901  cgcgggcacg gcggggctgc gggagccggc cgcgccgggg ccgccctgcc cgccgagctc
  961  gcccacccgg ccgccgagtg cgtggatccc gccgtggtct ccccctttcc cgtgaacaag
 1021  cgcgagccag cgcccgtgcc cgcagccccg gccagtgccc cggcggcggg ccctgcggtc
 1081  gcctcggggg cgggtattgc cgccccagcc ggggcccggg gggtcgcccc tccgcgccca
 1141  ggcggccgcc agaccagcgg cggcgaccac aaggccctca gtacctccgg agaggacacc
 1201  ctgagcgatt cagatgatga agatgatgaa gaggaagatg aagaggaaga atcgacgtg
 1261  gtcactgtgg agaagcggcg ttcctcctcc aacaccaagg ctgtcaccac attcaccatc
 1321  actgtgcgtc ccaagaacgc agccctgggt cccggagggg ctcagtccag cgagctgatc
 1381  ctcaaacgat gccttccat ccaccagcag cacaactatg ccgcccctc tccctacgtg
 1441  gagagtgagg atgcaccccc acagaagaag ataaagagcg aggcgtcccc acgtccgctc
 1501  aagagtgtca tccccccaaa ggctaagagc ttgagccccc gaaactctga ctcggaggac
 1561  agtgagcgtc gcagaaacca caacatcctg gagcgccagc gccgcaacga ccttcggtcc
 1621  agctttctca cgctcaggga ccacgtgccg gagttggtaa agaatgagaa ggccgccaag
 1681  gtggtcattt tgaaaaaggc cactgagtat gtccactccc tccaggccga ggagcaccag
 1741  cttttgctgg aaaaggaaaa attgcaggca agacagcagc agttgctaaa gaaaattgaa
 1801  cacgctcgga cttgctagac gcttctcaaa actggacagt cactgccact ttgcacattt
 1861  tgattttttt tttaaacaaa cattgtgttg acattaagaa tgttggttta ctttcaaatc
 1921  ggtcccctgt cgagttcggc tctgggtggg cagtaggacc accagtgtgg ggttctgctg
 1981  ggaccttgga gagcctgcat cccaggatgc tgggtggccc tgcagcctcc tccacctcac
 2041  ctccatgaca gcgctaaacg ttggtgacgg ttgggagcct ctggggctgt gaagtcacc
 2101  ttgtgtgttc caagtttcca acaacagaa agtcattcct tctttttaaa atggtgctta
 2161  agttccagca gatgccacat aagggggtttg ccatttgata cccctgggga catttctgt
 2221  aaataccatt gacacatccg ccttttgtat acatcctggg taatgagagg tggcttttgc
 2281  ggccagtatt agactggaag ttcataccta agtactgtaa taatacctca atgtttgagg
 2341  agcatgtttt gtatacaaat atattgttaa tctctgttat gtactgtact aattcttaca
 2401  ctgcctgtat actttagtat gacgctgata cataactaaa tttgatactt atattttcgt
 2461  atgaaaatga gttgtgaaag ttttgagtag atattacttt atcacttttt gaactaagaa
 2521  acttttgtaa agaaatttac tatatatata tgccttttc ctagcctgtt tcttcctgtt
 2581  aatgtatttg ttcatgtttg gtgcatagaa ctgggtaaat gcaaagttct gtgtttaatt
 2641  tcttcaaaat gtatatattt agtgctgcat cttatagcac tttgaaatac ctcatgttta
 2701  tgaaaataaa tagcttaaaa ttaaatgaaa aaaaaa
```

SEQ ID NO: 37-MYCN, isoform X1
Protein sequence:
```
    1  mpscststmp gmicknpdle fdslqpcfyp deddfyfggp dstppgediw kkfellptpp
```

```
     61 lspsrgfaeh sseppswvte mllenelwgs paeedafglg glggltpnpv ilqdcmwsgf
    121 sareklerav seklqhgrgp ptagstaqsp gagaaspagr ghggaagagr agaaalpaela
    181 hpaaecvdpa vvfpfpvnkr epapvpaapa sapaagpava sgagiaapag apgvapprpg
    241 grqtsggdhk alstsgedtl sdsddeddee edeeeeidvv tvekrrsssn tkavttftit
    301 vrpknaalgp graqsselil krclpihqqh nyaapspyve sedappqkki kseasprplk
    361 svippkaksl sprnsdseds errrnhnile rqrrndlrss fltlrdhvpe lvknekaakv
    421 vilkkateyv hslqaeehql llekeklqar qqqllkkieh artc
SEQ ID NO: 38-MYCN, isoform X1
mRNA sequence:
      1 ctccaccttc gggagcagtg ggcagagtgg ggggcttgga gggaagattg gggaacctgg
     61 ttagaggggg cgcccattgc ctatcccctc ggtctgcccc gtttgcccac cctctccggt
    121 gtgtctgtcg gttgcagtgt tggaggtcgg cgccggcccc cgccttccgc gcccccacg
    181 ggaaggaagc accccggta ttaaaacgaa cggggcggaa agaagccctc agtcgccggc
    241 cgggaggcga gccgatgccg agctgctcca cgtccaccat gccgggcatg atctgcaaga
    301 acccagacct cgagtttgac tcgctacagc cctgcttcta cccggacgaa gatgacttct
    361 acttcggcgg ccccgactcg accccccgg ggaggacat ctggaagaag tttgagctgc
    421 tgcccacgcc cccgctgtcg cccagccgtg gcttcgcgga gcacagctcc gagcccccga
    481 gctgggtcac ggagatgctg cttgagaacg agctgtgggg cagcccggcc gaggaggacg
    541 cgttcggcct ggggggactg ggtggcctca ccccaacc ggtcatcctc caggactgca
    601 tgtggagcgg cttctccgcc cgcgagaagc tggagcgcgc cgtgagcgag aagctgcagc
    661 acggccgcgg gccgccaacc gccggttcca ccgcccagtc cccgggagcc ggcgccgcca
    721 gccctgcggg tcgcgggcac ggcggggctg cgggagccgg ccgcgccggg ccgccctgc
    781 ccgccgagct cgcccacccg gccgccgagt gcgtggatcc cgccgtggtc ttccccttc
    841 ccgtgaacaa gcgcgagcca gcgcccgtgc ccgcagcccc ggccagtgcc cggcggcgg
    901 gccctgcggt cgcctcgggg gcgggtattg ccgcccagc cggggccccg ggggtcgccc
    961 ctccgcgccc aggcggccgc cagaccagcg gcggcgacca caaggccctc agtacctccg
   1021 gagaggacac cctgagcgat tcagatgatg aagatgatga agaggaagat gaagaggaag
   1081 aaatcgacgt ggtcactgtg agaagcggc gttcctcctc caacaccaag gctgtcacca
   1141 cattcaccat cactgtgcgt cccaagaacg cagccctggg tcccggagg gctcagtcca
   1201 gcgagctgat cctcaaacga tgccttccca tccaccagca gcacaactat gccgccccct
   1261 ctccctacgt ggagagtgag gatgcacccc cacagaagaa gataaagagc gaggcgtccc
   1321 cacgtccgct caagagtgtc atccccccaa aggctaagag cttgagcccc cgaaactctg
   1381 actcggagga cagtgagcgt cgcagaaacc acaacatcct ggagcgccag cgccgcaacg
   1441 accttcggtc cagctttctc acgctcaggg accacgtgcc ggagttggta aagaatgaga
   1501 aggccgccaa ggtggtcatt ttgaaaaagg ccactgagta tgtccactcc ctccaggccg
   1561 aggagcacca gcttttgctg gaaaaggaaa aattgcaggc aagacagcag cagttgctaa
   1621 agaaaattga acacgctcgg acttgctaga cgcttctcaa aactggacag tcactgccac
   1681 tttgcacatt ttgatttttt ttttaaacaa acattgtgtt gacattaaga atgttggttt
   1741 acttttcaaat cggtcccctg tcgagttcgg ctctgggtgg gcagtaggac caccagtgtg
   1801 gggttctgct gggaccttgg agagcctgca tccaggatg ctgggtggcc ctgcagcctc
   1861 ctccacctca cctccatgac agcgctaaac gttggtgacg gttgggagcc tctggggctg
```

```
1921  ttgaagtcac cttgtgtgtt ccaagtttcc aaacaacaga aagtcattcc ttcttttaa 1981  aatggtgctt aagttccagc agatgccaca taaggggttt gccatttgat accctggg 2041  aacatttctg taaataccat tgacacatcc gccttttgta tacatcctgg gtaatgagag 2101  ataacttta caaccaatat taaactaaaa attcatacct aaatactata taatacctc 2161  aatgtttgag gagcatgttt tgtatacaaa tatattgtta atctctgtta tgtactgtac 2221  taattcttac actgcctgta tactttagta tgacgctgat acataactaa atttgatact 2281  tatattttcg tatgaaaatg agttgtgaaa gttttgagta gatattactt tatcactttt 2341  tgaactaaga aacttttgta aagaaattta ctatatatat atgccttttt cctagcctgt 2401  ttcttcctgt taatgtattt gttcatgttt ggtgcataga actgggtaaa tgcaaagttc 2461  tgtgtttaat ttcttcaaaa tgtatatatt tagtgctgca tcttatagca ctttgaaata 2521  cctcatgttt atgaaaataa atagcttaaa attaaatga
```

SEQ ID NO: 39-HES6, isoform a
Protein sequence:
```
  1  mappaapgrd rvgrededgw etrgdrkark plvekkrrar ineslqelrl llagaevqak
 61  lenaevlelt vrrvqgvlrg rarereqlqa easerfaagy iqcmhevhtf vstcqaidat
121  vaaellnhll esmplregss fqdllgdala gpprapgrsg wpaggapgsp ipsppgpgdd
181  lcsdleeape aelsqapaeg pdlvpaalgs lttaqiarsv wrpw
```

SEQ ID NO: 40-HES6, isoform a
mRNA sequence:
```
   1  gtcggccgcc ccgggcccgc gcggccaatc ggcgcattga gatgcaaata agcggctata
  61  aaaggggcgg gaccgcggcg ggccggaagc cgcgaggagc gcggacggct gggctgctgc
 121  tgggcggccg cggggcagcg gagggcgccg gcactccggt ccccgccgct ccccgtcccc
 181  gctgctccta gcccctgccg cgtcccggc ggagcgggca tggcgccacc cgcggcgcct
 241  ggccgggacc gtgtgggccg tgaggatgag gacggctggg agacgcgagg ggaccgcaag
 301  gcccggaagc ccctggtgga gaagaagcgg cgcgcgcgga tcaacgagag cctgcaggag
 361  ctgcgctgc tgctggcggg cgccgaggtg caggccaagc tggagaacgc cgaagtgctg
 421  gagctgacgg tgcggcgggt ccagggtgtg ctgcggggcc gggcgcgcga gcgcgagcag
 481  ctgcaggcgg aagcgagcga gcgcttcgct gccggctaca tccagtgcat gcacgaggtg
 541  cacacgttcg tgtccacgtg ccaggccatc gacgctaccg tcgctgccga gctcctgaac
 601  catctgctcg agtccatgcc gctgcgtgag ggcagcagct tccaggatct gctgggggac
 661  gccctggcgg ggccacctag agccctggga cggagtggct ggcctgcggg gggcgctccg
 721  ggatccccaa tacccagccc ccgggtcct ggggacgacc tgtgctccga cctggaggag
 781  gccctgagg ctgaactgag tcaggctcct gctgaggggc ccgacttggt gcccgcagcc
 841  ctgggcagcc tgaccacagc ccaaattgcc cggagtgtct ggaggccttg tgaccaatg
 901  ccagccagag tcctgcgggg gtgggcccgg cctcctgg atctcctccc tcctcccagg
 961  ggttcagatg tggtggggta gggccctgga agtctcccag gtcttcctc cctcctctga
1021  tggatggctt gcagggcagc ccctggtaac cagcccagtc aggccccagc ccgtttctt
1081  aagaaacttt tagggaccct gcagctctgg agtgggtgga gggagggagc tacgggcagg
1141  aggaagaatt ttgtagagct gccagcgctc tcccaggttc acccacccag gcttcaccag
1201  ccctgtgcgg gctctggggg cagaggtggc agaaatggtg ctgggcacta gtgttccagg
1261  cagccctggg ctaaacaaaa gcttgaactt gccacttcag cggggagatg agaggcaggt
```

-continued

```
     1321 gcactgagct gcactgccca gagctgtgat gctctgtaca tcttgtttgt agcacacttg 1381 agtttgtgta ttccattgac atcaaatgtg acaattttac taaataaaga attttggagt 1441 tagttaccct tgaaaaaaaa aaaaaaaaaa
```

SEQ ID NO: 41-HES6, isoform b
Protein sequence:
```
       1 mappaapgrd rvgrededgw etrgdrkark plvekkrrar ineslqelrl llagaeakle 61 naevleltvr rvqgvlrgra rereqlqaea serfaagyiq cmhevhtfvs tcqaidatva 121 aellnhlles mplregssfq dllgdalagp prapgrsgwp aggapgspip sppgpgddlc 181 sdleeapeae lsqapaegpd lvpaalgslt taqiarsvwr pw
```

SEQ ID NO: 42-HES6, isoform b
mRNA sequence:
```
       1 gtcggccgcc ccgggcccgc gcggccaatc ggcgcattga gatgcaaata agcggctata 61 aaggggcgg accgcggcg ggccggaagc cgcgaggagc gcggacggct gggctgctgc 121 tgggcggccg cggggcagcg gagggcgccg gcactccggt ccccgccgct ccccgtcccc 181 gctgctccta gccctgccg cgtcccggc ggagcgggca tggcgccacc cgcggcgcct 241 ggccgggacc gtgtgggccg tgaggatgag gacggctggg agacgcgagg ggaccgcaag 301 gcccggaagc ccctggtgga aagaagcgg cgcgcgcgga tcaacgagag cctgcaggag 361 ctgcggctgc tgctggcggg cgccgaggcc aagctggaga acgccgaagt gctggagctg 421 acggtgcggc gggtccaggg tgtgctgcgg ggccgggcgc gcgagcgcga gcagctgcag 481 gcggaagcga gcgagcgctt cgctgccggc tacatccagt gcatgcacga ggtgcacacg 541 ttcgtgtcca cgtgccaggc catcgacgct accgtcgctg ccgagctcct gaaccatctg 601 ctcgagtcca tgccgctgcg tgagggcagc agcttccagg atctgctggg ggacgccctg 661 gcggggccac ctagagcccc tggacggagt ggctggcctg cggggggcgc tccgggatcc 721 ccaatacca gcccccggg tcctggggac gacctgtgct ccgacctgga ggagcccct 781 gaggctgaac tgagtcaggc tcctgctgag gggcccgact ggtgcccgc agccctgggc 841 agcctgacca cagcccaaat tgcccggagt gtctggaggc cttggtgacc aatgccagcc 901 agagtcctgc gggggtgggc ccggcccctcc ctggatctcc tcctcctcc caggggttca 961 gatgtggtgg ggtagggccc tggaagtctc ccaggtcttc cctccctcct ctgatggatg 1021 gcttgcaggg cagccctctg taaccagccc agtcaggccc cagccccgtt tcttaagaaa 1081 cttttaggga ccctgcagct ctggagtggg tgagggagg gagctacggg caggaggaag 1141 aattttgtag agctgccagc gctctcccag gttcacccac ccaggcttca ccagccctgt 1201 gcgggctctg ggggcagagg tggcagaaat ggtgctgggc actagtgttc caggcagccc 1261 tgggctaaac aaaagcttga acttgccact tcagcgggga gatgagaggc aggtgcactg 1321 agctgcactg cccagagctg tgatgctctg tacatcttgt ttgtagcaca cttgagtttg 1381 tgtattccat tgacatcaaa tgtgacaatt ttactaaata aagaatttg gagttagtta 1441 cccttgaaaa aaaaaaaaaa aaaa
```

SEQ ID NO: 43-HES6, isoform c
Protein sequence:
```
       1 mappaapgrd rvgrededgw etrgdrkark plvekkrrar ineslqelrl llagaevqak 61 lenaevlelt sasscrrkra saslpatssa ctrctrscpr arpstlpslp ss
```

SEQ ID NO: 44-HES6, isoform c
mRNA sequence:
```
       1 gtcggccgcc ccgggcccgc gcggccaatc ggcgcattga gatgcaaata agcggctata 61 aaggggcgg accgcggcg ggccggaagc cgcgaggagc gcggacggct gggctgctgc
```

```
121  tgggcggccg cggggcagcg gagggcgccg gcactccggt ccccgccgct ccccgtcccc 181  gctgctccta gccctgccg cgtccccggc ggagcgggca tggcgccacc cgcggcgcct 241  ggccgggacc gtgtgggccg tgaggatgag gacggctggg agacgcgagg ggaccgcaag 301  gcccggaagc ccctggtgga aagaagcgg cgcgcgcgga tcaacgagag cctgcaggag 361  ctgcggctgc tgctggcggg cgccgaggtg caggccaagc tggagaacgc cgaagtgctg 421  gagctgacga gcgcgagcag ctgcaggcgg aagcgagcga gcgcttcgct gccggctaca 481  tccagtgcat gcacgaggtg cacacgttcg tgtccacgtg ccaggccatc gacgctaccg 541  tcgctgccga gctcctgaac catctgctcg agtccatgcc gctgcgtgag ggcagcagct 601  tccaggatct gctggggac gccctggcgg ggccacctag agccctgga cggagtggct 661  ggcctgcggg gggcgctccg ggatccccaa tacccagccc cccgggtcct ggggacgacc 721  tgtgctccga cctggaggag gcccctgagg ctgaactgag tcaggctcct gctgaggggc 781  ccgacttggt gcccgcagcc ctgggcagcc tgaccacagc ccaaattgcc cggagtgtct 841  ggaggccttg gtgaccaatg ccagccagag tcctgcgggg gtgggcccgg ccctccctgg 901  atctcctccc tcctcccagg ggttcagatg tggtgggta gggccctgga agtctcccag 961  gtcttccctc cctcctctga tggatggctt gcagggcagc ccctggtaac cagcccagtc 1021 aggccccagc cccgtttctt aagaaactt tagggaccct gcagctctgg agtgggtgga 1081 gggagggagc tacgggcagg aggaagaatt ttgtagagct gccagcgctc tcccaggttc 1141 acccacccag gcttcaccag ccctgtgcgg gctctggggg cagaggtggc agaaatggtg 1201 ctgggcacta gtgttccagg cagccctggg ctaaacaaaa gcttgaactt gccacttcag 1261 cggggagatg agaggcaggt gcactgagct gcactgccca gagctgtgat gctctgtaca 1321 tcttgtttgt agcacacttg agtttgtgta ttccattgac atcaaatgtg acaattttac 1381 taaataaaga attttggagt tagttacccct tgaaaaaaaa aaaaaaaaaa
```

Many modifications and other embodiments of the inventions set forth herein will come to mind to one skilled in the art to which the inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating a subject with a glioma comprising administering a composition comprising a nucleic acid inhibitor that specifically targets at least one cancer factor comprising NKX6.2.

2. A method of treating a subject with a glioma comprising administering a composition comprising a nucleic inhibitor that specifically targets at least one cancer factor selected from the group consisting of BASP1, NKX6.2, and STOX2 and a nucleic acid inhibitor that specifically targets at least one stemness factor selected from SOX8, HES6, and ASCL1, and wherein the composition comprises nucleic acid inhibitors that specifically target each of BASP1, NKX6.2, MYCN, and ASCL1.

3. The method of claim 2, wherein the composition further comprises nucleic acid inhibitors that specifically target each of SOX8 and OLIG2.

4. The method of claim 3, wherein the composition further comprises nucleic acid inhibitors that specifically target each of STOX2 and HES6.

5. A method of inhibiting a glioblastoma stem-like cell (GSC) by introducing a composition that comprises a nucleic acid inhibitor that specifically targets at least one cancer factor comprising NKX6.2 into the GSC.

6. A method of inhibiting a glioblastoma stem-like cell (GSC) by introducing a composition that comprises a nucleic acid inhibitor that specifically targets at least one cancer factor and a nucleic acid inhibitor that specifically targets at least one stemness factor into the GSC, wherein the at least one stemness factor is selected from SOX8, HES6, and ASCL, and wherein the composition comprises nucleic acid inhibitors that specifically target each of BASP1, NKX6.2, MYCN, and ASCL1.

7. The method of claim 6, wherein the composition further comprises nucleic acid inhibitors that specifically target each of SOX8 and OLIG2.

8. The method of claim 7, wherein the composition further comprising nucleic acid inhibitors that specifically target each of STOX2 and HES6.

9. A method of inhibiting a glioblastoma stem-like cell (GSC) by introducing a composition that comprises a nucleic acid inhibitor that specifically targets at least one cancer factor and a nucleic acid inhibitor that specifically targets at least one stemness factor into the GSC, wherein the cancer factor is selected from the group consisting of BASP1, NKX6.2, and STOX2, and the stemness factor is selected from the group consisting of SOX8, HES6, and ASCL1, and wherein the nucleic acid inhibitor that specifically targets the cancer factor is an antisense molecule that targets a nucleic acid molecule having the sequence of any of SEQ ID NOs: 2, 4, 6, 8, 10, 12, 22, 24, 26 and 28, or a fragment thereof.

10. A method of inhibiting a glioblastoma stem-like cell (GSC) by introducing a composition that comprises a nucleic acid inhibitor that specifically targets at least one cancer factor and a nucleic acid inhibitor that targets at least one stemness factor into the GSC, wherein the cancer factor is selected from the group consisting of BASP1, NKX6.2, and STOX2, and the stemness factor is selected from the group consisting of SOX8, HES6, and ASCL1, and wherein the nucleic acid inhibitor that specifically targets the stemness factor is an antisense molecule that targets a nucleic acid molecule having the sequence of any of SEQ ID NOs: 14, 16, 40, 42 and 44, or a fragment thereof.

* * * * *

SEQUENCE LISTING

```
<160> NUMBER OF SEQ ID NOS: 44

<210> SEQ ID NO 1
<211> LENGTH: 926
<212> TYPE: PRT
<213> ORGANISM: Artificial Sequence
<220> FEATURE:
<223> OTHER INFORMATION: Synthetic

<400> SEQUENCE: 1

Met Lys Lys Thr Arg Ser Thr Thr Leu Arg Arg Ala Trp Pro Ser Ser
1               5                   10                  15

Asp Phe Ser Asp Arg Ala Ser Asp Arg Met Arg Ser Arg Ser Glu Lys
            20                  25                  30

Asp Tyr Arg Leu His Lys Arg Phe Pro Ala Ala Phe Ala Pro Gln Ala
        35                  40                  45
```

-continued

```
Ser Arg Gly Tyr Met Thr Ser Gly Asp Val Ser Pro Ile Ser Met Ser
 50                  55                  60

Pro Ile Ser Gln Ser Gln Phe Ile Pro Leu Gly Glu Ile Leu Cys Leu
 65                  70                  75                  80

Ala Ile Ser Ala Met Asn Ser Ala Arg Lys Pro Val Thr Gln Glu Ala
                 85                  90                  95

Leu Met Glu His Leu Thr Thr Cys Phe Pro Gly Val Pro Thr Pro Ser
            100                 105                 110

Gln Glu Ile Leu Arg His Thr Leu Asn Thr Leu Val Arg Glu Arg Lys
        115                 120                 125

Ile Tyr Pro Thr Pro Asp Gly Tyr Phe Ile Val Thr Pro Gln Thr Tyr
130                 135                 140

Phe Ile Thr Pro Ser Leu Ile Arg Thr Asn Ser Lys Trp Tyr His Leu
145                 150                 155                 160

Asp Glu Arg Ile Pro Asp Arg Ser Gln Cys Thr Ser Pro Gln Pro Gly
                165                 170                 175

Thr Ile Thr Pro Ser Ala Ser Gly Cys Val Arg Glu Arg Thr Leu Pro
            180                 185                 190

Arg Asn His Cys Asp Ser Cys His Cys Cys Arg Glu Asp Val His Ser
        195                 200                 205

Thr His Ala Pro Thr Leu Gln Arg Lys Ser Ala Lys Asp Cys Lys Asp
210                 215                 220

Pro Tyr Cys Pro Pro Ser Leu Cys Gln Val Pro Pro Thr Glu Lys Ser
225                 230                 235                 240

Lys Ser Thr Val Asn Phe Ser Tyr Lys Thr Glu Thr Leu Ser Lys Pro
                245                 250                 255

Lys Asp Ser Glu Lys Gln Ser Lys Lys Phe Gly Leu Lys Leu Phe Arg
            260                 265                 270

Leu Ser Phe Lys Lys Asp Lys Thr Lys Gln Leu Ala Asn Phe Ser Ala
        275                 280                 285

Gln Phe Pro Pro Glu Glu Trp Pro Leu Arg Asp Glu Asp Thr Pro Ala
290                 295                 300

Thr Ile Pro Arg Glu Val Glu Met Glu Ile Ile Arg Arg Ile Asn Pro
305                 310                 315                 320

Asp Leu Thr Val Glu Asn Val Met Arg His Thr Ala Leu Met Lys Lys
                325                 330                 335

Leu Glu Glu Glu Lys Ala Gln Arg Ser Lys Ala Gly Ser Ser Ala His
            340                 345                 350

His Ser Gly Arg Ser Lys Lys Ser Arg Thr His Arg Lys Ser His Gly
        355                 360                 365

Lys Ser Arg Ser His Ser Lys Thr Arg Val Ser Lys Gly Asp Pro Ser
370                 375                 380

Asp Gly Ser His Leu Asp Ile Pro Ala Glu Arg Glu Tyr Asp Phe Cys
385                 390                 395                 400

Asp Pro Leu Thr Arg Val Pro Arg Glu Gly Cys Phe Ile Ile Glu His
                405                 410                 415

Lys Gly Asp Asn Phe Ile Met His Ser Asn Thr Asn Val Leu Glu Ser
            420                 425                 430

His Phe Pro Met Thr Pro Glu Trp Asp Val Ser Gly Glu Leu Ala Lys
        435                 440                 445

Arg Arg Thr Glu Met Pro Phe Pro Glu Pro Ser Arg Gly Ser Ser His
450                 455                 460

Ser Lys Val His Arg Ser His Ser His Thr Gln Asp Arg Arg Ser Arg
```

-continued

```
            465                 470                 475                 480
Asn Glu Arg Ser Asn Lys Ala Lys Glu Arg Ser Arg Ser Met Asp Asn
                    485                 490                 495
Ser Lys Gly Pro Leu Gly Ala Ser Ser Leu Gly Thr Pro Glu Asp Leu
                500                 505                 510
Ala Glu Gly Cys Ser Gln Asp Gln Thr Pro Ser Gln Ser Tyr Ile
            515                 520                 525
Asp Asp Ser Thr Leu Arg Pro Ala Gln Thr Val Ser Leu Gln Arg Ala
        530                 535                 540
His Ile Ser Ser Thr Ser Tyr Lys Glu Val Cys Ile Pro Glu Ile Val
545                 550                 555                 560
Ser Gly Ser Lys Glu Pro Ser Ser Ala Cys Ser Leu Leu Glu Pro Gly
                565                 570                 575
Lys Pro Pro Glu Ser Leu Pro Ser Tyr Gly Glu Leu Asn Ser Cys Pro
                580                 585                 590
Thr Lys Thr Ala Thr Asp Asp Tyr Phe Gln Cys Asn Thr Ser Ser Glu
            595                 600                 605
Thr Val Leu Thr Ala Pro Ser Pro Leu Gly Lys Asn Lys Glu Asp His
        610                 615                 620
Asp Thr Leu Thr Leu Ala Glu Gly Val Lys Lys Leu Ser Pro Ser Asp
625                 630                 635                 640
Arg Gln Val Pro His Ser Ser Arg Glu Pro Val Gly His Lys Glu Glu
                645                 650                 655
Ser Pro Lys Gly Pro Gly Gly Pro Ala Ser Gly Gly Val Ala
                660                 665                 670
Glu Gly Ile Ala Asn Gly Arg Leu Val Gln His His Gly Ala Glu Pro
            675                 680                 685
Ser Ser Leu Asp Lys Arg Lys Glu Ile Phe Ser Lys Asp Thr Leu Phe
        690                 695                 700
Lys Pro Leu His Ser Thr Leu Ser Val Asn Ser Tyr His Lys Ser Ser
705                 710                 715                 720
Leu Ser Leu Leu Lys Ser His Pro Lys Thr Pro Ala Asp Thr Leu Pro
                725                 730                 735
Gly Arg Cys Glu Lys Leu Glu Pro Ser Leu Gly Thr Ser Ala Ala Gln
                740                 745                 750
Ala Met Pro Ala Ser Gln Arg Gln Gln Glu Ser Gly Gly Asn Gln Glu
            755                 760                 765
Ala Ser Phe Asp Tyr Tyr Asn Val Ser Asp Asp Asp Ser Glu Glu
        770                 775                 780
Gly Ala Asn Lys Asn Thr Glu Glu Lys Asn Arg Glu Asp Val Gly
785                 790                 795                 800
Thr Met Gln Trp Leu Leu Glu Arg Glu Lys Glu Arg Asp Leu Gln Arg
                805                 810                 815
Lys Phe Glu Lys Asn Leu Thr Leu Leu Ala Pro Lys Glu Thr Asp Ser
                820                 825                 830
Ser Ser Asn Gln Arg Ala Thr His Ser Ala Arg Leu Asp Ser Met Asp
            835                 840                 845
Ser Ser Ser Ile Thr Val Asp Ser Gly Phe Asn Ser Pro Arg Thr Arg
        850                 855                 860
Glu Ser Leu Ala Ser Asn Thr Ser Ser Ile Val Glu Ser Asn Arg Arg
865                 870                 875                 880
Gln Asn Pro Ala Leu Ser Pro Ala His Gly Gly Ala Gly Pro Ala Phe
                885                 890                 895
```

```
Asn Phe Arg Ala Ser Ala Glu Pro Pro Thr Asn Glu Ala Glu Lys Leu
            900                 905                 910

Gln Lys Pro Ser Asn Cys Leu Gln Ala Ser Val Thr Ser Val
            915                 920                 925

<210> SEQ ID NO 2
<211> LENGTH: 10474
<212> TYPE: DNA
<213> ORGANISM: Artificial Sequence
<220> FEATURE:
<223> OTHER INFORMATION: Synthetic

<400> SEQUENCE: 2
gcagcgtagc gggctggcgg tgacttacac cgggactcca gagggagaga ggaagcgctg     60
caggccactt gcattgcgtc ttccaggctg cgtggacccg cgcccccggc gtgtgcggtt    120 gtggggagc tcgccgtggc ctcccctccc tctggcttta gcttcctttg gggttggcgc    180
aggtgggcca gcagcgcac cgcagatctc cccgttccca cgaaggctgg ctcgctgtct    240
ctctccgagc gggagggacc atcctaaaaa tatgtaaata tccaagcgct ggctccaggc    300
tggggcagct gccaaggtcc ccgcgccgcc gccgggtgtt ttacatgaaa atgagaagcc    360
tgatgggaac cgcgttctaa cttaaggcag cctggtgatt agcatgagac tgggcggctg    420
tcctgcttcc tgcccttcaa tagccgttcc gcgcgctcgc gccggagcag cgctgccgcc    480 gcgcggggt cgatcgcagg ctcggcgtcc ttggcagcca tggctccggc gccgcctcgg    540
ccagtaagta ggagcatgca tgtgtagggg gcacatgcgt gtcggcgcac ccacccagcc    600
atccacccgc gcgcacgcac agcgcccgga gcctcggcaa ggggaagatt gacgaggcgc    660
tgcagtcgcg gggacgacgc gggctcttcc tggattccgc aggagcccgc ccgccgcagc    720
tgctgtctgc agagcctgct cggatcctgt gcacacgcgc ccccgctcg agcctctgtg    780 atgaagactg tctcccgggg actgcagcgg aggcagagcc agccagcgcc ggggactgcg    840
ggccgtgcgg ctgataggcc cgcggggaca cgactcggac actgtcatcc ccacgcctcg    900
cgctgagctg cccggcgcgg agggtctgcc gccgccccct cggcctcccg cacgcccgat    960
cccgggtcag ccccggaggc ctcggctgcc tcatttgttt gggtcttttg tgccgtggct   1020
cccagttggc caagcactcc tgcgctgaat cgggccattg tctgcgctcc cattgccttc   1080
acgctgcaag tctcggcgcc cccacccgc ccgccccctc ccgcctcct ccggccggg    1140 gagcctccta acgtgccttt cccccagga atctggaagc tataagccgg gcggattgca   1200
aatgaagtgt aatgcattgt gggacgtgtg taaaatcgga gccttcgccg tggggtgtg    1260 ggggggcgtg gggagggccg gacccgccgc tggcggtgta gacgccgacg aggagggct    1320 gggaaaatgt gcgcagagtc cgcccgggtc gtgcccgccg tagacggatg aaggagcgcg   1380
ctgcgccccg gcgctgaggc cccgaggatc ggggcggcag gtcgccctcc ccaccatgaa   1440
gaagacccgg agcacaacct gcggcgagc ctggcctagc tcggatttct cggacccgggc  1500 ctcggaccgc atgaggtccc gcagcgagaa ggactaccgc ctgcacaagc gtttccccgc   1560
ggccttcgcg ccccaggctt cgcggggcta catgacatca ggtgatgtat cacccatcag   1620
tatgtctccc atcagtcagt ctcagtttat ccactcgggg gagatcctct gcttggccat   1680
ctcagcaatg aactcggcaa gaaagcctgt cacccaagaa gcactgatgg agcacctgac   1740
cacgtgcttc ccaggtgttc caacgccaag ccaagaaatt ctgcggcaca cgctgaacac   1800
gctggtacgg gagaggaaga tctacccaac tccagatggc tacttcatcg tgaccccaca   1860
```

```
gacttatttc ataactcctt ccctcataag aactaacagt aaatggtacc atttggacga   1920
gaggatacct gaccggtctc agtgcacctc tccgcaaccc gggaccatca cgccctctgc   1980
ctcaggctgt gtcagggaaa ggacattgcc ccgaaaccac tgcgactctt gccactgctg   2040
cagagaagac gtgcacagca cgcatgcacc caccctgcaa aggaagtctg ccaaggactg   2100
caaagaccct tactgtcccc cttctctgtg ccaggtgcca cccactgaaa agagcaaaag   2160
tactgtaaat ttttcctata agacagaaac tctctcaaaa cctaaagata gtgaaaagca   2220
gtcaaaaaaa ttcgggctaa agttattccg gttaagtttt aaaaaagaca agaccaaaca   2280
gctggccaat ttttctgccc agtttcctcc tgaagagtgg ccctgcgag acgaggacac    2340 gccagctacg atccctcggg aagtagagat ggaaatcatt aggcgcatta cccagacct    2400 gaccgtggaa aatgtcatgc ggcacaccgc gctcatgaag aaactggaag aagaaaaggc   2460
ccagaggagt aaagccgggt cctctgccca tcacagcgga aggagtaaaa agagtaggac   2520
tcatcggaag tcccatggaa agtctcggtc tcacagcaag acacgggtgt ctaaaggaga   2580
cccttccgac ggttcacatc tggatatccc agctgaaaga gagtatgact tttgtgatcc   2640
tcttaccagg gtgcccaggg agggctgctt catcattgaa cacaaaggag ataacttcat   2700
catgcacagc aacacaaacg tgctcgagtc ccacttcccc atgacaccag aatgggatgt   2760
gtctggtgaa ttggctaaaa ggagaactga gatgccttt cctgaacctt ctaggggaag    2820
ctcccactca aaagtgcacc gaagcccacg ccatacacag gaccggaggt ccaggaatga   2880
gagatccaac aaagccaagg agagatccag gtcgatggat aactccaaag ccctctggg    2940 tgcttcttct ctaggacgc cggaagacct tgctgaaggc tgcagccaag acgaccagac    3000
ccccagccaa tcctacattg acgacagtac tttaaggcct gcacagaccg ttagtctcca   3060
aagggctcac atttcgtcca caagctataa agaggtgtgt attccagaga tagtcagtgg   3120
cagcaaggaa ccgtccagcg cttgcagcct tttggagcca ggaaaaccac ccgagagttt   3180
gccatcctat ggcgaactca actcttgtcc aacaaaaaca gccacagatg actatttcca   3240
gtgcaacacc tctagtgaga cggtgctcac ggcaccatca cctctgggaa agaataagga   3300
ggaccatgac actctgactt tggcagaagg ggtgaaaaag ctctccccctt ctgataggca   3360 ggtcccccac tcctccaggg agcctgtggg gcacaaggag gagtcaccaa aagggccggg   3420
tgggggcccc gctgcttcgg gaggagtggc tgaagggatc gccaacggac gcctcgtcca   3480
gcaccatggt gccgagccca gcagcttgga caagaggaaa gagatattta gcaaagacac   3540
actgttcaaa cctcttcaca gcaccttgtc tgtaaacagc tatcacaagt cgagcctgtc   3600
cctcctcaaa tctcacccga agacacctgc tgacacattg ccaggccgat gtgagaaact   3660
ggaaccgtcc ctgggacct cggcggcaca agccatgcct gcttcccagc gtcagcagga    3720
gtcaggaggg aaccaggaag cctctttga ctattacaac gtctctgatg atgacgactc    3780
tgaggaaggg gcaaacaaga acacagagga ggagaaaaat agagaggacg taggcaccat   3840
gcagtggctc ctcgagcggg agaaggaaag agacttgcag aggaaatttg aaaagaacct   3900 caccccttctt gctccaaaag aaaccgacag cagcagcaac cagagagcca cccattcagc   3960
ccggctcgac agcatggaca gcagcagcat cacagtggac agtggattca actccccacg   4020
tactcgggag agcctggctt ccaacacatc aagcattgtt gaaagtaacc gtcgtcagaa   4080
ccccgctttg agcccggccc atggtggagc tggtccagcc ttcaacttcc gagcgagcgc   4140
ggagcccccg acaaatgaag ctgagaagct acagaaacct tccaactgct tgcaagcttc   4200
tgttactagc gtgtgattgt ccttctgcct cagatcttct gtctcattcg atacagcaaa   4260
```

-continued

```
gtttacgaca ctgggactga tgtttacatc tttggaaaga caagcatctc aaccacagtt    4320
tttgtgttta cttaaactgt gctgctaagt agggctaggg caaaaaaaca aaaaatcttt    4380
atttcagagt attgcttttc acatttatgg ctctgtagca actgagtaac agtagggtg     4440 atatgtatac ttttgcttca ctaattgtat ctgagcacac ataggaaagt ctagacactg    4500
taagtgtaat acgcattttc aatgtcatgc agttgccaat tccattttaa aatgccacag    4560
atgcgtgttg ctcccagtct gtggttaaac ggtgccacag aactgatcct tgacacttcc    4620
aaaaaaaaaa aaacaaaaca aaacaaaaaa aatttaaaaa aaaaaaacaa aaaacaaaac    4680
taagctacca cgaaatgtca aatgcaaggg tccaccttga gggaaataga tgccaaacta    4740
actagaaggg accccggccc tttgtgtgtg aattgtttat gcaccagtca tttttcactg    4800
tgagttttcg tgacactatt ttgcaggagc ccatggaagt gtgtgagaag gggtcgcaat    4860
ggagatcact gggagtgaat gttttcaggg ttttgttttg aagtgtcaca gatgcttgtc    4920
tgattttttt aaccttccgt gatcacaaac aggaatatag gcctttgaat ctgaagtgga    4980
caaaggaaag caatttccag tctggctggg gcacagcatt aggtgattga aaaggtgatg    5040
tggacttgta aaggtgtta ctcaaatatt gaaggaagag aatttcctcc ttgtgatact     5100
taggatgacc ctatcttact ctaatagata caataattag tttgtttaaa agcaaaatgt    5160
tctttgtgat acaaatgaag agtagggcct gaggatgtta ttctttctaa tggaaggaca    5220
taaatctatt ttatgtagtt ttaaatagaa tgcctaaatt aggctgtggg agataatttt    5280
tagtggttgt aggaaagagc aaatttaggg agtgttgaac ttcaggcctt ttattcctgg    5340
gaagatatgt atagagaaaa cttttaaaat aattttttgat tagaaatata catgtgccca    5400
tgtaataaac aacagaatgt gctcattctg ctagtgcggt ataatccgaa tttgtactcc    5460
cctaaaattt atcagaataa caattatgca tacatgaact atgccagagt aatgtttaca    5520
gatactttgt aaccaatttc aggaggcgtt tttagctgga tgtgtagtta attagaccaa    5580
cttatttcca aatggtttgt taacattttg ctttggttta caatgtcatg ttgaacacaa    5640
agaagaccca gcagcaaagg gatgaccaat aatttcatct tatagcaagg agacattcca    5700
acgttcccat gtttttatttt ctgagaacag tgggacagat ctgtagtaat ggaatattat    5760
ttgcaaaagg gttacatatg acacaagtaa gtgttctgac ataaagtttt atttagttca    5820
gtggcatgtg ctgttgggag ccatacacca taaaatatat atatcccaaa ataaatctag    5880 aatatttttca cctccaattt cagtaattgg catatgattt tgtgagacgca tctgtttttg    5940 tatgaggttt aatcactagc aatctgttta aagaatccag tcctatacac agttggactc    6000
attcttgaaa cctttaaatg ctccctcata gttttcagt tatttggaag ttgcattggg     6060
tcaaactgaa ctccttgagt ttggtgtaaa ttccttttt ctgcttatta tagtgaaact     6120
tcagcatgtt tcttagtaaa ctcccatacc attgaaatgc ttaagccagt tggctttcag    6180
tctcatgcct tatttcctcc aaggcatgcc tcaacgcatt gtttgtctca ttgcttaaat    6240
atgtccagaa ggaatgatca tgtatctaat agactacata gttggttccc ttggggagtt    6300
atatatcata cagttactaa atatttgtct aaattcattt tttccaaaaa cctgctctca    6360 aattttttctt ctactctcag ttcataaata atataaccat tgaaacaaca catcagcctc   6420
tagctgatcc tctgaaagta gccattgaaa taatcgaata ctgtgtgaac aggaaaggaa    6480
agcgttacct ttaagagaag ctttaaaata ggaatttatt gatatttcac aagatatagg    6540
tttacagaag acattattca aataaatatg tacactattt gcctgatgct atggggtaca    6600
```

```
taatttttta aaaactccct tagaccagca gccattagtg tagaaatgat ggactttaaa    6660
ggtgatacca tgtaagcaga tgttgcatat aaaaatattc ctgcctgaat ctgatcgaga    6720
ttcttgaatg ggggaggagt ggcagccggc agcacattgc aaatgtcatt cgaggtcacg    6780
gtgaggctct cggtcccgga acagtggggg cctcgccagg cgttgccagt atccctttcc    6840
tcctgtaaaa tcatagcttt gtgttacacg actgcttatc cagtcttagg gtttagcagc    6900
tgaaaggttt acaaaactga atctggttga atctctgtga aagggtcaac acatctgtcg    6960
gcattttgca cacttatgta ttattatgat acaacatatt actttatggt aattttatt    7020
tttacatata actacctcca taaatttgat gaaatggcag ccgtgtgtta aagtgtatcg    7080
ttcagaagag caaagttgaa cacttccttc aacattaggg catggcgtgc tgtgtgtgtc    7140
agtgattgcc tctgtggact catgactttc catcgccatg gctttctctt acgccgctgt    7200
ttggctttca gatgtaatcc tgtcttctcc tctcttcccc acgaaagcgc actcgatttt    7260
gttaggaatg aacggaagtt taaaaattct tgtgcccacc cccgccctcc acccattcct    7320
gttaaaagtt ctctggcgaa gagccaatgg gtgaacgtaa ttgaaagagc tatttactct    7380
tttgaaaatc tgatttgaag tctaagtttt cagtaacaga agacacacaa gcaatgtgga    7440
ctgccaagct tgaagcactt cgggctctgc cttcactcgc atgctaccat gtcgagccca    7500
aactccactt taattaaaag agctgtgctg tgaattccac aacttctgtt aaataatttg    7560
tattccatta tatatatttt gcacatctca ggggaccata atgaacatat gaaggggggg    7620
ggggtgccat caaatagaga aaacaaatag aagaggtgaa tggagactag ctggataaaa    7680
ataacaaatt acttcttctc tgatgttgtg aaggtcaggt tcaggaagca tcaattcaca    7740
gttaatccgg agtaacaatg atctgaacac cagctgttcc caggtccctc ttttcatag     7800
cccaaccagc atctaaaatg taaatttaaa ttacattgca gtcaccatgg ggagaagaaa    7860
cctgttcagt ggaagcagaa gcattgttcc ttttttaggt tggcgcagct ttgcaaaact    7920
ctacccagga taaccactt atcaccacca agtgtacttg aaaataaagt ttttaactta     7980
aattacaagc atattgctca taatacaata gtgatcattt tttgaaagtc ttgccattta    8040
taacatggga agtatttgga gcttcattta aaaaccaaca acaaccgata atgactttgc    8100
acgattcact ttgggatctc aaagtgcttc caaagcattc agatttacaa acaattcaca    8160
agacaggtca tctttgtaat acgcatactt acaacgaatt aacaaaagga gtgacttaag    8220
attctccagg aacacagtgg cagctattga tgatctgttt tctatctgtt tgatagagca    8280
tcatgagaaa tcacaaaata caatgctatt tttctgatgt gtgctaataa agtcaaagaa    8340
aacaaataca tcttgacact tttgtccatt ttcattaaaa aaaaaaaagt tcagggtgtt    8400
tggaatttta catctcagca caccttactg gtatcaatgg ataaagcggg tgattgacag    8460
atccacccaa atgccactgc agtcagaagc agatctggac acacccttgt ttacagtttc    8520
atattgggtt gctatagttc ccgtgctaaa tcaccagctt tcaggaacat gactgctcct    8580
ggcagtggaa ggtgctgaaa cagaaatttt aattaaaaac tttatcaagt actcttcaca    8640
gtgctgcttg gcaccataga aaatcagtac aatatatcga gccctacttt ggaggagctg    8700
gatttctgag ggagctgatc cagttctaag tgtcttctcg aattaggaga tagatgatct    8760
ttgatgggga tctcctccgt caccacaggc cagtcacaga accaactagc cacgtgctgc    8820
cagacctcag tgggcccaag caggagcaat ctcttctatc cccatctccc cccaggacca    8880
tcccgcccat tgtcaacgtc atccaggggct cttctggtag tgagtgactt ttctgcacat    8940
gtttagggct tgggggagct agaacacagg aaacatgaat gcaaaaggca tggaaaacac    9000
```

```
tgttttgctt tgggttagta aatgtgggc aggacaaaga ttactattgg tctgagcttt    9060
gccaagtgag atagaatcaa ctgtcacccc attcctttcc cagaaggtct tatggtatta   9120
aggatacatc cagtatttc ccacagattt ttattcaggc gatgtttcat aaattacata    9180
tatgaaaaca ttcattatta catttccttg tgtgtttcaa acagacattg gcaccttcct   9240
attgagttaa ttctctgcat cttttgcagc agcagcccac aaggagattc ccagagatgg   9300
ctcccctaac acacagtcct gtgattttac agttctatga cttacagttg atgattcaca   9360
agattcagga ttctacaaga ctcaaggggg aactaaactt tcttacgatt gtacatgatc   9420
agttataggg ctgtaatcat taattgttgg cttcaaatgt ggacacacac acacacacat   9480
catgccaagg agggaatggg gtgtttcaag tcaggcagcg atgattctgg aaggttggaa   9540
atgtaaggtt agaagcttgg ctggtcttag taaacttgtt cccttgctcc caccaagaag   9600
aggtaccaaa tgtgagacct gagatctcct ccaatatctg tcctctgcag ttccgggaaa   9660
ctaatcatga agtacacatg cagcagctcc tccacttcct ttcctccgag gtcctccttt   9720
ccattctccc acctagatac tgacacaccg ccacggtttc cacattggaa gggcagaaca   9780
ctgtgcagta tcgtgcacac ttgctgggtt aggaatagag ctgccctagg gtcaccttca   9840
tgcaagtatt gacagctaca aattaaagtc cttagagcag ttgacacaga tactacgttc   9900
tagaagagaa ttaaatttaa acgtcaagtt taaagggatc ataattctgc aggtatcttt   9960
ctctgagtga ctgaatgtga ctattgcatt agggtaaatg aattaagacg tgcaagtggg   10020
atttactgta tgttagaaag gagttttgca gccaagactg ccttgaataa aatgtgtttg   10080
cactgaaaaa aaattttaaa ttacttggtc tctggttgct gtaaaggtca tccaagatgg   10140
atgttctgtt tatattgtat agtatttcat atgaaataat tacagttcat gaaatgtctt   10200
ccctaatgtt actgatttat aacagcacat ttgtaacatg gttttttatcg tgtcagtgta   10260
ccatactgta aatgatgatt acttgtcatg cttagtataa taacttaaaa gaaaaaaaag   10320
gacagggatt tttgtaagtc tatatttgaa agtccctccc tatggtgata ctgtgttcat   10380
gttgtttatg tagtgttgtg tgaaatatcc attttggatt gtgttacttt ttaagatatt   10440
aaataacatt tggttatatg tcaaaaaaaa aaaa                               10474
```

<210> SEQ ID NO 3
<211> LENGTH: 992
<212> TYPE: PRT
<213> ORGANISM: Artificial Sequence
<220> FEATURE:
<223> OTHER INFORMATION: Synthetic

<400> SEQUENCE: 3

```
Met Pro Gly Lys Met Glu Lys Phe Leu Gln Ile Ala Pro His Ser Leu
1               5                   10                  15

Ala Ile Val Leu Gly Pro Ala Glu Ala Pro Ala Gly Glu Arg Pro Gly
            20                  25                  30

Ala Ala Arg Pro Ala Pro Ala Gln Pro Arg Gln Leu Ala Arg His
        35                  40                  45

His Ile Gly Tyr Glu Ile Phe Ala Asp Phe Lys Ala Glu Asn Met Gln
    50                  55                  60

His Phe Trp Asn Lys Lys Val Thr Ala Val Ala Glu Thr Phe Phe
65                  70                  75                  80

Leu Gly Trp Ile Asp Glu Gln Val Leu Leu Ile Gln Gly Lys Glu Glu
                85                  90                  95
```

```
His Leu Glu Ala Leu Arg Glu Gly Trp Thr Arg Arg Ala Leu Arg Pro
                100                 105                 110

Pro Ser Gly Phe His Ile Arg Cys Leu Gly Asp Val Ser Pro Ile Ser
            115                 120                 125

Met Ser Pro Ile Ser Gln Ser Gln Phe Ile Pro Leu Gly Glu Ile Leu
    130                 135                 140

Cys Leu Ala Ile Ser Ala Met Asn Ser Ala Arg Lys Pro Val Thr Gln
145                 150                 155                 160

Glu Ala Leu Met Glu His Leu Thr Thr Cys Phe Pro Gly Val Pro Thr
                165                 170                 175

Pro Ser Gln Glu Ile Leu Arg His Thr Leu Asn Thr Leu Val Arg Glu
            180                 185                 190

Arg Lys Ile Tyr Pro Thr Pro Asp Gly Tyr Phe Ile Val Thr Pro Gln
        195                 200                 205

Thr Tyr Phe Ile Thr Pro Ser Leu Ile Arg Thr Asn Ser Lys Trp Tyr
    210                 215                 220

His Leu Asp Glu Arg Ile Pro Asp Arg Ser Gln Cys Thr Ser Pro Gln
225                 230                 235                 240

Pro Gly Thr Ile Thr Pro Ser Ala Ser Gly Cys Val Arg Glu Arg Thr
                245                 250                 255

Leu Pro Arg Asn His Cys Asp Ser Cys His Cys Cys Arg Glu Asp Val
            260                 265                 270

His Ser Thr His Ala Pro Thr Leu Gln Arg Lys Ser Ala Lys Asp Cys
        275                 280                 285

Lys Asp Pro Tyr Cys Pro Pro Ser Leu Cys Gln Val Pro Pro Thr Glu
290                 295                 300

Lys Ser Lys Ser Thr Val Asn Phe Ser Tyr Lys Thr Glu Thr Leu Ser
305                 310                 315                 320

Lys Pro Lys Asp Ser Glu Lys Gln Ser Lys Lys Phe Gly Leu Lys Leu
                325                 330                 335

Phe Arg Leu Ser Phe Lys Lys Asp Lys Thr Lys Gln Leu Ala Asn Phe
            340                 345                 350

Ser Ala Gln Phe Pro Pro Glu Glu Trp Pro Leu Arg Asp Glu Asp Thr
        355                 360                 365

Pro Ala Thr Ile Pro Arg Glu Val Glu Met Glu Ile Ile Arg Arg Ile
    370                 375                 380

Asn Pro Asp Leu Thr Val Glu Asn Val Met Arg His Thr Ala Leu Met
385                 390                 395                 400

Lys Lys Leu Glu Glu Lys Ala Gln Arg Ser Lys Ala Gly Ser Ser
                405                 410                 415

Ala His His Ser Gly Arg Ser Lys Ser Arg Thr His Arg Lys Ser
    420                 425                 430

His Gly Lys Ser Arg Ser His Ser Lys Thr Arg Val Ser Lys Gly Asp
        435                 440                 445

Pro Ser Asp Gly Ser His Leu Asp Ile Pro Ala Glu Arg Glu Tyr Asp
    450                 455                 460

Phe Cys Asp Pro Leu Thr Arg Val Pro Arg Glu Gly Cys Phe Ile Ile
465                 470                 475                 480

Glu His Lys Gly Asp Asn Phe Ile Met His Ser Asn Thr Asn Val Leu
                485                 490                 495

Glu Ser His Phe Pro Met Thr Pro Glu Trp Asp Val Ser Gly Glu Leu
            500                 505                 510

Ala Lys Arg Arg Thr Glu Met Pro Phe Pro Glu Pro Ser Arg Gly Ser
```

```
                515                 520                 525
Ser His Ser Lys Val His Arg Ser His Ser His Thr Gln Asp Arg Arg
530                 535                 540

Ser Arg Asn Glu Arg Ser Asn Lys Ala Lys Glu Arg Ser Arg Ser Met
545                 550                 555                 560

Asp Asn Ser Lys Gly Pro Leu Gly Ala Ser Leu Gly Thr Pro Glu
                565                 570                 575

Asp Leu Ala Glu Gly Cys Ser Gln Asp Gln Thr Pro Ser Gln Ser
                580                 585                 590

Tyr Ile Asp Asp Ser Thr Leu Arg Pro Ala Gln Thr Val Ser Leu Gln
                595                 600                 605

Arg Ala His Ile Ser Ser Thr Ser Tyr Lys Glu Val Cys Ile Pro Glu
610                 615                 620

Ile Val Ser Gly Ser Lys Glu Pro Ser Ser Ala Cys Ser Leu Leu Glu
625                 630                 635                 640

Pro Gly Lys Pro Pro Glu Ser Leu Pro Ser Tyr Gly Glu Leu Asn Ser
                645                 650                 655

Cys Pro Thr Lys Thr Ala Thr Asp Asp Tyr Phe Gln Cys Asn Thr Ser
                660                 665                 670

Ser Glu Thr Val Leu Thr Ala Pro Ser Pro Leu Gly Lys Asn Lys Glu
                675                 680                 685

Asp His Asp Thr Leu Thr Leu Ala Glu Gly Val Lys Lys Leu Ser Pro
690                 695                 700

Ser Asp Arg Gln Val Pro His Ser Ser Arg Glu Pro Val Gly His Lys
705                 710                 715                 720

Glu Glu Ser Pro Lys Gly Pro Gly Gly Pro Ala Ala Ser Gly Gly
                725                 730                 735

Val Ala Glu Gly Ile Ala Asn Gly Arg Leu Val Gln His His Gly Ala
                740                 745                 750

Glu Pro Ser Ser Leu Asp Lys Arg Lys Glu Ile Phe Ser Lys Asp Thr
                755                 760                 765

Leu Phe Lys Pro Leu His Ser Thr Leu Ser Val Asn Ser Tyr His Lys
                770                 775                 780

Ser Ser Leu Ser Leu Leu Lys Ser His Pro Lys Thr Pro Ala Asp Thr
785                 790                 795                 800

Leu Pro Gly Arg Cys Glu Lys Leu Glu Pro Ser Leu Gly Thr Ser Ala
                805                 810                 815

Ala Gln Ala Met Pro Ala Ser Gln Arg Gln Gln Glu Ser Gly Gly Asn
                820                 825                 830

Gln Glu Ala Ser Phe Asp Tyr Tyr Asn Val Ser Asp Asp Asp Ser
                835                 840                 845

Glu Glu Gly Ala Asn Lys Asn Thr Glu Glu Lys Asn Arg Glu Asp
                850                 855                 860

Val Gly Thr Met Gln Trp Leu Leu Glu Arg Glu Lys Glu Arg Asp Leu
865                 870                 875                 880

Gln Arg Lys Phe Glu Lys Asn Leu Thr Leu Leu Ala Pro Lys Glu Thr
                885                 890                 895

Asp Ser Ser Ser Asn Gln Arg Ala Thr His Ser Ala Arg Leu Asp Ser
                900                 905                 910

Met Asp Ser Ser Ile Thr Val Asp Ser Gly Phe Asn Ser Pro Arg
                915                 920                 925

Thr Arg Glu Ser Leu Ala Ser Asn Thr Ser Ser Ile Val Glu Ser Asn
                930                 935                 940
```

Arg Arg Gln Asn Pro Ala Leu Ser Pro Ala His Gly Gly Ala Gly Pro
945                 950                 955                 960

Ala Phe Asn Phe Arg Ala Ser Ala Glu Pro Pro Thr Asn Glu Ala Glu
            965                 970                 975

Lys Leu Gln Lys Pro Ser Asn Cys Leu Gln Ala Ser Val Thr Ser Val
        980                 985                 990

<210> SEQ ID NO 4
<211> LENGTH: 10582
<212> TYPE: DNA
<213> ORGANISM: Artificial Sequence
<220> FEATURE:
<223> OTHER INFORMATION: Synthetic

<400> SEQUENCE: 4

| | | | | | |
|---|---|---|---|---|---|
| acagtgagac | ctcgtctcaa | acacaaaaca | aacaaaaca | aaacaaaaca | aaccaaaaca | 60 |
| aaacaaaaca | aacacctcag | gtctttagac | ccgggtttag | tgactttttc | atgataataa | 120 |
| aatcacagga | cgccagcgga | aaacagttca | gttatttcta | ttccccaaaa | ctaggctgga | 180 |
| cattctgtgt | ttttcacggt | gtggtccgag | accaccagca | gcagcagtag | cagcagcatc | 240 |
| tgggaatttc | ttagaaattt | aaaaaaccgg | gttcctctag | acctactgaa | tcagaaactc | 300 |
| tgggaatggg | gcccagatac | ctgcgtttta | atacgtgttc | aggtgacggt | gatgcacgtt | 360 |
| gaaatttaaa | taccgctctg | ggtaaatgta | gcataactct | taatgcttct | tatgacaatc | 420 |
| atctcttttc | acatatgact | actagcctct | ctcgattaaa | atataagtca | tacagaattt | 480 |
| ggcacagaaa | caaacgtaag | gaattttctt | aaaagcatca | tcgttacctt | tcctggtaaa | 540 |
| tttctgtaac | ctcttcataa | accgagggtt | aatggttgat | tgggtttcct | ctagggtagg | 600 |
| ccaaagtata | tgctgaagac | aagagagtag | aattcctcaa | gagtttggga | ggagggactg | 660 |
| atgacaattt | ttggtggttg | actaagtttt | ttaaaaagcc | acttctaagg | gtacattcat | 720 |
| taaccagtca | gcgaatccac | ttgttccagc | gagaggtggg | aggtggggggc | aggggtggag | 780 |
| cgtggggagg | agcgacactc | gccgctccgg | aatccgtgcc | ttccaagtgt | cgccgttgcg | 840 |
| tcccccgcaa | ccccccgcttt | ctgatctccc | tcgaggccca | acacccaaag | gctcacccct | 900 |
| aggccatccg | cgctccccga | ccacctccct | cataggactc | cttgggattc | ctcaggccgc | 960 |
| gtccagccga | gggggttccc | gggcgcggtg | cgcactgccc | gcccctcac | tgcctcctcc | 1020 |
| cgcgtctccg | ccccccgcggg | gccgctgggc | gcccgggag | gcgagggtgc | cgaggccgga | 1080 |
| aaatgagcgc | tgcccgaagg | gtggcccgga | gctgcaggta | acgcggtcca | gagctcaggc | 1140 |
| cggagcgggc | cccgcacacc | gtcccttccc | cgcagcgacc | cgcgggctgc | gcccagggac | 1200 |
| tgcgccgggc | gccggggctg | cagggacgcg | ggcgcggggg | aggcgcggcc | agccctgccc | 1260 |
| tgggggacgg | tcgcgctccc | cgctggtctt | gcagccacgt | cccggcggct | gttcctggga | 1320 |
| gcggcgggag | gcggcctcgg | tgagccaggt | cggcgcggca | gatgcctggg | aagatggaga | 1380 |
| agtttctgca | gatcgcgcct | cactccctgg | ccatcgtcct | gggcccggca | gaggcgccgg | 1440 |
| cgggggaaag | gccaggggca | gcccggcccg | cgccccggc | ccagcccgc | cagctcgccc | 1500 |
| ggcaccacat | cggctacgag | atcttcgccg | acttcaaagc | cgagaacatg | cagcacttct | 1560 |
| ggaacaagaa | ggtcacggcc | gcggtggccg | agaccttctt | cctgggctgg | atcgacgagc | 1620 |
| aggtcctgct | gatccagggc | aaggaggaac | atctggaggc | gctgcgcgaa | ggctggacgc | 1680 |
| gccgggccct | gcggccgccc | tcgggcttcc | acatccgctg | cctgggtgat | gtatcaccca | 1740 |
| tcagtatgtc | tcccatcagt | cagtctcagt | ttattccact | cggggagatc | ctctgcttgg | 1800 |

-continued

```
ccatctcagc aatgaactcg gcaagaaagc ctgtcaccca agaagcactg atggagcacc    1860
tgaccacgtg cttcccaggt gttccaacgc caagccaaga aattctgcgg cacacgctga    1920
acacgctggt acgggagagg aagatctacc caactccaga tggctacttc atcgtgaccc    1980
cacagactta tttcataact ccttccctca taagaactaa cagtaaatgg taccatttgg    2040
acgagaggat acctgaccgg tctcagtgca cctctccgca acccgggacc atcacgccct    2100
ctgcctcagg ctgtgtcagg gaaaggacat tgccccgaaa ccactgcgac tcttgccact    2160
gctgcagaga agacgtgcac agcacgcatg cacccaccct gcaaaggaag tctgccaagg    2220
actgcaaaga cccttactgt cccccttctc tgtgccaggt gccacccact gaaaagagca    2280
aaagtactgt aaattttcc tataagacag aaactctctc aaaacctaaa gatagtgaaa     2340
agcagtcaaa aaaattcggg ctaaagttat tccggttaag ttttaaaaaa gacaagacca    2400
aacagctggc caattttct gcccagtttc ctcctgaaga gtggcccctg cgagacgagg     2460
acacgccagc tacgatccct cgggaagtag agatggaaat cattaggcgc attaacccag    2520
acctgaccgt ggaaaatgtc atgcggcaca ccgcgctcat gaagaaactg gaagaagaaa    2580
aggcccagag gagtaaagcc gggtcctctg cccatcacag cggaaggagt aaaaagagta    2640
ggactcatcg gaagtcccat ggaaagtctc ggtctcacag caagacacgg gtgtctaaag    2700
gagacccttc cgacggttca catctggata tcccagctga aagagagtat gacttttgtg    2760
atcctcttac cagggtgccc agggagggct gcttcatcat tgaacacaaa ggagataact    2820
tcatcatgca cagcaacaca aacgtgctcg agtcccactt ccccatgaca ccagaatggg    2880
atgtgtctgg tgaattggct aaaaggagaa ctgagatgcc ttttcctgaa ccttctaggg    2940
gaagctccca ctcaaaagtg caccgaagcc acagccatac acaggaccgg aggtccagga    3000
atgagagatc caacaaagcc aaggagagat ccaggtcgat ggataactcc aaaggccctc    3060
tgggtgcttc ttctctaggg acgccggaag accttgctga aggctgcagc caagacgacc    3120 agaccccag ccaatcctac attgacgaca gtactttaag gcctgcacag accgttagtc      3180
tccaaagggc tcacatttcg tccacaagct ataaagaggt gtgtattcca gagatagtca    3240
gtggcagcaa ggaaccgtcc agcgcttgca gccttttgga gccaggaaaa ccacccgaga    3300
gtttgccatc ctatggcgaa ctcaactctt gtccaacaaa aacagccaca gatgactatt    3360
tccagtgcaa cacctctagt gagacggtgc tcacggcacc atcacctctg ggaaagaata    3420
aggaggacca tgacactctg actttggcag aagggggtgaa aaagctctcc ccttctgata    3480
ggcaggtccc ccactcctcc agggagcctg tggggcacaa ggaggagtca ccaaaagggc    3540
cgggtggggg ccccgctgct tcgggaggag tggctgaagg gatcgccaac ggacgcctcg    3600
tccagcacca tggtgccgag cccagcagct tggacaagag gaaagagata tttagcaaag    3660
acacactgtt caacctcttt cacagcacct tgtctgtaaa cagctatcac aagtcgagcc    3720
tgtccctcct caaatctcac ccgaagacac ctgctgacac attgccaggc cgatgtgaga    3780
aactggaacc gtccctgggg acctcggcgg cacaagccat gcctgcttcc cagcgtcagc    3840
aggagtcagg agggaaccag gaagcctctt ttgactatta caacgtctct gatgatgacg    3900
actctgagga aggggcaaac aagaacacag aggaggagaa aaatagagag gacgtaggca    3960
ccatgcagtg gctcctcgag cgggagaagg aaagagactt gcagaggaaa tttgaaaaga    4020 acctcacccct tcttgctcca aaagaaaccg acagcagcag caaccagaga gccacccatt    4080
cagcccggct cgacagcatg gacagcagca gcatcacagt ggacagtgga ttcaactccc    4140
```

```
cacgtactcg ggagagcctg gcttccaaca catcaagcat tgttgaaagt aaccgtcgtc    4200
agaacccgc tttgagcccg gcccatggtg gagctggtcc agccttcaac ttccgagcga    4260
gcgcggagcc cccgacaaat gaagctgaga agctacagaa accttccaac tgcttgcaag    4320
cttctgttac tagcgtgtga ttgtccttct gcctcagatc ttctgtctca ttcgatacag    4380
caaagtttac gacactggga ctgatgttta catcttttgga aagacaagca tctcaaccac    4440
agttttgtg tttacttaaa ctgtgctgct aagtagggct agggcaaaaa aacaaaaaat    4500
ctttatttca gagtattgct tttcacattt atggctctgt agcaactgag taacagtagg    4560
ggtgatatgt atactttgc ttcactaatt gtatctgagc acacatagga aagtctagac    4620
actgtaagtg taatacgcat tttcaatgtc atgcagttgc caattccatt ttaaaatgcc    4680
acagatgcgt gttgctccca gtctgtggtt aaacggtgcc acagaactga tccttgacac    4740
ttccaaaaaa aaaaaaacaa aacaaaacaa aaaaatttta aaaaaaaaaa acaaaaaaca    4800
aaactaagct accacgaaat gtcaaatgca agggtccacc ttgagggaaa tagatgccaa    4860
actaactaga agggacccccg gcccctttgtg tgtgaattgt ttatgcacca gtcatttttc    4920
actgtgagtt tcgtgacac tattttgcag gagcccatgg aagtgtgtga aaggggtcg    4980
caatggagat cactgggagt gaatgttttc agggttttgt tttgaagtgt cacagatgct    5040
tgtctgattt ttttaacctt ccgtgatcac aaacaggaat ataggccttt gaatctgaag    5100
tggacaaagg aaaagcaattt ccagtctggc tggggcacag cattaggtga ttgaaaaggt    5160
gatgtggact tgtaaaaggt gttactcaaa tattgaagga agagaatttc ctccttgtga    5220
tacttaggat gaccctatct tactctaata gatacaataa ttagttttgtt taaaagcaaa    5280
atgttctttg tgatacaaat gaagagtagg gcctgaggat gttattcttt ctaatggaag    5340
gacataaatc tattttatgt agttttaaat agaatgccta aattaggctg tgggagataa    5400
tttttagtgg ttgtaggaaa gagcaaattt agggagtgtt gaacttcagg cctttttattc    5460
ctgggaagat atgtatagag aaaacttta aataattttt tgattagaaa tatacatgtg    5520
cccatgtaat aaacaacaga atgtgctcat tctgctagtg cggtataatc cgaatttgta    5580
ctccctaaa atttatcaga ataacaatta tgcatacatg aactatgcca gagtaatgtt    5640
tacagatact ttgtaaccaa tttcaggagg cgtttttagc tggatgtgta gttaattaga    5700
ccaacttatt tccaaatggt ttgttaacat tttgcttttgg tttacaatgt catgttgaac    5760
acaaagaaga cccagcagca aagggatgac caataatttc atcttatagc aaggagacat    5820
tccaacgttc ccatgtttta ttttctgaga acagtgggac agatctgtag taatggaata    5880
ttatttgcaa aagggttaca tatgacacaa gtaagtgttc tgacataaag ttttatttag    5940
ttcagtggca tgtgctgttg ggagccatac accataaaat atatatatcc caaataaat    6000
ctagaatatt ttcacctcca atttcagtaa ttggcatatg atttgtgaga cgcatctgtt    6060
tttgtatgag gttaatcac tagcaatctg tttaaagaat ccagtcctat acacagttgg    6120
actcattctt gaaaccttta aatgctccct catagttttt cagttatttg aagttgcat    6180
tgggtcaaac tgaactcctt gagtttggtg taaattcctt ttttctgctt attatagtga    6240
aacttcagca tgtttcttag taaactccca taccattgaa atgcttaagc cagttggctt    6300
tcagtctcat gccttatttc ctccaaggca tgcctcaacg cattgtttgt ctcattgctt    6360
aaatatgtcc agaaggaatg atcatgtatc taatagacta catagttggt tcccttgggg    6420
agttatatat catacagtta ctaaatattt gtctaaattc attttttcca aaaacctgct    6480
ctcaaatttt tcttctactc tcagttcata ataatataa ccattgaaac aacacatcag    6540
```

```
cctctagctg atcctctgaa agtagccatt gaaataatcg aatactgtgt gaacaggaaa    6600
ggaaagcgtt acctttaaga gaagctttaa aataggaatt tattgatatt tcacaagata    6660
taggtttaca gaagacatta ttcaaataaa tatgtacact atttgcctga tgctatgggg    6720
tacataattt tttaaaaact cccttagacc agcagccatt agtgtagaaa tgatggactt    6780
taaaggtgat accatgtaag cagatgttgc atataaaaat attcctgcct gaatctgatc    6840
gagattcttg aatggggggag gagtggcagc cggcagcaca ttgcaaatgt cattcgaggt    6900
cacggtgagg ctctcggtcc cggaacagtg ggggcctcgc caggcgttgc cagtatccct    6960
ttcctcctgt aaaatcatag ctttgtgtta cacgactgct tatccagtct tagggtttag    7020
cagctgaaag gtttacaaaa ctgaatctgg ttgaatctct gtgaaagggt caacacatct    7080
gtcggcattt tgcacactta tgtattatta tgatacaaca tattacttta tggtaatttt    7140
tatttttaca tataactacc tccataaatt tgatgaaatg gcagccgtgt gttaaagtgt    7200
atcgttcaga agagcaaagt tgaacacttc cttcaacatt agggcatggc gtgctgtgtg    7260
tgtcagtgat tgcctctgtg gactcatgac tttccatcgc catggctttc tcttacgccg    7320
ctgtttggct ttcagatgta atcctgtctt ctcctctctt ccccacgaaa gcgcactcga    7380
ttttgttagg aatgaacgga agtttaaaaa ttcttgtgcc caccccgcc ctccacccat    7440 tcctgttaaa agttctctgg cgaagagcca atgggtgaac gtaattgaaa gagctattta    7500
ctcttttgga aatctgattt gaagtctaag ttttcagtaa cagaagacac acaagcaatg    7560
tggactgcca agcttgaagc acttcgggct ctgccttcac tcgcatgcta ccatgtcgag    7620
cccaaactcc actttaatta aaagagctgt gctgtgaatt ccacaacttc tgttaaataa    7680
tttgtattcc attatatata ttttgcacat ctcaggggac cataatgaac atatgaaagg    7740
ggggggggtg ccatcaaata gagaaaacaa atagaagagg tgaatggaga ctagctggat    7800
aaaaataaca aattacttct tctctgatgt tgtgaaggtc aggttcagga agcatcaatt    7860
cacagttaat ccggagtaac aatgatctga acaccagctg ttcccaggtc cctcttttttc    7920 atagcccaac cagcatctaa aatgtaaatt taaattacat tgcagtcacc atggggagaa    7980
gaaacctgtt cagtggaagc agaagcattg ttcctttttt aggttggcgc agctttgcaa    8040
aactctaccc aggataaacc acttatcacc accaagtgta cttgaaaata aagttttttaa    8100 cttaaattac aagcatattg ctcataatac aatagtgatc attttttgaa agtcttgcca    8160
tttataacat gggcagtatt tggagcttca tttaaaaacc aacaacaacc gataatgact    8220
ttgcacgatt cactttggga tctcaaagtg cttccaaagc attcagattt acaaacaatt    8280
cacaagacag gtcatctttg taatacgcat acttacaacg aattaacaaa aggagtgact    8340
taagattctc caggaacaca gtggcagcta ttgatgatct gttttctatc tgtttgatag    8400
agcatcatga gaaatcacaa aatacaatgc tattttttctg atgtgtgcta ataaagtcaa    8460
agaaaacaaa tacatcttga cacttttgtc cattttcatt aaaaaaaaaa aagttcaggg    8520
tgtttggaat tttacatctc agcacacctt actggtatca atggataaag cgggtgattg    8580
acagatccac ccaaatgcca ctgcagtcag aagcagatct ggacacaccc ttgtttacag    8640
tttcatattg ggttgctata gttcccgtgc taaatcacca gctttcagga acatgactgc    8700
tcctggcagt ggaaggtgct gaaacagaaa ttttaattaa aaactttatc aagtactctt    8760
cacagtgctg cttggcacca tagaaaatca gtacaatata tcgagcccta ctttggagga    8820
gctggatttc tgagggagct gatccagttc taagtgtctt ctcgaattag gagatagatg    8880
```

| | |
|---|---|
| atctttgatg gggatctcct ccgtcaccac aggccagtca cagaaccaac tagccacgtg | 8940 |
| ctgccagacc tcagtgggcc caagcaggag caatctcttc tatcccccat ctcccccagg | 9000 |
| accatcccgc ccattgtcaa cgtcatccag ggctcttctg gtagtgagtg acttttctgc | 9060 |
| acatgtttag ggcttggggg agctagaaca caggaaacat gaatgcaaaa ggcatggaaa | 9120 |
| acactgtttt gctttgggtt agtaaaatgt gggcaggaca agattacta ttggtctgag | 9180 |
| ctttgccaag tgagatagaa tcaactgtca ccccattcct ttcccagaag gtcttatggt | 9240 |
| attaaggata catccagtat tttcccacag attttattc aggcgatgtt tcataaatta | 9300 |
| catatatgaa acattcatt attacatttc cttgtgtgtt tcaaacagac attggcacct | 9360 |
| tcctattgag ttaattctct gcatcttttg cagcagcagc ccacaaggag attcccagag | 9420 |
| atggctcccc taacacacag tcctgtgatt ttacagttct atgacttaca gttgatgatt | 9480 |
| cacaagattc aggattctac aagactcaag ggggaactaa actttcttac gattgtacat | 9540 |
| gatcagttat agggctgtaa tcattaattg ttggcttcaa atgtggacac acacacacac | 9600 |
| acatcatgcc aaggagggaa tggggtgttt caagtcaggc agcgatgatt ctggaaggtt | 9660 |
| ggaaatgtaa ggttagaagc ttggctggtc ttagtaaact tgttcccttg ctcccaccaa | 9720 |
| gaagaggtac caaatgtgag acctgagatc tcctccaata tctgtcctct gcagttccgg | 9780 |
| gaaactaatc atgaagtaca catgcagcag ctcctccact tcctttcctc cgaggtcctc | 9840 |
| cttttccattc tcccacctag atactgacac accgccacgg tttccacatt ggaagggcag | 9900 |
| aacactgtgc agtatcgtgc acacttgctg ggttaggaat agagctgccc tagggtcacc | 9960 |
| ttcatgcaag tattgacagc tacaaattaa agtccttaga gcagttgaca cagatactac | 10020 |
| gttctagaag agaattaaat ttaaacgtca agtttaaagg gatcataatt ctgcaggtat | 10080 |
| cttttctctga gtgactgaat gtgactattg cattagggta aatgaattaa gacgtgcaag | 10140 |
| tgggatttac tgtatgttag aaaggagttt tgcagccaag actgccttga ataaaatgtg | 10200 |
| tttgcactga aaaaaaattt taaattactt ggtctctggt tgctgtaaag gtcatccaag | 10260 |
| atggatgttc tgtttatatt gtatagtatt tcatatgaaa taattacagt tcatgaaatg | 10320 |
| tcttccctaa tgttactgat ttataacagc acatttgtaa catggttttt atcgtgtcag | 10380 |
| tgtaccatac tgtaaatgat gattacttgt catgcttagt ataataactt aaaagaaaaa | 10440 |
| aaaggacagg gatttttgta agtctatatt tgaaagtccc tccctatggt gatactgtgt | 10500 |
| tcatgttgtt tatgtagtgt tgtgtgaaat atccattttg gattgtgtta cttttttaaga | 10560 |
| tattaaataa catttggtta ta | 10582 |

<210> SEQ ID NO 5
<211> LENGTH: 929
<212> TYPE: PRT
<213> ORGANISM: Artificial Sequence
<220> FEATURE:
<223> OTHER INFORMATION: Synthetic

<400> SEQUENCE: 5

Met Pro Gly Lys Met Glu Lys Phe Leu Gln Ile Ala Pro His Ser Leu
1               5                   10                  15

Ala Ile Val Leu Gly Pro Ala Glu Ala Pro Ala Gly Glu Arg Pro Gly
            20                  25                  30

Ala Ala Arg Pro Ala Pro Pro Ala Gln Pro Arg Gln Leu Ala Arg His
        35                  40                  45

His Ile Gly Tyr Glu Ile Phe Ala Asp Phe Lys Ala Glu Asn Met Gln
    50                  55                  60

```
His Phe Trp Asn Lys Lys Val Thr Ala Ala Val Ala Glu Thr Phe Phe
 65                  70                  75                  80

Leu Gly Trp Ile Asp Glu Gln Val Leu Leu Ile Gln Gly Lys Glu Glu
                 85                  90                  95

His Leu Glu Ala Leu Arg Glu Gly Trp Thr Arg Arg Ala Leu Arg Pro
            100                 105                 110

Pro Ser Gly Phe His Ile Arg Cys Leu Gly Asp Val Ser Pro Ile Ser
        115                 120                 125

Met Ser Pro Ile Ser Gln Ser Gln Phe Ile Pro Leu Gly Glu Ile Leu
    130                 135                 140

Cys Leu Ala Ile Ser Ala Met Asn Ser Ala Arg Lys Pro Val Thr Gln
145                 150                 155                 160

Glu Ala Leu Met Glu His Leu Thr Thr Cys Phe Pro Gly Val Pro Thr
                165                 170                 175

Pro Ser Gln Glu Ile Leu Arg His Thr Leu Asn Thr Leu Val Arg Glu
            180                 185                 190

Arg Lys Ile Tyr Pro Thr Pro Asp Gly Tyr Phe Ile Val Thr Pro Gln
        195                 200                 205

Thr Tyr Phe Ile Thr Pro Ser Leu Ile Arg Thr Asn Ser Lys Trp Tyr
    210                 215                 220

His Leu Asp Glu Arg Ile Pro Asp Arg Ser Gln Cys Thr Ser Pro Gln
225                 230                 235                 240

Pro Gly Thr Ile Thr Pro Ser Ala Ser Gly Cys Val Arg Glu Arg Thr
                245                 250                 255

Leu Pro Arg Asn His Cys Asp Ser Cys His Cys Cys Arg Glu Asp Val
            260                 265                 270

His Ser Thr His Ala Pro Thr Leu Gln Arg Lys Ser Ala Lys Asp Cys
        275                 280                 285

Lys Asp Pro Tyr Cys Pro Pro Ser Leu Cys Gln Val Pro Pro Thr Glu
    290                 295                 300

Lys Ser Lys Ser Thr Val Asn Phe Ser Tyr Lys Thr Glu Thr Leu Ser
305                 310                 315                 320

Lys Pro Lys Asp Ser Glu Lys Gln Ser Lys Lys Phe Gly Leu Lys Leu
                325                 330                 335

Phe Arg Leu Ser Phe Lys Lys Asp Lys Thr Lys Gln Leu Ala Asn Phe
            340                 345                 350

Ser Ala Gln Phe Pro Pro Glu Glu Trp Pro Leu Arg Asp Glu Asp Thr
        355                 360                 365

Pro Ala Thr Ile Pro Arg Glu Val Glu Met Glu Ile Ile Arg Arg Ile
    370                 375                 380

Asn Pro Asp Leu Thr Val Glu Asn Val Met Arg His Thr Ala Leu Met
385                 390                 395                 400

Lys Lys Leu Glu Glu Glu Lys Ala Gln Arg Ser Lys Ala Gly Ser Ser
                405                 410                 415

Ala His His Ser Gly Arg Ser Lys Ser Arg Thr His Arg Lys Ser
            420                 425                 430

His Gly Lys Ser Arg Ser His Ser Lys Thr Arg Val Ser Lys Gly Asp
        435                 440                 445

Pro Ser Asp Gly Ser His Leu Asp Ile Pro Ala Glu Arg Glu Tyr Asp
    450                 455                 460

Phe Cys Asp Pro Leu Thr Arg Val Pro Arg Glu Gly Cys Phe Ile Ile
465                 470                 475                 480
```

-continued

```
Glu His Lys Gly Asp Asn Phe Ile Met His Ser Asn Thr Asn Val Leu
                485                 490                 495

Glu Ser His Phe Pro Met Thr Pro Glu Trp Asp Val Ser Gly Glu Leu
            500                 505                 510

Ala Lys Arg Arg Thr Glu Met Pro Phe Pro Glu Pro Ser Arg Gly Ser
        515                 520                 525

Ser His Ser Lys Val His Arg Ser His Ser His Thr Gln Asp Arg Arg
    530                 535                 540

Ser Arg Asn Glu Arg Ser Asn Lys Ala Lys Glu Arg Ser Arg Ser Met
545                 550                 555                 560

Asp Asn Ser Lys Gly Pro Leu Gly Ala Ser Ser Leu Gly Thr Pro Glu
                565                 570                 575

Asp Leu Ala Glu Gly Cys Ser Gln Asp Gln Thr Pro Ser Gln Ser
            580                 585                 590

Tyr Ile Asp Asp Ser Thr Leu Arg Pro Ala Gln Thr Val Ser Leu Gln
        595                 600                 605

Arg Ala His Ile Ser Ser Thr Ser Tyr Lys Glu Val Cys Ile Pro Glu
    610                 615                 620

Ile Val Ser Gly Ser Lys Glu Pro Ser Ser Ala Cys Ser Leu Leu Glu
625                 630                 635                 640

Pro Gly Lys Pro Pro Glu Ser Leu Pro Ser Tyr Gly Glu Leu Asn Ser
                645                 650                 655

Cys Pro Thr Lys Thr Ala Thr Asp Asp Tyr Phe Gln Cys Asn Thr Ser
            660                 665                 670

Ser Glu Thr Val Leu Thr Ala Pro Ser Pro Leu Gly Lys Asn Lys Glu
        675                 680                 685

Asp His Asp Thr Leu Thr Leu Ala Glu Gly Val Lys Lys Leu Ser Pro
    690                 695                 700

Ser Asp Arg Gln Val Pro His Ser Ser Arg Glu Pro Val Gly His Lys
705                 710                 715                 720

Glu Glu Ser Pro Lys Gly Pro Gly Gly Pro Ala Ala Ser Gly Gly
                725                 730                 735

Val Ala Glu Gly Ile Ala Asn Gly Arg Leu Val Gln His His Gly Ala
            740                 745                 750

Glu Pro Ser Ser Leu Asp Lys Arg Lys Glu Ile Phe Ser Lys Asp Thr
        755                 760                 765

Leu Phe Lys Pro Leu His Ser Thr Leu Ser Val Asn Ser Tyr His Lys
    770                 775                 780

Ser Ser Leu Ser Leu Lys Ser His Pro Lys Thr Pro Ala Asp Thr
785                 790                 795                 800

Leu Pro Gly Arg Cys Glu Lys Leu Glu Pro Ser Leu Gly Thr Ser Ala
                805                 810                 815

Ala Gln Ala Met Pro Ala Ser Gln Arg Gln Glu Ser Gly Gly Asn
            820                 825                 830

Gln Glu Ala Ser Phe Asp Tyr Tyr Asn Val Ser Asp Asp Asp Ser
        835                 840                 845

Glu Glu Gly Ala Asn Lys Asn Thr Glu Glu Lys Asn Arg Glu Asp
    850                 855                 860

Val Gly Thr Met Gln Trp Leu Leu Glu Arg Lys Glu Arg Asp Leu
865                 870                 875                 880

Gln Arg Lys Phe Glu Lys Asn Leu Thr Leu Leu Ala Pro Lys Glu Thr
                885                 890                 895

Asp Ser Ser Ser Asn Gln Arg Ala Thr His Ser Ala Arg Leu Asp Ser
```

```
            900                 905                 910
Met Asp Ser Ser Ser Ile Thr Val Asp Ser Gly Phe Asn Ser Pro Arg
        915                 920                 925
Asn

<210> SEQ ID NO 6
<211> LENGTH: 10631
<212> TYPE: DNA
<213> ORGANISM: Artificial Sequence
<220> FEATURE:
<223> OTHER INFORMATION: Synthetic

<400> SEQUENCE: 6
acagtgagac ctcgtctcaa acacaaaaca aaacaaaaca aaacaaaaca aaccaaaaca      60
aaacaaaaca aacacctcag gtctttagac ccggggtttag tgactttttc atgataataa    120
aatcacagga cgccagcgga aaacagttca gttatttcta ttccccaaaa ctaggctgga    180
cattctgtgt ttttcacggt gtggtccgag accaccagca gcagcagtag cagcagcatc    240
tgggaatttc ttagaaattt aaaaaaccgg gttcctctag acctactgaa tcagaaactc    300
tgggaatggg gcccagatac ctgcgtttta atacgtgttc aggtgacggt gatgcacgtt    360
gaaatttaaa taccgctctg ggtaaatgta gcataactct taatgcttct tatgacaatc    420 atctctttc acatatgact actagcctct ctcgattaaa atataagtca tacagaattt    480
ggcacagaaa caaacgtaag gaatttttctt aaaagcatca tcgttaccttt tcctggtaaa    540 tttctgtaac ctcttcataa accgagggtt aatggttgat tgggtttcct ctagggtagg    600
ccaaagtata tgctgaagac aagagagtag aattcctcaa gagtttggga ggagggactg    660
atgacaattt ttggtggttg actaagtttt ttaaaaagcc acttctaagg gtacattcat    720
taaccagtca gcgaatccac ttgttccagc gagaggtggg aggtggggc agggtggag    780 cgtggggagg agcgacactc gccgctccgg aatccgtgcc ttccaagtgt cgccgttgcg    840 tccccgcaa ccccgctttt ctgatctccc tcgaggccca acacccaaag gctcaccct    900 aggccatccg cgctccccga ccacctccct cataggactc cttgggattc ctcaggccgc    960
gtccagccga gggggttccc gggcgcggtg cgcactgccc gccccctcac tgcctcctcc   1020
cgcgtctccg ccccccgcggg gccgctggcg gccgggggag gcgaggtgc cgaggccgga   1080 aaatgagcgc tgcccgaagg gtgggcccgga gctgcaggta acgcggtcca gagctcaggc   1140
cggagcgggc cccgcacacc gtcccttccc cgcagcgacc cgcgggctgc gcccagggac   1200
tgcgccgggc gccggggctg cagggacgcg ggcgcggggg aggcgcggcc agccctgccc   1260
tgggggacgg tcgcgctccc cgctggtctt gcagccacgt cccggcggct gttcctggga   1320
gcggcgggag gcggcctcgg tgagccaggt cggcgcggca gatgcctggg aagatggaga   1380
agtttctgca gatcgcgcct cactccctgg ccatcgtcct gggcccggca gaggcgccgg   1440 cggggggaaag gccaggggca gcccggcccg cgccccggc ccagccccgc cagctcgccc   1500
ggcaccacat cggctacgag atcttcgccg acttcaaagc cgagaacatg cagcacttct   1560
ggaacaagaa ggtcacggcc gcggtggccg agaccttctt cctgggctgg atcgacgagc   1620
aggtcctgct gatccagggc aaggaggaac atctggagc gctgcgcgaa ggctggacgc   1680
gccgggccct gcggccgccc tcgggcttcc acatccgctg cctgggtgat gtatcaccca   1740
tcagtatgtc tccatcagt cagtctcagt ttattccact cggggagatc ctctgcttgg   1800
ccatctcagc aatgaactcg gcaagaaagc ctgtcaccca agaagcactg atggagcacc   1860
```

```
tgaccacgtg cttcccaggt gttccaacgc caagccaaga aattctgcgg cacacgctga    1920
acacgctggt acgggagagg aagatctacc caactccaga tggctacttc atcgtgaccc    1980
cacagactta tttcataact ccttccctca taagaactaa cagtaaatgg taccatttgg    2040
acgagaggat acctgaccgg tctcagtgca cctctccgca acccgggacc atcacgccct    2100
ctgcctcagg ctgtgtcagg gaaaggacat tgccccgaaa ccactgcgac tcttgccact    2160
gctgcagaga agacgtgcac agcacgcatg cacccaccct gcaaaggaag tctgccaagg    2220
actgcaaaga cccttactgt cccccttctc tgtgccaggt gccacccact gaaaagagca    2280
aaagtactgt aaattttcc tataagacag aaactctctc aaaacctaaa gatagtgaaa    2340
agcagtcaaa aaaattcggg ctaaagttat tccggttaag ttttaaaaaa gacaagacca    2400
aacagctggc caattttct gcccagtttc ctcctgaaga gtggcccctg cgagacgagg    2460
acacgccagc tacgatccct cgggaagtag agatggaaat cattaggcgc attaacccag    2520
acctgaccgt ggaaaatgtc atgcggcaca ccgcgctcat gaagaaactg aagaagaaa    2580
aggcccagag gagtaaagcc gggtcctctg cccatcacac cggaaggagt aaaaagagta    2640
ggactcatcg gaagtcccat ggaaagtctc ggtctcacag caagacacgg gtgtctaaag    2700
gagacccttc cgacggttca catctggata tcccagctga aagagagtat gacttttgtg    2760
atcctcttac cagggtgccc agggagggct gcttcatcat tgaacacaaa ggagataact    2820
tcatcatgca cagcaacaca aacgtgctcg agtcccactt ccccatgaca ccagaatggg    2880
atgtgtctgg tgaattggct aaaaggagaa ctgagatgcc ttttcctgaa ccttctaggg    2940
gaagctccca ctcaaaagtg caccgaagcc acagccatac acaggaccgg aggtccagga    3000
atgagagatc caacaaagcc aaggagagat ccaggtcgat ggataactcc aaaggccctc    3060
tgggtgcttc ttctctaggg acgccggaag accttgctga aggctgcagc caagacgacc    3120
agaccccccag ccaatcctac attgacgaca gtactttaag gcctgcacag accgttagtc    3180
tccaaagggc tcacatttcg tccacaagct ataaagaggt gtgtattcca gagatagtca    3240
gtggcagcaa ggaaccgtcc agcgcttgca gccttttgga gccaggaaaa ccacccgaga    3300
gtttgccatc ctatggcgaa ctcaactctt gtccaacaaa aacagccaca gatgactatt    3360
tccagtgcaa cacctctagt gagacggtgc tcacggcacc atcacctctg ggaaagaata    3420
aggaggacca tgacactctg actttggcag aaggggtgaa aaagctctcc ccttctgata    3480
ggcaggtccc ccactcctcc agggagcctg tggggcacaa ggaggagtca ccaaaagggc    3540
cgggtggggg ccccgctgct tcgggaggag tggctgaagg gatcgccaac ggacgcctcg    3600
tccagcacca tggtgccgag cccagcagct tggacaagag gaaagagata tttagcaaag    3660
acacactgtt caaacctctt cacagcacct tgtctgtaaa cagctatcac aagtcgagcc    3720
tgtccctcct caaatctcac ccgaagacac ctgctgacac attgccaggc cgatgtgaga    3780
aactggaacc gtccctgggg acctcggcgg cacaagccat gcctgcttcc cagcgtcagc    3840
aggagtcagg agggaaccag gaagcctctt ttgactatta caacgtctct gatgatgacg    3900
actctgagga aggggcaaac aagaacacag aggaggagaa aaatagagag gacgtaggca    3960
ccatgcagtg gctcctcgag cgggagaagg aaagagactt gcagaggaaa tttgaaaaga    4020
acctcacccct tcttgctcca aaagaaaccg acagcagcag caaccagaga gccacccatt    4080
cagcccggct cgacagcatg gacagcagca gcatcacagt ggacagtgga ttcaactccc    4140
cacggaattg aaaaaaatgt ttctgcacct gtagagatca ccaatctgga ctgtactcgg    4200
gagagcctgg cttccaacac atcaagcatt gttgaaagta accgtcgtca gaaccccgct    4260
```

```
ttgagcccgg cccatggtgg agctggtcca gccttcaact tccgagcgag cgcggagccc    4320
ccgacaaatg aagctgagaa gctacagaaa ccttccaact gcttgcaagc ttctgttact    4380
agcgtgtgat tgtccttctg cctcagatct tctgtctcat tcgatacagc aaagtttacg    4440
acactgggac tgatgtttac atctttggaa agacaagcat ctcaaccaca gttttttgtgt   4500
ttacttaaac tgtgctgcta agtagggcta gggcaaaaaa acaaaaaatc tttatttcag    4560
agtattgctt ttcacatttta tggctctgta gcaactgagt aacagtaggg gtgatatgta   4620
tacttttgct tcactaattg tatctgagca cataggaa agtctagaca ctgtaagtgt      4680
aatacgcatt ttcaatgtca tgcagttgcc aattccattt taaaatgcca cagatgcgtg   4740
ttgctcccag tctgtggtta aacggtgcca cagaactgat ccttgacact tccaaaaaaa  4800
aaaaaacaaa acaaaacaaa aaaaatttaa aaaaaaaaaa caaaaaacaa aactaagcta  4860
ccacgaaatg tcaaatgcaa gggtccacct tgagggaaat agatgccaaa ctaactagaa   4920
gggaccccgg cccctttgtgt gtgaattgtt tatgcaccag tcatttttca ctgtgagttt  4980
tcgtgacact attttgcagg agcccatgga agtgtgtgag aagggtcgc aatggagatc    5040
actgggagtg aatgttttca gggttttgtt ttgaagtgtc acagatgctt gtctgatttt   5100
tttaaccttc cgtgatcaca aacaggaata taggcctttg aatctgaagt ggacaaagga   5160
aagcaatttc cagtctggct ggggcacagc attaggtgat tgaaaaggtg atgtggactt   5220
gtaaaaggtg ttactcaaat attgaaggaa gagaatttcc tccttgtgat acttaggatg   5280
accctatctt actctaatag atacaataat tagtttgttt aaaagcaaaa tgttctttgt   5340
gatacaaatg aagagtaggg cctgaggatg ttattctttc taatggaagg acataaatct   5400
attttatgta gttttaaata gaatgcctaa attaggctgt gggagataat ttttagtggt  5460
tgtaggaaag agcaaattta gggagtgttg aacttcaggc ctttttattcc tgggaagata   5520
tgtatagaga aaactttaa aataattttt gattagaaat atacatgtgc ccatgtaata    5580
aacaacagaa tgtgctcatt ctgctagtgc ggtataatcc gaatttgtac tccctaaaa    5640
tttatcagaa taacaattat gcatacatga actatgccag agtaatgttt acagatactt   5700
tgtaaccaat ttcaggaggc gtttttagct ggatgtgtag ttaattagac caacttattt   5760
ccaaatggtt tgttaacatt ttgctttggt ttacaatgtc atgttgaaca caaagaagac   5820
ccagcagcaa agggatgacc aataaatttca tcttatagca aggagacatt ccaacgttcc   5880
catgttttat tttctgagaa cagtgggaca gatctgtagt aatggaatat tatttgcaaa    5940
agggttacat atgacacaag taagtgttct gacataaagt tttatttagt tcagtggcat    6000
gtgctgttgg gagccataca ccataaaata tatatatccc aaaataaatc tagaatattt   6060
tcacctccaa tttcagtaat tggcatatga tttgtgagac gcatctgttt ttgtatgagg    6120
tttaatcact agcaatctgt ttaaagaatc cagtcctata cacagttgga ctcattcttg    6180
aaacctttaa atgctccctc atagttttttc agttatttgg aagttgcatt gggtcaaact   6240
gaactccttg agtttggtgt aaattccttt tttctgctta ttatagtgaa acttcagcat   6300
gtttcttagt aaactcccat accattgaaa tgcttaagcc agttggcttt cagtctcatg    6360
ccttatttcc tccaaggcat gcctcaacgc attgtttgtc tcattgctta aatatgtcca   6420
gaaggaatga tcatgtatct aatagactac atagttggtt cccttgggga gttatatatc   6480
atacagttac taaatatttg tctaaattca ttttttccaa aaacctgctc tcaaattttt   6540
cttctactct cagttcataa ataatataac cattgaaaca acacatcagc ctctagctga   6600
```

```
tcctctgaaa gtagccattg aaataatcga atactgtgtg aacaggaaag gaaagcgtta    6660
cctttaagag aagctttaaa ataggaattt attgatattt cacaagatat aggtttacag    6720
aagacattat tcaaataaat atgtacacta tttgcctgat gctatggggt acataatttt    6780
ttaaaaactc ccttagacca gcagccatta gtgtagaaat gatggacttt aaaggtgata    6840
ccatgtaagc agatgttgca tataaaaata ttcctgcctg aatctgatcg agattcttga    6900
atgggggagg agtggcagcc ggcagcacat tgcaaatgtc attcgaggtc acggtgaggc    6960
tctcggtccc ggaacagtgg gggcctcgcc aggcgttgcc agtatccctt tcctcctgta    7020
aaatcatagc tttgtgttac acgactgctt atccagtctt agggtttagc agctgaaagg    7080
tttacaaaac tgaatctggt tgaatctctg tgaaagggtc aacacatctg tcggcatttt    7140
gcacacttat gtattattat gatacaacat attactttat ggtaattttt attttacat    7200 ataactacct ccataaattt gatgaaatgg cagccgtgtg ttaaagtgta tcgttcagaa    7260
gagcaaagtt gaacacttcc ttcaacatta gggcatggcg tgctgtgtgt gtcagtgatt    7320
gcctctgtgg actcatgact ttccatcgcc atggctttct cttacgccgc tgtttggctt    7380
tcagatgtaa tcctgtcttc tcctctcttc cccacgaaag cgcactcgat tttgttagga    7440
atgaacggaa gtttaaaaat tcttgtgccc accccgccc tccacccatt cctgttaaaa    7500
gttctctggc gaagagccaa tgggtgaacg taattgaaag agctatttac tcttttggaa    7560
atctgatttg aagtctaagt tttcagtaac agaagacaca caagcaatgt ggactgccaa    7620
gcttgaagca cttcgggctc tgccttcact cgcatgctac catgtcgagc ccaaactcca    7680 cttttaattaa aagagctgtg ctgtgaattc cacaacttct gttaaataat ttgtattcca    7740
ttatatatat tttgcacatc tcaggggacc ataatgaaca tatgaaaggg gggggggtgc    7800
catcaaatag agaaaacaaa tagaagaggt gaatggagac tagctggata aaaataacaa    7860
attacttctt ctctgatgtt gtgaaggtca ggttcaggaa gcatcaattc acagttaatc    7920
cggagtaaca atgatctgaa caccagctgt tcccaggtcc ctcttttca tagcccaacc    7980 agcatctaaa atgtaaattt aaattacatt gcagtcacca tggggagaag aaacctgttc    8040
agtggaagca gaagcattgt tccttttta ggttggcgca gctttgcaaa actctaccca    8100
ggataaacca cttatcacca ccaagtgtac ttgaaaataa agttttaac ttaaattaca    8160 agcatattgc tcataataca atagtgatca tttttgaaa gtcttgccat ttataacatg    8220
ggcagtattt ggagcttcat ttaaaaacca acaacaaccg ataatgactt tgcacgattc    8280
actttgggat ctcaaagtgc ttccaaagca ttcagattta caacaattc acaagacagg    8340 tcatctttgt aatacgcata cttacaacga attaacaaaa ggagtgactt aagattctcc    8400
aggaacacag tggcagctat tgatgatctg ttttctatct gtttgataga gcatcatgag    8460
aaatcacaaa atacaatgct atttttctga tgtgtgctaa taaagtcaaa gaaaacaaat    8520
acatcttgac acttttgtcc attttcatta aaaaaaaaaa agttcagggt gtttggaatt    8580
ttacatctca gcacaccta ctggtatcaa tggataaagc gggtgattga cagatccacc    8640
caaatgccac tgcagtcaga agcagatctg gacacaccct tgtttacagt ttcatattgg    8700
gttgctatag ttcccgtgct aaatcaccag ctttcaggaa catgactgct cctggcagtg    8760
gaaggtgctg aaacagaaat tttaattaaa aactttatca agtactcttc acagtgctgc    8820
ttggcaccat agaaaatcag tacaatatat cgagccctac tttggaggag ctggatttct    8880
gagggagctg atccagttct aagtgtcttc tcgaattagg atagatga tctttgatgg    8940 ggatctcctc cgtcaccaca ggccagtcac agaaccaact agccacgtgc tgccagacct    9000
```

```
cagtgggccc aagcaggagc aatctcttct atcccccatc tcccccagga ccatcccgcc    9060
cattgtcaac gtcatccagg gctcttctgg tagtgagtga cttttctgca catgtttagg    9120
gcttgggga  gctagaacac aggaaacatg aatgcaaaag gcatggaaaa cactgttttg    9180
ctttgggtta gtaaaatgtg gcaggacaa  agattactat tggtctgagc tttgccaagt   9240
gagatagaat caactgtcac cccattcctt tcccagaagg tcttatggta ttaaggatac    9300
atccagtatt ttcccacaga tttttattca ggcgatgttt cataaattac atatatgaaa    9360
acattcatta ttacatttcc ttgtgtgttt caaacagaca ttggcacctt cctattgagt    9420
taattctctg catcttttgc agcagcagcc cacaaggaga ttcccagaga tggctcccct    9480
aacacacagt cctgtgattt tacagttcta tgacttacag ttgatgattc acaagattca    9540
ggattctaca agactcaagg gggaactaaa ctttcttacg attgtacatg atcagttata    9600
gggctgtaat cattaattgt tggcttcaaa tgtggacaca cacacacaca catcatgcca    9660
aggagggaat ggggtgtttc aagtcaggca gcgatgattc tggaaggttg gaaatgtaag    9720
gttagaagct tggctggtct tagtaaactt gttcccttgc tcccaccaag aagaggtacc    9780
aaatgtgaga cctgagatct cctccaatat ctgtcctctg cagttccggg aaactaatca    9840
tgaagtacac atgcagcagc cctccacttt cctttcctcc gaggtcctcc tttccattct    9900
cccacctaga tactgacaca ccgccacggt ttccacattg aagggcaga  acactgtgca    9960
gtatcgtgca cacttgctgg gttaggaata gagctgccct agggtcacct tcatgcaagt   10020
attgacagct acaaattaaa gtccttagag cagttgacac agatactacg ttctagaaga   10080
gaattaaatt taaacgtcaa gtttaaaggg atcataattc tgcaggtatc tttctctgag   10140
tgactgaatg tgactattgc attagggtaa atgaattaag acgtgcaagt gggatttact   10200
gtatgttaga aaggagtttt gcagccaaga ctgccttgaa taaaatgtgt ttgcactgaa   10260
aaaaaatttt aaattacttg gtctctggtt gctgtaaagg tcatccaaga tggatgttct   10320
gtttatattg tatagtattt catatgaaat aattacagtt catgaaatgt cttccctaat   10380
gttactgatt tataacagca catttgtaac atggttttta tcgtgtcagt gtaccatact   10440
gtaaatgatg attacttgtc atgcttagta taataactta aagaaaaaa  aaggacaggg   10500
atttttgtaa gtctatattt gaaagtccct ccctatggtg atactgtgtt catgttgttt   10560
atgtagtgtt gtgtgaaata tccatttgg  attgtgttac ttttttaagat attaaataac   10620
atttggttat a                                                        10631
```

<210> SEQ ID NO 7
<211> LENGTH: 928
<212> TYPE: PRT
<213> ORGANISM: Artificial Sequence
<220> FEATURE:
<223> OTHER INFORMATION: Synthetic

<400> SEQUENCE: 7

Met Pro Gly Lys Met Glu Lys Phe Leu Gln Ile Ala Pro His Ser Leu
1               5                   10                  15

Ala Ile Val Leu Gly Pro Ala Glu Ala Pro Ala Gly Glu Arg Pro Gly
            20                  25                  30

Ala Ala Arg Pro Ala Pro Pro Ala Gln Pro Arg Gln Leu Ala Arg His
        35                  40                  45

His Ile Gly Tyr Glu Ile Phe Ala Asp Phe Lys Ala Glu Asn Met Gln
    50                  55                  60

His Phe Trp Asn Lys Lys Val Thr Ala Ala Val Ala Glu Thr Phe Phe
65                  70                  75                  80

Leu Gly Trp Ile Asp Glu Gln Val Leu Leu Ile Gln Gly Lys Glu Glu
            85                  90                  95

His Leu Glu Ala Leu Arg Glu Gly Trp Thr Arg Arg Ala Leu Arg Pro
        100                 105                 110

Pro Ser Gly Phe His Ile Arg Cys Leu Gly Asp Val Ser Pro Ile Ser
        115                 120                 125

Met Ser Pro Ile Ser Gln Ser Gln Phe Ile Pro Leu Gly Glu Ile Leu
    130                 135                 140

Cys Leu Ala Ile Ser Ala Met Asn Ser Ala Arg Lys Pro Val Thr Gln
145                 150                 155                 160

Glu Ala Leu Met Glu His Leu Thr Thr Cys Phe Pro Gly Val Pro Thr
                165                 170                 175

Pro Ser Gln Glu Ile Leu Arg His Thr Leu Asn Thr Leu Val Arg Glu
        180                 185                 190

Arg Lys Ile Tyr Pro Thr Pro Asp Gly Tyr Phe Ile Val Thr Pro Gln
        195                 200                 205

Thr Tyr Phe Ile Thr Pro Ser Leu Ile Arg Thr Asn Ser Lys Trp Tyr
210                 215                 220

His Leu Asp Glu Arg Ile Pro Asp Arg Ser Gln Cys Thr Ser Pro Gln
225                 230                 235                 240

Pro Gly Thr Ile Thr Pro Ser Ala Ser Gly Cys Val Arg Glu Arg Thr
            245                 250                 255

Leu Pro Arg Asn His Cys Asp Ser Cys His Cys Cys Arg Glu Asp Val
        260                 265                 270

His Ser Thr His Ala Pro Thr Leu Gln Arg Lys Ser Ala Lys Asp Cys
        275                 280                 285

Lys Asp Pro Tyr Cys Pro Pro Ser Leu Cys Gln Val Pro Pro Thr Glu
    290                 295                 300

Lys Ser Lys Ser Thr Val Asn Phe Ser Tyr Lys Thr Glu Thr Leu Ser
305                 310                 315                 320

Lys Pro Lys Asp Ser Glu Lys Gln Ser Lys Lys Phe Gly Leu Lys Leu
            325                 330                 335

Phe Arg Leu Ser Phe Lys Lys Asp Lys Thr Lys Gln Leu Ala Asn Phe
        340                 345                 350

Ser Ala Gln Phe Pro Pro Glu Glu Trp Pro Leu Arg Asp Glu Asp Thr
        355                 360                 365

Pro Ala Thr Ile Pro Arg Glu Val Glu Met Glu Ile Ile Arg Arg Ile
    370                 375                 380

Asn Pro Asp Leu Thr Val Glu Asn Val Met Arg His Thr Ala Leu Met
385                 390                 395                 400

Lys Lys Leu Glu Glu Glu Lys Ala Gln Arg Ser Lys Ala Gly Ser Ser
            405                 410                 415

Ala His His Ser Gly Arg Ser Lys Lys Ser Arg Thr His Arg Lys Ser
        420                 425                 430

His Gly Lys Ser Arg Ser His Ser Lys Thr Arg Val Ser Lys Gly Asp
        435                 440                 445

Pro Ser Asp Gly Ser His Leu Asp Ile Pro Ala Glu Arg Glu Tyr Asp
    450                 455                 460

Phe Cys Asp Pro Leu Thr Arg Val Pro Arg Glu Gly Cys Phe Ile Ile
465                 470                 475                 480

Glu His Lys Gly Asp Asn Phe Ile Met His Ser Asn Thr Asn Val Leu

-continued

```
                485                 490                 495
Glu Ser His Phe Pro Met Thr Pro Glu Trp Asp Val Ser Gly Glu Leu
                500                 505                 510
Ala Lys Arg Arg Thr Glu Met Pro Phe Pro Glu Pro Ser Arg Gly Ser
                515                 520                 525
Ser His Ser Lys Val His Arg Ser His Ser His Thr Gln Asp Arg Arg
                530                 535                 540
Ser Arg Asn Glu Arg Ser Asn Lys Ala Lys Glu Arg Ser Arg Ser Met
545                 550                 555                 560
Asp Asn Ser Lys Gly Pro Leu Gly Ala Ser Ser Leu Gly Thr Pro Glu
                565                 570                 575
Asp Leu Ala Glu Gly Cys Ser Gln Asp Gln Thr Pro Ser Gln Ser
                580                 585                 590
Tyr Ile Asp Asp Ser Thr Leu Arg Pro Ala Gln Thr Val Ser Leu Gln
                595                 600                 605
Arg Ala His Ile Ser Ser Thr Ser Tyr Lys Glu Val Cys Ile Pro Glu
                610                 615                 620
Ile Val Ser Gly Ser Lys Glu Pro Ser Ser Ala Cys Ser Leu Leu Glu
625                 630                 635                 640
Pro Gly Lys Pro Pro Glu Ser Leu Pro Ser Tyr Gly Glu Leu Asn Ser
                645                 650                 655
Cys Pro Thr Lys Thr Ala Thr Asp Asp Tyr Phe Gln Cys Asn Thr Ser
                660                 665                 670
Ser Glu Thr Val Leu Thr Ala Pro Ser Pro Leu Gly Lys Asn Lys Glu
                675                 680                 685
Asp His Asp Thr Leu Thr Leu Ala Glu Gly Val Lys Lys Leu Ser Pro
                690                 695                 700
Ser Asp Arg Gln Val Pro His Ser Ser Arg Glu Pro Val Gly His Lys
705                 710                 715                 720
Glu Glu Ser Pro Lys Gly Pro Gly Gly Gly Pro Ala Ala Ser Gly Gly
                725                 730                 735
Val Ala Glu Gly Ile Ala Asn Gly Arg Leu Val Gln His His Gly Ala
                740                 745                 750
Glu Pro Ser Ser Leu Asp Lys Arg Lys Glu Ile Phe Ser Lys Asp Thr
                755                 760                 765
Leu Phe Lys Pro Leu His Ser Thr Leu Ser Val Asn Ser Tyr His Lys
                770                 775                 780
Ser Ser Leu Ser Leu Lys Ser His Pro Lys Thr Pro Ala Asp Thr
785                 790                 795                 800
Leu Pro Gly Arg Cys Glu Lys Leu Glu Pro Ser Leu Gly Thr Ser Ala
                805                 810                 815
Ala Gln Ala Met Pro Ala Ser Gln Arg Gln Glu Ser Gly Gly Asn
                820                 825                 830
Gln Glu Ala Ser Phe Asp Tyr Tyr Asn Val Ser Asp Asp Asp Ser
                835                 840                 845
Glu Glu Gly Ala Asn Lys Asn Thr Glu Glu Lys Asn Arg Glu Asp
                850                 855                 860
Val Gly Thr Met Gln Trp Leu Leu Glu Arg Glu Lys Glu Arg Asp Leu
865                 870                 875                 880
Gln Arg Lys Phe Glu Lys Asn Leu Thr Leu Leu Ala Pro Lys Glu Thr
                885                 890                 895
Asp Ser Ser Ser Asn Gln Arg Ala Thr His Ser Ala Arg Leu Asp Ser
                900                 905                 910
```

Met Asp Ser Ser Ser Ile Thr Val Asp Ser Gly Phe Asn Ser Pro Arg
        915                 920                 925

<210> SEQ ID NO 8
<211> LENGTH: 4148
<212> TYPE: DNA
<213> ORGANISM: Artificial Sequence
<220> FEATURE:
<223> OTHER INFORMATION: Synthetic

<400> SEQUENCE: 8

| | | | | |
|---|---|---|---|---|
| acagtgagac | ctcgtctcaa | acacaaaaca | aaacaaaaca | aaacaaaaca aaccaaaaca | 60 |
| aaacaaaaca | aacacctcag | gtctttagac | ccgggtttag | tgactttttc atgataataa | 120 |
| aatcacagga | cgccagcgga | aaacagttca | gttatttcta | ttccccaaaa ctaggctgga | 180 |
| cattctgtgt | ttttcacggt | gtggtccgag | accaccagca | gcagcagtag cagcagcatc | 240 |
| tgggaatttc | ttagaaattt | aaaaaaccgg | gttcctctag | acctactgaa tcagaaactc | 300 |
| tgggaatggg | gcccagatac | ctgcgtttta | atacgtgttc | aggtgacggt gatgcacgtt | 360 |
| gaaatttaaa | taccgctctg | ggtaaatgta | gcataactct | taatgcttct tatgacaatc | 420 |
| atctcttttc | acatatgact | actagcctct | ctcgattaaa | atataagtca tacagaattt | 480 |
| ggcacagaaa | caaacgtaag | gaattttctt | aaaagcatca | tcgttacctt tcctggtaaa | 540 |
| tttctgtaac | ctcttcataa | accgagggtt | aatggttgat | tgggtttcct ctagggtagg | 600 |
| ccaaagtata | tgctgaagac | aagagagtag | aattcctcaa | gagtttggga ggagggactg | 660 |
| atgacaattt | ttggtggttg | actaagtttt | ttaaaaagcc | acttctaagg gtacattcat | 720 |
| taaccagtca | gcgaatccac | ttgttccagc | gagaggtggg | aggtgggggc aggggtggag | 780 |
| cgtggggagg | agcgacactc | gccgctccgg | aatccgtgcc | ttccaagtgt cgccgttgcg | 840 |
| tcccccgcaa | ccccgctttc | ctgatctccc | tcgaggccca | acccaaag gctcacccct | 900 |
| aggccatccg | cgctccccga | ccacctccct | cataggactc | cttgggattc tcaggccgc | 960 |
| gtccagccga | ggggttccc | gggcgcggtg | cgcactgccc | gccccctcac tgcctcctcc | 1020 |
| cgcgtctccg | ccccccgcggg | gccgctgggc | gccggggag | cgagggtgc cgaggccgga | 1080 |
| aaatgagcgc | tgcccgaagg | gtggcccgga | gctgcaggta | acgcggtcca gagctcaggc | 1140 |
| cggagcgggc | cccgcacacc | gtcccttccc | cgcagcgacc | cgcggggctgc gcccagggac | 1200 |
| tgcgccgggc | gccccgggctg | cagggacgcg | ggcgcggggg | aggcgcggcc agccctgccc | 1260 |
| tgggggacgg | tcgcgctccc | cgctggtctt | gcagccacgt | cccggcggct gttcctggga | 1320 |
| gcggcgggag | gcggcctcgg | tgagccaggt | cggcgcggca | gatgcctggg aagatggaga | 1380 |
| agtttctgca | gatcgcgcct | cactccctgg | ccatcgtcct | gggcccggca gaggcgccgg | 1440 |
| cgggggaaag | gccaggggca | gcccggcccg | cgccccggc | ccagccccgc cagctcgccc | 1500 |
| ggcaccacat | cggctacgag | atcttcgccg | acttcaaagc | cgagaacatg cagcacttct | 1560 |
| ggaacaagaa | ggtcacggcc | gcggtggccg | agaccttctt | cctgggctgg atcgacgagc | 1620 |
| aggtcctgct | gatccagggc | aaggaggaac | atctggaggc | gctgcgcgaa ggctggacgc | 1680 |
| gccgggccct | gcggccgccc | tcgggcttcc | acatccgctg | cctgggtgat gtatcaccca | 1740 |
| tcagtatgtc | tcccatcagt | cagtctcagt | ttattccact | cggggagatc ctctgcttgg | 1800 |
| ccatctcagc | aatgaactcg | gcaagaaagc | ctgtcaccca | agaagcactg atggagcacc | 1860 |
| tgaccacgtg | cttcccaggt | gttccaacgc | caagccaaga | aattctgcgg cacacgctga | 1920 |
| acacgctggt | acgggagagg | aagatctacc | caactccaga | tggctacttc atcgtgaccc | 1980 |

-continued

```
cacagactta tttcataact ccttccctca taagaactaa cagtaaatgg taccatttgg    2040
acgagaggat acctgaccgg tctcagtgca cctctccgca acccgggacc atcacgccct    2100
ctgcctcagg ctgtgtcagg gaaaggacat tgccccgaaa ccactgcgac tcttgccact    2160
gctgcagaga agacgtgcac agcacgcatg cacccaccct gcaaaggaag tctgccaagg    2220
actgcaaaga cccttactgt cccccttctc tgtgccaggt gccacccact gaaaagagca    2280
aaagtactgt aaattttttcc tataagacag aaactctctc aaaacctaaa gatagtgaaa    2340
agcagtcaaa aaaattcggg ctaaagttat tccggttaag ttttaaaaaa gacaagacca    2400
aacagctggc caatttttct gcccagtttc ctcctgaaga gtggcccctg cgagacgagg    2460
acacgccagc tacgatccct cgggaagtag agatggaaat cattaggcgc attaacccag    2520
acctgaccgt ggaaaatgtc atgcggcaca ccgcgctcat gaagaaactg gaagaagaaa    2580
aggcccagag gagtaaagcc gggtcctctg cccatcacag cggaaggagt aaaaagagta    2640
ggactcatcg gaagtcccat ggaaagtctc ggtctcacag caagacacgg gtgtctaaag    2700
gagacccttc cgacggttca catctggata tcccagctga agagagtat gacttttgtg     2760 atcctcttac cagggtgccc agggagggct gcttcatcat tgaacacaaa ggagataact    2820
tcatcatgca cagcaacaca aacgtgctcg agtcccactt ccccatgaca ccagaatggg    2880
atgtgtctgg tgaattggct aaaaggagaa ctgagatgcc ttttcctgaa ccttctaggg    2940
gaagctccca ctcaaaagtg caccgaagcc acagccatac acaggaccgg aggtccagga    3000
atgagagatc caacaaagcc aaggagagat ccaggtcgat ggataactcc aaaggccctc    3060
tgggtgcttc ttctctaggg acgccggaag accttgctga aggctgcagc caagacgacc    3120 agaccccccag ccaatcctac attgacgaca gtactttaag gcctgcacag accgttagtc    3180
tccaaagggc tcacatttcg tccacaagct ataaagaggt gtgtattcca gagatagtca    3240
gtggcagcaa ggaaccgtcc agcgcttgca gccttttgga gccaggaaaa ccacccgaga    3300
gtttgccatc ctatggcgaa ctcaactctt gtccaacaaa aacagccaca gatgactatt    3360
tccagtgcaa cacctctagt gagacggtgc tcacggcacc atcacctctg ggaaagaata    3420
aggaggacca tgacactctg actttggcag aagggggtgaa aaagctctcc ccttctgata    3480
ggcaggtccc ccactcctcc agggagcctg tggggcacaa ggaggagtca ccaaagggc     3540 cgggtggggg ccccgctgct tcgggaggag tggctgaagg gatcgccaac ggacgcctcg    3600
tccagcacca tggtgccgag cccagcagct tggacaagag gaaagagata tttagcaaag    3660
acacactgtt caaacctctt cacagcacct tgtctgtaaa cagctatcac aagtcgagcc    3720
tgtccctcct caaatctcac ccgaagacac ctgctgacac attgccaggc cgatgtgaga    3780
aactggaacc gtccctgggg acctcggcgg cacaagccat gcctgcttcc cagcgtcagc    3840
aggagtcagg agggaaccag gaagcctctt ttgactatta caacgtctct gatgatgacg    3900
actctgagga aggggcaaac aagaacacag aggaggagaa aaatagagag gacgtaggca    3960
ccatgcagtg gctcctcgag cgggagaagg aaagagactt gcagaggaaa tttgaaaaga    4020
acctcaccct tcttgctcca aaagaaaccg acagcagcag caaccagaga gccacccatt    4080
cagcccggct cgacagcatg gacagcagca gcatcacagt ggacagtgga ttcaactccc    4140
cacggtag                                                            4148
```

<210> SEQ ID NO 9
<211> LENGTH: 880
<212> TYPE: PRT

<213> ORGANISM: Artificial Sequence
<220> FEATURE:
<223> OTHER INFORMATION: Synthetic

<400> SEQUENCE: 9

```
Met Phe Gly Gln Lys Lys His Lys His Gly Asp Val Ser Pro Ile Ser
1               5                   10                  15

Met Ser Pro Ile Ser Gln Ser Gln Phe Ile Pro Leu Gly Glu Ile Leu
            20                  25                  30

Cys Leu Ala Ile Ser Ala Met Asn Ser Ala Arg Lys Pro Val Thr Gln
                35                  40                  45

Glu Ala Leu Met Glu His Leu Thr Thr Cys Phe Pro Gly Val Pro Thr
50                  55                  60

Pro Ser Gln Glu Ile Leu Arg His Thr Leu Asn Thr Leu Val Arg Glu
65                  70                  75                  80

Arg Lys Ile Tyr Pro Thr Pro Asp Gly Tyr Phe Ile Val Thr Pro Gln
                85                  90                  95

Thr Tyr Phe Ile Thr Pro Ser Leu Ile Arg Thr Asn Ser Lys Trp Tyr
            100                 105                 110

His Leu Asp Glu Arg Ile Pro Asp Arg Ser Gln Cys Thr Ser Pro Gln
        115                 120                 125

Pro Gly Thr Ile Thr Pro Ser Ala Ser Gly Cys Val Arg Glu Arg Thr
    130                 135                 140

Leu Pro Arg Asn His Cys Asp Ser Cys His Cys Arg Glu Asp Val
145                 150                 155                 160

His Ser Thr His Ala Pro Thr Leu Gln Arg Lys Ser Ala Lys Asp Cys
                165                 170                 175

Lys Asp Pro Tyr Cys Pro Pro Ser Leu Cys Gln Val Pro Pro Thr Glu
            180                 185                 190

Lys Ser Lys Ser Thr Val Asn Phe Ser Tyr Lys Thr Glu Thr Leu Ser
        195                 200                 205

Lys Pro Lys Asp Ser Glu Lys Gln Ser Lys Lys Phe Gly Leu Lys Leu
    210                 215                 220

Phe Arg Leu Ser Phe Lys Lys Asp Lys Thr Lys Gln Leu Ala Asn Phe
225                 230                 235                 240

Ser Ala Gln Phe Pro Pro Glu Glu Trp Pro Leu Arg Asp Glu Asp Thr
                245                 250                 255

Pro Ala Thr Ile Pro Arg Glu Val Glu Met Glu Ile Ile Arg Arg Ile
            260                 265                 270

Asn Pro Asp Leu Thr Val Glu Asn Val Met Arg His Thr Ala Leu Met
        275                 280                 285

Lys Lys Leu Glu Glu Glu Lys Ala Gln Arg Ser Lys Ala Gly Ser Ser
    290                 295                 300

Ala His His Ser Gly Arg Ser Lys Lys Ser Arg Thr His Arg Lys Ser
305                 310                 315                 320

His Gly Lys Ser Arg Ser His Ser Lys Thr Arg Val Ser Lys Gly Asp
                325                 330                 335

Pro Ser Asp Gly Ser His Leu Asp Ile Pro Ala Glu Arg Glu Tyr Asp
            340                 345                 350

Phe Cys Asp Pro Leu Thr Arg Val Pro Arg Glu Gly Cys Phe Ile Ile
        355                 360                 365

Glu His Lys Gly Asp Asn Phe Ile Met His Ser Asn Thr Asn Val Leu
    370                 375                 380

Glu Ser His Phe Pro Met Thr Pro Glu Trp Asp Val Ser Gly Glu Leu
```

-continued

```
            385                 390                 395                 400
        Ala Lys Arg Arg Thr Glu Met Pro Phe Pro Glu Pro Ser Arg Gly Ser
                        405                 410                 415

Ser His Ser Lys Val His Arg Ser His Ser His Thr Gln Asp Arg Arg
                        420                 425                 430

Ser Arg Asn Glu Arg Ser Asn Lys Ala Lys Glu Arg Ser Arg Ser Met
                        435                 440                 445

Asp Asn Ser Lys Gly Pro Leu Gly Ala Ser Ser Leu Gly Thr Pro Glu
                        450                 455                 460

Asp Leu Ala Glu Gly Cys Ser Gln Asp Gln Thr Pro Ser Gln Ser
        465                 470                 475                 480

Tyr Ile Asp Asp Ser Thr Leu Arg Pro Ala Gln Thr Val Ser Leu Gln
                        485                 490                 495

Arg Ala His Ile Ser Ser Thr Ser Tyr Lys Glu Val Cys Ile Pro Glu
                        500                 505                 510

Ile Val Ser Gly Ser Lys Glu Pro Ser Ser Ala Cys Ser Leu Leu Glu
                        515                 520                 525

Pro Gly Lys Pro Pro Glu Ser Leu Pro Ser Tyr Gly Glu Leu Asn Ser
                        530                 535                 540

Cys Pro Thr Lys Thr Ala Thr Asp Asp Tyr Phe Gln Cys Asn Thr Ser
        545                 550                 555                 560

Ser Glu Thr Val Leu Thr Ala Pro Ser Pro Leu Gly Lys Asn Lys Glu
                        565                 570                 575

Asp His Asp Thr Leu Thr Leu Ala Glu Gly Val Lys Lys Leu Ser Pro
                        580                 585                 590

Ser Asp Arg Gln Val Pro His Ser Ser Arg Glu Pro Val Gly His Lys
                        595                 600                 605

Glu Glu Ser Pro Lys Gly Pro Gly Gly Pro Ala Ala Ser Gly Gly
                        610                 615                 620

Val Ala Glu Gly Ile Ala Asn Gly Arg Leu Val Gln His His Gly Ala
        625                 630                 635                 640

Glu Pro Ser Ser Leu Asp Lys Arg Lys Glu Ile Phe Ser Lys Asp Thr
                        645                 650                 655

Leu Phe Lys Pro Leu His Ser Thr Leu Ser Val Asn Ser Tyr His Lys
                        660                 665                 670

Ser Ser Leu Ser Leu Leu Lys Ser His Pro Lys Thr Pro Ala Asp Thr
                        675                 680                 685

Leu Pro Gly Arg Cys Glu Lys Leu Glu Pro Ser Leu Gly Thr Ser Ala
                        690                 695                 700

Ala Gln Ala Met Pro Ala Ser Gln Arg Gln Glu Ser Gly Gly Asn
        705                 710                 715                 720

Gln Glu Ala Ser Phe Asp Tyr Tyr Asn Val Ser Asp Asp Asp Ser
                        725                 730                 735

Glu Glu Gly Ala Asn Lys Asn Thr Glu Glu Lys Asn Arg Glu Asp
                        740                 745                 750

Val Gly Thr Met Gln Trp Leu Leu Glu Arg Glu Lys Glu Arg Asp Leu
                        755                 760                 765

Gln Arg Lys Phe Glu Lys Asn Leu Thr Leu Ala Pro Lys Glu Thr
                        770                 775                 780

Asp Ser Ser Ser Asn Gln Arg Ala Thr His Ser Ala Arg Leu Asp Ser
        785                 790                 795                 800

Met Asp Ser Ser Ser Ile Thr Val Asp Ser Gly Phe Asn Ser Pro Arg
                        805                 810                 815
```

```
Thr Arg Glu Ser Leu Ala Ser Asn Thr Ser Ser Ile Val Glu Ser Asn
            820                 825                 830

Arg Arg Gln Asn Pro Ala Leu Ser Pro Ala His Gly Gly Ala Gly Pro
        835                 840                 845

Ala Phe Asn Phe Arg Ala Ser Ala Glu Pro Pro Thr Asn Glu Ala Glu
850                 855                 860

Lys Leu Gln Lys Pro Ser Asn Cys Leu Gln Ala Ser Val Thr Ser Val
865                 870                 875                 880

<210> SEQ ID NO 10
<211> LENGTH: 9713
<212> TYPE: DNA
<213> ORGANISM: Artificial Sequence
<220> FEATURE:
<223> OTHER INFORMATION: Synthetic

<400> SEQUENCE: 10
```

| | | | | | |
|---|---|---|---|---|---|
| ggtgctgggt | gagctccacc | gctgcccggg | ctgcgagcct | gacggctgtg | tgtcgggaat | 60 |
| gacgagaccc | aggcttgcaa | agacttgcac | ggcaactgga | atttatgaca | aatagctcac | 120 |
| tgcagctaaa | ctttgataca | gtgtacagta | gaaccgcctg | ttacacacag | gagggagacg | 180 |
| cgtccttcgt | caccatgcaa | agccagcctt | aacacaacat | aggaaaatgt | ggcaggtctc | 240 |
| taattacgga | ctgagaacaa | gcagaagagg | agtgacactg | cagattccga | ggcactgcag | 300 |
| tgggatgttg | gctcagcaag | tggctgtgat | gtacgggata | ggcatggaac | aggattccag | 360 |
| ctgttccatg | caaataggat | aaaagaatgg | taaagaggat | tcctttttt | ttccctcctc | 420 |
| aaaacgttac | cagcaaagta | cattcacaga | gccttttaa | ggtgccttt | gccagctttt | 480 |
| gaactgaact | tgtaccagta | tctcaagccc | tgaattgtaa | gaagagctga | gagttctgga | 540 |
| actcattttt | aaaaagtaga | tctacgaaga | ttctaggacg | tccgtttctg | ttactggctc | 600 |
| cttcttgtgc | ttggatgcag | ctccctagca | tgcaccaggc | tttagcgtca | gtgctacctg | 660 |
| ggggatggag | ccagtccaga | aagggccagt | cacatccatc | tcatagctca | ccctgtcaca | 720 |
| gaagaaaaga | gagcatgttt | cctttctcca | ctgtcagagg | tctcttcttt | ctgcatagca | 780 |
| gtttgcatct | tcagagcaac | gttgaggatg | ctgagtcagg | tttaaaggat | gtttggtcag | 840 |
| aaaaaacaca | agcatggtga | tgtatcaccc | atcagtatgt | ctcccatcag | tcagtctcag | 900 |
| tttattccac | tcggggagat | cctctgcttg | gccatctcag | caatgaactc | ggcaagaaag | 960 |
| cctgtcaccc | aagaagcact | gatggagcac | ctgaccacgt | gcttcccagg | tgttccaacg | 1020 |
| ccaagccaag | aaattctgcg | gcacacgctg | aacacgctgg | tacgggagag | gaagatctac | 1080 |
| ccaactccag | atggctactt | catcgtgacc | ccacagactt | atttcataac | tccttccctc | 1140 |
| ataagaacta | acagtaaatg | gtaccatttg | gacgagagga | tacctgaccg | gtctcagtgc | 1200 |
| acctctccgc | aacccgggac | catcacgccc | tctgcctcag | gctgtgtcag | ggaaaggaca | 1260 |
| ttgccccgaa | accactgcga | ctcttgccac | tgctgcagag | aagacgtgca | cagcacgcat | 1320 |
| gcacccaccc | tgcaaaggaa | gtctgccaag | gactgcaaag | acccttactg | tccccttct | 1380 |
| ctgtgccagg | tgccaccac | tgaaaagagc | aaaagtactg | taaattttc | ctataagaca | 1440 |
| gaaactctct | caaaacctaa | agatagtgaa | agcagtcaa | aaaaattcgg | gctaaagtta | 1500 |
| ttccggttaa | gttttaaaaa | agacaagacc | aaacagctgg | ccaattttc | tgcccagttt | 1560 |
| cctcctgaag | agtggcccct | gcgagacgag | gacacgccag | ctacgatccc | tcgggaagta | 1620 |
| gagatggaaa | tcattaggcg | cattaaccca | gacctgaccg | tggaaaatgt | catgcggcac | 1680 |

-continued

```
accgcgctca tgaagaaact ggaagaagaa aaggcccaga ggagtaaagc cgggtcctct   1740
gcccatcaca gcggaaggag taaaaagagt aggactcatc ggaagtccca tggaaagtct   1800
cggtctcaca gcaagacacg ggtgtctaaa ggagacccct ccgacggttc acatctggat   1860
atcccagctg aaagagagta tgacttttgt gatcctctta ccagggtgcc cagggagggc   1920
tgcttcatca ttgaacacaa aggagataac ttcatcatgc acagcaacac aaacgtgctc   1980
gagtcccact tccccatgac accagaatgg gatgtgtctg gtgaattggc taaaaggaga   2040
actgagatgc cttttcctga accttctagg ggaagctccc actcaaaagt gcaccgaagc   2100
cacagccata cacaggaccg gaggtccagg aatgagagat ccaacaaagc caggagaga   2160 tccaggtcga tggataactc caaaggccct ctgggtgctt cttctctagg gacgccggaa   2220
gaccttgctg aaggctgcag ccaagacgac cagaccccca gccaatccta cattgacgac   2280
agtactttaa ggcctgcaca gaccgttagt ctccaaaggg ctcacatttc gtccacaagc   2340
tataaagagg tgtgtattcc agagatagtc agtggcagca aggaaccgtc cagcgcttgc   2400
agccttttgg agccaggaaa accacccgag agtttgccat cctatggcga actcaactct   2460
tgtccaacaa aaacagccac agatgactat ttccagtgca cacctctag tgagacggtg   2520 ctcacggcac catcacctct gggaaagaat aaggaggacc atgacactct gactttggca   2580
gaaggggtga aaaagctctc cccttctgat aggcaggtcc cccactcctc cagggagcct   2640
gtggggcaca aggaggagtc accaaaaggg ccgggtgggg gccccgctgc ttcgggagga   2700
gtggctgaag ggatcgccaa cggacgcctc gtccagcacc atggtgccga gcccagcagc   2760
ttggacaaga ggaaagagat atttagcaaa gacacactgt tcaaacctct tcacagcacc   2820
ttgtctgtaa acagctatca caagtcgagc ctgtccctcc tcaaatctca cccgaagaca   2880
cctgctgaca cattgccagg ccgatgtgag aaactggaac cgtccctggg gacctcggcg   2940
gcacaagcca tgcctgcttc ccagcgtcag caggagtcag gagggaacca ggaagcctct   3000
tttgactatt acaacgtctc tgatgatgac gactctgagg aaggggcaaa caagaacaca   3060
gaggaggaga aaaatagaga ggacgtaggc accatgcagt ggctcctcga gcgggagaag   3120
gaaagagact tgcagaggaa atttgaaaag aacctcaccc ttcttgctcc aaaagaaacc   3180
gacagcagca gcaaccagag agccacccat tcagcccggc tcgacagcat ggacagcagc   3240
agcatcacag tggacagtgg attcaactcc ccacgtactc gggagagcct ggcttccaac   3300
acatcaagca ttgttgaaag taaccgtcgt cagaaccccg ctttgagccc ggcccatggt   3360
ggagctggtc cagccttcaa cttccgagcg agcgcggagc ccccgacaaa tgaagctgag   3420
aagctacaga aaccttccaa ctgcttgcaa gcttctgtta ctagcgtgtg attgtccttc   3480
tgcctcagat cttctgtctc attcgataca gcaaagttta cgacactggg actgatgttt   3540
acatctttgg aaagacaagc atctcaacca cagttttgt gtttacttaa actgtgctgc   3600
taagtagggc tagggcaaaa aaacaaaaaa tctttatttc agagtattgc ttttcacatt   3660
tatggctctg tagcaactga gtaacagtag gggtgatatg tatactttg cttcactaat   3720 tgtatctgag cacacatagg aaagtctaga cactgtaagt gtaatacgca ttttcaatgt   3780
catgcagttg ccaattccat tttaaaatgc cacagatgcg tgttgctccc agtctgtggt   3840
taaacggtgc cacagaactg atccttgaca cttccaaaaa aaaaaaaaca aaacaaaaca   3900 aaaaaattt aaaaaaaaaa aacaaaaaac aaaactaagc taccacgaaa tgtcaaatgc   3960
aagggtccac cttgagggaa atagatgcca aactaactag aagggacccc ggcccttgt   4020 gtgtgaattg tttatgcacc agtcattttt cactgtgagt tttcgtgaca ctattttgca   4080
```

```
ggagcccatg gaagtgtgtg agaagggtc gcaatggaga tcactgggag tgaatgtttt    4140
cagggttttg ttttgaagtg tcacagatgc ttgtctgatt tttttaacct tccgtgatca    4200
caaacaggaa tataggcctt tgaatctgaa gtggacaaag gaaagcaatt tccagtctgg    4260
ctggggcaca gcattaggtg attgaaaagg tgatgtggac ttgtaaaagg tgttactcaa    4320
atattgaagg aagagaattt cctccttgtg atacttagga tgaccctatc ttactctaat    4380
agatacaata attagtttgt ttaaaagcaa aatgttcttt gtgatacaaa tgaagagtag    4440
ggcctgagga tgttattctt tctaatggaa ggacataaat ctattttatg tagttttaaa    4500
tagaatgcct aaattaggct gtgggagata attttttagtg gttgtaggaa agagcaaatt    4560
tagggagtgt tgaacttcag gccttttatt cctgggaaga tatgtataga gaaaactttt    4620
aaaataattt ttgattagaa atatacatgt gcccatgtaa taaacaacag aatgtgctca    4680
ttctgctagt gcggtataat ccgaatttgt actccctaa aatttatcag aataacaatt    4740
atgcatacat gaactatgcc agagtaatgt ttacagatac tttgtaacca atttcaggag    4800 gcgttttag ctggatgtgt agttaattag accaacttat ttccaaatgg tttgttaaca    4860
ttttgctttg gttacaaatg tcatgttgaa cacaaagaag acccagcagc aaagggatga    4920
ccaataattt catcttatag caaggagaca ttccaacgtt cccatgtttt attttctgag    4980
aacagtggga cagatctgta gtaatggaat attatttgca aaagggttac atatgacaca    5040
agtaagtgtt ctgacataaa gttttattta gttcagtggc atgtgctgtt gggagccata    5100
caccataaaa tatatatc ccaaaataaa tctagaatat tttcacctcc aatttcagta    5160
attggcatat gatttgtgag acgcatctgt ttttgtatga ggtttaatca ctagcaatct    5220
gtttaaagaa tccagtccta tacacagttg gactcattct tgaaaccttt aaatgctccc    5280
tcatagtttt tcagttattt ggaagttgca ttgggtcaaa ctgaactcct tgagtttggt    5340
gtaaattcct ttttctgct tattatagtg aaacttcagc atgtttctta gtaaactccc    5400
ataccattga aatgcttaag ccagttggct ttcagtctca tgccttattt cctccaaggc    5460
atgcctcaac gcattgtttg tctcattgct taaatatgtc cagaaggaat gatcatgtat    5520
ctaatagact acatagttgg ttcccttggg gagttatata tcatacagtt actaaatatt    5580
tgtctaaatt cattttttcc aaaaacctgc tctcaaattt ttcttctact ctcagttcat    5640
aaataatata accattgaaa caacacatca gcctctagct gatcctctga aagtagccat    5700
tgaaataatc gaatactgtg tgaacaggaa aggaaagcgt tacctttaag agaagcttta    5760
aaataggaat ttattgatat ttcacaagat ataggtttac agaagacatt attcaaataa    5820
atatgtacac tatttgcctg atgctatggg gtacataatt ttttaaaaac tcccttagac    5880
cagcagccat tagtgtagaa atgatggact ttaaaggtga taccatgtaa gcagatgttg    5940
catataaaaa tattcctgcc tgaatctgat cgagattctt gaatggggga ggagtggcag    6000
ccggcagcac attgcaaatg tcattcgagg tcacggtgag gctctcggtc ccggaacagt    6060
gggggcctcg ccaggcgttg ccagtatccc tttcctcctg taaaatcata gctttgtgtt    6120
acacgactgc ttatccagtc ttagggttta gcagctgaaa ggtttacaaa actgaatctg    6180
gttgaatctc tgtgaaaggg tcaacacatc tgtcggcatt ttgcacactt atgtattatt    6240
atgatacaac atattacttt atggtaattt ttatttttac atataactac ctccataaat    6300
ttgatgaaat ggcagccgtg tgttaaagtg tatcgttcag aagagcaaag ttgaacactt    6360
ccttcaacat tagggcatgg cgtgctgtgt gtgtcagtga ttgcctctgt ggactcatga    6420
```

-continued

| | | | | | |
|---|---|---|---|---|---|
| ctttccatcg | ccatggcttt | ctcttacgcc | gctgtttggc | tttcagatgt | aatcctgtct | 6480 |
| tctcctctct | tccccacgaa | agcgcactcg | attttgttag | gaatgaacgg | aagtttaaaa | 6540 |
| attcttgtgc | ccaccccgc | cctccaccca | ttcctgttaa | aagttctctg | gcgaagagcc | 6600 |
| aatgggtgaa | cgtaattgaa | agagctattt | actcttttgg | aaatctgatt | tgaagtctaa | 6660 |
| gttttcagta | acagaagaca | cacaagcaat | gtggactgcc | aagcttgaag | cacttcgggc | 6720 |
| tctgccttca | ctcgcatgct | accatgtcga | gcccaaactc | cactttaatt | aaaagagctg | 6780 |
| tgctgtgaat | tccacaactt | ctgttaaata | atttgtattc | cattatatat | attttgcaca | 6840 |
| tctcagggga | ccataatgaa | catatgaaag | ggggggggt | gccatcaaat | agagaaaaca | 6900 |
| aatagaagag | gtgaatggag | actagctgga | taaaataac | aaattacttc | ttctctgatg | 6960 |
| ttgtgaaggt | caggttcagg | aagcatcaat | tcacagttaa | tccggagtaa | caatgatctg | 7020 |
| aacaccagct | gttcccaggt | ccctcttttt | catagcccaa | ccagcatcta | aaatgtaaat | 7080 |
| ttaaattaca | ttgcagtcac | catggggaga | agaaacctgt | tcagtggaag | cagaagcatt | 7140 |
| gttcctttt | taggttggcg | cagctttgca | aaactctacc | caggataaac | cacttatcac | 7200 |
| caccaagtgt | acttgaaaat | aaagttttta | acttaaatta | caagcatatt | gctcataata | 7260 |
| caatagtgat | catttttga | aagtcttgcc | atttataaca | tgggcagtat | ttggagcttc | 7320 |
| atttaaaaac | caacaacaac | cgataatgac | tttgcacgat | tcactttggg | atctcaaagt | 7380 |
| gcttccaaag | cattcagatt | tacaaacaat | tcacaagaca | ggtcatcttt | gtaatacgca | 7440 |
| tacttacaac | gaattaacaa | aaggagtgac | ttaagattct | ccaggaacac | agtggcagct | 7500 |
| attgatgatc | tgttttctat | ctgtttgata | gagcatcatg | agaaatcaca | aaatacaatg | 7560 |
| ctattttct | gatgtgtgct | aataaagtca | aagaaaacaa | atacatcttg | acactttgt | 7620 |
| ccattttcat | taaaaaaaa | aaagttcagg | gtgtttggaa | ttttacatct | cagcacacct | 7680 |
| tactggtatc | aatggataaa | gcgggtgatt | gacagatcca | cccaaatgcc | actgcagtca | 7740 |
| gaagcagatc | tggacacacc | cttgtttaca | gtttcatatt | gggttgctat | agttcccgtg | 7800 |
| ctaaatcacc | agctttcagg | aacatgactg | ctcctggcag | tggaaggtgc | tgaaacagaa | 7860 |
| atttttaatta | aaaactttat | caagtactct | tcacagtgct | gcttggcacc | atagaaaatc | 7920 |
| agtacaatat | atcgagccct | actttggagg | agctggattt | ctgagggagc | tgatccagtt | 7980 |
| ctaagtgtct | tctcgaatta | ggagatagat | gatctttgat | ggggatctcc | tccgtcacca | 8040 |
| caggccagtc | acagaaccaa | ctagccacgt | gctgccagac | ctcagtgggc | ccaagcagga | 8100 |
| gcaatctctt | ctatccccca | tctcccccag | gaccatcccg | cccattgtca | acgtcatcca | 8160 |
| gggctcttct | ggtagtgagt | gacttttctg | cacatgttta | gggcttgggg | gagctagaac | 8220 |
| acaggaaaca | tgaatgcaaa | aggcatggaa | aacactgttt | tgctttgggt | tagtaaaatg | 8280 |
| tgggcaggac | aaagattact | attggtctga | gctttgccaa | gtgagataga | atcaactgtc | 8340 |
| accccattcc | tttcccagaa | ggtcttatgg | tattaaggat | acatccagta | ttttcccaca | 8400 |
| gatttttatt | caggcgatgt | ttcataaatt | acatatatga | aaacattcat | tattacattt | 8460 |
| ccttgtgtgt | ttcaaacaga | cattggcacc | ttcctattga | gttaattctc | tgcatctttt | 8520 |
| gcagcagcag | cccacaagga | gattcccaga | gatggctccc | ctaacacaca | gtcctgtgat | 8580 |
| tttacagttc | tatgacttac | agttgatgat | tcacaagatt | caggattcta | caagactcaa | 8640 |
| ggggaacta | aactttctta | cgattgtaca | tgatcagtta | tagggctgta | atcattaatt | 8700 |
| gttggcttca | aatgtggaca | cacacacaca | cacatcatgc | caaggaggga | atggggtgtt | 8760 |
| tcaagtcagg | cagcgatgat | tctggaaggt | tggaaatgta | aggttagaag | cttggctggt | 8820 |

```
cttagtaaac ttgttccctt gctcccacca agaagaggta ccaaatgtga gacctgagat    8880
ctcctccaat atctgtcctc tgcagttccg ggaaactaat catgaagtac acatgcagca    8940
gctcctccac ttcctttcct ccgaggtcct cctttccatt ctcccaccta gatactgaca    9000
caccgccacg gttccacat tggaagggca gaacactgtg cagtatcgtg cacacttgct    9060
gggttaggaa tagagctgcc ctagggtcac cttcatgcaa gtattgacag ctacaaatta    9120
aagtccttag agcagttgac acagatacta cgttctagaa gagaattaaa tttaaacgtc    9180
aagtttaaag ggatcataat tctgcaggta tctttctctg agtgactgaa tgtgactatt    9240
gcattagggt aaatgaatta agacgtgcaa gtgggattta ctgtatgtta gaaaggagtt    9300
ttgcagccaa gactgccttg aataaaatgt gtttgcactg aaaaaaaatt ttaaattact    9360
tggtctctgg ttgctgtaaa ggtcatccaa gatggatgtt ctgtttatat tgtatagtat    9420
ttcatatgaa ataattacag ttcatgaaat gtcttcccta atgttactga tttataacag    9480
cacatttgta acatggtttt tatcgtgtca gtgtaccata ctgtaaatga tgattacttg    9540
tcatgcttag tataataact taaaagaaaa aaaaggacag ggattttttgt aagtctatat    9600 ttgaaagtcc ctccctatgg tgatactgtg ttcatgttgt ttatgtagtg ttgtgtgaaa    9660
tatccatttt ggattgtgtt acttttaag atattaaata catttggtt ata              9713
```

<210> SEQ ID NO 11
<211> LENGTH: 879
<212> TYPE: PRT
<213> ORGANISM: Artificial Sequence
<220> FEATURE:
<223> OTHER INFORMATION: Synthetic

<400> SEQUENCE: 11

```
Met Glu Pro Val Gln Lys Gly Pro Gly Asp Val Ser Pro Ile Ser Met
1               5                   10                  15

Ser Pro Ile Ser Gln Ser Gln Phe Ile Pro Leu Gly Glu Ile Leu Cys
            20                  25                  30

Leu Ala Ile Ser Ala Met Asn Ser Ala Arg Lys Pro Val Thr Gln Glu
        35                  40                  45

Ala Leu Met Glu His Leu Thr Thr Cys Phe Pro Gly Val Pro Thr Pro
    50                  55                  60

Ser Gln Glu Ile Leu Arg His Thr Leu Asn Thr Leu Val Arg Glu Arg
65                  70                  75                  80

Lys Ile Tyr Pro Thr Pro Asp Gly Tyr Phe Ile Val Thr Pro Gln Thr
                85                  90                  95

Tyr Phe Ile Thr Pro Ser Leu Ile Arg Thr Asn Ser Lys Trp Tyr His
            100                 105                 110

Leu Asp Glu Arg Ile Pro Asp Arg Ser Gln Cys Thr Ser Pro Gln Pro
        115                 120                 125

Gly Thr Ile Thr Pro Ser Ala Ser Gly Cys Val Arg Glu Arg Thr Leu
    130                 135                 140

Pro Arg Asn His Cys Asp Ser Cys His Cys Arg Glu Asp Val His
145                 150                 155                 160

Ser Thr His Ala Pro Thr Leu Gln Arg Lys Ser Ala Lys Asp Cys Lys
                165                 170                 175

Asp Pro Tyr Cys Pro Pro Ser Leu Cys Gln Val Pro Pro Thr Glu Lys
            180                 185                 190

Ser Lys Ser Thr Val Asn Phe Ser Tyr Lys Thr Glu Thr Leu Ser Lys
        195                 200                 205
```

```
Pro Lys Asp Ser Glu Lys Gln Ser Lys Lys Phe Gly Leu Lys Leu Phe
    210                 215                 220
Arg Leu Ser Phe Lys Lys Asp Lys Thr Lys Gln Leu Ala Asn Phe Ser
225                 230                 235                 240
Ala Gln Phe Pro Pro Glu Glu Trp Pro Leu Arg Asp Glu Asp Thr Pro
                245                 250                 255
Ala Thr Ile Pro Arg Glu Val Glu Met Glu Ile Ile Arg Arg Ile Asn
            260                 265                 270
Pro Asp Leu Thr Val Glu Asn Val Met Arg His Thr Ala Leu Met Lys
        275                 280                 285
Lys Leu Glu Glu Glu Lys Ala Gln Arg Ser Lys Ala Gly Ser Ser Ala
    290                 295                 300
His His Ser Gly Arg Ser Lys Lys Ser Arg Thr His Arg Lys Ser His
305                 310                 315                 320
Gly Lys Ser Arg Ser His Ser Lys Thr Arg Val Ser Lys Gly Asp Pro
                325                 330                 335
Ser Asp Gly Ser His Leu Asp Ile Pro Ala Glu Arg Glu Tyr Asp Phe
            340                 345                 350
Cys Asp Pro Leu Thr Arg Val Pro Arg Glu Gly Cys Phe Ile Ile Glu
        355                 360                 365
His Lys Gly Asp Asn Phe Ile Met His Ser Asn Thr Asn Val Leu Glu
    370                 375                 380
Ser His Phe Pro Met Thr Pro Glu Trp Asp Val Ser Gly Glu Leu Ala
385                 390                 395                 400
Lys Arg Arg Thr Glu Met Pro Phe Pro Glu Pro Ser Arg Gly Ser Ser
                405                 410                 415
His Ser Lys Val His Arg Ser His Ser His Thr Gln Asp Arg Arg Ser
            420                 425                 430
Arg Asn Glu Arg Ser Asn Lys Ala Lys Glu Arg Ser Arg Ser Met Asp
        435                 440                 445
Asn Ser Lys Gly Pro Leu Gly Ala Ser Ser Leu Gly Thr Pro Glu Asp
    450                 455                 460
Leu Ala Glu Gly Cys Ser Gln Asp Asp Gln Thr Pro Ser Gln Ser Tyr
465                 470                 475                 480
Ile Asp Asp Ser Thr Leu Arg Pro Ala Gln Thr Val Ser Leu Gln Arg
                485                 490                 495
Ala His Ile Ser Ser Thr Ser Tyr Lys Glu Val Cys Ile Pro Glu Ile
            500                 505                 510
Val Ser Gly Ser Lys Glu Pro Ser Ser Ala Cys Ser Leu Leu Glu Pro
        515                 520                 525
Gly Lys Pro Pro Glu Ser Leu Pro Ser Tyr Gly Glu Leu Asn Ser Cys
    530                 535                 540
Pro Thr Lys Thr Ala Thr Asp Asp Tyr Phe Gln Cys Asn Thr Ser Ser
545                 550                 555                 560
Glu Thr Val Leu Thr Ala Pro Ser Pro Leu Gly Lys Asn Lys Glu Asp
                565                 570                 575
His Asp Thr Leu Thr Leu Ala Glu Gly Val Lys Lys Leu Ser Pro Ser
            580                 585                 590
Asp Arg Gln Val Pro His Ser Ser Arg Glu Pro Val Gly His Lys Glu
        595                 600                 605
Glu Ser Pro Lys Gly Pro Gly Gly Pro Ala Ser Gly Gly Val
    610                 615                 620
```

Ala Glu Gly Ile Ala Asn Gly Arg Leu Val Gln His His Gly Ala Glu
625                 630                 635                 640

Pro Ser Ser Leu Asp Lys Arg Lys Glu Ile Phe Ser Lys Asp Thr Leu
            645                 650                 655

Phe Lys Pro Leu His Ser Thr Leu Ser Val Asn Ser Tyr His Lys Ser
            660                 665                 670

Ser Leu Ser Leu Leu Lys Ser His Pro Lys Thr Pro Ala Asp Thr Leu
            675                 680                 685

Pro Gly Arg Cys Glu Lys Leu Glu Pro Ser Leu Gly Thr Ser Ala Ala
            690                 695                 700

Gln Ala Met Pro Ala Ser Gln Arg Gln Gln Glu Ser Gly Gly Asn Gln
705                 710                 715                 720

Glu Ala Ser Phe Asp Tyr Tyr Asn Val Ser Asp Asp Asp Ser Glu
            725                 730                 735

Glu Gly Ala Asn Lys Asn Thr Glu Glu Lys Asn Arg Glu Asp Val
            740                 745                 750

Gly Thr Met Gln Trp Leu Leu Glu Arg Glu Lys Glu Arg Asp Leu Gln
            755                 760                 765

Arg Lys Phe Glu Lys Asn Leu Thr Leu Leu Ala Pro Lys Glu Thr Asp
770                 775                 780

Ser Ser Ser Asn Gln Arg Ala Thr His Ser Ala Arg Leu Asp Ser Met
785                 790                 795                 800

Asp Ser Ser Ile Thr Val Asp Ser Gly Phe Asn Ser Pro Arg Thr
            805                 810                 815

Arg Glu Ser Leu Ala Ser Asn Thr Ser Ser Ile Val Glu Ser Asn Arg
            820                 825                 830

Arg Gln Asn Pro Ala Leu Ser Pro Ala His Gly Gly Ala Gly Pro Ala
            835                 840                 845

Phe Asn Phe Arg Ala Ser Ala Glu Pro Pro Thr Asn Glu Ala Glu Lys
850                 855                 860

Leu Gln Lys Pro Ser Asn Cys Leu Gln Ala Ser Val Thr Ser Val
865                 870                 875

<210> SEQ ID NO 12
<211> LENGTH: 9619
<212> TYPE: DNA
<213> ORGANISM: Artificial Sequence
<220> FEATURE:
<223> OTHER INFORMATION: Synthetic

<400> SEQUENCE: 12
tcaattttaa tgtgtgtgtt ctctcttcaa gcatctggag gtatgtgccc ttttacctt      60 tttcatgatt aaaaaaatat gagttggtgc taatgcatgg gagggacct gggcccttg     120 gagaggagag tgtgcccctc gccacccgc gcctgggta cattctgacc tcgcgtctcc     180
gcactgcaca gacaaaggag cctgcacaga caaacagagg ctgtagcttt tcttggagcg    240
atgactcatt tcagttcaca aaggattctg ggcagggcag tgagaagtca ggttggctga    300
tccgtccctg tgacttcact ttgcagagaa caagcagaag aggagtgaca ctgcagattc    360
cgaggcactg cagtgggatg ttggctcagc aagtggctgt gatgtacggg ataggcatgg    420
aacaggattc cagctgttcc atgcaaatag gataaagaa tggtaaagag gattcctttt    480 ttttccctc ctcaaaacgt taccagcaaa gtacattcac agagccttt taaggtgcct    540 tttgccagct tttgaactga acttgtacca gtatctcaag ccctgaattg taagaagagc    600
tgagagttct ggaactcatt tttaaaaagt agatctacga agattctagg acgtccgttt    660

```
ctgttactgg ctccttcttg tgcttggatg cagctccta gcatgcacca ggctttagcg      720
tcagtgctac ctgggggatg gagccagtcc agaaagggcc aggtgatgta tcacccatca      780
gtatgtctcc catcagtcag tctcagttta ttccactcgg ggagatcctc tgcttggcca      840
tctcagcaat gaactcggca agaaagcctg tcacccaaga agcactgatg gagcacctga      900
ccacgtgctt cccaggtgtt ccaacgccaa gccaagaaat tctgcggcac acgctgaaca      960
cgctggtacg ggagaggaag atctacccaa ctccagatgg ctacttcatc gtgaccccac     1020
agacttattt cataactcct tccctcataa gaactaacag taaatggtac catttggacg     1080
agaggatacc tgaccggtct cagtgcacct tccgcaaccc gggaccatc acgccctctg      1140 cctcaggctg tgtcagggaa aggacattgc cccgaaacca ctgcgactct tgccactgct     1200
gcagagaaga cgtgcacagc acgcatgcac ccaccctgca aaggaagtct gccaaggact     1260
gcaaagaccc ttactgtccc ccttctctgt gccaggtgcc acccactgaa aagagcaaaa     1320
gtactgtaaa ttttcctat aagacagaaa ctctctcaaa acctaaagat agtgaaaagc      1380
agtcaaaaaa attcgggcta aagttattcc ggttaagttt taaaaagac aagaccaaac      1440 agctggccaa tttttctgcc cagtttcctc ctgaagagtg gccctgcga gacgaggaca     1500 cgccagctac gatccctcgg gaagtagaga tggaaatcat taggcgcatt aacccagacc     1560
tgaccgtgga aaatgtcatg cggcacaccg cgctcatgaa gaaactggaa gaagaaaagg     1620
cccagaggag taaagccggg tcctctgccc atcacagcgg aaggagtaaa agagtagga      1680 ctcatcggaa gtcccatgga aagtctcggt ctcacagcaa gacacgggtg tctaaaggag     1740 accccttccga cggttcacat ctggatatcc cagctgaaag agagtatgac ttttgtgatc     1800
ctcttaccag ggtgcccagg gagggctgct tcatcattga acacaaagga gataacttca     1860
tcatgcacag caacacaaac gtgctcgagt cccacttccc catgacacca gaatgggatg     1920
tgtctggtga attggctaaa aggagaactg agatgccttt tcctgaacct tctagggga      1980 gctcccactc aaaagtgcac cgaagccaca gccatacaca ggaccggagg tccaggaatg     2040
agagatccaa caaagccaag gagagatcca ggtcgatgga taactccaaa ggccctctgg     2100
gtgcttcttc tctagggacg ccggaagacc ttgctgaagg ctgcagccaa gacgaccaga     2160 ccccccagcca atcctacatt gacgacagta ctttaaggcc tgcacagacc gttagtctcc     2220
aaagggctca catttcgtcc acaagctata aagaggtgtg tattccagag atagtcagtg     2280
gcagcaagga accgtccagc gcttgcagcc ttttggagcc aggaaaacca cccgagagtt     2340
tgccatccta tggcgaactc aactcttgtc aacaaaaaac agccacagat gactattcc      2400 agtgcaacac ctctagtgag acggtgctca cggcaccatc acctctggga aagaataagg     2460
aggaccatga cactctgact ttggcagaag gggtgaaaaa gctctcccct tctgataggc     2520
aggtccccca ctcctccagg gagcctgtgg ggcacaagga ggagtcacca aaagggccgg     2580 gtggggccc cgctgcttcg ggaggagtgg ctgaagggat cgccaacgga cgcctcgtcc     2640
agcaccatgg tgccgagccc agcagcttgg acaagaggaa agagatattt agcaaagaca     2700
cactgttcaa acctcttcac agcaccttgt ctgtaaacag ctatcacaag tcgagcctgt     2760
ccctcctcaa atctcacccg aagacacctg ctgcacatt gccaggccga tgtgagaaac     2820
tggaaccgtc cctggggacc tcggcggcac aagccatgcc tgcttcccag cgtcagcagg     2880
agtcaggagg gaaccaggaa gcctcttttg actattacaa cgtctctgat gatgacgact     2940
ctgaggaagg ggcaaacaag aacacagagg aggagaaaaa tagagaggac gtaggcacca     3000
```

```
tgcagtggct cctcgagcgg gagaaggaaa gagacttgca gaggaaattt gaaaagaacc    3060
tcacccttct tgctccaaaa gaaaccgaca gcagcagcaa ccagagagcc acccattcag    3120
cccggctcga cagcatggac agcagcagca tcacagtgga cagtggattc aactccccac    3180
gtactcggga gagcctggct tccaacacat caagcattgt tgaaagtaac cgtcgtcaga    3240
accccgcttt gagcccggcc catggtggag ctggtccagc cttcaacttc cgagcgagcg    3300
cggagccccc gacaaatgaa gctgagaagc tacagaaacc ttccaactgc ttgcaagctt    3360
ctgttactag cgtgtgattg tccttctgcc tcagatcttc tgtctcattc gatacagcaa    3420
agtttacgac actgggactg atgtttacat ctttggaaag acaagcatct caaccacagt    3480
ttttgtgttt acttaaactg tgctgctaag tagggctagg gcaaaaaaac aaaaaatctt    3540
tatttcagag tattgctttt cacatttatg gctctgtagc aactgagtaa cagtaggggt    3600
gatatgtata cttttgcttc actaattgta tctgagcaca cataggaaag tctagacact    3660
gtaagtgtaa tacgcatttt caatgtcatg cagttgccaa ttccatttta aaatgccaca    3720
gatgcgtgtt gctcccagtc tgtggttaaa cggtgccaca gaactgatcc ttgacacttc    3780
caaaaaaaaa aaacaaaac aaaacaaaaa aatttaaaa aaaaaaaaca aaaaacaaaa    3840
ctaagctacc acgaaatgtc aaatgcaagg gtccaccttg agggaaatag atgccaaact    3900
aactagaagg gaccccggcc ctttgtgtgt gaattgttta tgcaccagtc attttttcact    3960 gtgagttttc gtgacactat tttgcaggag cccatgaag tgtgtgagaa ggggtcgcaa     4020
tggagatcac tgggagtgaa tgttttcagg gttttgtttt gaagtgtcac agatgcttgt    4080
ctgatttttt taaccttccg tgatcacaaa caggaatata ggcctttgaa tctgaagtgg    4140
acaaaggaaa gcaatttcca gtctggctgg ggcacagcat taggtgattg aaaaggtgat    4200
gtggacttgt aaaaggtgtt actcaaatat tgaaggaaga gaatttcctc cttgtgatac    4260
ttaggatgac cctatcttac tctaatagat acaataatta gtttgtttaa aagcaaaatg    4320
ttctttgtga tacaaatgaa gagtagggcc tgaggatgtt attctttcta atggaaggac    4380
ataaatctat tttatgtagt tttaaataga atgcctaaat taggctgtgg gagataatttt    4440 ttagtggttg taggaaagag caaatttagg gagtgttgaa cttcaggcct tttattcctg    4500
ggaagatatg tatagagaaa acttttaaaa taattttttga ttagaaatat acatgtgccc    4560
atgtaataaa caacagaatg tgctcattct gctagtgcgg tataatccga atttgtactc    4620
ccctaaaatt tatcagaata acaattatgc atacatgaac tatgccagag taatgtttac    4680
agatactttg taaccaattt caggaggcgt tttagctgg atgtgtagtt aattagacca     4740
acttatttcc aaatggtttg ttaacatttt gctttggttt acaatgtcat gttgaacaca    4800
aagaagaccc agcagcaaag ggatgaccaa taatttcatc ttatagcaag agacattcc     4860 aacgttccca tgttttattt tctgagaaca gtgggacaga tctgtagtaa tggaatatta    4920
tttgcaaaag ggttacatat gacacaagta agtgttctga cataaagttt tatttagttc    4980
agtggcatgt gctgttggga gccatacacc ataaaatata tatatcccaa aataaatcta   5040
gaatattttc acctccaatt tcagtaattg gcatatgatt tgtgagacgc atctgttttt    5100
gtatgaggtt taatcactag caatctgttt aaagaatcca gtcctataca cagttggact   5160
cattcttgaa acctttaaat gctccctcat agttttttcag ttatttggaa gttgcattgg   5220
gtcaaactga actccttgag tttggtgtaa attccttttt tctgcttatt atagtgaaac    5280
ttcagcatgt ttcttagtaa actcccatac cattgaaatg cttaagccag ttggctttca   5340
gtctcatgcc ttatttcctc caaggcatgc ctcaacgcat tgtttgtctc attgcttaaa   5400
```

```
tatgtccaga aggaatgatc atgtatctaa tagactacat agttggttcc cttggggagt    5460
tatatatcat acagttacta aatatttgtc taaattcatt ttttccaaaa acctgctctc    5520
aaattttcct tctactctca gttcataaat aatataacca ttgaaacaac acatcagcct    5580
ctagctgatc ctctgaaagt agccattgaa ataatcgaat actgtgtgaa caggaaagga    5640
aagcgttacc tttaagagaa gctttaaaat aggaatttat tgatatttca caagatatag    5700
gtttacagaa gacattattc aaataaatat gtacactatt tgcctgatgc tatggggtac    5760 ataattttt aaaaactccc ttagaccagc agccattagt gtagaaatga tggactttaa    5820
aggtgatacc atgtaagcag atgttgcata taaaaatatt cctgcctgaa tctgatcgag    5880
attcttgaat gggggaggag tggcagccgg cagcacattg caaatgtcat tcgaggtcac    5940
ggtgaggctc tcggtcccgg aacagtgggg gcctcgccag gcgttgccag tatccctttc    6000
ctcctgtaaa atcatagctt tgtgttacac gactgcttat ccagtcttag ggtttagcag    6060
ctgaaaggtt tacaaaactg aatctggttg aatctctgtg aaagggtcaa cacatctgtc    6120
ggcattttgc acacttatgt attattatga tacaacatat tactttatgg taattttat    6180 ttttacatat aactacctcc ataaatttga tgaaatggca gccgtgtgtt aaagtgtatc    6240
gttcagaaga gcaaagttga acacttcctt caacattagg gcatggcgtg ctgtgtgtgt    6300
cagtgattgc ctctgtggac tcatgacttt ccatcgccat ggctttctct tacgccgctg    6360
tttggctttc agatgtaatc ctgtcttctc ctctcttccc cacgaaagcg cactcgattt    6420
tgttaggaat gaacggaagt ttaaaaattc ttgtgcccac ccccgccctc cacccattcc    6480
tgttaaaagt tctctggcga agagccaatg ggtgaacgta attgaaagag ctatttactc    6540
ttttggaaat ctgatttgaa gtctaagttt tcagtaacag aagacacaca agcaatgtgg    6600
actgccaagc ttgaagcact tcgggctctg ccttcactcg catgctacca tgtcgagccc    6660
aaactccact ttaattaaaa gagctgtgct gtgaattcca caacttctgt taaataattt    6720
gtattccatt atatatattt tgcacatctc aggggaccat aatgaacata tgaaagggggg    6780 gggggtgcca tcaaatagag aaaacaaata gaagaggtga atggagacta gctggataaa    6840
aataacaaat tacttcttct ctgatgttgt gaaggtcagg ttcaggaagc atcaattcac    6900
agttaatccg gagtaacaat gatctgaaca ccagctgttc ccaggtccct cttttttcata    6960 gcccaaccag catctaaaat gtaaatttaa attacattgc agtcaccatg gggagaagaa    7020
acctgttcag tggaagcaga agcattgttc cttttttagg ttggcgcagc tttgcaaaac    7080
tctacccagg ataaaccact tatcaccacc aagtgtactg gaaaataaag ttttaacttt    7140
aaattacaag catattgctc ataatacaat agtgatcatt ttttgaaagt cttgccattt    7200
ataacatggg cagtatttgg agcttcattt aaaaaccaac aacaaccgat aatgactttg    7260
cacgattcac tttgggatct caaagtgctt ccaaagcatt cagatttaca aacaattcac    7320
aagacaggtc atctttgtaa tacgcatact tacaacgaat taacaaaagg agtgacttaa    7380
gattctccag gaacacagtg gcagctattg atgatctgtt ttctatctgt ttgatagagc    7440
atcatgagaa atcacaaaat acaatgctat ttttctgatg tgtgctaata aagtcaaaga    7500
aaacaaatac atcttgacac ttttgtccat tttcattaaa aaaaaaaag ttcagggtgt    7560 ttggaatttt acatctcagc acaccttact ggtatcaatg gataaagcgg gtgattgaca    7620
gatccaccca aatgccactg cagtcagaag cagatctgga cacacccttg tttacagttt    7680
catattgggt tgctatagtt cccgtgctaa atcaccagct ttcaggaaca tgactgctcc    7740
```

```
tggcagtgga aggtgctgaa acagaaattt taattaaaaa ctttatcaag tactcttcac    7800
agtgctgctt ggcaccatag aaaatcagta caatatatcg agccctactt tggaggagct    7860
ggatttctga gggagctgat ccagttctaa gtgtcttctc gaattaggag atagatgatc    7920
tttgatgggg atctcctccg tcaccacagg ccagtcacag aaccaactag ccacgtgctg    7980
ccagacctca gtgggcccaa gcaggagcaa tctcttctat cccccatctc ccccaggacc    8040
atcccgccca ttgtcaacgt catccagggc tcttctggta gtgagtgact tttctgcaca    8100
tgtttagggc ttgggggagc tagaacacag gaaacatgaa tgcaaaggc atggaaaaca     8160 ctgtttttgct ttgggttagt aaaatgtggg caggacaaag attactattg gtctgagctt   8220
tgccaagtga gatagaatca actgtcaccc cattcctttc ccagaaggtc ttatggtatt    8280
aaggatacat ccagtatttt cccacagatt tttattcagg cgatgtttca taaattacat    8340
atatgaaaac attcattatt acatttcctt gtgtgtttca aacagacatt ggcaccttcc    8400
tattgagtta attctctgca tcttttgcag cagcagccca caaggagatt cccagagatg    8460
gctcccctaa cacacagtcc tgtgatttta cagttctatg acttacagtt gatgattcac    8520
aagattcagg attctacaag actcaagggg gaactaaact ttcttacgat tgtacatgat    8580
cagttatagg gctgtaatca ttaattgttg gcttcaaatg tggacacaca cacacacaca    8640
tcatgccaag gagggaatgg ggtgtttcaa gtcaggcagc gatgattctg gaaggttgga    8700
aatgtaaggt tagaagcttg gctggtctta gtaaacttgt tcccttgctc ccaccaagaa    8760
gaggtaccaa atgtgagacc tgagatctcc tccaatatct gtcctctgca gttccgggaa    8820
actaatcatg aagtacacat gcagcagctc ctccacttcc tttcctccga ggtcctcctt    8880
tccattctcc cacctagata ctgacacacc gccacggttt ccacattgga agggcagaac    8940
actgtgcagt atcgtgcaca cttgctgggt taggaataga gctgccctag ggtcaccttc    9000
atgcaagtat tgacagctac aaattaaagt ccttagagca gttgacacag atactacgtt    9060
ctagaagaga attaaattta aacgtcaagt ttaaagggat cataattctg caggtatctt    9120
tctctgagtg actgaatgtg actattgcat tagggtaaat gaattaagac gtgcaagtgg    9180
gatttactgt atgttagaaa ggagttttgc agccaagact gccttgaata aaatgtgttt    9240
gcactgaaaa aaaattttaa attacttggt ctctggttgc tgtaaaggtc atccaagatg    9300
gatgttctgt ttatattgta tagtatttca tatgaaataa ttacagttca tgaaatgtct    9360
tccctaatgt tactgattta taacagcaca tttgtaacat ggttttttatc gtgtcagtgt    9420 accatactgt aaatgatgat tacttgtcat gcttagtata ataacttaaa agaaaaaaaa    9480
ggacagggat ttttgtaagt ctatatttga aagtccctcc ctatggtgat actgtgttca    9540
tgttgtttat gtagtgttgt gtgaaatatc cattttggat tgtgttactt tttaagatat    9600
taaataacat ttggttata                                                 9619
```

<210> SEQ ID NO 13
<211> LENGTH: 446
<212> TYPE: PRT
<213> ORGANISM: Artificial Sequence
<220> FEATURE:
<223> OTHER INFORMATION: Synthetic

<400> SEQUENCE: 13

Met Leu Asp Met Ser Glu Ala Arg Ser Gln Pro Pro Cys Ser Pro Ser
1               5                   10                  15

Gly Thr Ala Ser Ser Met Ser His Val Glu Asp Ser Asp Ser Asp Ala
            20                  25                  30

```
Pro Pro Ser Pro Ala Gly Ser Glu Gly Leu Gly Arg Ala Gly Val Ala
        35                  40                  45
Val Gly Gly Ala Arg Gly Asp Pro Ala Glu Ala Ala Asp Glu Arg Phe
 50                  55                  60
Pro Ala Cys Ile Arg Asp Ala Val Ser Gln Val Leu Lys Gly Tyr Asp
 65                  70                  75                  80
Trp Ser Leu Val Pro Met Pro Val Arg Gly Gly Gly Gly Ala Leu
                 85                  90                  95
Lys Ala Lys Pro His Val Lys Arg Pro Met Asn Ala Phe Met Val Trp
                100                 105                 110
Ala Gln Ala Ala Arg Arg Lys Leu Ala Asp Gln Tyr Pro His Leu His
            115                 120                 125
Asn Ala Glu Leu Ser Lys Thr Leu Gly Lys Leu Trp Arg Leu Leu Ser
130                 135                 140
Glu Ser Glu Lys Arg Pro Phe Val Glu Ala Glu Arg Leu Arg Val
145                 150                 155                 160
Gln His Lys Lys Asp His Pro Asp Tyr Lys Tyr Gln Pro Arg Arg Arg
                165                 170                 175
Lys Ser Ala Lys Ala Gly His Ser Asp Ser Asp Ser Gly Ala Glu Leu
            180                 185                 190
Gly Pro His Pro Gly Gly Gly Ala Val Tyr Lys Ala Glu Ala Gly Leu
        195                 200                 205
Gly Asp Gly His His His Gly Asp His Thr Gly Gln Thr His Gly Pro
210                 215                 220
Pro Thr Pro Pro Thr Thr Pro Lys Thr Glu Leu Gln Gln Ala Gly Ala
225                 230                 235                 240
Lys Pro Glu Leu Lys Leu Glu Gly Arg Arg Pro Val Asp Ser Gly Arg
                245                 250                 255
Gln Asn Ile Asp Phe Ser Asn Val Asp Ile Ser Glu Leu Ser Ser Glu
            260                 265                 270
Val Met Gly Thr Met Asp Ala Phe Asp Val His Glu Phe Asp Gln Tyr
        275                 280                 285
Leu Pro Leu Gly Gly Pro Ala Pro Pro Glu Pro Gly Gln Ala Tyr Gly
        290                 295                 300
Gly Ala Tyr Phe His Ala Gly Ala Ser Pro Val Trp Ala His Lys Ser
305                 310                 315                 320
Ala Pro Ser Ala Ser Ala Ser Pro Thr Glu Thr Gly Pro Pro Arg Pro
                325                 330                 335
His Ile Lys Thr Glu Gln Pro Ser Pro Gly His Tyr Gly Asp Gln Pro
            340                 345                 350
Arg Gly Ser Pro Asp Tyr Gly Ser Cys Ser Gly Gln Ser Ser Ala Thr
        355                 360                 365
Pro Ala Ala Pro Ala Gly Pro Phe Ala Gly Ser Gln Gly Asp Tyr Gly
        370                 375                 380
Asp Leu Gln Ala Ser Ser Tyr Tyr Gly Ala Tyr Pro Gly Tyr Ala Pro
385                 390                 395                 400
Gly Leu Tyr Gln Tyr Pro Cys Phe His Ser Pro Arg Arg Pro Tyr Ala
                405                 410                 415
Ser Pro Leu Leu Asn Gly Leu Ala Leu Pro Pro Ala His Ser Pro Thr
            420                 425                 430
Ser His Trp Asp Gln Pro Val Tyr Thr Thr Leu Thr Arg Pro
        435                 440                 445
```

<210> SEQ ID NO 14
<211> LENGTH: 3049
<212> TYPE: DNA
<213> ORGANISM: Artificial Sequence
<220> FEATURE:
<223> OTHER INFORMATION: Synthetic

<400> SEQUENCE: 14

| | | | | | |
|---|---|---|---|---|---|
| ggcgagggtc | ggggccaccg | cgcggcgacc | tcgggtcccg | gagcgaccgc | agggcagccc | 60 |
| cgggcgccgg | ccccggtgcg | cgtctcctgt | gcgcgcccct | ccgcgcgcgg | ccccgatgct | 120 |
| ggacatgagc | gaggcccgct | cccagccgcc | ctgcagcccg | tccggcaccg | ccagctccat | 180 |
| gtcgcacgtg | gaggactcgg | actcggacgc | gccgccgtct | ccgccggct | ccgagggcct | 240 |
| gggccgcgcg | ggggtcgcgg | tggggggcgc | ccggggcgac | ccggcggagg | cggcggacga | 300 |
| gcgcttcccg | gcctgcatcc | gcgacgccgt | gtcgcaggtg | ctcaagggct | acgactggag | 360 |
| tctggtgccc | atgccggtgc | gcggcggcg | cggcggcgcg | ctcaaagcca | agccgcatgt | 420 |
| gaagcggccc | atgaacgcat | tcatggtgtg | ggcgcaggcg | gcgcgccgca | agctggccga | 480 |
| ccagtacccg | cacctgcaca | acgccgagct | cagcaagacg | ctgggcaagc | tgtggcgctt | 540 |
| gctgagcgag | agcgagaagc | ggcccttcgt | ggaggaggca | gagcgccttc | gcgtgcagca | 600 |
| caagaaggac | caccccgact | acaagtacca | gccacggcgc | aggaagagcg | ccaaagccgg | 660 |
| ccacagcgac | tccgactcgg | gcgcggagct | gggaccccac | cctggcggcg | gtgccgtgta | 720 |
| caaggctgaa | gcagggcttg | agatgggca | ccaccatggc | gaccacacag | ggcagaccca | 780 |
| cgggccgccc | accccgccca | ccaccccaa | gacggagctg | cagcaggcgg | gcgccaagcc | 840 |
| ggagctgaag | ctggagggac | gccggccggt | ggacagcggg | cgccagaaca | tcgacttcag | 900 |
| caacgtggac | atctcggagc | tcagcagcga | ggtcatgggc | accatggacg | ccttcgacgt | 960 |
| ccacgagttc | gaccagtacc | tgcccctggg | cggccccgcc | cacccgagc | cgggccaggc | 1020 |
| ctatggggc | gcctacttcc | acgccggggc | gtccccgtg | tgggcccaca | agagtgcccc | 1080 |
| gtcggcctcc | gcgtcgccca | ccgagacggg | tcccccacgg | ccgcacatca | agacggagca | 1140 |
| gccgagcccc | ggccactacg | gcgaccagcc | ccgaggctcg | cccgactacg | gttcctgcag | 1200 |
| cggccagtcc | agcgccaccc | cggccgcccc | cgccggcccc | ttcgccggct | cacagggcga | 1260 |
| ctatggcgac | ctgcaggcct | ccagctacta | tggtgcctac | cctggctacg | cacccggcct | 1320 |
| ctaccagtac | ccctgcttcc | actcgccgcg | ccggccctac | gcctcacccc | tgctcaacgg | 1380 |
| cctggccctg | ccgccgccc | acagcccac | cagtcactgg | gaccagccgg | tgtacaccac | 1440 |
| cctgaccagg | ccctgagggc | ccagccgcgg | ggagggactc | gcaggcgtca | gggggcagcc | 1500 |
| ttgtcccggc | ccagtgtgtg | tgaccagggc | gggaggggcc | ccagtggctg | agctccaagt | 1560 |
| gcctgctgaa | gtctgcaggg | aaacacgctt | gctgcccgtg | gccctcggcc | tccagatggc | 1620 |
| cacacctctg | ccgacgacgg | accagctccc | tctcccttct | atctttcttt | ttgaggtggt | 1680 |
| gggattattc | cacaaagaag | ggctgccgtt | tggtccctct | tccgtgagga | ctggcggcac | 1740 |
| cagcaccttc | gctttgcatc | tcggtagagg | agaaacggca | gcacagccca | aggaccaaag | 1800 |
| gagggggtgg | cagggccctt | gcagggcgct | gtgaggtcca | ggccggtctt | ggcgccgaga | 1860 |
| gccctgcac | tcaaggccac | attccctcga | caacggctgc | acgggctgtc | cgggatccgg | 1920 |
| ggtgtctgtc | cgcagactgg | gatgagtcta | ctcgagcatc | tccggaccct | gcctgtcaga | 1980 |
| tctgaggtgt | ctccttgctg | gcagagtgcg | ctcacgcgag | ggctggctgt | gatgaacaca | 2040 |
| tctctctttt | attttatgt | ttttgataat | tttatttttt | gaagcttaaa | tgtgtttctt | 2100 |

-continued

```
ctgaaagctg ttaaagatgt atttatgttc tgtgttattt tatctttaat taatgaggta    2160
attcgggcaa agagtagaat ttaagacaaa acgaagctg ggaagcttcc cttgagggca     2220
ggcaggaggt ggagttgcag ctgttggccg gcatcacgtt gctcgttgct cggcttatgg    2280
gaggccgccc tggagggccc ggaggtccca aggtccctgg gaggactggg cccctcatgc    2340
ctcgagcttg gcaaccgaaa acccgaggga ggagaaggga cctgccttgt gacatctctg    2400
atcaggttgg ggtgccccag cacccagtac cagtttgggg tttgggaagc aggactccgt    2460
ccctgtcccc gactgtgcca cgtggtagga cacataggac acaggaattc ctgggtcctt    2520
gcccatgact gtgccatgtg gtaggacaca ggacacagga attcctggaa agtggtggct    2580
tcagaagtga tcttggctcg caggcaccag tgccacctac caagctgtga aactaaacct    2640
tctccactaa acgtcgttag ggcctcagtt ctagacgagt cataccgat tcacctgcac     2700
tgcttcccct gtgtgctgag catagagcat acaatagcgc ctacttcacg gaaacttgtg   2760
cctttaaact ttgtaaactt aaacacagcc gagaagttgc ttctttgtac tttttctact    2820
tttcctactt ttttgtagaa aaaaaagata atgcctctgc ttctatttct ctgggggtgg    2880
gggtgggggc cggagccgt cgcagacccg tttcatgcag cgtctccctt ggcaccgcgt     2940
tcggaggacg caccctcact cccctgctgc cttcactcct ttctgaccaa gcaacgctaa    3000
cttttgtaca gatcgatttg ataaaattaa acaaagtgct ttttatgga               3049
```

<210> SEQ ID NO 15
<211> LENGTH: 236
<212> TYPE: PRT
<213> ORGANISM: Artificial Sequence
<220> FEATURE:
<223> OTHER INFORMATION: Synthetic

<400> SEQUENCE: 15

```
Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Ala Pro
    50                  55                  60

Gln Leu Arg Pro Ala Ala Asp Gly Gln Pro Ser Gly Gly Gly His Lys
65                  70                  75                  80

Ser Ala Pro Lys Gln Val Lys Arg Gln Arg Ser Ser Pro Glu Leu
                85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
        115                 120                 125

Asn Arg Val Lys Leu Val Asn Leu Gly Phe Ala Thr Leu Arg Glu His
    130                 135                 140

Val Pro Asn Gly Ala Ala Asn Lys Lys Met Ser Lys Val Glu Thr Leu
145                 150                 155                 160

Arg Ser Ala Val Glu Tyr Ile Arg Ala Leu Gln Gln Leu Leu Asp Glu
                165                 170                 175

His Asp Ala Val Ser Ala Ala Phe Gln Ala Gly Val Leu Ser Pro Thr
            180                 185                 190
```

```
Ile Ser Pro Asn Tyr Ser Asn Asp Leu Asn Ser Met Ala Gly Ser Pro
        195                 200                 205

Val Ser Ser Tyr Ser Ser Asp Glu Gly Ser Tyr Asp Pro Leu Ser Pro
    210                 215                 220

Glu Glu Gln Glu Leu Leu Asp Phe Thr Asn Trp Phe
225                 230                 235

<210> SEQ ID NO 16
<211> LENGTH: 2490
<212> TYPE: DNA
<213> ORGANISM: Artificial Sequence
<220> FEATURE:
<223> OTHER INFORMATION: Synthetic

<400> SEQUENCE: 16
```

| | | | | | |
|---|---|---|---|---|---|
| agcactctct | cacttctggc | cagggaacgt | ggaaggcgca | ccgacaggga | tccggccagg | 60 |
| gagggcgagt | gaaagaagga | atcagaaag | gaagggagtt | aacaaaataa | taaaaacagc | 120 |
| ctgagccacg | gctggagaga | ccgagacccg | gcgcaagaga | gcgcagcctt | agtaggagag | 180 |
| gaacgcgaga | gcgcggcagag | gcgcgttcagc | actgacttttt | gctgctgctt | ctgcttttttt | 240 |
| ttttcttaga | aacaagaagg | cgccagcggc | agcctcacac | gcgagcgcca | cgcgaggctc | 300 |
| ccgaagccaa | cccgcgaagg | gaggagggga | gggaggagga | ggcggcgtgc | agggaggaga | 360 |
| aaaagcattt | tcactttttt | tgctcccact | ctaagaagtc | tcccggggat | tttgtatata | 420 |
| ttttttaact | tccgtcaggg | ctcccgcttc | atatttcctt | ttctttccct | ctctgttcct | 480 |
| gcacccaagt | tctctctgtg | tcccctcgc | gggccccgca | cctcgcgtcc | cggatcgctc | 540 |
| tgattccgcg | actccttggc | cgccgctgcg | catggaaagc | tctgccaaga | tggagagcgg | 600 |
| cggcgccggc | cagcagccc | agccgcagcc | ccagcagccc | ttcctgccgc | cgcagcctg | 660 |
| tttctttgcc | acggccgcag | ccgcggcggc | cgcagccgcc | gcagcggcag | cgcagagcgc | 720 |
| gcagcagcag | cagcagcagc | agcagcagca | gcagcaggcg | ccgcagctga | gaccggcggc | 780 |
| cgacggccag | ccctcagggg | gcggtcacaa | gtcagcgccc | aagcaagtca | agcgacagcg | 840 |
| ctcgtcttcg | cccgaactga | tgcgctgcaa | acgccggctc | aacttcagcg | gctttggcta | 900 |
| cagcctgccg | cagcagcagc | cggccgccgt | ggcgcgcgc | aacgagcgcg | agcgcaaccg | 960 |
| cgtcaagttg | gtcaacctgg | gctttgccac | ccttcgggag | cacgtcccca | acggcgcggc | 1020 |
| caacaagaag | atgagtaagg | tggagacact | gcgctcggcg | gtcgagtaca | tccgcgcgct | 1080 |
| gcagcagctg | ctggacgagc | atgacgcggt | gagcgccgcc | ttccaggcag | gcgtcctgtc | 1140 |
| gcccaccatc | tcccccaact | actccaacga | cttgaactcc | atggccggct | cgccggtctc | 1200 |
| atcctactcg | tcggacgagg | gctcttacga | cccgctcagc | ccgaggagc | aggagcttct | 1260 |
| cgacttcacc | aactggttct | gaggggctcg | gcctggtcag | gccctggtgc | gaatggactt | 1320 |
| tggaagcagg | gtgatcgcac | aacctgcatc | tttagtgctt | tcttgtcagt | ggcgttggga | 1380 |
| ggggagaaa | aggaaaagaa | aaaaaaaga | agaagaagaa | gaaagagaa | gaagaaaaa | 1440 |
| acgaaaacag | tcaaccaacc | ccatcgccaa | ctaagcgagg | catgcctgag | agacatggct | 1500 |
| ttcagaaaac | gggaagcgct | cagaacagta | tctttgcact | ccaatcattc | acggagatat | 1560 |
| gaagagcaac | tgggacctga | gtcaatgcgc | aaaatgcagc | ttgtgtgcaa | aagcagtggg | 1620 |
| ctcctggcag | aagggagcag | cacacgcgtt | atagtaactc | ccatcacctc | taacacgcac | 1680 |
| agctgaaagt | tcttgctcgg | gtcccttcac | ctcctcgccc | tttcttaaag | tgcagttctt | 1740 |
| agccctctag | aaacgagttg | gtgtctttcg | tctcagtagc | ccccacccca | ataagctgta | 1800 |

```
gacattggtt tacagtgaaa ctatgctatt ctcagcccct tgaaactctg cttctcctcc    1860
agggcccgat tcccaaaccc catggcttcc ctcacactgt cttttctacc attttcatta    1920
tagaatgctt ccaatctttt gtgaattttt tattataaaa aatctatttg tatctatcct    1980
aaccagttcg gggatatatt aagatatttt tgtacataag agagaaagag agagaaaaat    2040
ttatagaagt tttgtacaaa tggtttaaaa tgtgtatatc ttgatacttt aacatgtaat    2100
gctattacct ctgcatattt tagatgtgta gttcacctta caactgcaat tttccctatg    2160
tggttttgta aagaactctc ctcataggtg agatcaagag gccaccagtt gtacttcagc    2220
accaatgtgt cttactttat agaaatgttg ttaatgtatt aatgatgtta ttaaatactg    2280
ttcaagaaga acaaagttta tgcagctact gtccaaactc aaagtggcag ccagttggtt    2340
ttgataggtt gccttttgga gatttctatt actgcctttt tttttcttac tgttttatta    2400
caaacttaca aaaatatgta taaccctgtt ttatacaaac tagtttcgta ataaaacttt    2460 ttccttttt taaaatgaaa ataaaaaaaa                                      2490
```

<210> SEQ ID NO 17
<211> LENGTH: 323
<212> TYPE: PRT
<213> ORGANISM: Artificial Sequence
<220> FEATURE:
<223> OTHER INFORMATION: Synthetic

<400> SEQUENCE: 17

```
Met Asp Ser Asp Ala Ser Leu Val Ser Ser Arg Pro Ser Ser Glu
1               5                   10                  15

Pro Asp Asp Leu Phe Leu Pro Ala Arg Ser Lys Gly Ser Ser Gly Ser
            20                  25                  30

Ala Phe Thr Gly Gly Thr Val Ser Ser Thr Pro Ser Asp Cys Pro
        35                  40                  45

Pro Glu Leu Ser Ala Glu Leu Arg Gly Ala Met Gly Ser Ala Gly Ala
    50                  55                  60

His Pro Gly Asp Lys Leu Gly Gly Ser Gly Phe Lys Ser Ser Ser Ser
65                  70                  75                  80

Ser Thr Ser Ser Thr Ser Ser Ala Ala Ala Ser Ser Thr Lys Lys
                85                  90                  95

Asp Lys Lys Gln Met Thr Glu Pro Glu Leu Gln Gln Leu Arg Leu Lys
            100                 105                 110

Ile Asn Ser Arg Glu Arg Lys Arg Met His Asp Leu Asn Ile Ala Met
        115                 120                 125

Asp Gly Leu Arg Glu Val Met Pro Tyr Ala His Gly Pro Ser Val Arg
    130                 135                 140

Lys Leu Ser Lys Ile Ala Thr Leu Leu Leu Ala Arg Asn Tyr Ile Leu
145                 150                 155                 160

Met Leu Thr Asn Ser Leu Glu Glu Met Lys Arg Leu Val Ser Glu Ile
                165                 170                 175

Tyr Gly Gly His His Ala Gly Phe His Pro Ser Ala Cys Gly Gly Leu
            180                 185                 190

Ala His Ser Ala Pro Leu Pro Ala Ala Thr Ala His Pro Ala Ala Ala
        195                 200                 205

Ala His Ala Ala His His Pro Ala Val His His Pro Ile Leu Pro Pro
    210                 215                 220

Ala Ala Ala Ala Ala Ala Ala Ala Ala Ala Ala Ala Val Ser Ser
225                 230                 235                 240
```

```
Ala Ser Leu Pro Gly Ser Gly Leu Pro Ser Val Gly Ser Ile Arg Pro
            245                 250                 255

Pro His Gly Leu Leu Lys Ser Pro Ser Ala Ala Ala Ala Ala Pro Leu
        260                 265                 270

Gly Gly Gly Gly Gly Ser Gly Ala Ser Gly Gly Phe Gln His Trp
        275                 280                 285

Gly Gly Met Pro Cys Pro Cys Ser Met Cys Gln Val Pro Pro His
        290                 295                 300

His His Val Ser Ala Met Gly Ala Gly Ser Leu Pro Arg Leu Thr Ser
305                 310                 315                 320

Asp Ala Lys

<210> SEQ ID NO 18
<211> LENGTH: 2521
<212> TYPE: DNA
<213> ORGANISM: Artificial Sequence
<220> FEATURE:
<223> OTHER INFORMATION: Synthetic

<400> SEQUENCE: 18
aaaaaccggc cgagccccta aaggtgcgga tgcttattat agatcgacgc gacaccagcg      60
cccggtgcca ggttctcccc tgaggctttt cggagcgagc tcctcaaatc gcatccagat     120
tttcgggtcc gagggaagga ggaccctgcg aaagctgcga cgactatctt ccctggggc     180 catggactcg gacgccagcc tggtgtccag ccgcccgtcg tcgccagagc ccgatgacct     240
tttcctgccg gcccggagta agggcagcag cggcagcgcc ttcactgggg gcaccgtgtc     300
ctcgtccacc ccgagtgact gcccgccgga gctgagcgcg gagctgcgcg gcgctatggg     360
ctctgcgggc gcgcatcctg gggacaagct aggaggcagt ggcttcaagt catcctcgtc     420
cagcacctcg tcgtctacgt cgtcggcggc tgcgtcgtcc accaagaagg acaagaagca     480
aatgacagag ccggagctgc agcagctgcg tctcaagatc aacagccgcg agcgcaagcg     540
catgcacgac ctcaacatcg ccatggatgg cctccgcgag gtcatgccgt acgcacacgg     600
cccttcggtg cgcaagcttt ccaagatcgc cacgctgctg ctggcgcgca actacatcct     660
catgctcacc aactcgctgg aggagatgaa gcgactggtg agcgagatct acgggggcca     720
ccacgctggc ttccacccgt cggcctgcgg cggcctggcg cactccgcgc ccctgcccgc     780
cgccaccgcg caccccggcag cagcagcgca cgccgcacat caccccgcgg tgcaccaccc     840
catcctgccg cccgccgccg cagcggctgc tgccgccgct gcagccgcgg ctgtgtccag     900
cgcctctctg cccggatccg ggctgccgtc ggtcggctcc atccgtccac cgcacggcct     960
actcaagtct ccgtctgctg ccgcggccgc cccgctgggg gcgggggcg gcggcagtgg    1020 ggcgagcggg ggcttccagc actggggcgg catgccctgc ccctgcagca tgtgccaggt    1080
gccgccgccg caccaccacg tgtcggctat gggcgccggc agcctgccgc gcctcacctc    1140
cgacgccaag tgagccgact ggcgccggcg cgttctggcg acaggggagc caggggccgc    1200
ggggaagcga ggactggcct cgctgggct cgggagctct gtcgcgagga ggggcgcagg    1260
accatggact gggggtgggg catggtgggg attccagcat ctgcgaaccc aagcaatggg    1320
ggcgcccaca gagcagtggg gagtgagggg atgttctctc cgggacctga tcgagcgctg    1380
tctggcttta acctgagctg gtccagtaga catcgtttta tgaaaaggta ccgctgtgtg    1440
cattcctcac tagaactcat ccgaccccg accccacct ccgggaaaag attctaaaaa    1500
cttctttccc tgagagcgtg gcctgacttg cagactcggc ttgggcagca cttcgggggg    1560
```

-continued

```
ggaggggtg ttatgggagg gggacacatt ggggccttgc tcctcttcct cctttcttgg    1620
cgggtgggag actccgggta gccgcactgc agaagcaaca gcccgaccgc gccctccagg    1680
gtcgtccctg gcccaaggcc aggggccaca agttagttgg aagccggcgt tcggtatcag    1740
aagcgctgat ggtcatatcc aatctcaata tctgggtcaa tccacaccct cttagaactg    1800
tggccgttcc tccctgtctc tcgttgattt gggagaatat ggttttctaa taaatctgtg    1860
gatgttcctt cttcaacagt atgagcaagt ttatagacat tcagagtaga accacttgtg    1920
gattggaata acccaaaact gccgatttca ggggcgggtg cattgtagtt attattttaa    1980
aatagaaact accccaccga ctcatctttc cttctctaag cacaaagtga tttggttatt    2040
ttggtacctg agaacgtaac agaattaaaa ggcagttgct gtggaaacag tttgggttat    2100 ttggggttc tgttggcttt ttaaaatttt ctttttgga tgtgtaaatt tatcaatgat     2160
gaggtaagtg cgcaatgcta agctgtttgc tcacgtgact gccagcccca tcggagtcta    2220
agccggcttt cctctatttt ggtttatttt tgccacgttt aacacaaatg gtaaactcct    2280
ccacgtgctt cctgcgttcc gtgcaagccg cctcggcgct gcctgcgttg caaactgggc    2340
tttgtagcgt ctgccgtgta acacccttcc tctgatcgca ccgcccctcg cagagagtgt    2400
atcatctgtt ttattttgt aaaaacaaag tgctaaataa tatttattac ttgtttggtt    2460
gcaaaaacgg aataaatgac tgagtgttga gattttaaat aaaatttaaa gtaaaaaaaa   2520
a                                                                    2521
```

<210> SEQ ID NO 19
<211> LENGTH: 323
<212> TYPE: PRT
<213> ORGANISM: Artificial Sequence
<220> FEATURE:
<223> OTHER INFORMATION: Synthetic

<400> SEQUENCE: 19

```
Met Asp Ser Asp Ala Ser Leu Val Ser Ser Arg Pro Ser Pro Glu
1               5                   10                  15

Pro Asp Asp Leu Phe Leu Pro Ala Arg Ser Lys Gly Ser Ser Gly Ser
                20                  25                  30

Ala Phe Thr Gly Gly Thr Val Ser Ser Thr Pro Ser Asp Cys Pro
        35                  40                  45

Pro Glu Leu Ser Ala Glu Leu Arg Gly Ala Met Gly Ser Ala Gly Ala
    50                  55                  60

His Pro Gly Asp Lys Leu Gly Gly Ser Gly Phe Lys Ser Ser Ser Ser
65                  70                  75                  80

Ser Thr Ser Ser Ser Thr Ser Ser Ala Ala Ala Ser Ser Thr Lys Lys
                85                  90                  95

Asp Lys Lys Gln Met Thr Glu Pro Glu Leu Gln Gln Leu Arg Leu Lys
                100                 105                 110

Ile Asn Ser Arg Glu Arg Lys Arg Met His Asp Leu Asn Ile Ala Met
            115                 120                 125

Asp Gly Leu Arg Glu Val Met Pro Tyr Ala His Gly Pro Ser Val Arg
        130                 135                 140

Lys Leu Ser Lys Ile Ala Thr Leu Leu Leu Ala Arg Asn Tyr Ile Leu
145                 150                 155                 160

Met Leu Thr Asn Ser Leu Glu Glu Met Lys Arg Leu Val Ser Glu Ile
                165                 170                 175

Tyr Gly Gly His His Ala Gly Phe His Pro Ser Ala Cys Gly Gly Leu
            180                 185                 190
```

```
Ala His Ser Ala Pro Leu Pro Ala Thr Ala His Pro Ala Ala Ala
            195                 200                 205

Ala His Ala Ala His His Pro Ala Val His His Pro Ile Leu Pro Pro
    210                 215                 220

Ala Ala Ala Ala Ala Ala Ala Ala Ala Ala Ala Ala Val Ser Ser
225                 230                 235                 240

Ala Ser Leu Pro Gly Ser Gly Leu Pro Ser Val Gly Ser Ile Arg Pro
            245                 250                 255

Pro His Gly Leu Leu Lys Ser Pro Ser Ala Ala Ala Ala Pro Leu
        260                 265                 270

Gly Gly Gly Gly Gly Gly Ser Gly Ala Ser Gly Gly Phe Gln His Trp
            275                 280                 285

Gly Gly Met Pro Cys Pro Cys Ser Met Cys Gln Val Pro Pro Pro His
        290                 295                 300

His His Val Ser Ala Met Gly Ala Gly Ser Leu Pro Arg Leu Thr Ser
305                 310                 315                 320

Asp Ala Lys

<210> SEQ ID NO 20
<211> LENGTH: 2722
<212> TYPE: DNA
<213> ORGANISM: Artificial Sequence
<220> FEATURE:
<223> OTHER INFORMATION: Synthetic

<400> SEQUENCE: 20
ggatgcttat tatagatcga cgcgacacca gcgcccggtg ccaggttctc ccctgaggct      60
tttcggagcg agctcctcaa atcgcatcca gagtaagtgt ccccgcccca cagcagccgc    120
agcctagatc ccagggacag actctcctca actcggctgt gacccagaat gctccgatac    180 aggggggtctg gatccctact ctgcgggcca tttctccaga gcgactttgc tcttctgtcc    240
tccccacact caccgctgca tctccctcac caaaagcgag aagtcggagc gacaacagct    300
ctttctgccc aagccccagt cagctgtttt cgggtccgag ggaaggagga ccctgcgaaa    360
gctgcgacga ctatcttccc ctggggccat ggactcggac gccagcctgg tgtccagccg    420
cccgtcgtcg ccagagcccg atgacctttt tctgccggcc cggagtaagg gcagcagcgg    480
cagcgccttc actgggggca ccgtgtcctc gtccaccccg agtgactgcc cgccggagct    540
gagcgccgag ctgcgcggcg ctatgggctc tgcgggcgcg catcctgggg acaagctagg    600
aggcagtggc ttcaagtcat cctcgtccag cacctcgtcg tctacgtcgt cggcggctgc    660
gtcgtccacc aagaaggaca agaagcaaat gacagagccg gagctgcagc agctgcgtct    720
caagatcaac agccgcgagc gcaagcgcat gcacgacctc aacatcgcca tggatggcct    780
ccgcgaggtc atgccgtacg cacacggccc ttcggtgcgc aagctttcca agatcgccac    840
gctgctgctg gcgcgcaact acatcctcat gctcaccaac tcgctggagg agatgaagcg    900
actggtgagc gagatctacg ggggccacca cgctggcttc acccgtcgg cctgcggcgg    960 cctggcgcac tccgcgcccc tgccgccgc caccgcgcac ccggcagcag cagcgcacgc   1020
cgcacatcac cccgcggtgc accacccat cctgccgccc gccgccgcag cggctgctgc   1080
cgccgctgca gccgcggctg tgtccagcgc ctctctgccc ggatccgggc tgccgtcggt   1140
cggctccatc cgtccaccgc acggcctact caagtctccg tctgctgccg cggccgcccc   1200 gctgggggc ggggcggcg gcagtggggc gagcgggggc ttccagcact ggggcggcat    1260
```

```
gccctgcccc tgcagcatgt gccaggtgcc gccgccgcac caccacgtgt cggctatggg    1320
cgccggcagc ctgccgcgcc tcacctccga cgccaagtga gccgactggc gccggcgcgt    1380
tctggcgaca ggggagccag gggccgcggg gaagcgagga ctggcctgcg ctgggctcgg    1440
gagctctgtc gcgaggaggg gcgcaggacc atggactggg ggtggggcat ggtggggatt    1500
ccagcatctg cgaacccaag caatgggggc gcccacagag cagtggggag tgaggggatg    1560
ttctctccgg gacctgatcg agcgctgtct ggctttaacc tgagctggtc cagtagacat    1620
cgttttatga aaaggtaccg ctgtgtgcat tcctcactag aactcatccg accccgacc     1680
cccacctccg ggaaaagatt ctaaaaactt ctttccctga gagcgtggcc tgacttgcag    1740
actcggcttg ggcagcactt cggggggga ggggtgtta tgggaggggg acacattggg      1800
gccttgctcc tcttcctcct ttcttggcgg gtgggagact ccgggtagcc gcactgcaga    1860
agcaacagcc cgaccgcgcc ctccagggtc gtccctggcc caaggccagg ggccacaagt    1920
tagttggaag ccggcgttcg gtatcagaag cgctgatggt catatccaat ctcaatatct    1980
gggtcaatcc acaccctctt agaactgtgg ccgttcctcc ctgtctctcg ttgatttggg    2040
agaatatggt tttctaataa atctgtggat gttccttctt caacagtatg agcaagttta    2100
tagacattca gagtagaacc acttgtggat tggaataacc caaaactgcc gatttcaggg    2160
gcgggtgcat tgtagttatt attttaaaat agaaactacc ccaccgactc atctttcctt    2220
ctctaagcac aaagtgattt ggttattttg gtacctgaga acgtaacaga attaaaaggc    2280
agttgctgtg gaaacagttt gggttatttg ggggttctgt tggcttttta aaattttctt    2340
ttttggatgt gtaaatttat caatgatgag gtaagtgcgc aatgctaagc tgtttgctca    2400
cgtgactgcc agccccatcg gagtctaagc cggcttttcct ctattttggt ttattttttgc   2460
cacgtttaac acaaatggta aactcctcca cgtgcttcct gcgttccgtg caagccgcct    2520
cggcgctgcc tgcgttgcaa actgggcttt gtagcgtctg ccgtgtaaca cccttcctct    2580
gatcgcaccg cccctcgcag agagtgtatc atctgtttta tttttgtaaa aacaaagtgc    2640
taaataatat ttattacttg tttggttgca aaaacggaat aaatgactga gtgttgagat    2700
tttaaataaa atttaaagta aa                                              2722
```

<210> SEQ ID NO 21
<211> LENGTH: 227
<212> TYPE: PRT
<213> ORGANISM: Artificial Sequence
<220> FEATURE:
<223> OTHER INFORMATION: Synthetic

<400> SEQUENCE: 21

Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Ala Glu Pro
        35                  40                  45

Ala Glu Ala Lys Glu Gly Lys Glu Lys Pro Asp Gln Asp Ala Glu Gly
    50                  55                  60

Lys Ala Glu Glu Lys Glu Gly Glu Lys Asp Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly

```
            100                 105                 110
Pro Ala Gly Gly Glu Ala Pro Lys Ala Glu Ala Ala Ala
        115                 120                 125
Pro Ala Glu Ser Ala Ala Pro Ala Ala Gly Glu Glu Pro Ser Lys Glu
        130                 135                 140
Glu Gly Glu Pro Lys Lys Thr Glu Ala Pro Ala Ala Pro Ala Ala Gln
145                 150                 155                 160
Glu Thr Lys Ser Asp Gly Ala Pro Ala Ser Asp Ser Lys Pro Gly Ser
                165                 170                 175
Ser Glu Ala Ala Pro Ser Ser Lys Glu Thr Pro Ala Ala Thr Glu Ala
                180                 185                 190
Pro Ser Ser Thr Pro Lys Ala Gln Gly Pro Ala Ala Ser Ala Glu Glu
                195                 200                 205
Pro Lys Pro Val Glu Ala Pro Ala Ala Asn Ser Asp Gln Thr Val Thr
        210                 215                 220
Val Lys Glu
225

<210> SEQ ID NO 22
<211> LENGTH: 1902
<212> TYPE: DNA
<213> ORGANISM: Artificial Sequence
<220> FEATURE:
<223> OTHER INFORMATION: Synthetic

<400> SEQUENCE: 22
ggcactgggc aggaagggga gggggagcga gcgcgagaaa tgcagaggct gcagcggcgg      60
cggcggcggc agtagcggca gcggcgacga cggcggcggc agcgctccaa ctggctcctc     120
gctccgggct ccgccgtcga gccgggagag agcctccgcc agcggccagg caccagccag     180
acgacgccag cgaccccggc tctcggcgg caccgcgcta actcaggggc tgcataggca      240
cccagagccg aactccaaga tgggaggcaa gctcagcaag aagaagaagg gctacaatgt     300
gaacgacgag aaagccaagg agaaagacaa gaaggccgag ggcgcggcga cggaagagga     360
ggggaccccg aaggagagtg agccccaggc ggccgcagag cccgccgagg ccaaggaggg     420
caaggagaag cccgaccagg acgccgaggg caaggccgag gagaaggagg gcgagaagga     480
cgcggcggct gccaaggagg aggccccgaa ggcggagccc gagaagacgg agggcgcggc     540
agaggccaag gctgagcccc gaaggcgcc cgagcaggag caggcggccc ccggccccgc     600
tgcgggcggc gaggccccca agctgctga ggcgccgcg gccccggccg agagcgcggc      660
ccctgccgcc ggggaggagc ccagcaagga ggaagggga cccaaaaaga ctgaggcgcc     720
cgcagctcct gccgcccagg agaccaaaag tgacggggcc ccagcttcag actcaaaacc     780
cggcagctcg gaggctgccc cctcttccaa ggagaccccc gcagccacgg aagcgcctag     840
ttccacaccc aaggcccagg gccccgcagc ctctgcagaa gagcccaagc cggtggaggc     900
cccggcagct aattccgacc aaaccgtaac cgtgaaagag tgacaaggac agcctatagg     960
aaaaacaata ccacttaaaa caatctcctc tctctctctc tctctctctc tctatctctc    1020
tctctatctc ctctctctct ctcctctcct atctctcctc tctctctctc ctatactaac    1080
ttgtttcaaa ttggaagtaa tgatatgtat tgcccaagga aaatacagg atgttgtccc     1140
atcaagggag ggaggggtg ggagaatcca aatagtattt ttgtgggaa atatctaata      1200
taccttcagt caactttacc aagaagtcct ggatttccaa gatccgcgtc tgaaagtgca    1260
gtacatcgtt tgtacctgaa actgccgcca catgcactcc tccaccgctg agagttgaat    1320
```

```
agcttttctt ctgcaatggg agttgggagt gatgcgtttg attctgccca cagggcctgt    1380
gccaaggcaa tcagatcttt atgagagcag tattttctgt gttttctttt taatttacag    1440
cctttcttat tttgatattt ttttaatgtt gtggatgaat gccagctttc agacagagcc    1500
cacttagctt gtccacatgg atctcaatgc caatcctcca ttcttcctct ccagatattt    1560
ttgggagtga caaacattct ctcatcctac ttagcctacc tagatttctc atgacgagtt    1620
aatgcatgtc cgtggttggg tgcacctgta gttctgttta ttggtcagtg gaaatgaaaa    1680
aaaaaaaaaa aaaagtctg cgttcattgc agttccagtt tctcttccat tctgtgtcac     1740
agacaccaac acaccactca ttggaaaatg gaaaaaaaaa acaaaaaaaa aacaaaaaaa    1800
tgtacaatgg atgcattgaa attatatgta attgtataaa tggtgcaaca gtaataaagt    1860
taaacaatta aaagaagta ataaagacaa aaaaaaaaa aa                         1902
```

<210> SEQ ID NO 23
<211> LENGTH: 227
<212> TYPE: PRT
<213> ORGANISM: Artificial Sequence
<220> FEATURE:
<223> OTHER INFORMATION: Synthetic

<400> SEQUENCE: 23

```
Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Ala Glu Pro
        35                  40                  45

Ala Glu Ala Lys Glu Gly Lys Glu Lys Pro Asp Gln Asp Ala Glu Gly
    50                  55                  60

Lys Ala Glu Glu Lys Glu Gly Glu Lys Asp Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Gly Gly Glu Ala Pro Lys Ala Ala Glu Ala Ala Ala
        115                 120                 125

Pro Ala Glu Ser Ala Ala Pro Ala Gly Glu Glu Pro Ser Lys Glu
    130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205

Pro Lys Pro Val Glu Ala Pro Ala Ala Asn Ser Asp Gln Thr Val Thr
    210                 215                 220

Val Lys Glu
225
```

<210> SEQ ID NO 24
<211> LENGTH: 1727

<212> TYPE: DNA
<213> ORGANISM: Artificial Sequence
<220> FEATURE:
<223> OTHER INFORMATION: Synthetic

<400> SEQUENCE: 24

| | | | | | |
|---|---|---|---|---|---|
| gcgcaactcg | tttgcagcgg | cgcagcccag | acgcgcctgc | agctggggct | caccccaacc | 60 |
| tcgctgccag | ccgagaactc | caagatggga | ggcaagctca | gcaagaagaa | gaagggctac | 120 |
| aatgtgaacg | acgagaaagc | caaggagaaa | gacaagaagg | ccgagggcgc | ggcgacggaa | 180 |
| gaggagggga | ccccgaagga | gagtgagccc | caggcggccg | cagagcccgc | cgaggccaag | 240 |
| gagggcaagg | agaagcccga | ccaggacgcc | gagggcaagg | ccgaggagaa | ggagggcgag | 300 |
| aaggacgcgg | cggctgccaa | ggaggaggcc | ccgaaggcgg | agcccgagaa | gacggagggc | 360 |
| gcggcagagg | ccaaggctga | gccccgaag | gcgcccgagc | aggagcaggc | ggcccccggc | 420 |
| cccgctgcgg | gcggcgaggc | ccccaaagct | gctgaggccg | ccgcggcccc | ggccgagagc | 480 |
| gcggcccctg | ccgccgggga | ggagcccagc | aaggaggaag | gggaacccaa | aaagactgag | 540 |
| gcgcccgcag | ctcctgccgc | ccaggagacc | aaaagtgacg | gggccccagc | ttcagactca | 600 |
| aaacccggca | gctcggaggc | tgcccccctct | tccaaggaga | ccccgcagc | cacggaagcg | 660 |
| cctagttcca | cacccaaggc | ccagggcccc | gcagcctctg | cagaagagcc | caagccggtg | 720 |
| gaggccccgg | cagctaattc | cgaccaaacc | gtaaccgtga | agagtgaca | aggacagcct | 780 |
| ataggaaaaa | caataccact | taaaacaatc | tcctctctct | ctctctctct | ctctctctat | 840 |
| ctctctctct | atctcctctc | tctctctcct | tcctatctc | tcctctctct | ctctcctata | 900 |
| ctaacttgtt | tcaaattgga | agtaatgata | tgtattgccc | aaggaaaaat | acaggatgtt | 960 |
| gtcccatcaa | gggagggagg | gggtgggaga | atccaaatag | tattttgtg | gggaaatatc | 1020 |
| taatatacct | tcagtcaact | ttaccaagaa | gtcctggatt | tccaagatcc | gcgtctgaaa | 1080 |
| gtgcagtaca | tcgtttgtac | ctgaaactgc | cgccacatgc | actcctccac | cgctgagagt | 1140 |
| tgaatagctt | ttcttctgca | atgggagttg | ggagtgatgc | gtttgattct | gcccacaggg | 1200 |
| cctgtgccaa | ggcaatcaga | tctttatgag | agcagtattt | tctgtgtttt | cttttttaatt | 1260 |
| tacagccttt | cttattttga | tatttttta | atgttgtgga | tgaatgccag | ctttcagaca | 1320 |
| gagcccactt | agcttgtcca | catggatctc | aatgccaatc | ctccattctt | cctctccaga | 1380 |
| tattttggg | agtgacaaac | attctctcat | cctacttagc | ctacctagat | ttctcatgac | 1440 |
| gagttaatgc | atgtccgtgg | ttgggtgcac | ctgtagttct | gtttattggt | cagtggaaat | 1500 |
| gaaaaaaaa | aaaaaaaaa | gtctgcgttc | attgcagttc | cagttctct | tccattctgt | 1560 |
| gtcacagaca | ccaacacacc | actcattgga | aaatggaaaa | aaaaacaaa | aaaaaaacaa | 1620 |
| aaaaatgtac | aatggatgca | ttgaaattat | atgtaattgt | ataaatggtg | caacagtaat | 1680 |
| aaagttaaac | aattaaaaag | aagtaataaa | gacaaaaaaa | aaaaaaa | | 1727 |

<210> SEQ ID NO 25
<211> LENGTH: 277
<212> TYPE: PRT
<213> ORGANISM: Artificial Sequence
<220> FEATURE:
<223> OTHER INFORMATION: Synthetic

<400> SEQUENCE: 25

Met Asp Thr Asn Arg Pro Gly Ala Phe Val Leu Ser Ser Ala Pro Leu
1               5                   10                  15

Ala Ala Leu His Asn Met Ala Glu Met Lys Thr Ser Leu Phe Pro Tyr

```
            20                  25                  30
Ala Leu Gln Gly Pro Ala Gly Phe Lys Ala Pro Ala Leu Gly Gly Leu
         35                  40                  45

Gly Ala Gln Leu Pro Leu Gly Thr Pro His Gly Ile Ser Asp Ile Leu
     50                  55                  60

Gly Arg Pro Val Gly Ala Gly Gly Gly Leu Gly Gly Leu Pro
 65                  70                  75                  80

Arg Leu Asn Gly Leu Ala Ser Ser Ala Gly Val Tyr Phe Gly Pro Ala
                 85                  90                  95

Ala Ala Val Ala Arg Gly Tyr Pro Lys Pro Leu Ala Glu Leu Pro Gly
             100                 105                 110

Arg Pro Pro Ile Phe Trp Pro Gly Val Val Gln Gly Ala Pro Trp Arg
         115                 120                 125

Asp Pro Arg Leu Ala Gly Pro Ala Pro Ala Gly Val Leu Asp Lys
     130                 135                 140

Asp Gly Lys Lys Lys His Ser Arg Pro Thr Phe Ser Gly Gln Gln Ile
145                 150                 155                 160

Phe Ala Leu Glu Lys Thr Phe Glu Gln Thr Lys Tyr Leu Ala Gly Pro
                 165                 170                 175

Glu Arg Ala Arg Leu Ala Tyr Ser Leu Gly Met Thr Glu Ser Gln Val
             180                 185                 190

Lys Val Trp Phe Gln Asn Arg Arg Thr Lys Trp Arg Lys Arg His Ala
         195                 200                 205

Ala Glu Met Ala Ser Ala Lys Lys Lys Gln Asp Ser Asp Ala Glu Lys
     210                 215                 220

Leu Lys Val Gly Gly Ser Asp Ala Glu Asp Asp Glu Tyr Asn Arg
225                 230                 235                 240

Pro Leu Asp Pro Asn Ser Asp Asp Glu Lys Ile Thr Arg Leu Leu Lys
                 245                 250                 255

Lys His Lys Pro Ser Asn Leu Ala Leu Val Ser Pro Cys Gly Gly Gly
             260                 265                 270

Ala Gly Asp Ala Leu
         275

<210> SEQ ID NO 26
<211> LENGTH: 1019
<212> TYPE: DNA
<213> ORGANISM: Artificial Sequence
<220> FEATURE:
<223> OTHER INFORMATION: Synthetic

<400> SEQUENCE: 26
gccgcgcgca aacttcccgg gccggcgggc aggggcggcg gcggcggggc ccggatggga      60
gcccgggccg gcggcggcgg cgcccatgga cactaaccgc ccgggcgcgt tcgtgctgag     120
cagtgccccg ctggccgcgc tgcacaacat ggccgagatg aagacgtcgc tgttccccta     180
cgcgctgcag gtccggccg gcttcaaggc gccccgcgctg gggggcctgg gcgcgcagct     240
cccgctcggg accccgcacg gcatcagcga catcctgggc cggcccgtgg gcgcggcggg     300 cggggggcctc ctggggggc tgccccggct caacgggctc cgtcgtccg ccggcgttta     360 cttcgggccc gcggccgctg tggcgcgcgg ctaccccaag cccctggccg agctgccggg     420
gcgcccgccc atcttctggc ccggcgtggt gcagggcgcg ccctggaggg acccgcgtct     480
ggctggcccg gccccggccg gcggcgtcct ggacaaggac gggaagaaga agcactcgcg     540
cccgaccttc tcgggccagc agatcttcgc gctggagaaa accttcgagc agaccaagta     600
```

```
cctggcgggc ccggagcgcg cgcgtctcgc ctactcgctg ggcatgaccg agagccaggt    660
gaaggtctgg ttccagaacc gccggaccaa gtggcgcaag cggcacgcgg cggagatggc    720
gtcggccaag aagaagcagg actcggacgc cgagaagctg aaggtgggcg gctcggacgc    780
ggaggacgac gacgaataca accggcccct ggacccaaac tcggacgacg agaagatcac    840
gcggctgctc aagaagcaca aaccctcgaa cttggcgctg gtcagcccgt gcggcggcgg    900 cgcggggac gccttgtgag gacccgcggg gtggggcga atctatttt gcagaatccg    960 ggggcggccc cgggtgggcg cgagtcgctt tgtatcatca ataaattatt taacgggtc    1019
```

<210> SEQ ID NO 27
<211> LENGTH: 277
<212> TYPE: PRT
<213> ORGANISM: Artificial Sequence
<220> FEATURE:
<223> OTHER INFORMATION: Synthetic

<400> SEQUENCE: 27

```
Met Asp Thr Asn Arg Pro Gly Ala Phe Val Leu Ser Ser Ala Pro Leu
1               5                   10                  15

Ala Ala Leu His Asn Met Ala Glu Met Lys Thr Ser Leu Phe Pro Tyr
            20                  25                  30

Ala Leu Gln Gly Pro Ala Gly Phe Lys Ala Pro Ala Leu Gly Gly Leu
        35                  40                  45

Gly Ala Gln Leu Pro Leu Gly Thr Pro His Gly Ile Ser Asp Ile Leu
    50                  55                  60

Gly Arg Pro Val Gly Ala Ala Gly Gly Gly Leu Gly Gly Leu Pro
65                  70                  75                  80

Arg Leu Asn Gly Leu Ala Ser Ser Ala Gly Val Tyr Phe Gly Pro Ala
                85                  90                  95

Ala Ala Val Ala Arg Gly Tyr Pro Lys Pro Leu Ala Glu Leu Pro Gly
            100                 105                 110

Arg Pro Pro Ile Phe Trp Pro Gly Val Val Gln Gly Ala Pro Trp Arg
        115                 120                 125

Asp Pro Arg Leu Ala Gly Pro Ala Pro Ala Gly Gly Val Leu Asp Lys
    130                 135                 140

Asp Gly Lys Lys Lys His Ser Arg Pro Thr Phe Ser Gly Gln Gln Ile
145                 150                 155                 160

Phe Ala Leu Glu Lys Thr Phe Glu Gln Thr Lys Tyr Leu Ala Gly Pro
                165                 170                 175

Glu Arg Ala Arg Leu Ala Tyr Ser Leu Gly Met Thr Glu Ser Gln Val
            180                 185                 190

Lys Val Trp Phe Gln Asn Arg Arg Thr Lys Trp Arg Lys Arg His Ala
        195                 200                 205

Val Glu Met Ala Ser Ala Lys Lys Lys Gln Asp Ser Asp Ala Glu Lys
    210                 215                 220

Leu Lys Val Gly Gly Ser Asp Ala Glu Asp Asp Glu Tyr Asn Arg
225                 230                 235                 240

Pro Leu Asp Pro Asn Ser Asp Asp Glu Lys Ile Thr Arg Leu Leu Lys
                245                 250                 255

Lys His Lys Pro Ser Asn Leu Ala Leu Val Ser Pro Cys Gly Gly Gly
            260                 265                 270

Ala Gly Asp Ala Leu
        275
```

<210> SEQ ID NO 28
<211> LENGTH: 1538
<212> TYPE: DNA
<213> ORGANISM: Artificial Sequence
<220> FEATURE:
<223> OTHER INFORMATION: Synthetic

<400> SEQUENCE: 28

| | | | | | |
|---|---|---|---|---|---|
| cgcaaacttc | ccgggccggc | gggcaggggc | ggcggcggcg | gggcccggat | gggagcccgg | 60 |
| gccggcggcg | gcggcgccca | tggacactaa | ccgcccgggc | gcgttcgtgc | tgagcagtgc | 120 |
| cccgctggcc | gcgctgcaca | acatggccga | gatgaagacg | tcgctgttcc | cctacgcgct | 180 |
| gcagggtccg | gccggcttca | aggcgcccgc | gctgggggc | ctgggcgcgc | agctcccgct | 240 |
| cgggaccccg | cacggcatca | gcgacatcct | gggccggccc | gtgggcgcgg | cgggcggggg | 300 |
| cctcctgggg | gggctgcccc | ggctcaacgg | gctcgcgtcg | tccgccggcg | tttacttcgg | 360 |
| gcccgcggcc | gctgtggcgc | gcggctaccc | caagcccctg | gccgagctgc | cggggcgccc | 420 |
| gcccatcttc | tggcccggcg | tggtgcaggg | cgcgccctgg | agggaccgc | gtctggctgg | 480 |
| cccggcccg | gccggcggcg | tcctggacaa | ggacgggaag | aagaagcact | cgcgcccgac | 540 |
| cttctcgggc | cagcagatct | cgcgctgga | gaaaaccttc | gagcagacca | agtacctggc | 600 |
| gggcccggag | cgcgcgcgtc | tcgcctactc | gctgggcatg | accgagagcc | aggtgaaggt | 660 |
| ctggttccag | aaccgccgga | ccaagtggcg | caagcggcac | gcggtggaga | tggcgtcggc | 720 |
| caagaagaag | caggactcgg | acgccgagaa | gctgaaggtg | ggcggctcgg | acgcggagga | 780 |
| cgacgacgaa | tacaaccggc | ccctggaccc | caactcggac | gacgagaaga | tcacgcggct | 840 |
| gctcaagaag | cacaaaccct | cgaacttggc | gctggtcagc | ccgtgcggcg | cggcgcggg | 900 |
| ggacgccttg | tgaggacccg | cggggtgggg | gcgaatctat | ttttgcagaa | tccggggcg | 960 |
| gccccgggtg | ggcgcgagtc | gctttgtatc | atcaataaat | tatttaacgg | gtccccgtcg | 1020 |
| gagccgtcgc | tccggagcct | gcgccgcgtg | tttcttccgt | ctcgaacccg | gagcgaggcg | 1080 |
| gccccctcccc | ggccccggct | tcgcccctgc | gccgcctcg | ggtcctccgg | gttccggtg | 1140 |
| cggaggctgc | gggccccggg | caggcgcgag | gaggcggcga | aggcgcaggg | aagggggcccg | 1200 |
| gcccgcggga | aggaaccgca | gcgacagccg | ccaggagccc | gggacggagc | cggggacgga | 1260 |
| gcagcaggaa | ccagaccggt | cacttccaaa | ggccctcag | aacgaccaac | agctgaaacc | 1320 |
| cgcggggcgg | actccgtgtt | gaaccgcgga | cagcggcaac | cacagcagcg | acacggacct | 1380 |
| gtgcttccac | caagaacaga | ttccgcagcg | gacagcagtc | acttgcagtg | gtagtattta | 1440 |
| tcccacacaa | acacccagct | aatgccttca | cccggtccag | gaactctgta | gtgttctaaa | 1500 |
| gtaaaatcaa | taaacatac | atttgtgttt | catcaaca | | | 1538 |

<210> SEQ ID NO 29
<211> LENGTH: 464
<212> TYPE: PRT
<213> ORGANISM: Artificial Sequence
<220> FEATURE:
<223> OTHER INFORMATION: Synthetic

<400> SEQUENCE: 29

Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp

```
              35                  40                  45
Ile Trp Lys Lys Phe Glu Leu Leu Pro Thr Pro Pro Leu Ser Pro Ser
 50                  55                  60

Arg Gly Phe Ala Glu His Ser Ser Glu Pro Pro Ser Trp Val Thr Glu
 65                      70                  75                  80

Met Leu Leu Glu Asn Glu Leu Trp Gly Ser Pro Ala Glu Glu Asp Ala
                     85                  90                  95

Phe Gly Leu Gly Gly Leu Gly Gly Leu Thr Pro Asn Pro Val Ile Leu
                100                 105                 110

Gln Asp Cys Met Trp Ser Gly Phe Ser Ala Arg Glu Lys Leu Glu Arg
                115                 120                 125

Ala Val Ser Glu Lys Leu Gln His Gly Arg Gly Pro Pro Thr Ala Gly
                130                 135                 140

Ser Thr Ala Gln Ser Pro Gly Ala Gly Ala Ala Ser Pro Ala Gly Arg
145                 150                 155                 160

Gly His Gly Gly Ala Gly Ala Gly Arg Ala Gly Ala Ala Leu Pro
                165                 170                 175

Ala Glu Leu Ala His Pro Ala Ala Glu Cys Val Asp Pro Ala Val Val
                180                 185                 190

Phe Pro Phe Pro Val Asn Lys Arg Glu Pro Ala Pro Val Pro Ala Ala
                195                 200                 205

Pro Ala Ser Ala Pro Ala Ala Gly Pro Ala Val Ala Ser Gly Ala Gly
210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Asp Glu Asp Glu Glu Glu Asp
                260                 265                 270

Glu Glu Glu Glu Ile Asp Val Val Thr Val Glu Lys Arg Arg Ser Ser
                275                 280                 285

Ser Asn Thr Lys Ala Val Thr Thr Phe Thr Ile Thr Val Arg Pro Lys
290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
                340                 345                 350

Glu Ala Ser Pro Arg Pro Leu Lys Ser Val Ile Pro Pro Lys Ala Lys
                355                 360                 365

Ser Leu Ser Pro Arg Asn Ser Asp Ser Glu Asp Ser Glu Arg Arg Arg
                370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
                420                 425                 430

Leu Gln Ala Glu Glu His Gln Leu Leu Leu Glu Lys Glu Lys Leu Gln
                435                 440                 445

Ala Arg Gln Gln Gln Leu Leu Lys Lys Ile Glu His Ala Arg Thr Cys
450                 455                 460
```

<210> SEQ ID NO 30
<211> LENGTH: 3046
<212> TYPE: DNA
<213> ORGANISM: Artificial Sequence
<220> FEATURE:
<223> OTHER INFORMATION: Synthetic

<400> SEQUENCE: 30

| | | | | | |
|---|---|---|---|---|---|
| gctttcctct | cctttctccc | tccccttgt | ctgcgccaca | gccccttct | ctccccgccc | 60 |
| cccgggtgtg | tcagattttt | cagttaataa | tatccccga | gcttcaaagc | gcaggctgtg | 120 |
| acagtcatct | gtctggacgc | gctgggtgga | tgcgggggc | tcctgggaac | tgtgttggag | 180 |
| ccgagcaagc | gctagccagg | cgcaagcgcg | cacagactgt | agccatccga | ggacaccccc | 240 |
| gcccccggg | cccacccgga | gacacccgcg | cagaatcgcc | tccggatccc | ctgcagtcgg | 300 |
| cgggaggtaa | ggagcagggc | ttgcaaaccg | cccggcgccc | agggaagcga | cgagcgccgg | 360 |
| ggcaaggcaa | gccctggacg | ggattgcgac | gtgcgcaccg | ggcgcccta a| tatgcccggg | 420 |
| ggactgtttc | tgcttccgaa | acaaaaccat | ctctgggttt | tcccagaaaa | gccagttcca | 480 |
| gccccgaagg | catcctggct | agaggagacc | cgccctaatc | cttttgcagc | ccttaccggg | 540 |
| gggagtaatg | gcttctgcga | aaagaaattc | cctcggctct | agaagatctg | tctgtgtttg | 600 |
| agctgtcgga | gagccgtgtt | ggaggtcggc | gccggcccc | gccttccgcg | ccccccacgg | 660 |
| gaaggaagca | ccccggtat | taaaacgaac | ggggcggaaa | gaagccctca | gtcgccggcc | 720 |
| gggaggcgag | ccgatgccga | gctgctccac | gtccaccatg | ccgggcatga | tctgcaagaa | 780 |
| cccagacctc | gagtttgact | cgctacagcc | ctgcttctac | ccggacgaag | atgacttcta | 840 |
| cttcggcggc | cccgactcga | cccccccggg | ggaggacatc | tggaagaagt | ttgagctgct | 900 |
| gcccacgccc | ccgctgtcgc | ccagccgtgg | cttcgcggag | cacagctccg | agcccccgag | 960 |
| ctgggtcacg | gagatgctgc | ttgagaacga | gctgtgggc | agcccggccg | aggaggacgc | 1020 |
| gttcggcctg | gggggactgg | gtggcctcac | ccccaacccg | gtcatcctcc | aggactgcat | 1080 |
| gtggagcggc | ttctccgccc | gcgagaagct | ggagcgcgcc | gtgagcgaga | gctgcagca | 1140 |
| cggccgcggg | ccgccaaccg | ccggttccac | cgcccagtcc | ccgggagccg | cgccgccag | 1200 |
| ccctgcgggt | cgcgggcacg | gcggggctgc | gggagccggc | cgcgccgggg | ccgccctgcc | 1260 |
| cgccgagctc | gcccacccgg | ccgccgagtg | cgtggatccc | gccgtggtct | tcccctttcc | 1320 |
| cgtgaacaag | cgcgagccag | cgcccgtgcc | cgcagccccg | gccagtgccc | ggcggcggg | 1380 |
| ccctgcggtc | gcctcggggg | cgggtattgc | cgccccagcc | ggggcccgg | gggtcgcccc | 1440 |
| tccgcgccca | ggcggccgcc | agaccagcgg | cggcgaccac | aaggccctca | gtacctccgg | 1500 |
| agaggacacc | ctgagcgatt | cagatgatga | agatgatgaa | gaggaagatg | aagaggaaga | 1560 |
| aatcgacgtg | gtcactgtgg | agaagcggcg | ttcctcctcc | aacaccaagg | ctgtcaccac | 1620 |
| attcaccatc | actgtgcgtc | ccaagaacgc | agccctgggt | cccggagggg | ctcagtccag | 1680 |
| cgagctgatc | ctcaaaacgat | gccttcccat | ccaccagcag | cacaactatg | ccgcccctc | 1740 |
| tccctacgtg | gagagtgagg | atgcaccccc | acagaagaag | ataaagagcg | aggcgtcccc | 1800 |
| acgtccgctc | aagagtgtca | tccccccaaa | ggctaagagc | ttgagccccc | gaaactctga | 1860 |
| ctcggaggac | agtgagcgtc | gcagaaacca | caacatcctg | gagcgccagc | gccgcaacga | 1920 |
| ccttcggtcc | agctttctca | cgctcaggga | ccacgtgccg | gagttggtaa | agaatgagaa | 1980 |
| ggccgccaag | gtggtcattt | tgaaaaaggc | cactgagtat | gtccactccc | tccaggccga | 2040 |

-continued

```
ggagcaccag cttttgctgg aaaaggaaaa attgcaggca agacagcagc agttgctaaa    2100
gaaaattgaa cacgctcgga cttgctagac gcttctcaaa actggacagt cactgccact    2160
ttgcacattt tgatttttt tttaaacaaa cattgtgttg acattaagaa tgttggttta     2220
ctttcaaatc ggtcccctgt cgagttcggc tctgggtggg cagtaggacc accagtgtgg    2280
ggttctgctg ggaccttgga gagcctgcat cccaggatgc tgggtggccc tgcagcctcc    2340
tccacctcac ctccatgaca gcgctaaacg ttggtgacgg ttgggagcct ctggggctgt    2400
tgaagtcacc ttgtgtgttc caagtttcca acaacagaa agtcattcct tcttttaaa     2460 atggtgctta agttccagca gatgccacat aaggggtttg ccatttgata cccctgggga    2520
acatttctgt aaataccatt gacacatccg ccttttgtat acatcctggg taatgagagg    2580
tggcttttgc ggccagtatt agactggaag ttcatacccta agtactgtaa taatacctca   2640
atgtttgagg agcatgtttt gtatacaaat atattgttaa tctctgttat gtactgtact    2700
aattcttaca ctgcctgtat actttagtat gacgctgata cataactaaa tttgatactt    2760
atattttcgt atgaaaatga gttgtgaaag ttttgagtag atattacttt atcactttt    2820 gaactaagaa acttttgtaa agaaatttac tatatatata tgcctttttc ctagcctgtt    2880
tcttcctgtt aatgtatttg ttcatgtttg gtgcatagaa ctgggtaaat gcaaagttct    2940
gtgtttaatt tcttcaaaat gtatatattt agtgctgcat cttatagcac tttgaaatac    3000
ctcatgttta tgaaaataaa tagcttaaaa ttaaatgaaa aaaaaa                   3046
```

<210> SEQ ID NO 31
<211> LENGTH: 464
<212> TYPE: PRT
<213> ORGANISM: Artificial Sequence
<220> FEATURE:
<223> OTHER INFORMATION: Synthetic

<400> SEQUENCE: 31

```
Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp
        35                  40                  45

Ile Trp Lys Lys Phe Glu Leu Leu Pro Thr Pro Pro Leu Ser Pro Ser
    50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140

Ser Thr Ala Gln Ser Pro Gly Ala Gly Ala Ser Pro Ala Gly Arg
145                 150                 155                 160

Gly His Gly Gly Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190
```

```
Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Glu Asp Asp Glu Glu Asp
            260                 265                 270

Glu Glu Glu Glu Ile Asp Val Val Thr Val Glu Lys Arg Arg Ser Ser
                275                 280                 285

Ser Asn Thr Lys Ala Val Thr Thr Phe Thr Ile Thr Val Arg Pro Lys
    290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
        355                 360                 365

Ser Leu Ser Pro Arg Asn Ser Asp Ser Glu Asp Ser Glu Arg Arg Arg
    370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
            420                 425                 430

Leu Gln Ala Glu Glu His Gln Leu Leu Leu Glu Lys Glu Lys Leu Gln
        435                 440                 445

Ala Arg Gln Gln Gln Leu Leu Lys Lys Ile Glu His Ala Arg Thr Cys
    450                 455                 460

<210> SEQ ID NO 32
<211> LENGTH: 2736
<212> TYPE: DNA
<213> ORGANISM: Artificial Sequence
<220> FEATURE:
<223> OTHER INFORMATION: Synthetic

<400> SEQUENCE: 32
gctttcctct cctttctccc tccccttgt ctgcgccaca gccccttct ctcccgccc      60 cccgggtgtg tcagattttt cagttaataa tatcccccga gcttcaaagc gcaggctgtg    120
acagtcatct gtctggacgc gctggtgga tgcggggggc tcctgggaac tgtgttggag     180
ccgagcaagc gctagccagg cgcaagcgcg cacagactgt agccatccga ggacaccccc    240 gccccccgg cccacccgga gacacccgcg cagaatcgcc tccggatccc ctgcagtcgg     300
cgggagtgtt ggaggtcggc gccggccccc gccttccgcg ccccccacgg gaaggaagca    360
cccccggtat taaaacgaac ggggcggaaa gaagccctca gtcgccggcc gggaggcgag    420
ccgatgccga gctgctccac gtccaccatg ccgggcatga tctgcaagaa cccagacctc    480
gagtttgact cgctacagcc ctgcttctac ccggacgaag atgacttcta cttcggcggc    540
```

```
cccgactcga ccccccgggg ggaggacatc tggaagaagt ttgagctgct gcccacgccc    600
ccgctgtcgc ccagccgtgg cttcgcggag cacagctccg agcccccgag ctgggtcacg    660
gagatgctgc ttgagaacga gctgtggggc agcccggccg aggaggacgc gttcggcctg    720
gggggactgg gtggcctcac ccccaacccg gtcatcctcc aggactgcat gtggagcggc    780
ttctccgccc gcgagaagct ggagcgcgcc gtgagcgaga agctgcagca cggccgcggg    840
ccgccaaccg ccggttccac ccgcccagtc ccggggagcc gcgccgccag ccctgcgggt    900
cgcgggcacg gcggggctgc gggagccggc cgcgccgggg ccgccctgcc cgccgagctc    960
gcccacccgg ccgccgagtg cgtggatccc gccgtggtct tccccttcc cgtgaacaag    1020 cgcgagccag cgcccgtgcc cgcagccccg gccagtgccc cggcggcggg ccctgcggtc    1080
gcctcggggg cgggtattgc cgccccagcc ggggccccgg gggtcgcccc tccgcgccca    1140
ggcggccgcc agaccagcgg cggcgaccac aaggccctca gtacctccgg agaggacacc    1200
ctgagcgatt cagatgatga agatgatgaa gaggaagatg aagaggaaga atcgacgtg    1260 gtcactgtgg agaagcggcg ttcctcctcc aacaccaagg ctgtcaccac attcaccatc    1320
actgtgcgtc ccaagaacgc agccctgggt cccgggaggg ctcagtccag cgagctgatc    1380
ctcaaacgat gccttcccat ccaccagcag cacaactatg ccgcccctc tccctacgtg    1440 gagagtgagg atgcaccccc acagaagaag ataaagagcg aggcgtcccc acgtccgctc    1500
aagagtgtca tcccccaaa ggctaagagc ttgagccccc gaaactctga ctcggaggac    1560
agtgagcgtc gcagaaacca caacatcctg gagcgccagc gccgcaacga ccttcggtcc    1620
agctttctca cgctcaggga ccacgtgccg gagttggtaa agaatgagaa ggccgccaag    1680
gtggtcattt tgaaaaaggc cactgagtat gtccactccc tccaggccga ggagcaccag    1740
cttttgctgg aaaaggaaaa attgcaggca agacagcagc agttgctaaa gaaaattgaa    1800
cacgctcgga cttgctagac gcttctcaaa actggacagt cactgccact ttgcacattt    1860 tgatttttt tttaaacaaa cattgtgttg acattaagaa tgttggttta ctttcaaatc    1920
ggtcccctgt cgagttcggc tctgggtggg cagtaggacc accagtgtgg ggttctgctg    1980
ggaccttgga gagcctgcat cccaggatgc tgggtggccc tgcagcctcc tccacctcac    2040
ctccatgaca cgctaaacg ttggtgacgg ttgggagcct ctggggctgt gaagtcacc    2100 ttgtgtgttc caagtttcca aacaacagaa agtcattcct tctttttaaa atggtgctta    2160
agttccagca gatgccacat aaggggtttg ccatttgata cccctgggga acatttctgt    2220
aaataccatt gacacatccg ccttttgtat acatcctggg taatgagagg tggcttttgc    2280
ggccagtatt agactggaag ttcataccta agtactgtaa taatacctca atgtttgagg    2340
agcatgtttt gtatacaaat atattgttaa tctctgttat gtactgtact aattcttaca    2400
ctgcctgtat actttagtat gacgctgata cataactaaa tttgatactt atattttcgt    2460
atgaaaatga gttgtgaaag ttttgagtag atattacttt atcacttttt gaactaagaa    2520 actttgtaa agaaatttac tatatatata tgccttttc ctagcctgtt tcttcctgtt    2580
aatgtatttg ttcatgtttg gtgcatagaa ctgggtaaat gcaaagttct gtgtttaatt    2640 tcttcaaat gtatatattt agtgctgcat cttatagcac tttgaaatac ctcatgttta    2700
tgaaaataaa tagcttaaaa ttaaatgaaa aaaaaa                              2736

<210> SEQ ID NO 33
<211> LENGTH: 253
<212> TYPE: PRT
```

<213> ORGANISM: Artificial Sequence
<220> FEATURE:
<223> OTHER INFORMATION: Synthetic

<400> SEQUENCE: 33

```
Met Arg Gly Ala Pro Gly Asn Cys Val Gly Ala Glu Gln Ala Leu Ala
1               5                   10                  15

Arg Arg Lys Arg Ala Gln Thr Val Ala Ile Arg Gly His Pro Arg Pro
            20                  25                  30

Pro Gly Pro Pro Gly Asp Thr Arg Ala Glu Ser Pro Pro Asp Pro Leu
        35                  40                  45

Gln Ser Ala Gly Asp Asp Glu Asp Glu Glu Asp Glu Glu Glu
    50                  55                  60

Glu Ile Asp Val Val Thr Val Glu Lys Arg Arg Ser Ser Ser Asn Thr
65                  70                  75                  80

Lys Ala Val Thr Thr Phe Thr Ile Thr Val Arg Pro Lys Asn Ala Ala
                85                  90                  95

Leu Gly Pro Gly Arg Ala Gln Ser Ser Glu Leu Ile Leu Lys Arg Cys
            100                 105                 110

Leu Pro Ile His Gln Gln His Asn Tyr Ala Ala Pro Ser Pro Tyr Val
        115                 120                 125

Glu Ser Glu Asp Ala Pro Pro Gln Lys Lys Ile Lys Ser Glu Ala Ser
    130                 135                 140

Pro Arg Pro Leu Lys Ser Val Ile Pro Lys Ala Lys Ser Leu Ser
145                 150                 155                 160

Pro Arg Asn Ser Asp Ser Glu Asp Ser Glu Arg Arg Arg Asn His Asn
                165                 170                 175

Ile Leu Glu Arg Gln Arg Arg Asn Asp Leu Arg Ser Ser Phe Leu Thr
            180                 185                 190

Leu Arg Asp His Val Pro Glu Leu Val Lys Asn Glu Lys Ala Ala Lys
        195                 200                 205

Val Val Ile Leu Lys Lys Ala Thr Glu Tyr Val His Ser Leu Gln Ala
    210                 215                 220

Glu Glu His Gln Leu Leu Leu Glu Lys Glu Lys Leu Gln Ala Arg Gln
225                 230                 235                 240

Gln Gln Leu Leu Lys Lys Ile Glu His Ala Arg Thr Cys
                245                 250
```

<210> SEQ ID NO 34
<211> LENGTH: 1829
<212> TYPE: DNA
<213> ORGANISM: Artificial Sequence
<220> FEATURE:
<223> OTHER INFORMATION: Synthetic

<400> SEQUENCE: 34

```
gctttcctct cctttctccc tccccttgt ctgcgccaca gccccttct ctcccgccc      60 cccgggtgtg tcagatttt cagttaataa tatcccccga gcttcaaagc gcaggctgtg   120
acagtcatct gtctggacgc gctgggtgga tgcggggggc tcctgggaac tgtgttggag   180
ccgagcaagc gctagccagg cgcaagcgcg cacagactgt agccatccga ggacaccccc   240 gccccccgg cccacccgga gacacccgcg cagaatcgcc tccggatccc ctgcagtcgg   300
cgggagatga tgaagatgat gaagaggaag atgaagagga agaaatcgac gtggtcactg   360
tggagaagcg gcgttcctcc tccaacacca aggctgtcac cacattcacc atcactgtgc   420
gtcccaagaa cgcagccctg gtcccgggga gggctcagtc cagcgagctg atcctcaaac   480
```

```
gatgccttcc catccaccag cagcacaact atgccgcccc ctctccctac gtggagagtg      540
aggatgcacc cccacagaag aagataaaga gcgaggcgtc cccacgtccg ctcaagagtg      600 tcatccccc  aaaggctaag agcttgagcc cccgaaactc tgactcggag gacagtgagc      660
gtcgcagaaa ccacaacatc ctggagcgcc agcgccgcaa cgaccttcgg tccagctttc      720
tcacgctcag ggaccacgtg ccggagttgg taaagaatga aaggccgcc  aaggtggtca      780 ttttgaaaaa ggccactgag tatgtccact ccctccaggc cgaggagcac cagcttttgc      840
tggaaaagga aaaattgcag gcaagacagc agcagttgct aaagaaaatt gaacacgctc      900
ggacttgcta gacgcttctc aaaactggac agtcactgcc actttgcaca tttgatttt       960 ttttttaaac aaacattgtg ttgacattaa gaatgttggt ttactttcaa atcggtcccc     1020
tgtcgagttc ggctctgggt gggcagtagg accaccagtg tggggttctg ctgggacctt     1080
ggagagcctg catcccagga tgctgggtgg ccctgcagcc tcctccacct cacctccatg     1140
acagcgctaa acgttggtga cggttgggag cctctggggc tgttgaagtc accttgtgtg     1200
ttccaagttt ccaaacaaca gaaagtcatt ccttcttttt aaaatggtgc ttaagttcca     1260
gcagatgcca cataaggggt ttgccatttg atacccctgg ggaacatttc tgtaaatacc     1320
attgacacat ccgcctttg tatacatcct gggtaatgag aggtggcttt gcggccagt       1380 attagactgg aagttcatac ctaagtactg taataatacc tcaatgtttg aggagcatgt     1440
tttgtataca aatatattgt taatctctgt tatgtactgt actaattctt acactgcctg     1500
tatactttag tatgacgctg atacataact aaatttgata cttatattt  cgtatgaaaa     1560 tgagttgtga agttttgag  tagatattac tttatcactt tttgaactaa gaaacttttg     1620
taaagaaatt tactatatat atatgccttt tcctagcct  gtttcttcct gttaatgtat     1680
ttgttcatgt ttggtgcata gaactgggta aatgcaaagt tctgtgttta atttcttcaa     1740
aatgtatata tttagtgctg catcttatag cactttgaaa tacctcatgt ttatgaaaat     1800
aaatagctta aaattaaatg aaaaaaaaa                                       1829
```

<210> SEQ ID NO 35
<211> LENGTH: 112
<212> TYPE: PRT
<213> ORGANISM: Artificial Sequence
<220> FEATURE:
<223> OTHER INFORMATION: Synthetic

<400> SEQUENCE: 35

Met Arg Gly Ala Pro Gly Asn Cys Val Gly Ala Glu Gln Ala Leu Ala
1               5                   10                  15

Arg Arg Lys Arg Ala Gln Thr Val Ala Ile Arg Gly His Pro Arg Pro
            20                  25                  30

Pro Gly Pro Pro Gly Asp Thr Arg Ala Glu Ser Pro Asp Pro Leu
        35                  40                  45

Gln Ser Ala Gly Val Leu Glu Val Gly Ala Gly Pro Arg Leu Pro Arg
    50                  55                  60

Pro Pro Arg Glu Gly Ser Thr Pro Gly Ile Lys Thr Asn Gly Ala Glu
65                  70                  75                  80

Arg Ser Pro Gln Ser Pro Ala Gly Arg Arg Ala Asp Ala Glu Leu Leu
                85                  90                  95

His Val His His Ala Gly His Asp Leu Gln Glu Pro Arg Pro Arg Val
            100                 105                 110

```
<210> SEQ ID NO 36
<211> LENGTH: 2736
<212> TYPE: DNA
<213> ORGANISM: Artificial Sequence
<220> FEATURE:
<223> OTHER INFORMATION: Synthetic

<400> SEQUENCE: 36
gctttcctct cctttctccc tccccttgt ctgcgccaca gccccttct ctccccgccc      60 cccgggtgtg tcagattttt cagttaataa tatcccccga gcttcaaagc gcaggctgtg    120
acagtcatct gtctggacgc gctgggtgga tgcgggggc tcctgggaac tgtgttggag    180
ccgagcaagc gctagccagg cgcaagcgcg cacagactgt agccatccga ggacaccccc    240 gccccccgg cccacccgga cacccgcg cagaatcgcc tccggatccc ctgcagtcgg      300
cgggagtgtt ggaggtcggc gccggccccc gccttccgcg ccccccacgg gaaggaagca    360 ccccggtat taaacgaac ggggcggaaa gaagccctca gtcgccggcc gggaggcgag      420
ccgatgccga gctgctccac gtccaccatg ccgggcatga tctgcaagaa cccagacctc    480
gagtttgact cgctacagcc ctgcttctac ccggacgaag atgacttcta cttcggcggc    540
cccgactcga cccccgggg ggaggacatc tggaagaagt ttgagctgct gcccacgccc    600
ccgctgtcgc ccagccgtgg cttcgcggag cacagctccg agccccgag ctgggtcacg      660 gagatgctgc ttgagaacga gctgtggggc agcccggccg aggaggacgc gttcggcctg    720
gggggactgg gtggcctcac ccccaacccg gtcatcctcc aggactgcat gtggagcggc    780
ttctccgccc gcgagaagct ggagcgcgcc gtgagcgaga agctgcagca cggccgcggg    840
ccgccaaccg ccggttccac cgcccagtcc ccgggagccg gcgccgccag ccctgcgggt    900
cgcgggcacg gcggggctgc gggagccggc gcgccggggg ccgccctgcc cgccgagctc    960
gcccacccgg ccgccgagtg cgtggatccc gccgtggtct tccccttcc cgtgaacaag   1020 cgcgagccag cgcccgtgcc cgcagccccg gccgtgcccc cggcggcggg ccctgcggtc    1080
gcctcggggg cgggtattgc cgccccagcc ggggccccgg gggtcgcccc tccgcgccca    1140
ggcggccgcc agaccagcgg cggcgaccac aaggccctca gtacctccgg agaggacacc    1200
ctgagcgatt cagatgatga agatgatgaa gaggaagatg aagaggaaga atcgacgtg    1260 gtcactgtgg agaagcggcg ttcctcctcc aacaccaagg ctgtcaccac attcaccatc    1320
actgtgcgtc caagaacgc agccctgggt cccggggggg ctcagtccag cgagctgatc    1380
ctcaaacgat gccttcccat ccaccagcag cacaactatg ccgccccctc tccctacgtg    1440
gagagtgagg atgcacccccc acagaagaag ataaagagcg aggcgtcccc acgtccgctc    1500
aagagtgtca tcccccaaa ggctaagagc ttgagccccc gaaactctga ctcggaggac    1560
agtgagcgtc gcagaaacca caacatcctg gagcgccagc gccgcaacga ccttcggtcc    1620
agctttctca cgctcaggga ccacgtgccg gagttggtaa agaatgagaa ggccgccaag    1680
gtggtcattt tgaaaaaggc cactgagtat gtccactccc tccaggccga ggagcaccag    1740
cttttgctgg aaaaggaaaa attgcaggca agacagcagc agttgctaaa gaaaattgaa    1800
cacgctcgga cttgctagac gcttctcaaa actggacagt cactgccact ttgcacattt    1860 tgatttttt tttaaacaaa cattgtgttg acattaagaa tgttggttta ctttcaaatc    1920
ggtcccctgt cgagttcggc tctggtggg cagtaggacc accagtgtgg ggttctgctg    1980
ggaccttgga gagcctgcat cccaggatgc tgggtggccc tgcagcctcc tccacctcac    2040
ctccatgaca gcgctaaacg ttggtgacgg ttggagcct ctggggctgt tgaagtcacc    2100
```

```
ttgtgtgttc caagtttcca acaacagaa agtcattcct tcttttaaa atggtgctta    2160 agttccagca gatgccacat aagggggttg ccatttgata cccctgggga acatttctgt    2220
aaataccatt gacacatccg cctttgtat acatcctggg taatgagagg tggcttttgc    2280
ggccagtatt agactggaag ttcataccta agtactgtaa taatacctca atgtttgagg    2340
agcatgtttt gtatacaaat atattgttaa tctctgttat gtactgtact aattcttaca    2400
ctgcctgtat actttagtat gacgctgata cataactaaa tttgatactt atattttcgt    2460
atgaaaatga gttgtgaaag ttttgagtag atattacttt atcacttttt gaactaagaa    2520
acttttgtaa agaaatttac tatatatata tgccttttc ctagcctgtt tcttcctgtt    2580
aatgtatttg ttcatgtttg gtgcatagaa ctgggtaaat gcaagttct gtgtttaatt    2640 tcttcaaaat gtatatattt agtgctgcat cttatagcac tttgaaatac ctcatgttta    2700
tgaaaataaa tagcttaaaa ttaaatgaaa aaaaaa                               2736
```

<210> SEQ ID NO 37
<211> LENGTH: 464
<212> TYPE: PRT
<213> ORGANISM: Artificial Sequence
<220> FEATURE:
<223> OTHER INFORMATION: Synthetic

<400> SEQUENCE: 37

```
Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp
        35                  40                  45

Ile Trp Lys Lys Phe Glu Leu Leu Pro Thr Pro Leu Ser Pro Ser
    50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140

Ser Thr Ala Gln Ser Pro Gly Ala Gly Ala Ser Pro Ala Gly Arg
145                 150                 155                 160

Gly His Gly Gly Ala Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255
```

Glu Asp Thr Leu Ser Asp Ser Asp Glu Asp Glu Glu Glu Asp
        260                 265                 270

Glu Glu Glu Glu Ile Asp Val Val Thr Val Glu Lys Arg Arg Ser Ser
            275                 280                 285

Ser Asn Thr Lys Ala Val Thr Thr Phe Thr Ile Thr Val Arg Pro Lys
        290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
        355                 360                 365

Ser Leu Ser Pro Arg Asn Ser Asp Ser Glu Asp Ser Glu Arg Arg Arg
        370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
            420                 425                 430

Leu Gln Ala Glu Glu His Gln Leu Leu Leu Glu Lys Glu Lys Leu Gln
        435                 440                 445

Ala Arg Gln Gln Gln Leu Leu Lys Lys Ile Glu His Ala Arg Thr Cys
    450                 455                 460

<210> SEQ ID NO 38
<211> LENGTH: 2559
<212> TYPE: DNA
<213> ORGANISM: Artificial Sequence
<220> FEATURE:
<223> OTHER INFORMATION: Synthetic

<400> SEQUENCE: 38
ctccaccttc gggagcagtg ggcagagtgg ggggcttgga gggaagattg gggaacctgg     60 ttagagggg cgcccattgc ctatcccctc ggtctgcccc gtttgcccac cctctccggt    120
gtgtctgtcg gttgcagtgt tggaggtcgg cgccggcccc cgccttccgc gccccccacg    180
ggaaggaagc accccggta ttaaaacgaa cggggcggaa agaagccctc agtcgccggc    240
cgggaggcga gccgatgccg agctgctcca cgtccaccat gccgggcatg atctgcaaga    300
acccagacct cgagtttgac tcgctacagc cctgcttcta cccggacgaa gatgacttct    360
acttcggcgg ccccgactcg acccccccgg gggaggacat ctggaagaag tttgagctgc    420
tgcccacgcc cccgctgtcg cccagccgtg gcttcgcgga gcacagctcc gagccccga    480 gctgggtcac ggagatgctg cttgagaacg agctgtgggg cagcccggcc gaggaggacg    540
cgttcggcct gggggactg ggtggcctca ccccaaccc ggtcatcctc caggactgca    600
tgtggagcgc cttctccgcc cgcgagaagc tggagcgcgc cgtgagcgag aagctgcagc    660 acggccgcg gccgccaacc gccggttcca ccgcccagtc cccgggagcc ggcgccgcca    720
gccctgcggg tcgcgggcac ggcggggctg cgggagccgg ccgcgccggg gccgccctgc    780
ccgccgagct cgcccacccg gccgcgagt cgtggatcc cgccgtggtc ttccccttc    840 ccgtgaacaa gcgcgagcca gcgcccgtgc ccgcagcccc ggccagtgcc ccggcggcgg    900

```
gccctgcggt cgcctcgggg gcgggtattg ccgccccagc cggggccccg ggggtcgccc    960
ctccgcgccc aggcggccgc cagaccagcg gcggcgacca caaggccctc agtacctccg   1020
gagaggacac cctgagcgat tcagatgatg aagatgatga agaggaagat gaagaggaag   1080
aaatcgacgt ggtcactgtg gagaagcggc gttcctcctc aacaccaag gctgtcacca    1140 cattcaccat cactgtgcgt cccaagaacg cagccctggg tcccggggagg gctcagtcca   1200 gcgagctgat cctcaaacga tgccttccca tccaccagca gcacaactat gccgccccct   1260
ctccctacgt ggagagtgag gatgcacccc cacagaagaa gataaagagc gaggcgtccc   1320
cacgtccgct caagagtgtc atccccccaa aggctaagag cttgagcccc cgaaactctg   1380
actcggagga cagtgagcgt cgcagaaacc acaacatcct ggagcgccag cgccgcaacg   1440
accttcggtc cagcttttctc acgctcaggg accacgtgcc ggagttggta aagaatgaga   1500
aggccgccaa ggtggtcatt ttgaaaaagg ccactgagta tgtccactcc ctccaggccg   1560
aggagcacca gcttttgctg gaaaaggaaa aattgcaggc aagacagcag cagttgctaa   1620
agaaaattga acacgctcgg acttgctaga cgcttctcaa aactggacag tcactgccac   1680
tttgcacatt ttgattttttt ttttaaacaa acattgtgtt gacattaaga atgttggttt   1740
actttcaaat cggtcccctg tcgagttcgg ctctgggtgg gcagtaggac caccagtgtg   1800
gggttctgct gggaccttgg agagcctgca tcccaggatg ctgggtggcc ctgcagcctc   1860
ctccacctca cctccatgac agcgctaaac gttggtgacg gttgggagcc tctggggctg   1920
ttgaagtcac cttgtgtgtt ccaagtttcc aaacaacaga aagtcattcc ttcttttttaa   1980 aatggtgctt aagttccagc agatgccaca taaggggttt gccatttgat acccctgggg   2040
aacatttctg taaataccat tgacacatcc gccttttgta tacatcctgg gtaatgagag   2100
gtggcttttg cggccagtat tagactggaa gttcatacct aagtactgta ataataccctc   2160 aatgtttgag gagcatgttt tgtatacaaa tatattgtta atctctgtta tgtactgtac   2220
taattcttac actgcctgta tactttagta tgacgctgat acataactaa atttgatact   2280
tatattttcg tatgaaaatg agttgtgaaa gttttgagta gatattactt tatcactttt   2340
tgaactaaga aacttttgta aagaaattta ctatatatat atgccttttt cctagcctgt   2400
ttcttcctgt taatgtattt gttcatgttt ggtgcataga actgggtaaa tgcaaagttc   2460
tgtgtttaat ttcttcaaaa tgtatatatt tagtgctgca tcttatagca ctttgaaata   2520
cctcatgttt atgaaaataa atagcttaaa attaaatga                          2559
```

<210> SEQ ID NO 39
<211> LENGTH: 224
<212> TYPE: PRT
<213> ORGANISM: Artificial Sequence
<220> FEATURE:
<223> OTHER INFORMATION: Synthetic

<400> SEQUENCE: 39

Met Ala Pro Pro Ala Ala Pro Gly Arg Asp Arg Val Gly Arg Glu Asp
1               5                   10                  15

Glu Asp Gly Trp Glu Thr Arg Gly Asp Arg Lys Ala Arg Lys Pro Leu
            20                  25                  30

Val Glu Lys Lys Arg Arg Ala Arg Ile Asn Glu Ser Leu Gln Glu Leu
        35                  40                  45

Arg Leu Leu Leu Ala Gly Ala Glu Val Gln Ala Lys Leu Glu Asn Ala
    50                  55                  60

| | | | | | | | | | | | | | | | |
|---|---|---|---|---|---|---|---|---|---|---|---|---|---|---|---|
|Glu|Val|Leu|Glu|Leu|Thr|Val|Arg|Arg|Val|Gln|Gly|Val|Leu|Arg|Gly|
|65| | | | |70| | | |75| | | | |80| |

Arg Ala Arg Glu Arg Glu Gln Leu Gln Ala Glu Ala Ser Glu Arg Phe
            85                  90                  95

Ala Ala Gly Tyr Ile Gln Cys Met His Glu Val His Thr Phe Val Ser
            100                 105                 110

Thr Cys Gln Ala Ile Asp Ala Thr Val Ala Ala Glu Leu Leu Asn His
            115                 120                 125

Leu Leu Glu Ser Met Pro Leu Arg Glu Gly Ser Ser Phe Gln Asp Leu
130                 135                 140

Leu Gly Asp Ala Leu Ala Gly Pro Pro Arg Ala Pro Gly Arg Ser Gly
145                 150                 155                 160

Trp Pro Ala Gly Gly Ala Pro Gly Ser Pro Ile Pro Ser Pro Pro Gly
            165                 170                 175

Pro Gly Asp Asp Leu Cys Ser Asp Leu Glu Glu Ala Pro Glu Ala Glu
            180                 185                 190

Leu Ser Gln Ala Pro Ala Glu Gly Pro Asp Leu Val Pro Ala Ala Leu
            195                 200                 205

Gly Ser Leu Thr Thr Ala Gln Ile Ala Arg Ser Val Trp Arg Pro Trp
210                 215                 220

<210> SEQ ID NO 40
<211> LENGTH: 1470
<212> TYPE: DNA
<213> ORGANISM: Artificial Sequence
<220> FEATURE:
<223> OTHER INFORMATION: Synthetic

<400> SEQUENCE: 40

| | | | | | |
|---|---|---|---|---|---|
|gtcggccgcc|ccgggcccgc|gcggccaatc|ggcgcattga|gatgcaaata|agcggctata|60|
|aaagggcgg|gaccgcggcg|ggccggaagc|cgcgaggagc|gcggacggct|gggctgctgc|120|
|tgggcggccg|cggggcagcg|gagggcgccg|gcactccggt|ccccgccgct|ccccgtcccc|180|
|gctgctccta|gccccctgccg|cgtccccggc|ggagcgggca|tggcgccacc|cgcggcgcct|240|
|ggccgggacc|gtgtgggccg|tgaggatgag|gacggctggg|agacgcgagg|ggaccgcaag|300|
|gcccggaagc|ccctggtgga|gaagaagcgg|cgcgcgcgga|tcaacgagag|cctgcaggag|360|
|ctgcggctgc|tgctggcggg|cgccgaggtg|caggccaagc|tggagaacgc|cgaagtgctg|420|
|gagctgacgg|tgcggcgggt|ccagggtgtg|ctgcggggcc|gggcgcgcga|gcgcgagcag|480|
|ctgcaggcgg|aagcgagcga|gcgcttcgct|gccggctaca|tccagtgcat|gcacgaggtg|540|
|cacacgttcg|tgtccacgtg|ccaggccatc|gacgctaccg|tcgctgccga|gctcctgaac|600|
|catctgctcg|agtccatgcc|gctgcgtgag|ggcagcagct|tccaggatct|gctgggggac|660|
|gccctggcgg|ggccacctag|agcccctgga|cggagtggct|ggcctgcggg|gggcgctccg|720|
|ggatccccaa|tacccagccc|cccgggtcct|ggggacgacc|tgtgctccga|cctggaggag|780|
|gccccctgagg|ctgaactgag|tcaggctcct|gctgaggggc|ccgacttggt|gcccgcagcc|840|
|ctgggcagcc|tgaccacagc|ccaaattgcc|cggagtgtct|ggaggccttg|gtgaccaatg|900|
|ccagccagag|tcctgcgggg|gtgggcccgg|ccctccctgg|atctcctccc|tcctcccagg|960|
|ggttcagatg|tggtggggta|gggccctgga|agtctcccag|gtcttccctc|cctcctctga|1020|
|tggatggctt|gcagggcagc|ccctggtaac|cagcccagtc|aggcccccagc|ccgtttctt|1080|
|aagaaacttt|tagggacccct|gcagctctgg|agtgggtgga|gggagggagc|tacgggcagg|1140|
|aggaagaatt|ttgtagagct|gccagcgctc|tcccaggttc|acccacccag|gcttcaccag|1200|

```
ccctgtgcgg gctctggggg cagaggtggc agaaatggtg ctgggcacta gtgttccagg    1260
cagcccgggg ctaaacaaaa gcttgaactt gccacttcag cggggagatg agaggcaggt    1320
gcactgagct gcactgccca gagctgtgat gctctgtaca tcttgtttgt agcacacttg    1380
agtttgtgta ttccattgac atcaaatgtg acaattttac taaataaaga attttggagt    1440
tagttaccct tgaaaaaaaa aaaaaaaaaa                                     1470
```

<210> SEQ ID NO 41
<211> LENGTH: 222
<212> TYPE: PRT
<213> ORGANISM: Artificial Sequence
<220> FEATURE:
<223> OTHER INFORMATION: Synthetic

<400> SEQUENCE: 41

```
Met Ala Pro Pro Ala Ala Pro Gly Arg Asp Arg Val Gly Arg Glu Asp
1               5                   10                  15

Glu Asp Gly Trp Glu Thr Arg Gly Asp Arg Lys Ala Arg Lys Pro Leu
            20                  25                  30

Val Glu Lys Lys Arg Arg Ala Arg Ile Asn Glu Ser Leu Gln Glu Leu
        35                  40                  45

Arg Leu Leu Leu Ala Gly Ala Glu Ala Lys Leu Glu Asn Ala Glu Val
    50                  55                  60

Leu Glu Leu Thr Val Arg Arg Val Gln Gly Val Leu Arg Gly Arg Ala
65                  70                  75                  80

Arg Glu Arg Glu Gln Leu Gln Ala Glu Ala Ser Glu Arg Phe Ala Ala
                85                  90                  95

Gly Tyr Ile Gln Cys Met His Glu Val His Thr Phe Val Ser Thr Cys
            100                 105                 110

Gln Ala Ile Asp Ala Thr Val Ala Ala Glu Leu Leu Asn His Leu Leu
        115                 120                 125

Glu Ser Met Pro Leu Arg Glu Gly Ser Ser Phe Gln Asp Leu Leu Gly
    130                 135                 140

Asp Ala Leu Ala Gly Pro Pro Arg Ala Pro Gly Arg Ser Gly Trp Pro
145                 150                 155                 160

Ala Gly Gly Ala Pro Gly Ser Pro Ile Pro Ser Pro Gly Pro Gly
                165                 170                 175

Asp Asp Leu Cys Ser Asp Leu Glu Glu Ala Pro Glu Ala Glu Leu Ser
            180                 185                 190

Gln Ala Pro Ala Glu Gly Pro Asp Leu Val Pro Ala Ala Leu Gly Ser
        195                 200                 205

Leu Thr Thr Ala Gln Ile Ala Arg Ser Val Trp Arg Pro Trp
    210                 215                 220
```

<210> SEQ ID NO 42
<211> LENGTH: 1464
<212> TYPE: DNA
<213> ORGANISM: Artificial Sequence
<220> FEATURE:
<223> OTHER INFORMATION: Synthetic

<400> SEQUENCE: 42

```
gtcggccgcc ccgggcccgc gcggccaatc ggcgcattga gatgcaaata agcggctata    60 aaagggggcgg gaccgcggcg ggccggaagc cgcgaggagc gcggacggct gggctgctgc   120
tgggcggccg cggggcagcg gagggcgccg gcactccggt ccccgccgct ccccgtcccc   180
```

```
gctgctccta gccctgccg cgtccccggc ggagcgggca tggcgccacc cgcggcgcct    240
ggccgggacc gtgtgggccg tgaggatgag gacggctggg agacgcgagg ggaccgcaag    300
gcccggaagc ccctggtgga aagaagcgg cgcgcgcgga tcaacgagag cctgcaggag    360
ctgcggctgc tgctggcggg cgccgaggcc aagctggaga cgccgaagt gctggagctg    420 acggtgcggc gggtccaggg tgtgctgcgg ggccgggcgc gcgagcgcga gcagctgcag    480
gcggaagcga gcgagcgctt cgctgccggc tacatccagt gcatgcacga ggtgcacacg    540
ttcgtgtcca cgtgccaggc catcgacgct accgtcgctg ccgagctcct gaaccatctg    600
ctcgagtcca tgccgctgcg tgagggcagc agcttccagg atctgctggg ggacgccctg    660
gcggggccac ctagagcccc tggacggagt ggctggcctg cgggggggcgc tccgggatcc    720 ccaatacccca gcccccgggg tcctggggac gacctgtgct ccgacctgga ggaggcccct    780
gaggctgaac tgagtcaggc tcctgctgag gggcccgact tggtgccgc agccctgggc    840 agcctgacca cagcccaaat tgcccggagt gtctggaggc cttggtgacc aatgccagcc    900
agagtcctgc gggggtgggc ccggcccctcc ctggatctcc tccctcctcc cagggttca     960 gatgtggtgg ggtagggccc tggaagtctc ccaggtcttc cctccctcct ctgatggatg    1020
gcttgcaggg cagcccctgg taaccagccc agtcaggccc cagccccgtt tcttaagaaa    1080
cttttaggga ccctgcagct ctggagtggg tggagggagg gagctacggg caggaggaag    1140
aattttgtag agctgccagc gctctcccag gttcacccac ccaggcttca ccagccctgt    1200
gcgggctctg ggggcagagg tggcagaaat ggtgctgggc actagtgttc caggcagccc    1260
tgggctaaac aaaagcttga acttgccact tcagcgggga gatgagaggc aggtgcactg    1320
agctgcactg cccagagctg tgatgctctg tacatcttgt ttgtagcaca cttgagtttg    1380
tgtattccat tgacatcaaa tgtgacaatt ttactaaata aagaatttg gagttagtta    1440 cccttgaaaa aaaaaaaaaa aaaa                                          1464
```

<210> SEQ ID NO 43
<211> LENGTH: 112
<212> TYPE: PRT
<213> ORGANISM: Artificial Sequence
<220> FEATURE:
<223> OTHER INFORMATION: Synthetic

<400> SEQUENCE: 43

Met Ala Pro Pro Ala Ala Pro Gly Arg Asp Arg Val Gly Arg Glu Asp
1               5                   10                  15

Glu Asp Gly Trp Glu Thr Arg Gly Asp Arg Lys Ala Arg Lys Pro Leu
            20                  25                  30

Val Glu Lys Lys Arg Arg Ala Arg Ile Asn Glu Ser Leu Gln Glu Leu
        35                  40                  45

Arg Leu Leu Leu Ala Gly Ala Glu Val Gln Ala Lys Leu Glu Asn Ala
    50                  55                  60

Glu Val Leu Glu Leu Thr Ser Ala Ser Cys Arg Arg Lys Arg Ala
65                  70                  75                  80

Ser Ala Ser Leu Pro Ala Thr Ser Ser Ala Cys Thr Arg Cys Thr Arg
                85                  90                  95

Ser Cys Pro Arg Ala Arg Pro Ser Thr Leu Pro Ser Leu Pro Ser Ser
            100                 105                 110

<210> SEQ ID NO 44
<211> LENGTH: 1430
<212> TYPE: DNA

<213> ORGANISM: Artificial Sequence
<220> FEATURE:
<223> OTHER INFORMATION: Synthetic

<400> SEQUENCE: 44

```
gtcggccgcc ccgggcccgc gcggccaatc ggcgcattga gatgcaaata agcggctata      60
aaaggggcgg daccgcggcg ggccggaagc cgcgaggagc gcggacggct gggctgctgc     120
tgggcggccg cggggcagcg gagggcgccg gcactccggt ccccgccgct ccccgtcccc     180
gctgctccta gccoctgccg cgtccccggc ggagcgggca tggcgccacc cgcggcgcct     240
ggccgggacc gtgtgggccg tgaggatgag gacggctggg agacgcgagg ggaccgcaag     300
gcccggaagc ccctggtgga gaagaagcgg cgcgcgcgga tcaacgagag cctgcaggag     360
ctgcggctgc tgctggcggg cgccgaggtg caggccaagc tggagaacgc cgaagtgctg     420
gagctgacga gcgcgagcag ctgcaggcgg aagcgagcga gcgcttcgct gccggctaca     480
tccagtgcat gcacgaggtg cacacgttcg tgtccacgtg ccaggccatc gacgctaccg     540
tcgctgccga gctcctgaac catctgctcg agtccatgcc gctgcgtgag ggcagcagct     600
tccaggatct gctgggggac gccctggcgg ggccacctag agccctgga cggagtggct     660
ggcctgcggg gggcgctccg ggatccccaa tacccagccc ccgggtcct ggggacgacc     720
tgtgctccga cctggaggag gcccctgagg ctgaactgag tcaggctcct gctgaggggc     780
ccgacttggt gcccgcagcc ctgggcagcc tgaccacagc ccaaattgcc cggagtgtct     840
ggaggccttg gtgaccaatg ccagccagag tcctgcgggg gtgggccgg ccctccctgg     900
atctcctccc tcctcccagg ggttcagatg tggtggggta gggccctgga agtctcccag     960
gtcttccctc cctcctctga tggatggctt gcagggcagc ccctggtaac cagcccagtc    1020
aggccccagc cccgtttctt aagaaacttt tagggaccct gcagctctgg agtgggtgga    1080
gggagggagc tacgggcagg aggaagaatt ttgtagagct gccagcgctc tcccaggttc    1140
acccacccag gcttcaccag ccctgtgcgg gctctggggg cagaggtggc agaaatggtg    1200
ctgggcacta gtgttccagg cagccctggg ctaaacaaaa gcttgaactt gccacttcag    1260
cggggagatg agaggcaggt gcactgagct gcactgccca gagctgtgat gctctgtaca    1320
tcttgtttgt agcacacttg agtttgtgta ttccattgac atcaaatgtg acaatttac     1380
taaataaaga attttggagt tagttaccct tgaaaaaaaa aaaaaaaaa                1430
```